United States Patent
Dong et al.

(10) Patent No.: US 10,736,966 B2
(45) Date of Patent: Aug. 11, 2020

(54) BRUSH-POLY (GLYCOAMIDOAMINE)-LIPIDS AND USES THEREOF

(71) Applicant: Massachusetts Institute of Technology, Cambridge, MA (US)

(72) Inventors: Yizhou Dong, Dublin, OH (US); Joseph R. Dorkin, Somerville, MA (US); Robert S. Langer, Newton, MA (US); Daniel Griffith Anderson, Framingham, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 601 days.

(21) Appl. No.: 14/825,127

(22) Filed: Aug. 12, 2015

(65) Prior Publication Data

US 2016/0067346 A1    Mar. 10, 2016

Related U.S. Application Data

(60) Provisional application No. 62/036,492, filed on Aug. 12, 2014.

(51) Int. Cl.
*A61K 38/18* (2006.01)
*A61K 9/127* (2006.01)
(Continued)

(52) U.S. Cl.
CPC ...... *A61K 47/48207* (2013.01); *A61K 9/1273* (2013.01); *A61K 38/1816* (2013.01);
(Continued)

(58) Field of Classification Search
None
See application file for complete search history.

(56) References Cited

U.S. PATENT DOCUMENTS 5,393,795 A * 2/1995 Hedstrand ............ C08G 73/028
                                                521/134

FOREIGN PATENT DOCUMENTS

WO    WO 2002/031025 A2    4/2002
WO    WO 2004/106411 A2    12/2004
(Continued)

OTHER PUBLICATIONS

Lee et al, Bioconjugate Chem. 19:428-440, 2008.*
(Continued)

*Primary Examiner* — Alma Pipic
(74) *Attorney, Agent, or Firm* — Wolf, Greenfield & Sacks, P.C.

(57) ABSTRACT

The present disclosure provides brush-poly(glycoamidoamine)-lipids (PGALs) (e.g., polymers of any one of Formulae (I)-(IV)) and methods of preparing the PGALs. A described PGAL may include poly(glycoamidoamine)-derived moieties (e.g.,

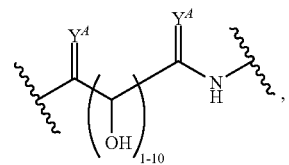

such as

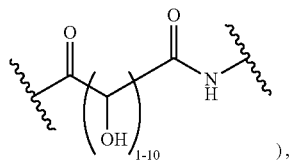

which may assist the PGAL and/or a complex of the PGAL and an agent to pass through cell membranes or be taken up by cells. Also provided are compositions including a described PGAL and an agent (e.g., polynucleotide, small molecule, peptide, or protein). The present disclosure also provides methods, kits, and uses that include or involve the PGALs or compositions for delivering an agent to a subject, tissue, or cell and/or for treating and/or preventing in a subject a range of diseases, such as genetic diseases, proliferative diseases, hematological diseases, neurological diseases, immunological diseases, gastrointestinal diseases, respiratory diseases, painful conditions, psychiatric disorders, musculoskeletal diseases, genitourinary diseases, and metabolic disorders

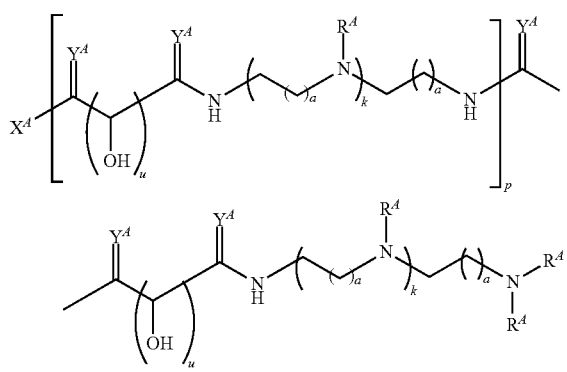

27 Claims, 6 Drawing Sheets

(51) Int. Cl.
| | |
|---|---|
| C08G 69/48 | (2006.01) |
| C08G 69/50 | (2006.01) |
| A61K 47/48 | (2006.01) |
| C08G 73/00 | (2006.01) |
| C08L 79/00 | (2006.01) |
| A61K 47/60 | (2017.01) |
| A61K 47/69 | (2017.01) |
| A61K 47/54 | (2017.01) |
| A61K 47/59 | (2017.01) |
| A61K 48/00 | (2006.01) |
| C12N 15/113 | (2010.01) |

(52) U.S. Cl.
CPC .......... *A61K 47/544* (2017.08); *A61K 47/554* (2017.08); *A61K 47/595* (2017.08); *A61K 47/60* (2017.08); *A61K 47/6915* (2017.08); *A61K 47/6935* (2017.08); *A61K 48/00* (2013.01); *C08G 69/48* (2013.01); *C08G 69/50* (2013.01); *C08G 73/00* (2013.01); *C08L 79/00* (2013.01); *C12N 15/1137* (2013.01); *A61K 48/0041* (2013.01); *C12N 2310/14* (2013.01); *C12N 2320/32* (2013.01)

(56) References Cited

FOREIGN PATENT DOCUMENTS

| WO | WO 2006/138380 A2 | | 12/2006 |
|---|---|---|---|
| WO | WO 07/143659 | * | 12/2007 |
| WO | WO 2007/143659 A2 | | 12/2007 |
| WO | WO 2008/011561 A2 | | 1/2008 |
| WO | WO 2010/053572 A2 | | 5/2010 |
| WO | WO 10/129709 | * | 11/2010 |
| WO | WO 2013/063468 A1 | | 5/2013 |

OTHER PUBLICATIONS

Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.

Berge et al., Pharmaceutical salts. J Pharm Sci. Jan. 1977;66(1):1-19.

Damen et al., Delivery of DNA and siRNA by novel gemini-like amphiphilic peptides. J Control Release. Jul. 1, 2010;145(1):33-9. doi:10.1016/j.jconrel.2010.03.028. Epub Apr. 8, 2010.

Davis et al., Evidence of RNAi in humans from systemically administered siRNA via targeted nanoparticles. Nature. Apr. 15, 2010;464(7291):1067-70. doi: 10.1038/nature08956. Epub Mar. 21, 2010.

Liu et al., Hydroxyl stereochemistry and amine number within poly(glycoamidoamine)s affect intracellular DNA delivery. J Am Chem Soc. Mar. 9, 2005;127(9):3004-15.

Liu et al., New poly(d-glucaramidoamine)s induce DNA nanoparticle formation and efficient gene delivery into mammalian cells. J Am Chem Soc. Jun. 23, 2004;126(24):7422-3.

McLendon et al., Poly(glycoamidoamine) vehicles promote pDNA uptake through multiple routes and efficient gene expression via caveolae-mediated endocytosis. Mol Pharm. Jun. 7, 2010;7(3):738-50. doi: 10.1021/mp900282e.

Morris et al., Lentiviral-mediated delivery of siRNAs for antiviral therapy.Gene Ther. Mar. 2006;13(6):553-8.

Peer et al., Nanocarriers as an emerging platform for cancer therapy. Nat Nanotechnol. Dec. 2007;2(12):751-60. doi: 10.1038/nnano.2007.387.

Sen, Surfactin: biosynthesis, genetics and potential applications. Adv Exp Med Biol. 2010;672:316-23.

Whitehead et al., Knocking down barriers: advances in siRNA delivery. Nat Rev Drug Discov. Feb. 2009;8(2):129-38. doi: 10.1038/nrd2742.

International Search Report and Written Opinion for PCT/US2015/044921, dated Dec. 7, 2015.

Dahlman et al., In vivo endothelial siRNA delivery using polymeric nanoparticles with low molecular weight. Nat Nanotechnol. Aug. 2014;9(8):648-55.

Dong et al., Lipopeptide nanoparticles for potent and selective siRNA delivery in rodents and nonhuman primates. Proc Natl Acad Sci U S A. Mar. 18, 2014;111(11):3955-60.

Ingle et al., Poly(glycoamidoamine)s: a broad class of carbohydrate-containing polycations for nucleic acid delivery. Trends in Biotech. Sep. 2011; 29(9):443-53.

Taori et al., DNA delivery in vitro via surface release from multilayer assemblies with poly(glycoamidoamine)s. Acta Biomater. Mar. 2009;5(3):925-33.

International Preliminary Report on Patentability for PCT/US2015/044921, dated Feb. 23, 2017.

* cited by examiner

BRUSH-POLY (GLYCOAMIDOAMINE)-LIPIDS AND USES THEREOF

RELATED APPLICATIONS

This application claims priority under 35 U.S.C. § 119(e) to U.S. Provisional Application, U.S. Ser. No. 62/036,492, filed Aug. 12, 2014, which is incorporated herein by reference.

GOVERNMENT SUPPORT

This invention was made with Government support under grant number EB000244 awarded by the National Institutes of Health. The Government has certain rights in the invention.

BACKGROUND OF THE INVENTION

The ability to silence genes via RNA interference (RNAi) was reported by Mello and Fire in 1998. See Fire et al., *Nature* (1998) 391:806-811. Since then, scientists have rushed to take advantage of the enormous therapeutic potential driven by targeted gene knockdown. This is evidenced by the fact that the first report of small interfering RNA (siRNA) mediated RNAi in human beings was reported only twelve years after the phenomenon was described in *Caenorhabditis elegans*. See Davis et al., *Nature* (2010) 464: 1067-1070. The advantages of siRNA therapeutics include high target selectivity and specificity, and the potential to target pathways currently believed to be "undruggable" for the treatment of genetic diseases without effective therapy. siRNA therapeutics has shown promising results for the treatment of various diseases, such as hepatic carcinoma, hypercholesterolemia, refractory anemia, and familial amyloid neuropathy.

However, the efficient delivery of siRNA is still a challenge in the development of siRNA therapeutics. Due to issues associated with delivery efficiency and toxicity, the clinical use of siRNA requires safer and more effective delivery systems. It is understood that the development of genetic drugs is slowed by the inability to deliver nucleic acids effectively in vivo. When unprotected, genetic materials injected into the bloodstream can be degraded by deoxyribonucleases (DNAases) and ribonucleases (RNAases), or, if not degraded, the genetic materials can stimulate an immune response. See, e.g., Whitehead et al., *Nature Reviews Drug Discovery* (2009) 8:129-138; Robbins et al., *Oligonucleotides* (2009) 19:89-102. Intact siRNA must then enter the cytosol, where the antisense strand is incorporated into the RNA-induced silencing complex (RISC) (Whitehead et al., supra). The RISC associates with and degrades complementary mRNA sequences, thereby preventing translation of the target mRNA into protein, i.e., "silencing" the gene.

To overcome difficulties in the delivery of polynucleotides, polynucleotides have been complexed with a wide variety of delivery systems, including polymers, lipids, inorganic nanoparticles, and viruses. See, e.g., Peer et al., *Nature Nanotechnology*, (2007) 2:751-760. However, despite promising data from ongoing clinical trials for the treatment of respiratory syncytial virus infection and liver cancers (see, e.g., Zamora et al., *Am. J. Respir. Crit. Care Med*. (2011) 183:531-538), the clinical use of siRNA continues to require development of safer and more effective delivery systems. Toward this end, numerous lipid-like molecules have been developed including poly β-amino esters and amino alcohol lipids. See, e.g., International PCT Patent Application Publications, WO 2002/031025, WO 2004/106411, WO 2008/011561, WO 2007/143659, WO 2006/138380, WO 2010/053572, and WO 2013/063468. Amino acid, peptide, and polypeptide-derived lipids have also been studied for a variety of applications, including use as therapeutics, biosurfactants, and nucleotide delivery systems. See, e.g., Giuliani et al., *Cellular and Molecular Life Sciences* (2011) 68:2255-2266; Ikeda et al., *Current Medicinal Chemistry* (2007) 14: 111263-1275; Sen, *Advances in Experimental Medicine and Biology* (2010) 672:316-323; and Damen et al., *Journal of Controlled Release* (2010) 145:33-39.

But still there remains a need for new materials and systems for the effective delivery of siRNAs, other nucleic acids, and other agents including small molecule and proteins to cells.

SUMMARY OF THE INVENTION

The present disclosure provides brush-poly(glycoamidoamine)-lipids (PGALs) (e.g., polymers of any one of Formulae (I)-(IV) (e.g., Formulae (I), (I'), (I''), (II), (II'), (II''), (III), (III'), (III''), and (IV)) and methods of preparing the polymers. The polymers described herein are useful in delivering an agent (e.g., a polynucleotide (e.g., RNA (e.g., siRNA or mRNA) or DNA), small molecule, peptide, or protein) to a subject, tissue (e.g., liver, spleen, lung, kidney, pancreas, heart, muscle, or prostate), or cell. In certain embodiments, a polymer described herein includes glycoamido-derived moieties (e.g.,

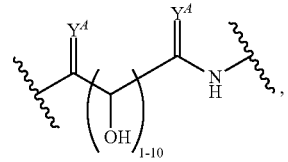

such as glycoamido moieties

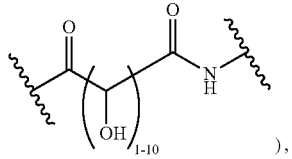

), amino moieties, and lipid moieties ("lipid tails") (e.g., substituted or unsubstituted alkyl or substituted or unsubstituted alkenyl moieties) (e.g., $R^{A1}$, $R^{B1}$, or $R^{C1}$). The amino moieties of the described polymers may be protonated to form positively charged ammonium cations that may bind to an agent that includes negatively charged moieties, such as the phosphate groups in the backbone of a polynucleotide. The lipid moieties of a described polymer are typically hydrophobic and may assist the described polymer and/or a complex of the described polymer and the agent to pass through cell membranes or be taken up by cells. The glycoamido moieties of a described polymer may improve the ability of the described polymer and/or a complex of the described polymer and the agent to pass through cell membranes or be taken up by cells. For example, the glycoamido moieties are hydrophilic, and the described polymers bearing these moieties may be more soluble and/or have a greater ability to get into a cell. Moreover, the glycoamido moieties may be recognized by membrane transport proteins that lead to the uptake of the described polymers and any agent associated with the polymer into cells. As a result, the described polymers with glycoamido moieties attached may be efficiently transported into cells. Additionally, the amide groups (e.g.,

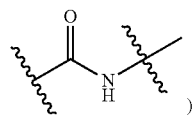
)

of the glycoamido moieties may be hydrolyzed in a cell to give rise to polyamines (e.g., 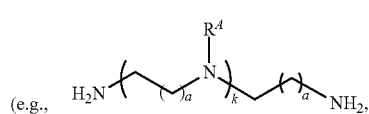

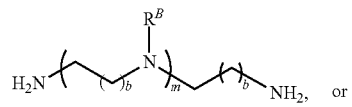, or

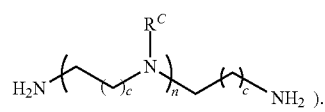 ).

The polyamines may no longer be recognized by membrane transport proteins and, therefore, may be retained inside the cell. The polyamines may also remain in the cell because the polyamines are too polar (e.g., when the polyamines are protonated and positively charged) to pass through the cell membrane to get out of the cell. The polymers may also be able to form lipid nanoparticles (LNPs), microparticles, micelles, liposomes, lipoplexes, and other forms.

Also described herein are compositions (e.g., pharmaceutical compositions) including a polymer described herein and optionally an agent. The present disclosure also provides methods and kits using the polymers or compositions for delivering an agent to a subject, tissue, or cell and for treating and/or preventing a range of diseases, such as genetic diseases, proliferative diseases, hematological diseases, neurological diseases, gastrointestinal diseases (e.g., liver diseases), immunological diseases (e.g., autoimmune diseases), spleen diseases, respiratory diseases (e.g., lung diseases), painful conditions, psychiatric disorders, musculoskeletal diseases, genitourinary diseases, and metabolic disorders.

In one aspect, the present disclosure provides polymers of any one of Formulae (I), (I'), and (I"):

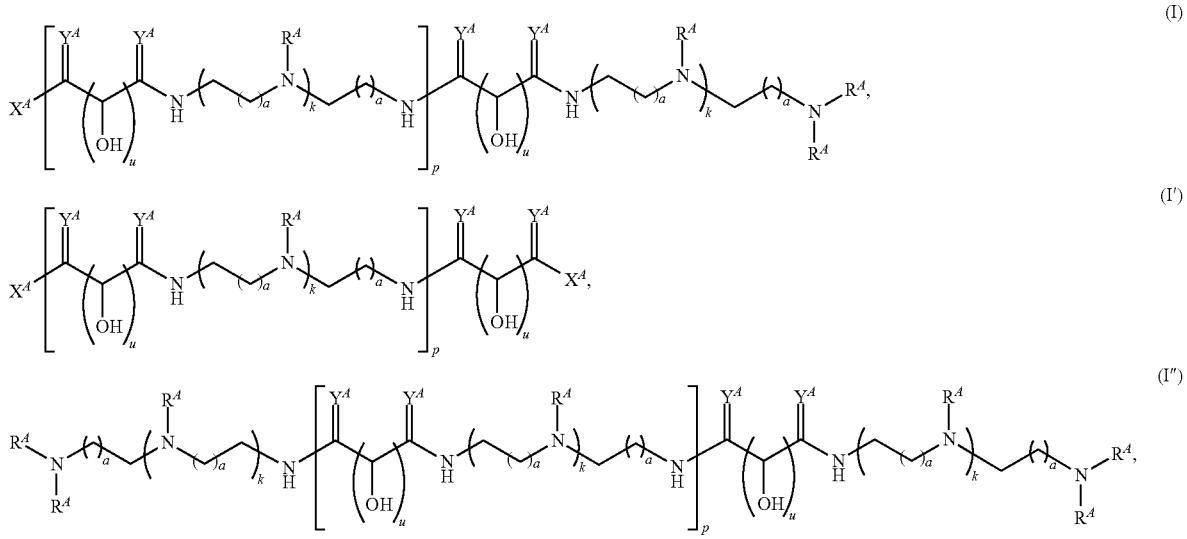

and salts, solvates, hydrates, polymorphs, co-crystals, tautomers, stereoisomers, and isotopically labeled derivatives, wherein each instance of $R^A$ is independently hydrogen, a moiety of the formula:

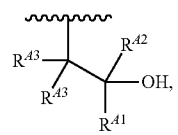

or a moiety of the formula:

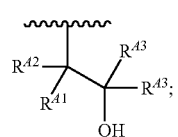

at least one instance of $R^A$ is of the formula:
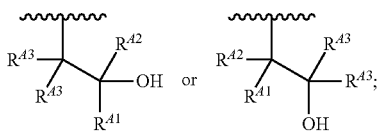
and each instance of $R^{A1}$ is independently hydrogen, substituted or unsubstituted alkyl, or substituted or unsubstituted alkenyl. $X^A$, $R^{A2}$, $R^{A3}$, a, k, p, and u are as described herein.
Exemplary polymers of Formula (I) include, but are not limited to:
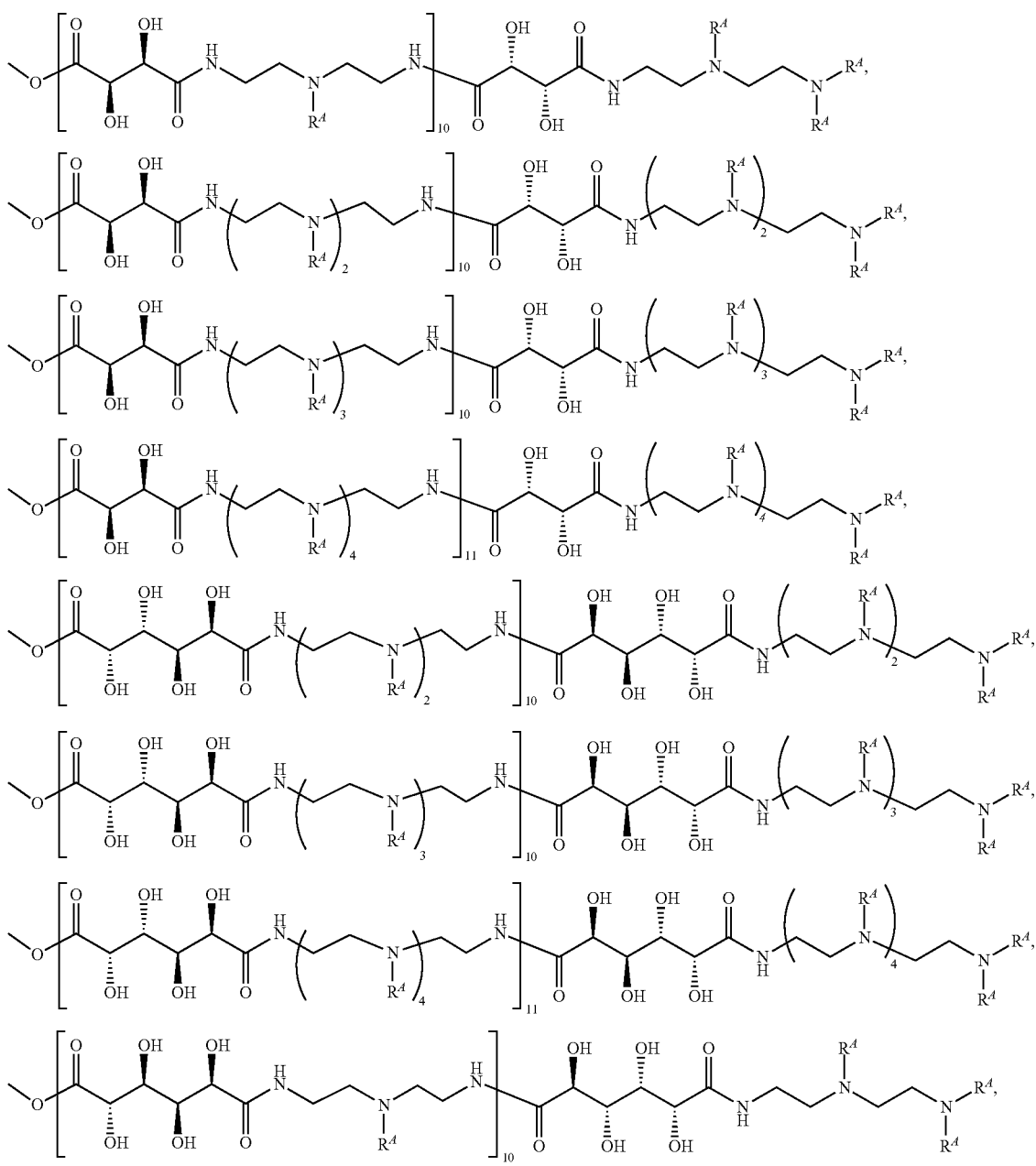

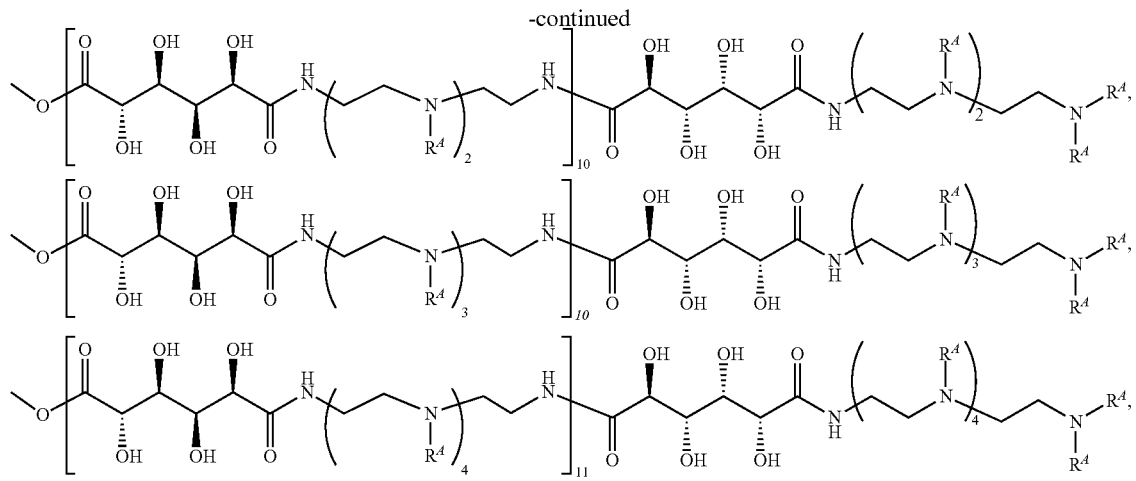

and salts, solvates, hydrates, polymorphs, co-crystals, tautomers, stereoisomers, and isotopically labeled derivatives thereof, wherein each instance of $R^A$ is independently H, a moiety of the formula:

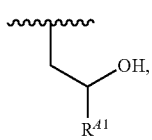

or a moiety of the formula:

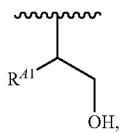

wherein: at least one instance of $R^A$ is of the formula:

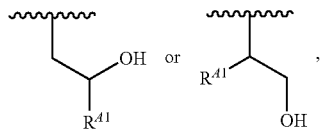

and each instance of $R^{A1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$.

Exemplary polymers of any one of Formulae (I), (I'), and (I'') also include the polymers shown in Table 7, and salts, solvates, hydrates, polymorphs, co-crystals, tautomers, stereoisomers, and isotopically labeled derivatives thereof.

In another aspect, the present disclosure provides polymers of any one of Formulae (II), (II'), and (II''):

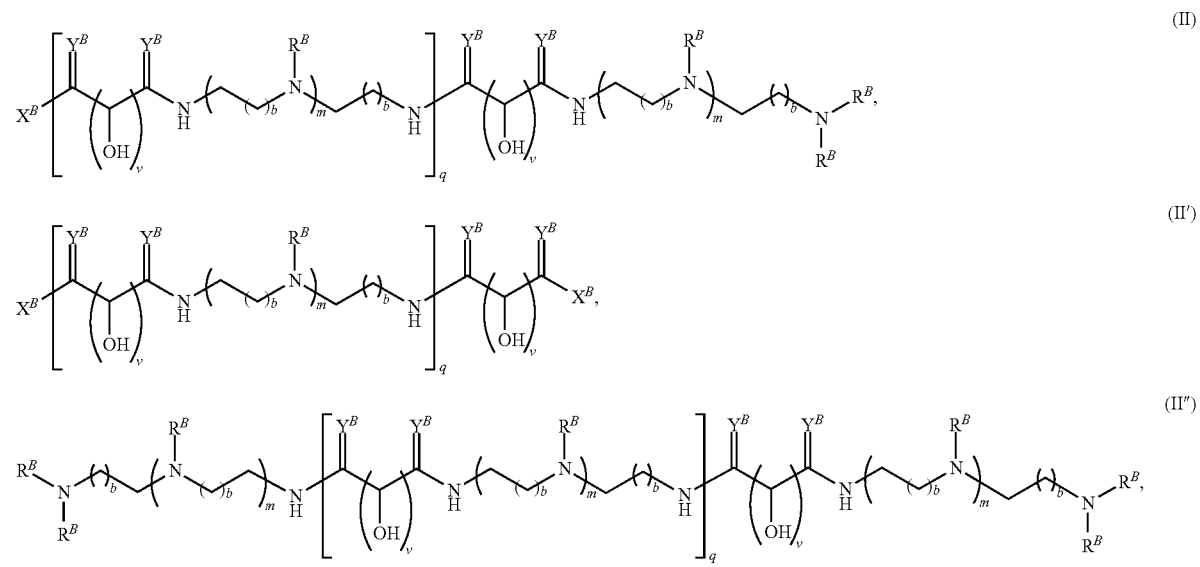

and salts, solvates, hydrates, polymorphs, co-crystals, tautomers, stereoisomers, and isotopically labeled derivatives thereof, wherein each instance of $R^B$ is independently hydrogen or a moiety of the formula:

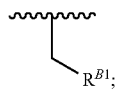

at least one instance of $R^B$ is of the formula:

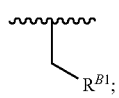

and each instance of $R^{B1}$ is independently substituted or unsubstituted alkyl or substituted or unsubstituted alkenyl. $X^B$, b, m, q, and v are as described herein.

In another aspect, the present disclosure provides polymers of any one of Formulae (III), (III'), and (III''):

at least one instance of $R^C$ is of the formula:

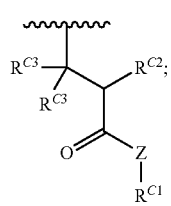

and each instance of $R^{C1}$ is independently hydrogen, substituted or unsubstituted alkyl, or substituted or unsubstituted alkenyl. $X^C$, Z, c, n, r, and w are as described herein.

In another aspect, the present disclosure provides polymers of Formula (IV):

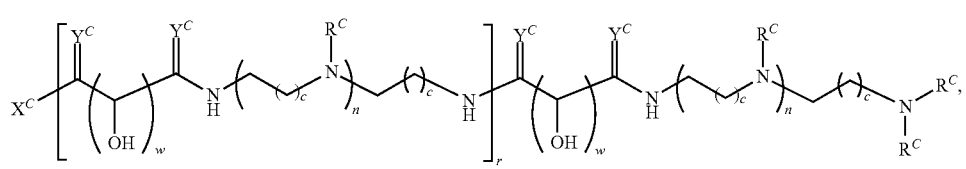

(III)

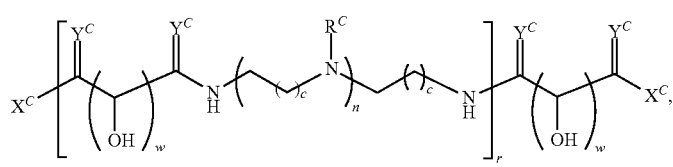

(III')

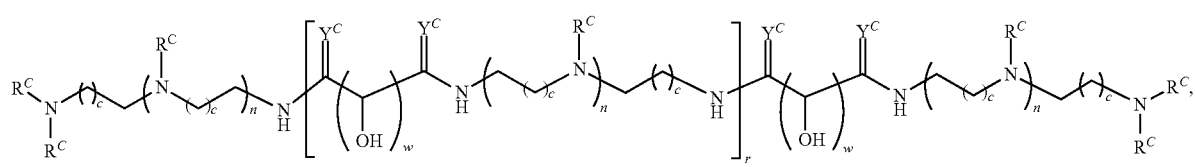

(III'')

and salts, solvates, hydrates, polymorphs, co-crystals, tautomers, stereoisomers, and isotopically labeled derivatives thereof, wherein each instance of $R^C$ is independently hydrogen or a moiety of the formula:

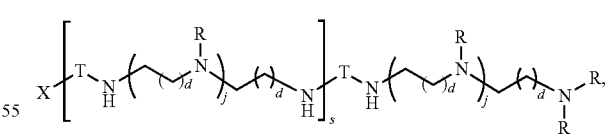

(IV)

and salts, solvates, hydrates, polymorphs, co-crystals, tautomers, stereoisomers, and isotopically labeled derivatives thereof, wherein each instance of T is a divalent carbohydrate moiety; each instance of R is independently $R^A$, $R^B$, or $R^C$; and X, d, j, and s are as described herein.

Another aspect of the present disclosure relates to methods of preparing polymers of any one of Formulae (I), (I'), and (I''), and salts thereof, the methods including reacting a polymer of Formula (A1), (A3), (A4), or a salt thereof, with an epoxide of Formula (A2) to provide the polymer of any one of Formulae (I), (I'), and (I"), or a salt thereof:

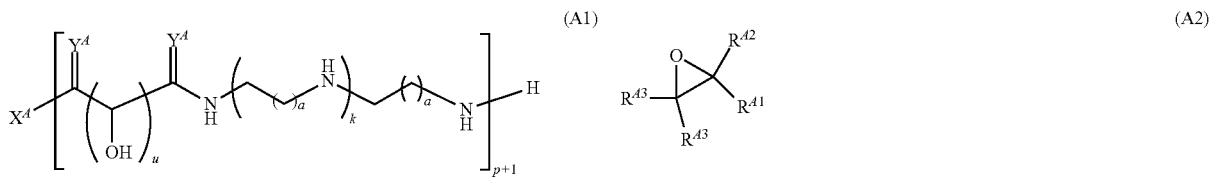
(A1)

(A2)

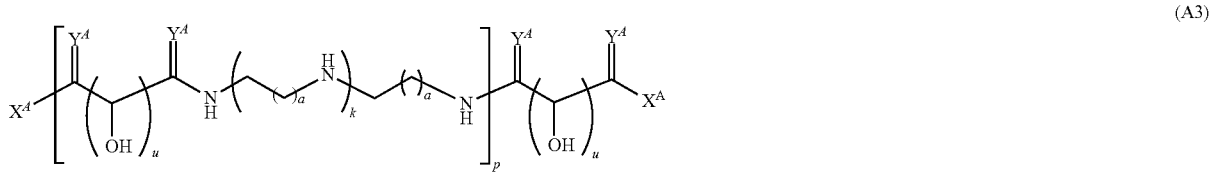
(A3)

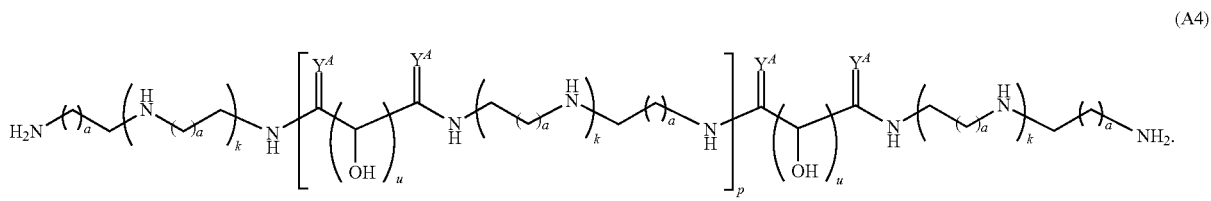
(A4)

Another aspect of the present disclosure relates to methods of preparing the polymers of any one of Formulae (II), (II'), and (II"), and salts thereof, the methods including reacting a polymer of Formula (B1), (B4), (B5), or a salt thereof, with an aldehyde of Formula (B2) in the presence of a reductant to provide the polymer of any one of Formulae (II), (II'), and (II"), or a salt thereof:

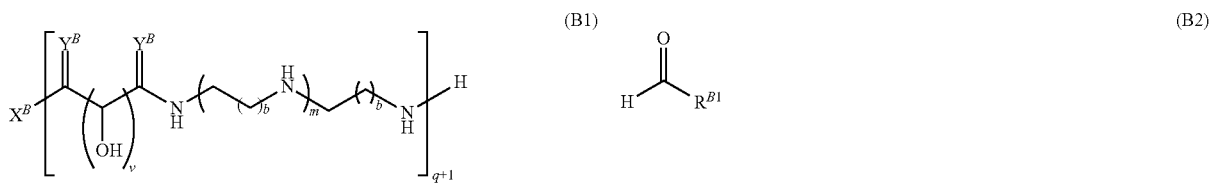
(B1)

(B2)

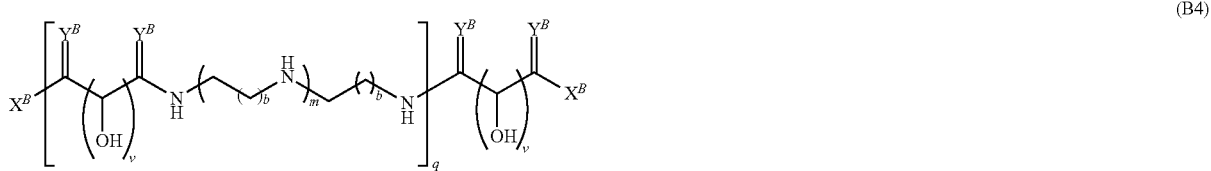
(B4)

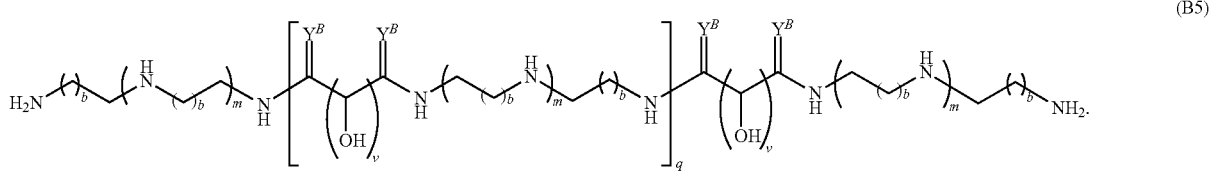
(B5)

Another aspect of the present disclosure relates to methods of preparing the polymers of Formula (II), and salts thereof, the methods including reducing a polymer of Formula (B3), or a salt thereof, with a reductant to provide the polymer of Formula (II), or a salt thereof:

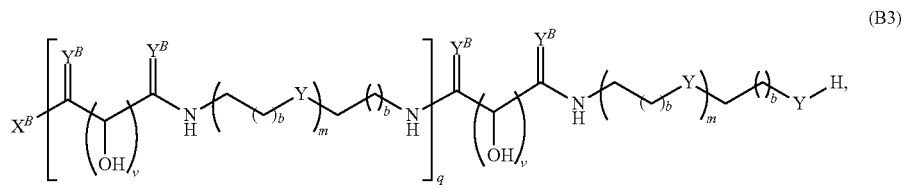
(B3)

wherein each instance of Y is independently —NH— or a moiety of the formula:

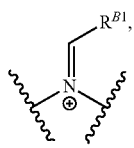

wherein at least one instance of Y is a moiety of the formula:

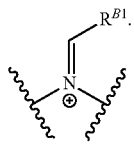

In certain embodiments, the reductant is a borohydride, borane, silane, alcohol, or $H_2$.

Another aspect of the present disclosure relates to methods of preparing the polymers of any one of Formulae (III), (III'), and (III"), and salts thereof, the methods including reacting a polymer of Formula (C1), (C3), (C4), or a salt thereof, with a compound of Formula (C2) to provide the polymer of any one of Formulae (III), (III'), and (III"), or a salt thereof:

described compositions are thought to be useful for delivering an agent to a subject, tissue, or cell. A described composition including a polymer described herein may be in the form of particles (e.g., nanoparticles, microparticles, micelles, or liposomes). In certain embodiments, the lipid moieties of a polymer described herein are substantially on the outside of a particle described herein. In certain embodiments, the amino moieties of a polymer described herein are substantially within a particle described herein. An agent may be encapsulated within the particle described herein and may get transported through the cell membranes (e.g., into or out of a cell). The particle may dissociate and release the agent to a cell (e.g., a target cell) or tissue (e.g., a target tissue).

The compositions described herein (e.g., pharmaceutical compositions) may also be useful in treating a range of diseases (e.g., genetic diseases, proliferative diseases, hematological diseases, neurological diseases, gastrointestinal diseases (e.g., liver diseases), spleen diseases, respiratory diseases (e.g., lung diseases), painful conditions, psychiatric disorders, musculoskeletal diseases, genitourinary diseases, musculoskeletal diseases, genitourinary diseases, musculoskeletal diseases, genitourinary diseases, and metabolic disorders) in a subject in need thereof. In certain embodiments, a composition described herein includes a therapeutically effective amount of an agent (e.g., a pharmaceutical or diagnostic agent).

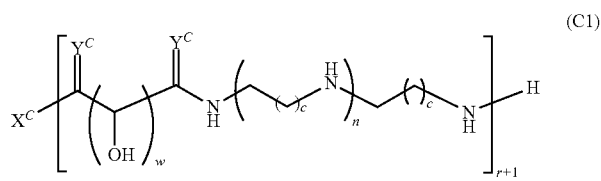 (C1)

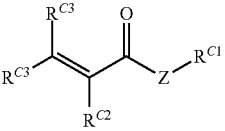 (C2)

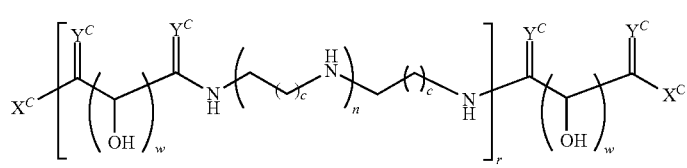 (C3)

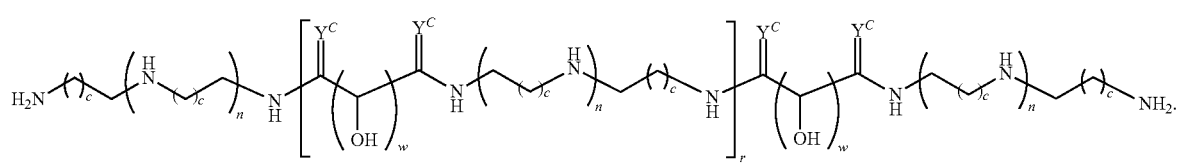 (C4)

In yet another aspect, the present disclosure provides compositions (e.g., pharmaceutical compositions) comprising a polymer described herein and optionally an excipient (e.g., a pharmaceutically acceptable excipient). The The compositions described herein (e.g., pharmaceutical compositions) may also be useful in preventing a variety of diseases (e.g., genetic diseases, proliferative diseases, hematological diseases, neurological diseases, gastrointestinal diseases (e.g., liver diseases), spleen diseases, respiratory diseases (e.g., lung diseases), painful conditions, psychiatric disorders, musculoskeletal diseases, genitourinary diseases, and metabolic disorders) in a subject in need thereof. In certain embodiments, a composition described herein includes a prophylactically effective amount of the agent.

Another aspect of the present disclosure relates to methods of delivering an agent to a subject. In certain embodiments, the method of delivering an agent comprises administering to a subject (e.g., a human) a composition described herein that includes the agent.

Another aspect of the present disclosure relates to methods of delivering an agent to a tissue. In certain embodiments, the method of delivering an agent comprises contacting a tissue (e.g., a liver, spleen, or lung) with a composition described herein that includes the agent. In certain embodiments, the agent is selectively delivered to a target tissue, compared to the delivery of the agent to a non-target tissue.

Another aspect of the present disclosure relates to methods of delivering an agent to a cell. In certain embodiments, the method of delivering an agent comprises contacting a cell with a composition described herein that includes the agent. The cell may be in vitro or in vivo. In certain embodiments, the agent is selectively delivered to a target cell, compared to the delivery of the agent to a non-target cell.

Another aspect of the disclosure relates to methods of increasing the exposure or concentration of an agent in a subject, tissue, or cell.

In another aspect, the present disclosure provides methods of treating and/or preventing a disease in a subject in need thereof. In certain embodiments, the methods of treating a disease comprise administering to the subject a therapeutically effective amount of a pharmaceutical composition described herein that includes a pharmaceutical agent. In certain embodiments, the methods of preventing a disease comprise administering to the subject a prophylactically effective amount of a pharmaceutical composition described herein that includes a pharmaceutical agent.

In certain embodiments, the disease that is treated or prevented by a described method is a genetic disease, proliferative disease, hematological disease, neurological disease, gastrointestinal disease (e.g., liver disease), spleen disease, respiratory disease (e.g., lung disease), painful condition, psychiatric disorder, musculoskeletal disease, genitourinary disease, or metabolic disorder. Another aspect of the disclosure relates to methods of screening a library of polymers described herein to identify a polymer that is useful in a method described herein (e.g., a polymer useful for delivering a polynucleotide to a subject, tissue, or cell).

In yet another aspect, the present disclosure provides polymers and compositions described herein for use in a method of the present disclosure (e.g., a method of delivering an agent to a subject; a method of delivering an agent to a tissue; a method of delivering an agent to a cell; a method of increasing the exposure or concentration of an agent in a subject, tissue, or cell; a method of treating a disease in a subject in need thereof; or a method of preventing a disease in a subject in need thereof).

Another aspect of the present disclosure relates to kits comprising a container with a polymer or composition described herein. The kits may include a single dose or multiple doses of the composition. The kits may be useful in a method described herein. In certain embodiments, a kit of the disclosure further includes instructions for using the polymer or composition (e.g., for administering the polymer or composition to a subject (e.g., as required by a regulatory agency)).

The details of one or more embodiments of the disclosure are set forth herein. Other features, objects, and advantages of the disclosure will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Compounds (e.g., polymers) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$alkenyl"). In some embodiments, an alkenyl group has 2 to 8 carbon atoms ("$C_{2-8}$alkenyl"). In some embodiments, an alkenyl group has 2 to 7 carbon atoms ("$C_{2-7}$alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is unspecified (e.g., —CH=CHCH$_3$ or

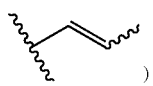
)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$carbocyclyl"). In some embodiments, a carbocyclyl group has 3 to 8 ring carbon atoms ("$C_{3-8}$carbocyclyl"). In some embodiments, a carbocyclyl group has 3 to 7 ring carbon atoms ("$C_{3-7}$carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

The term "heteroaryl" refers to a radical of a 5-14 membered monocyclic or polycyclic (e.g., bicyclic, tricyclic) 4n+2 aromatic ring system (e.g., having 6, 10, or 14 it electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to being substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group) if not otherwise provided explicitly. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$alkyl)(C$_{1-6}$ alkyl), —N(OH)(C$_{1-6}$ alkyl), —NH(OH), —SH, —SC$_{1-6}$alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)

($C_{1-6}$ alkyl), —N($C_{1-6}$ alkyl)C(=O)($C_{1-6}$ alkyl), —NHCO$_2$ ($C_{1-6}$ alkyl), —NHC(=O)N($C_{1-6}$ alkyl)$_2$, —NHC(=O)NH ($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$, —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X is a counterion.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), tert-butoxycarbonyl, methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate, alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_1$-4 alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The polymers of any one of Formulae (I)-(IV) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot yH_2O$, wherein R is the compound and wherein y is a number greater than 0. A given compound may form more than one type of hydrates, including, e.g., monohydrates (y is 1), lower hydrates (y is a number greater than 0 and smaller than 1, e.g., hemihydrates ($R.0.5H_2O$)), and polyhydrates (y is a number greater than 1, e.g., dihydrates ($R.2H_2O$) and hexahydrates ($R.6H_2O$)).

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (–)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "lipophilic" or "hydrophobic" refers to the ability of a compound to dissolve, or the ability of a moiety of a compound to assist the compound in dissolving in fats, oils, lipids, and/or non-polar solvents (e.g., hexane or toluene). Lipophilic moieties include, but are not limited to, substituted or unsubstituted, branched or unbranched alkyl groups having 1 to 50 carbon atoms. In certain embodiments, the lipophilic moiety is an alkyl group including at least 1, at least 6, at least 12, at least 18, at least 24, at least 36, or at least 50 carbon atoms. In certain embodiments, the lipophilic moiety is an alkyl group including at most 50, at most 36, at most 24, at most 18, at most 12, or at most 6 carbon atoms. Combinations of the above-referenced ranges (e.g., at least about 1 and at most about 24 carbon atoms) are also within the scope of the disclosure. In certain embodiments, the lipophilic moiety is unsubstituted alkyl. In certain embodiments, the lipophilic moiety is unsubstituted and unbranched alkyl. In certain embodiments, the lipophilic moiety is unsubstituted and unbranched $C_{1-24}$ alkyl. In certain embodiments, the lipophilic moiety is unsubstituted and unbranched $C_{6-24}$ alkyl. In certain embodiments, the lipophilic moiety is unsubstituted and unbranched $C_{12-24}$ alkyl.

The term "polymer" refers to a compound comprising two or more repeating structural units. In certain embodiments, a polymer is naturally occurring. In certain embodiments, a polymer is synthetic (i.e., not naturally occurring).

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an α anomer, the —OH substituent on the anomeric carbon rests on the opposite side (trans) of the ring from the —CH₂OH side branch. The alternative form, in which the —CH₂OH substituent and the anomeric hydroxyl are on the same side (cis) of the plane of the ring, is called a β anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

The term "divalent carbohydrate moiety" refers to a divalent moiety, or a derivative thereof, wherein the divalent moiety is formed by removing two hydrogen atoms from a carbohydrate (e.g., from a —CH₂—, —C(=O)H, and/or —OH group of a carbohydrate). When a point of attachment is a carbon atom that includes at least one hydrogen atom and is substituted with a —OH moiety, the —OH moiety may be derivatized to form =O. For example, the divalent moiety of the formula:

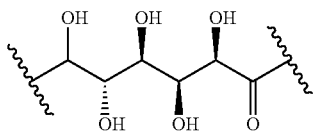 [SMILES: *C(=O)[C@H](O)[C@@H](O)[C@H](O)[C@H](O)C(*)O]

is a divalent carbohydrate moiety, which is formed by removing the two hydrogen atoms H$^a$ and H$^b$ from the carbohydrate of the formula:

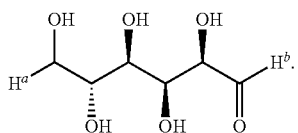

The divalent moiety of the formula:

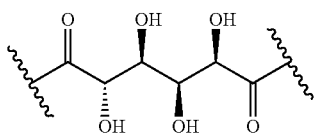 [SMILES: *C(=O)[C@@H](O)[C@@H](O)[C@H](O)[C@@H](O)C(*)=O]

is also a divalent carbohydrate moiety, which is a derivative of the divalent carbohydrate moiety

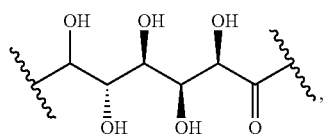 [SMILES: *C(=O)[C@H](O)[C@@H](O)[C@H](O)[C@H](O)C(*)O]

where the moiety

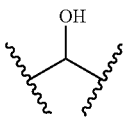

is derivatized to form the moiety

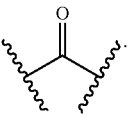

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present disclosure.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. The proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "gene" refers to a nucleic acid fragment that expresses a protein, including regulatory sequences preceding (5' non-coding sequences) and following (3' non-coding sequences) the coding sequence. "Native gene" refers to a gene as found in nature with its own regulatory sequences. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonucleotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the subject will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Any type of plasmid, cosmid, yeast artificial chromosome, or viral vector can be used to prepare the recombinant DNA construct that can be introduced directly into the tissue site.

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "recombinant nucleic acid molecule" is a nucleic acid molecule that has undergone a molecular biological manipulation, i.e., non-naturally occurring nucleic acid molecule or genetically engineered nucleic acid molecule. Furthermore, the term "recombinant DNA molecule" refers to a nucleic acid sequence which is not naturally occurring, or can be made by the artificial combination of two otherwise separated segments of nucleic acid sequence, i.e., by ligating together pieces of DNA that are not normally continuous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., *Molecular Cloning*, second edition, Cold Spring Harbor Laboratory, Plainview, N.Y.; (1989), or Ausubel et al., *Current Protocols in Molecular Biology*, Current Protocols (1989), and *DNA Cloning: A Practical Approach*, Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design.

The term "pDNA," "plasmid DNA," or "plasmid" refers to a small DNA molecule that is physically separate from, and can replicate independently of, chromosomal DNA within a cell. Plasmids can be found in all three major domains: Archaea, Bacteria, and Eukarya. In nature, plasmids carry genes that may benefit survival of the subject (e.g., antibiotic resistance) and can frequently be transmitted from one bacterium to another (even of another species) via horizontal gene transfer. Artificial plasmids are widely used as vectors in molecular cloning, serving to drive the replication of recombinant DNA sequences within host subjects. Plasmid sizes may vary from 1 to over 1,000 kbp. Plasmids are considered replicons, capable of replicating autonomously within a suitable host.

"RNA transcript" refers to the product resulting from RNA polymerase-catalyzed transcription of a DNA sequence. When the RNA transcript is a complementary copy of the DNA sequence, it is referred to as the primary transcript, or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template. The cDNA can be single-stranded or converted to double-stranded form using, for example, the Klenow fragment of DNA polymerase I.

A sequence "complementary" to a portion of an RNA, refers to a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The terms "nucleic acid" or "nucleic acid sequence", "nucleic acid molecule", "nucleic acid fragment" or "polynucleotide" may be used interchangeably with "gene", "mRNA encoded by a gene" and "cDNA".

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "gene silencing" refers to an epigenetic process of gene regulation where a gene is "switched off" by a mechanism other than genetic modification. That is, a gene which would be expressed (i.e., "turned on") under normal circumstances is switched off by machinery in the cell. Gene silencing occurs when RNA is unable to make a protein during translation. Genes are regulated at either the transcriptional or post-transcriptional level. Transcriptional gene silencing is the result of histone modifications, creating an environment of heterochromatin around a gene that makes it inaccessible to transcriptional machinery (e.g., RNA polymerase and transcription factors). Post-transcriptional gene silencing is the result of mRNA of a particular gene being destroyed or blocked. The destruction of the mRNA prevents translation and thus the formation of a gene product (e.g., a protein). A common mechanism of post-transcriptional gene silencing is RNAi.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals, aggregates, composites, pulverized, milled or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having a characteristic dimension of less than about 1 micrometer and at least about 1 nanometer, where the characteristic dimension of the particle is the smallest cross-sectional dimension of the particle.

The term "microparticle" refers to a particle having a characteristic dimension of less than about 1 millimeter and at least about 1 micrometer, where the characteristic dimension of the particle is the smallest cross-sectional dimension of the particle.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile.

The term "target tissue" refers to any biological tissue of a subject (including a group of cells, a body part, or an organ) or a part thereof, including blood and/or lymph vessels, which is the object to which a compound, particle, and/or composition of the disclosure is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. In certain embodiments, the target tissue is the spleen. In certain embodiments, the target tissue is the kidney, pancreas, heart, muscle, or prostate. A "non-target tissue" is any biological tissue of a subject (including a group of cells, a body part, or an organ) or a part thereof, including blood and/or lymph vessels, which is not a target tissue.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellisvan Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders—Fourth Edition* (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., type 1 diabetes, type 2 diabetes, gestational diabetes), hyperglycemia, hyperinsulinemia, insulin resistance, and obesity.

The term "musculoskeletal disease" or "MSD" refers to an injury and/or pain in a subject's joints, ligaments, muscles, nerves, tendons, and structures that support limbs, neck, and back. In certain embodiments, an MSD is a degenerative disease. In certain embodiments, an MSD includes an inflammatory condition. Body parts of a subject that may be associated with MSDs include upper and lower back, neck, shoulders, and extremities (arms, legs, feet, and hands). In certain embodiments, an MSD is a bone disease, such as achondroplasia, acromegaly, bone callus, bone demineralization, bone fracture, bone marrow disease, bone marrow neoplasm, dyskeratosis congenita, leukemia (e.g., hairy cell leukemia, lymphocytic leukemia, myeloid leukemia, Philadelphia chromosome-positive leukemia, plasma cell leukemia, stem cell leukemia), systemic mastocytosis, myelodysplastic syndromes, paroxysmal nocturnal hemoglobinuria, myeloid sarcoma, myeloproliferative disorders, multiple myeloma, polycythemia vera, pearson marrow-pancreas syndrome, bone neoplasm, bone marrow neoplasm, Ewing sarcoma, osteochondroma, osteoclastoma, osteosarcoma, brachydactyly, Camurati-Engelmann syndrome, Craniosynostosis, Crouzon craniofacial dysostosis, dwarfism, achondroplasia, bloom syndrome, Cockayne syndrome, Ellis-van Creveld syndrome, Seckel syndrome, spondyloepiphyseal dysplasia, spondyloepiphyseal dysplasia congenita, Werner syndrome, hyperostosis, osteophyte, Klippel-Trenaunay-Weber syndrome, Marfan syndrome, McCune-Albright syndrome, osteitis, osteoarthritis, osteochondritis, osteochondrodysplasia, Kashin-Beck disease, Leri-Weill dyschondrosteosis, osteochondrosis, osteodystrophy, osteogenesis imperfecta, osteolysis, Gorham-Stout syndrome, osteomalacia, osteomyelitis, osteonecrosis, osteopenia, osteopetrosis, osteoporosis, osteosclerosis, otospondylomegaepiphyseal dysplasia, pachydermoperiostosis, Paget disease of bone, Polydactyly, Meckel syndrome, rickets, Rothmund-Thomson syndrome, Sotos syndrome, spondyloepiphyseal dysplasia, spondyloepiphyseal dysplasia congenita, syndactyly, Apert syndrome, syndactyly type II, or Werner syndrome. In certain embodiments, an MSD is a cartilage disease, such as cartilage neoplasm, osteochondritis, osteochondrodysplasia, Kashin-Beck disease, or Leri-Weill dyschondrosteosis. In certain embodiments, an MSD is hernia, such as intervertebral disk hernia. In certain embodiments, an MSD is a joint disease, such as arthralgia, arthritis (e.g., gout (e.g., Kelley-Seegmiller syndrome, Lesch-Nyhan syndrome), Lyme disease, osteoarthritis, psoriatic arthritis, reactive arthritis, rheumatic fever, rheumatoid arthritis, Felty syndrome, synovitis, Blau syndrome, nail-patella syndrome, spondyloarthropathy, reactive arthritis, Stickler syndrome, synovial membrane disease, synovitis, or Blau syndrome. In certain embodiments, an MSD is Langer-Giedion syndrome. In certain embodiments, an MSD is a muscle disease, such as Barth syndrome, mitochondrial encephalomyopathy, MELAS syndrome, MERRF syndrome, MNGIE syndrome, mitochondrial myopathy, Kearns-Sayre syndrome, myalgia, fibromyalgia, polymyalgia rheumatica, myoma, myositis, dermatomyositis, neuromuscular disease, Kearns-Sayre syndrome, muscular dystrophy, myasthenia, congenital myasthenic syndrome, Lambert-Eaton myasthenic syndrome, myasthenia gravis, myotonia, myotonia congenita, spinal muscular atrophy, tetany, ophthalmoplegia, or rhabdomyolysis. In certain embodiments, an MSD is Proteus syndrome. In certain embodiments, an MSD is a rheumatic diseases, such as arthritis (e.g., gout (e.g., Kelley-Seegmiller syndrome, Lesch-Nyhan lyme disease)), osteoarthritis, psoriatic arthritis, reactive arthritis, rheumatic fever, rheumatoid arthritis, Felty syndrome, synovitis, Blau syndrome, gout (e.g., Kelley-Seegmiller syndrome, Lesch-Nyhan syndrome), polymyalgia rheumatica, rheumatic fever, rheumatic heart disease, or Sjogren syndrome. In certain embodiments, an MSD is Schwartz-Jampel syndrome. In certain embodiments, an MSD is a skeleton disease, such as Leri-Weill dyschondrosteosis, skeleton malformations, Melnick-Needles syndrome, pachydermoperiostosis, Rieger syndrome, spinal column disease, intervertebral disk hernia, scoliosis, spina bifida, spondylitis, ankylosing spondylitis, spondyloarthropathy, reactive arthritis, spondyloepiphyseal dysplasia, spondyloepiphyseal dysplasia congenita, or spondylosis.

BRIEF DESCRIPTION OF THE DRAWINGS

FIG. 3A: Expression of EPO in mouse serum for the nanoparticles at a dose of 0.3 mg/kg of mRNA. Data shown is mean±s.d. (n=3). Nanoparticles of TarN3C10 demonstrated EPO expression over one thousand fold higher than free mRNA. FIG. 3B: Biodistribution evaluated by luciferase expression in several organs. The TarN3C10-mRNA treated mice demonstrated one thousand fold higher luciferase expression in the liver and spleen compared to the group treated with free luciferase mRNA (normalized by tissue weight). Data shown is mean±s.d. (n=5). FIG. 3C: Cryo-TEM of TarN3C10 without mRNA. FIG. 3D and FIG. 3E: Cryo-TEM of TarN3C10 nanoparticles formulated with mRNA. The TarN3C10 nanoparticles form round spherical objects (FIG. 3D), and the addition of mRNA leads to formation of more complex structures (FIG. 3E). Scale bar is 100 nm for all cryo-TEM images.

DETAILED DESCRIPTION OF CERTAIN EMBODIMENTS OF THE INVENTION

Figure 1A:
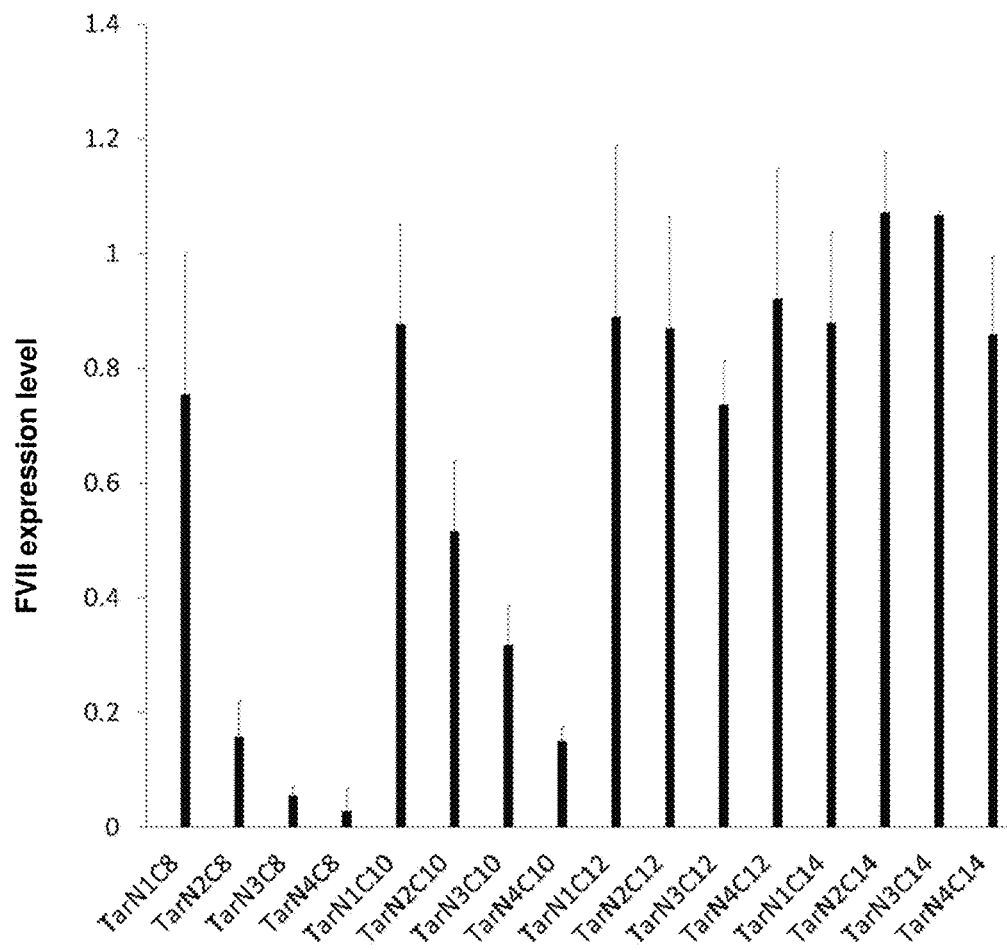
FIGS. 1A to 1C show exemplary expression levels of Factor VII (FVII) in C57BL/6 mice treated with FVII siRNA and a polymer described herein.

The present disclosure provides brush-poly(glycoamidoamine)-lipids (PGALs) and uses thereof. In one aspect, described herein are polymers of any one of Formulae (I)-(IV), and salts, solvates, hydrates, polymorphs, co-crystals, tautomers, stereoisomers, and isotopically labeled derivatives thereof. Also described herein are compositions including a polymer described herein and optionally an excipient. In certain embodiments, the compositions further include an agent (e.g., a polynucleotide (e.g., RNA or DNA), small molecule, peptide, or protein). The polymers and compositions have been found to be able to deliver effectively and efficiently an agent to a subject, tissue, or cell. In certain embodiments, the compositions are useful in delivering (e.g., selectively delivering) the agent to a subject, tissue (e.g., liver, spleen, or lung), or cell. The compositions (e.g., pharmaceutical compositions) may also be useful in treating and/or preventing a variety of diseases (e.g., genetic diseases, proliferative diseases, hematological diseases, neurological diseases, gastrointestinal diseases (e.g., liver diseases), spleen diseases, respiratory diseases (e.g., lung diseases), painful conditions, psychiatric disorders, musculoskeletal diseases, genitourinary diseases, and metabolic disorders) in a subject in need thereof. The PGALs described herein were shown to deliver erythropoietin (EPO) mRNA in mice. The PGALs did not show toxicity based on analysis of tissue histology, systemic cytokine levels, and liver enzyme chemistry. The PGALs are more potent than reported non-viral intravenous mRNA delivery systems.

Polymers

In one aspect, the present disclosure provides polymers of Formula (I):

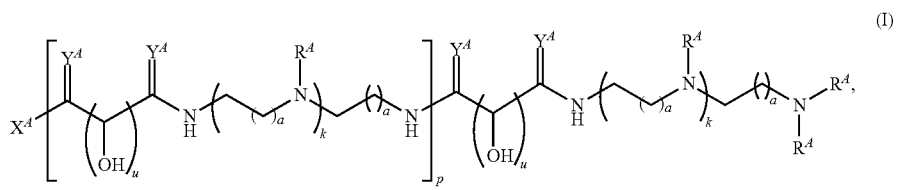

and salts, solvates, hydrates, polymorphs, co-crystals, tautomers, stereoisomers, and isotopically labeled derivatives thereof, wherein:

$X^A$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $—OR^{XA}$, $—N(R^{XA})_2$, $—SR^{XA}$, $—C(=NR^{XA})R^{XA}$, $—C(=NR^{XA})OR^{XA}$, $—C(=NR^{XA})N(R^{XA})_2$, $—C(=O)R^{XA}$, $—C(=O)OR^{XA}$, or $—C(=O)N(R^{XA})_2$, wherein each instance of $R^{XA}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{XA}$ are joined to form a substituted or unsubstituted heterocyclic or substituted or unsubstituted heteroaryl ring;

each instance of $Y^A$ is independently =O, =S, or =NR$^{YA}$, wherein each instance of $R^{YA}$ is independently hydrogen, substituted or unsubstituted $C_{1-6}$ alkyl, or a nitrogen protecting group;

each instance of $R^A$ is independently hydrogen, a moiety of the formula:

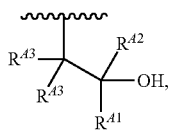

or a moiety of the formula:

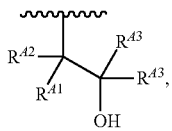

wherein: at least one instance of $R^A$ is of the formula:

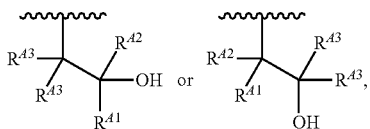

and each instance of $R^{A1}$ is independently hydrogen, substituted or unsubstituted alkyl, or substituted or unsubstituted alkenyl; each instance of $R^{A2}$ is independently hydrogen or substituted or unsubstituted alkyl; and each instance of $R^{A3}$ is independently hydrogen or substituted or unsubstituted alkyl;

each instance of a is 1, 2, 3, 4, or 5;

each instance of k is 0, 1, 2, 3, 4, 5, or 6;

each instance of u is 1, 2, 3, 4, 5, 6, 7, 8, 9, or 10; and p is an integer between 1 and 1000, inclusive.

In another aspect, the present disclosure provides polymers of Formula (I'):

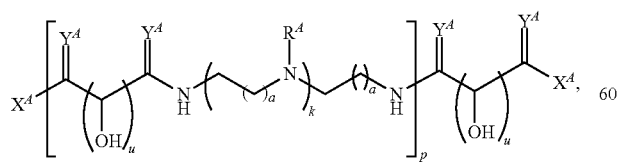

and salts, solvates, hydrates, polymorphs, co-crystals, tautomers, stereoisomers, and isotopically labeled derivatives thereof, wherein:

each instance of $X^A$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{XA}$, —N(R$^{XA}$)$_2$, —SR$^{XA}$, —C(=NR$^{XA}$)R$^{XA}$, —C(=NR$^{XA}$)OR$^{XA}$, —C(=NR$^{XA}$)N(R$^{XA}$)$_2$, —C(=O)R$^{XA}$, —C(=O)OR$^{XA}$, or —C(=O)N(R$^{XA}$)$_2$, wherein each instance of $R^{XA}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{XA}$ are joined to form a substituted or unsubstituted heterocyclic or substituted or unsubstituted heteroaryl ring;

each instance of $Y^A$ is independently =O, =S, or =NR$^{YA}$, wherein each instance of $R^{YA}$ is independently hydrogen, substituted or unsubstituted $C_{1-6}$ alkyl, or a nitrogen protecting group;

each instance of $R^A$ is independently hydrogen, a moiety of the formula:

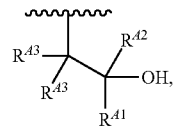

or a moiety of the formula:

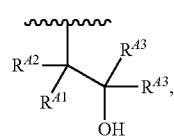

wherein: at least one instance of $R^A$ is of the formula:

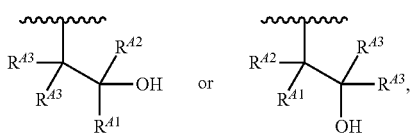

and each instance of $R^{A1}$ is independently hydrogen, substituted or unsubstituted alkyl, or substituted or unsubstituted alkenyl; each instance of $R^{A2}$ is independently hydrogen or substituted or unsubstituted alkyl; and each instance of $R^{A3}$ is independently hydrogen or substituted or unsubstituted alkyl;

each instance of a is 1, 2, 3, 4, or 5;
each instance of k is 0, 1, 2, 3, 4, 5, or 6;
each instance of u is 1, 2, 3, 4, 5, 6, 7, 8, 9, or 10; and
p is an integer between 1 and 1000, inclusive.

In another aspect, the present disclosure provides polymers of Formula (I″):

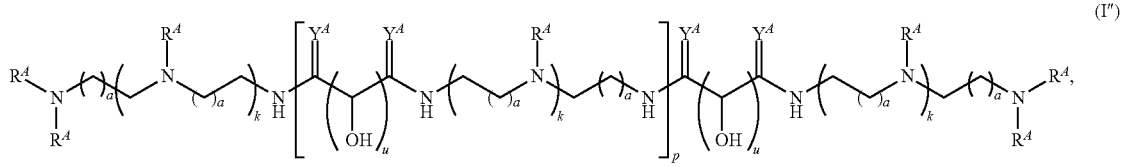

and salts, solvates, hydrates, polymorphs, co-crystals, tautomers, stereoisomers, and isotopically labeled derivatives thereof, wherein:

each instance of $Y^A$ is independently =O, =S, or =$NR^{YA}$, wherein each instance of $R^{YA}$ is independently hydrogen, substituted or unsubstituted $C_{1-6}$ alkyl, or a nitrogen protecting group;

each instance of $R^A$ is independently hydrogen, a moiety of the formula:

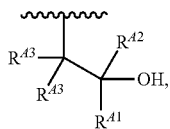

or a moiety of the formula:

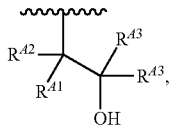

wherein: at least one instance of $R^A$ is of the formula:

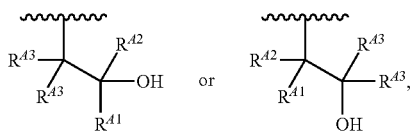

and each instance of $R^{A1}$ is independently hydrogen, substituted or unsubstituted alkyl, or substituted or unsubstituted alkenyl; each instance of $R^{A2}$ is independently hydrogen or substituted or unsubstituted alkyl; and each instance of $R^{A3}$ is independently hydrogen or substituted or unsubstituted alkyl;

each instance of a is 1, 2, 3, 4, or 5;
each instance of k is 0, 1, 2, 3, 4, 5, or 6;
each instance of u is 1, 2, 3, 4, 5, 6, 7, 8, 9, or 10; and p is an integer between 1 and 1000, inclusive.

Any one of Formulae (I), (I′), and (I″) includes more than one hydroxyl moieties. In certain embodiments, all instances of the hydroxyl moieties are of the same configuration. In certain embodiments, at least two instances of the hydroxyl moieties are of different configurations. In certain embodiments, at least one instance of the hydroxyl moieties is of the R-configuration. In certain embodiments, at least one instance of the hydroxyl moieties is of the S-configuration.

Formula (I) includes end group $X^A$. In certain embodiments, $X^A$ is substituted alkyl. In certain embodiments, $X^A$ is unsubstituted alkyl. In certain embodiments, $X^A$ is unsubstituted $C_{1-6}$ alkyl. In certain embodiments, $X^A$ is substituted $C_{1-6}$ alkyl. In certain embodiments, $X^A$ is $C_{1-6}$ alkyl substituted with at least one halogen. In certain embodiments, $X^A$ is —$CH_3$. In certain embodiments, $X^A$ is substituted methyl. In certain embodiments, $X^A$ is —$CH_2F$. In certain embodiments, $X^A$ is —$CHF_2$. In certain embodiments, $X^A$ is —$CF_3$. In certain embodiments, $X^A$ is ethyl. In certain embodiments, $X^A$ is propyl. In certain embodiments, $X^A$ is butyl. In certain embodiments, $X^A$ is pentyl. In certain embodiments, $X^A$ is hexyl. In certain embodiments, $X^A$ is halogen or substituted or unsubstituted $C_{1-6}$ alkyl. In certain embodiments, $X^A$ is substituted alkenyl. In certain embodiments, $X^A$ is unsubstituted alkenyl. In certain embodiments, $X^A$ is substituted alkynyl. In certain embodiments, $X^A$ is unsubstituted alkynyl. In certain embodiments, $X^A$ is substituted carbocyclyl. In certain embodiments, $X^A$ is unsubstituted carbocyclyl. In certain embodiments, $X^A$ is saturated carbocyclyl. In certain embodiments, $X^A$ is unsaturated carbocyclyl. In certain embodiments, $X^A$ is monocyclic carbocyclyl. In certain embodiments, $X^A$ is 3- to 7-membered, monocyclic carbocyclyl. In certain embodiments, $X^A$ is substituted heterocyclyl. In certain embodiments, $X^A$ is unsubstituted heterocyclyl. In certain embodiments, $X^A$ is saturated heterocyclyl. In certain embodiments, $X^A$ is unsaturated heterocyclyl. In certain embodiments, $X^A$ is heterocyclyl, wherein one, two, or three atoms of the heterocyclic ring system are independently selected from the group consisting of nitrogen, oxygen, and sulfur. In certain embodiments, $X^A$ is monocyclic heterocyclyl. In certain embodiments, $X^A$ is 3- to 7-membered, monocyclic heterocyclyl. In certain embodiments, $X^A$ is substituted aryl. In certain embodiments, $X^A$ is unsubstituted aryl. In certain embodiments, $X^A$ is 6- to 10-membered aryl. In certain embodiments, $X^A$ is substituted phenyl. In certain embodiments, $X^A$ is unsubstituted phenyl. In certain embodiments, $X^A$ is substituted heteroaryl. In certain embodiments, $X^A$ is unsubstituted heteroaryl. In certain embodiments, $X^A$ is heteroaryl, wherein one, two, three, or four atoms of the heteroaryl ring system are independently selected from the group consisting of nitrogen, oxygen, and sulfur. In certain embodiments, $X^A$ is monocyclic heteroaryl. In certain embodiments, $X^A$ is 5-membered, monocyclic heteroaryl. In certain embodiments, $X^A$ is 6-membered, monocyclic heteroaryl. In certain embodiments, $X^A$ is bicyclic heteroaryl, wherein the point of attachment may be on any atom of the bicyclic heteroaryl ring system, as valency permits. In certain embodiments, $X^A$ is 9- or 10-membered, bicyclic heteroaryl. In certain embodiments, $X^A$ is —$OR^{XA}$. In certain embodiments, $X^A$ is —OH. In certain embodiments, $X^A$ is —$OR^{XA}$, wherein $R^{XA}$ is substituted or unsubstituted $C_{1-6}$ alkyl. In certain embodiments, $X^A$ is —OMe. In certain embodiments, $X^A$ is —OEt, —OPr, —OBu, or —OBn. In certain embodiments, $X^A$ is —OPh. In certain embodiments, $X^A$ is —$SR^{XA}$. In certain embodiments, $X^A$ is —SH. In certain embodiments, $X^A$ is —SMe. In certain embodiments, $X^A$ is —$N(R^{XA})_2$. In certain embodiments, $X^A$ is —$NH_2$. In certain embodiments, $X^A$ is —NHMe. In certain embodiments, $X^A$ is —$NMe_2$. In certain embodiments, $X^A$ is —$OR^{XA}$ or —$N(R^{XA})_2$. In certain embodiments, $X^A$ is —$C(=NR^{XA})R^{XA}$, —$C(=NR^{XA})OR^{XA}$, or —$C(=NR^{XA})N(R^{XA})_2$. In certain embodiments, $X^A$ is —$C(=O)R^{XA}$ or —$C(=O)OR^{XA}$. In certain embodiments, $X^A$ is —$C(=O)N(R^{XA})_2$. In certain embodiments, $X^A$ is —$C(=O)NMe_2$, —$C(=O)NHMe$, or —$C(=O)NH_2$.

Formula (I') includes end groups $X^A$. In certain embodiments, all instances of $X^A$ are the same. In certain embodiments, two instances of $X^A$ are not the same. In certain embodiments, at least one instance of $X^A$ is substituted alkyl. In certain embodiments, at least one instance of $X^A$ is unsubstituted alkyl. In certain embodiments, at least one instance of $X^A$ is unsubstituted $C_{1-6}$ alkyl. In certain embodiments, at least one instance of $X^A$ is substituted $C_{1-6}$ alkyl. In certain embodiments, at least one instance of $X^A$ is $C_{1-6}$ alkyl substituted with at least one halogen. In certain embodiments, at least one instance of $X^A$ is —$CH_3$. In certain embodiments, at least one instance of $X^A$ is substituted methyl. In certain embodiments, at least one instance of $X^A$ is —$CH_2F$. In certain embodiments, at least one instance of $X^A$ is —$CHF_2$. In certain embodiments, at least one instance of $X^A$ is —$CF_3$. In certain embodiments, at least one instance of $X^A$ is ethyl. In certain embodiments, at least one instance of $X^A$ is propyl. In certain embodiments, at least one instance of $X^A$ is butyl. In certain embodiments, at least one instance of $X^A$ is pentyl. In certain embodiments, at least one instance of $X^A$ is hexyl. In certain embodiments, at least one instance of $X^A$ is halogen or substituted or unsubstituted $C_{1-6}$ alkyl. In certain embodiments, at least one instance of $X^A$ is substituted alkenyl. In certain embodiments, at least one instance of $X^A$ is unsubstituted alkenyl. In certain embodiments, at least one instance of $X^A$ is substituted alkynyl. In certain embodiments, at least one instance of $X^A$ is unsubstituted alkynyl. In certain embodiments, at least one instance of $X^A$ is substituted carbocyclyl. In certain embodiments, at least one instance of $X^A$ is unsubstituted carbocyclyl. In certain embodiments, at least one instance of $X^A$ is saturated carbocyclyl. In certain embodiments, at least one instance of $X^A$ is unsaturated carbocyclyl. In certain embodiments, at least one instance of $X^A$ is monocyclic carbocyclyl. In certain embodiments, at least one instance of $X^A$ is 3- to 7-membered, monocyclic carbocyclyl. In certain embodiments, at least one instance of $X^A$ is substituted heterocyclyl. In certain embodiments, at least one instance of $X^A$ is unsubstituted heterocyclyl. In certain embodiments, at least one instance of $X^A$ is saturated heterocyclyl. In certain embodiments, at least one instance of $X^A$ is unsaturated heterocyclyl. In certain embodiments, at least one instance of $X^A$ is heterocyclyl, wherein one, two, or three atoms of the heterocyclic ring system are independently selected from the group consisting of nitrogen, oxygen, and sulfur. In certain embodiments, at least one instance of $X^A$ is monocyclic heterocyclyl. In certain embodiments, at least one instance of $X^A$ is 3- to 7-membered, monocyclic heterocyclyl. In certain embodiments, at least one instance of $X^A$ is substituted aryl. In certain embodiments, at least one instance of $X^A$ is unsubstituted aryl. In certain embodiments, at least one instance of $X^A$ is 6- to 10-membered aryl. In certain embodiments, at least one instance of $X^A$ is substituted phenyl. In certain embodiments, at least one instance of $X^A$ is unsubstituted phenyl. In certain embodiments, at least one instance of $X^A$ is substituted heteroaryl. In certain embodiments, at least one instance of $X^A$ is unsubstituted heteroaryl. In certain embodiments, at least one instance of $X^A$ is heteroaryl, wherein one, two, three, or four atoms of the heteroaryl ring system are independently selected from the group consisting of nitrogen, oxygen, and sulfur. In certain embodiments, at least one instance of $X^A$ is monocyclic heteroaryl. In certain embodiments, at least one instance of $X^A$ is 5-membered, monocyclic heteroaryl. In certain embodiments, at least one instance of $X^A$ is 6-membered, monocyclic heteroaryl. In certain embodiments, at least one instance of $X^A$ is bicyclic heteroaryl, wherein the point of attachment may be on any atom of the bicyclic heteroaryl ring system, as valency permits. In certain embodiments, at least one instance of $X^A$ is 9- or 10-membered, bicyclic heteroaryl. In certain embodiments, at least one instance of $X^A$ is —$OR^{XA}$. In certain embodiments, at least one instance of $X^A$ is —OH. In certain embodiments, at least one instance of $X^A$ is —$OR^{XA}$, wherein $R^{XA}$ is substituted or unsubstituted $C_{1-6}$ alkyl. In certain embodiments, at least one instance of $X^A$ is —OMe. In certain embodiments, at least one instance of $X^A$ is —OEt, —OPr, —OBu, or —OBn. In certain embodiments, at least one instance of $X^A$ is —OPh. In certain embodiments, at least one instance of $X^A$ is —$SR^{XA}$. In certain embodiments, at least one instance of $X^A$ is —SH. In certain embodiments, at least one instance of $X^A$ is —SMe. In certain embodiments, at least one instance of $X^A$ is —$N(R^{XA})_2$. In certain embodiments, at least one instance of $X^A$ is —$NH_2$. In certain embodiments, at least one instance of $X^A$ is —NHMe. In certain embodiments, at least one instance of $X^A$ is —$NMe_2$. In certain embodiments, at least one instance of $X^A$ is —$OR^{XA}$ or —$N(R^{XA})_2$. In certain embodiments, at least one instance of $X^A$ is —$C(=NR^{XA})R^{XA}$, —$C(=NR^{XA})OR^{XA}$, or —$C(=NR^{XA})N(R^{XA})_2$. In certain embodiments, at least one instance of $X^A$ is —$C(=O)R^{XA}$ or —$C(=O)OR^{XA}$. In certain embodiments, at least one instance of $X^A$ is —$C(=O)N(R^{XA})_2$. In certain embodiments, at least one instance of $X^A$ is —$C(=O)NMe_2$, —$C(=O)NHMe$, or —$C(=O)NH_2$.

For any of the $X^A$ that include an $R^{XA}$ moiety described herein, any of the following embodiments for $R^{XA}$ may be applicable. In certain embodiments, $R^{XA}$ is H. In certain embodiments, $R^{XA}$ is substituted acyl. In certain embodiments, $R^{XA}$ is unsubstituted acyl. In certain embodiments, $R^{XA}$ is acetyl. In certain embodiments, $R^{XA}$ is substituted alkyl. In certain embodiments, $R^{XA}$ is unsubstituted alkyl. In certain embodiments, $R^{XA}$ is unsubstituted $C_{1-6}$ alkyl. In certain embodiments, $R^{XA}$ is methyl. In certain embodiments, $R^{XA}$ is ethyl. In certain embodiments, $R^{XA}$ is propyl. In certain embodiments, $R^{XA}$ is butyl. In certain embodiments, $R^{XA}$ is pentyl. In certain embodiments, $R^{XA}$ is hexyl. In certain embodiments, $R^{XA}$ is substituted alkenyl. In certain embodiments, $R^{XA}$ is unsubstituted alkenyl. In certain embodiments, $R^{XA}$ is substituted alkynyl. In certain embodiments, $R^{XA}$ is unsubstituted alkynyl. In certain embodiments, $R^{XA}$ is substituted or unsubstituted carbocyclyl. In certain embodiments, $R^{XA}$ is saturated carbocyclyl. In certain embodiments, $R^{XA}$ is unsaturated carbocyclyl. In certain embodiments, $R^{XA}$ is 3- to 7-membered, monocyclic carbocyclyl. In certain embodiments, $R^{XA}$ is substituted or unsubstituted heterocyclyl. In certain embodiments, $R^{XA}$ is saturated heterocyclyl. In certain embodiments, $R^{XA}$ is unsaturated heterocyclyl. In certain embodiments, $R^{XA}$ is heterocyclyl, wherein one, two, or three atoms of the heterocyclic ring system are independently selected from the group consisting of nitrogen, oxygen, and sulfur. In certain embodiments, $R^{XA}$ is 3- to 7-membered, monocyclic heterocyclyl. In certain embodiments, $R^{XA}$ is substituted or unsubstituted aryl. In certain embodiments, $R^{XA}$ is 6- to 10-membered aryl. In certain embodiments, $R^{XA}$ is monocyclic aryl. In certain embodiments, $R^{XA}$ is substituted phenyl. In certain embodiments, $R^{XA}$ is unsubstituted phenyl. In certain embodiments, $R^{XA}$ is bicyclic aryl. In certain embodiments, $R^{XA}$ is substituted or unsubstituted heteroaryl. In certain embodiments, $R^{XA}$ is heteroaryl, wherein one, two, three, or four atoms of the heteroaryl ring system are independently selected from the group consisting of nitrogen, oxygen, and sulfur. In certain embodiments, $R^{XA}$ is monocyclic heteroaryl. In certain embodiments, $R^{XA}$ is 5- or 6-membered, monocyclic heteroaryl. In certain embodiments, $R^{XA}$ is bicyclic heteroaryl, wherein the point of attachment may be on any atom of the bicyclic heteroaryl ring system, as valency permits. In certain embodiments, $R^{XA}$ is a nitrogen protecting group when attached to a nitrogen atom. In certain embodiments, $R^{XA}$ is Bn, Boc, Cbz, Fmoc, trifluoroacetyl, triphenylmethyl, acetyl, or Ts when attached to a nitrogen atom. In certain embodiments, $R^{XA}$ is an oxygen protecting group when attached to an oxygen atom. In certain embodiments, $R^{XA}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{XA}$ is a sulfur protecting group when attached to a sulfur atom. In certain embodiments, $R^{XA}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{XA}$ are joined to form a substituted or unsubstituted heterocyclic ring. In certain embodiments, two instances of $R^{XA}$ are joined to form a saturated or unsaturated heterocyclic ring. In certain embodiments, two instances of $R^{XA}$ are joined to form a heterocyclic ring, wherein one, two, or three atoms of the heterocyclic ring system are independently selected from the group consisting of nitrogen, oxygen, and sulfur. In certain embodiments, two instances of $R^{XA}$ are joined to form a 3- to 7-membered, monocyclic heterocyclic ring. In certain embodiments, two instances of $R^{XA}$ are joined to form a substituted or unsubstituted heteroaryl ring. In certain embodiments, two instances of $R^{XA}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

Any one of Formulae (I), (I'), and (I") includes $Y^A$ moieties. In certain embodiments, all instances of $Y^A$ are the same. In certain embodiments, at least two instances of $Y^A$ are different from each other. In certain embodiments, at least one instance of $Y^A$ is =O. In certain embodiments, each instance of $Y^A$ is =O. In certain embodiments, at least one instance of $Y^A$ is =S. In certain embodiments, at least one instance of $Y^A$ is =$NR^{YA}$. In certain embodiments, at least one instance of $Y^A$ is =NH. In certain embodiments, at least one instance of $Y^A$ is =N(substituted or unsubstituted $C_{1-6}$ alkyl, e.g., methyl).

In certain embodiments, all instances of $R^{YA}$ are the same. In certain embodiments, at least two instances of $R^{YA}$ are different from each other. In certain embodiments, at least one instance of $R^{YA}$ is H. In certain embodiments, at least one instance of $R^{YA}$ is substituted or unsubstituted $C_{1-6}$ alkyl.

In certain embodiments, at least one instance of $R^{YA}$ is methyl. In certain embodiments, at least one instance of $R^{YA}$ is ethyl, propyl, butyl, pentyl, or hexyl. In certain embodiments, at least one instance of $R^{YA}$ is a nitrogen protecting group (e.g., Bn, Boc, Cbz, Fmoc, trifluoroacetyl, triphenylmethyl, acetyl, or Ts).

Any one of Formulae (I), (I'), and (I") includes substituents $R^A$. In certain embodiments, at least about 10%, at least about 20%, at least about 30%, or at least about 40% of the total instances of $R^A$ are the same. In certain embodiments, at least about 50% of the total instances of $R^A$ are the same. In certain embodiments, at least about 60% of the total instances of $R^A$ are the same. In certain embodiments, at least about 70% of the total instances of $R^A$ are the same. In certain embodiments, at least about 80% of the total instances of $R^A$ are the same. In certain embodiments, at least about 90% of the total instances of $R^A$ are the same. In certain embodiments, at least about 95% of the total instances of $R^A$ are the same. In certain embodiments, all instances of $R^A$ are the same. In certain embodiments, at least two instances of $R^A$ are different from each other. In certain embodiments, at least one instance of $R^A$ is H. In certain embodiments, at least one instance of $R^A$ is of the formula:

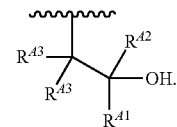

In certain embodiments, at least one instance of $R^A$ is of the formula:

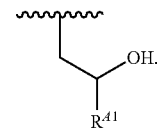

In certain embodiments, at least one instance of $R^A$ is of the formula:

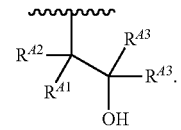

In certain embodiments, at least one instance of $R^A$ is of the formula:

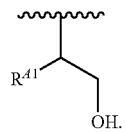

In certain embodiments, at least one instance of $R^A$ is of the formula:

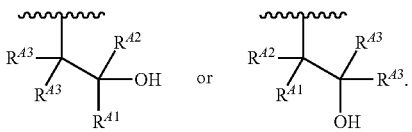

In certain embodiments, at least about 10%, at least about 20%, at least about 30%, at least about 40%, at least about 50%, at least about 60%, at least about 70%, at least about 80%, at least about 90%, or at least about 95% of the total instances of $R^A$ are independently of the formula:

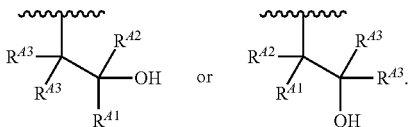

In certain embodiments, all instances of $R^A$ are independently of the formula:

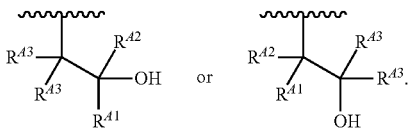

In certain embodiments, at least one instance of $R^A$ is of the formula:

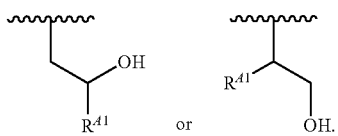

In certain embodiments, at least about 10%, at least about 20%, at least about 30%, at least about 40%, at least about 50%, at least about 60%, at least about 70%, at least about 80%, at least about 90%, or at least about 95% of the total instances of $R^A$ are independently of the formula:

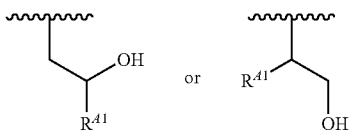

In certain embodiments, all instances of $R^A$ are independently of the formula:

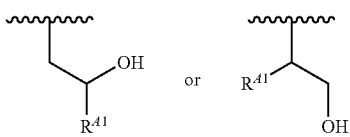

In certain embodiments, each instance of $R^A$ is independently H, a moiety of the formula:

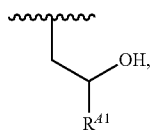

or a moiety of the formula:

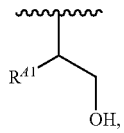

wherein: at least one instance of $R^A$ is of the formula:

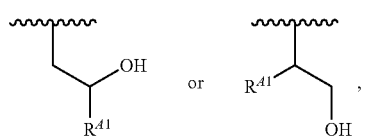

and each instance of $R^{41}$ is independently unsubstituted $C_{4-18}$ alkyl.

Each instance of $R^A$ in any one of Formulae (I), (I'), and (I") includes one or more substituents $R^{41}$. In certain embodiments, all instances of $R^{41}$ are the same. In certain embodiments, all instances of $R^{41}$ that are not hydrogen are the same. In certain embodiments, at least two instances of $R^{41}$ are different from each other. In certain embodiments, at least one instance of $R^{41}$ is H. In certain embodiments, each instance of $R^{41}$ is H. In certain embodiments, at least one instance of $R^{41}$ is substituted alkyl. In certain embodiments, at least one instance of $R^{41}$ is unsubstituted alkyl. In certain embodiments, each instance of $R^{41}$ is independently substituted or unsubstituted $C_{1-30}$ alkyl. In certain embodiments, at least one instance of $R^{41}$ is substituted $C_{1-30}$ alkyl. In certain embodiments, at least one instance of $R^{41}$ is a moiety shown in Table 2. In certain embodiments, each instance of $R^{41}$ is independently a moiety shown in Table 2. In certain embodiments, each instance of $R^{41}$ is a moiety shown in Table 2. In certain embodiments, at least one instance of $R^{41}$ is $C_{1-30}$ alkyl substituted with one or more halogen. In certain embodiments, at least one instance of $R^{41}$ is $C_{1-30}$ alkyl substituted with one or more fluorine. In certain embodiments, at least one instance of $R^{41}$ is $C_{1-30}$ perfluoroalkyl. In certain embodiments, at least one instance of $R^{41}$ is unsubstituted $C_{1-30}$ alkyl. In certain embodiments, at least one instance of $R^{41}$ is a moiety shown in Table 1. In certain embodiments, each instance of $R^{41}$ is independently a moiety shown in Table 1. In certain embodiments, each instance of $R^{41}$ is a moiety shown in Table 1. In certain embodiments, at least one instance of $R^{41}$ is unsubstituted and unbranched $C_{1-30}$ alkyl. In certain embodiments, each instance of $R^{41}$ is independently substituted or unsubstituted $C_{4-22}$ alkyl (e.g., substituted or unsubstituted $C_{4-18}$ alkyl). In certain embodiments, at least one instance of $R^{41}$ is substituted $C_{4-18}$ alkyl. In certain embodiments, at least one instance of $R^{41}$ is $C_{4-18}$ alkyl substituted with one or more halogen. In certain embodiments, at least one instance of $R^{41}$ is $C_{4-18}$ alkyl substituted with one or more fluorine. In certain embodiments, at least one instance of $R^{A1}$ is $C_{4-18}$ perfluoroalkyl. In certain embodiments, at least one instance of $R^{A1}$ is unsubstituted $C_{4-18}$ alkyl. In certain embodiments, at least one instance of $R^{A1}$ is unsubstituted and unbranched $C_{4-18}$ alkyl. In certain embodiments, each instance of $R^{A1}$ is independently substituted or unsubstituted $C_{6-14}$ alkyl. In certain embodiments, at least one instance of $R^{A1}$ is substituted $C_{6-14}$ alkyl. In certain embodiments, at least one instance of $R^{A1}$ is $C_{6-14}$ alkyl substituted with one or more halogen. In certain embodiments, at least one instance of $R^{A1}$ is $C_{6-14}$ alkyl substituted with one or more fluorine. In certain embodiments, at least one instance of $R^{A1}$ is $C_{6-14}$ perfluoroalkyl. In certain embodiments, at least one instance of $R^{A1}$ is unsubstituted $C_{6-14}$ alkyl. In certain embodiments, at least one instance of $R^{A1}$ is unsubstituted and unbranched $C_{6-14}$ alkyl. In certain embodiments, each instance of $R^{A1}$ is independently $n\text{-}C_6H_{13}$, $n\text{-}C_8H_{17}$, $n\text{-}C_{10}H_{21}$, $n\text{-}C_{12}H_{25}$. In certain embodiments, each instance of $R^{A1}$ is $n\text{-}C_6H_{13}$, $n\text{-}C_8H_{17}$, $n\text{-}C_{10}H_{21}$, $n\text{-}C_{12}H_{25}$.

TABLE 1

Exemplary unsubstituted alkyl moieties.

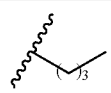

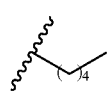

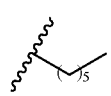

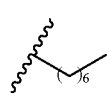

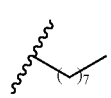

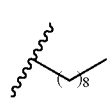

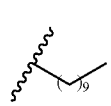

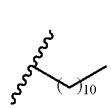

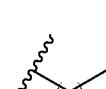

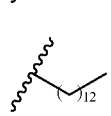

TABLE 1-continued

Exemplary unsubstituted alkyl moieties.

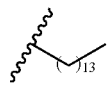

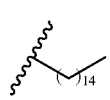

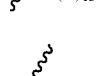

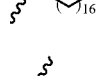

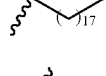

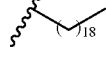

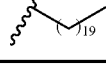

TABLE 2

Exemplary substituted alkyl moieties.

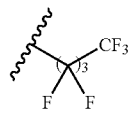

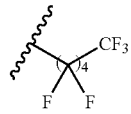

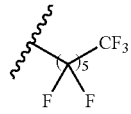

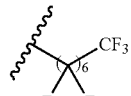

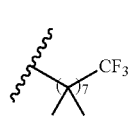

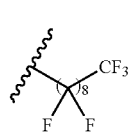

TABLE 2-continued

Exemplary substituted alkyl moieties.

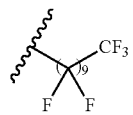

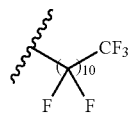

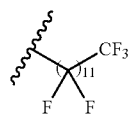

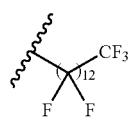

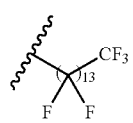

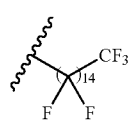

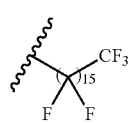

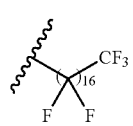

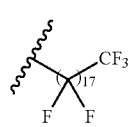

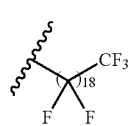

TABLE 2-continued

Exemplary substituted alkyl moieties.

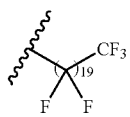

In certain embodiments, at least one instance of $R^{A1}$ is substituted alkenyl. In certain embodiments, at least one instance of $R^{A1}$ is unsubstituted alkenyl. In certain embodiments, each instance of $R^{A1}$ is independently substituted or unsubstituted $C_{2-30}$ alkenyl. In certain embodiments, at least one instance of $R^{A1}$ is substituted $C_{2-30}$ alkenyl. In certain embodiments, at least one instance of $R^{A1}$ is $C_{2-30}$ alkenyl substituted with one or more halogen. In certain embodiments, at least one instance of $R^{A1}$ is $C_{2-30}$ alkenyl substituted with one or more fluorine. In certain embodiments, at least one instance of $R^{A1}$ is $C_{2-30}$ perfluoroalkenyl. In certain embodiments, at least one instance of $R^{A1}$ is unsubstituted $C_{2-30}$ alkenyl. In certain embodiments, at least one instance of $R^{A1}$ is a moiety shown in Table 3. In certain embodiments, each instance of $R^{A1}$ is independently a moiety shown in Table 3. In certain embodiments, each instance of $R^{A1}$ is a moiety shown in Table 3. In certain embodiments, at least one instance of $R^{A1}$ is unsubstituted and unbranched $C_{2-30}$ alkenyl. In certain embodiments, each instance of $R^{A1}$ is independently substituted or unsubstituted $C_{4-18}$ alkenyl. In certain embodiments, at least one instance of $R^{A1}$ is substituted $C_{4-18}$ alkenyl. In certain embodiments, at least one instance of $R^{A1}$ is $C_{4-18}$ alkenyl substituted with one or more halogen. In certain embodiments, at least one instance of $R^{A1}$ is $C_{4-18}$ alkenyl substituted with one or more fluorine. In certain embodiments, at least one instance of $R^{A1}$ is $C_{4-18}$ perfluoroalkenyl. In certain embodiments, at least one instance of $R^{A1}$ is unsubstituted $C_{4-18}$ alkenyl. In certain embodiments, at least one instance of $R^{A1}$ is unsubstituted and unbranched $C_{4-18}$ alkenyl. In certain embodiments, each instance of $R^{A1}$ is independently substituted or unsubstituted $C_{6-14}$ alkenyl. In certain embodiments, at least one instance of $R^{A1}$ is substituted $C_{6-14}$ alkenyl. In certain embodiments, at least one instance of $R^{A1}$ is $C_{6-14}$ alkenyl substituted with one or more halogen. In certain embodiments, at least one instance of $R^{A1}$ is $C_{6-14}$ alkenyl substituted with one or more fluorine. In certain embodiments, at least one instance of $R^{A1}$ is $C_{6-14}$ perfluoroalkenyl. In certain embodiments, at least one instance of $R^{A1}$ is unsubstituted $C_{6-14}$ alkenyl. In certain embodiments, at least one instance of $R^{A1}$ is unsubstituted and unbranched $C_{6-14}$ alkenyl.

TABLE 3

Exemplary unsubstituted alkenyl moieties.

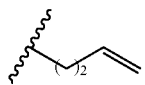

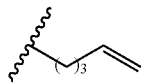

TABLE 3-continued
Exemplary unsubstituted alkenyl moieties.
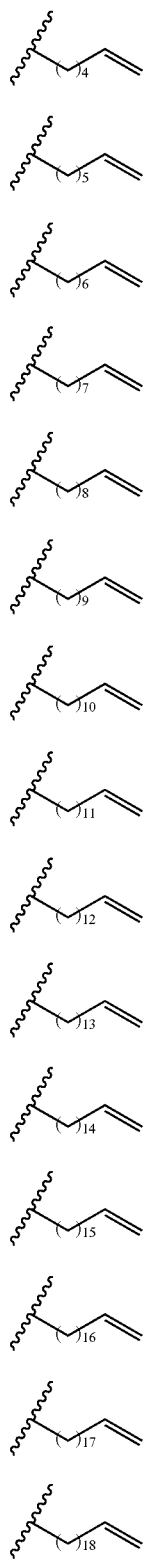
—(CH$_2$)$_7$CH=CH(CH$_2$)$_3$CH$_3$
—(CH$_2$)$_7$CH=CH(CH$_2$)$_5$CH$_3$
—(CH$_2$)$_4$CH=CH(CH$_2$)$_8$CH$_3$
—(CH$_2$)$_7$CH=CH(CH$_2$)$_7$CH$_3$ TABLE 3-continued Exemplary unsubstituted alkenyl moieties.

—(CH$_2$)$_7$CH=CHCH$_2$CH=CH(CH$_2$)$_4$CH$_3$
—(CH$_2$)$_7$CH=CHCH$_2$CH=CHCH$_2$CH=CHCH$_2$CH$_3$
—(CH$_2$)$_3$CH=CHCH$_2$CH=CHCH$_2$CH=CHCH$_2$CH=CH(CH$_2$)$_4$CH$_3$
—(CH$_2$)$_3$CH=CHCH$_2$CH=CHCH$_2$CH=CHCH$_2$CH=CHCH$_2$CH=CHCH$_2$CH$_3$
—(CH$_2$)$_{11}$CH=CH(CH$_2$)$_7$CH$_3$
—(CH$_2$)$_2$CH=CHCH$_2$CH=CHCH$_2$CH=CHCH$_2$CH=CHCH$_2$CH=CHCH$_2$CH=CH—CH$_2$CH$_3$

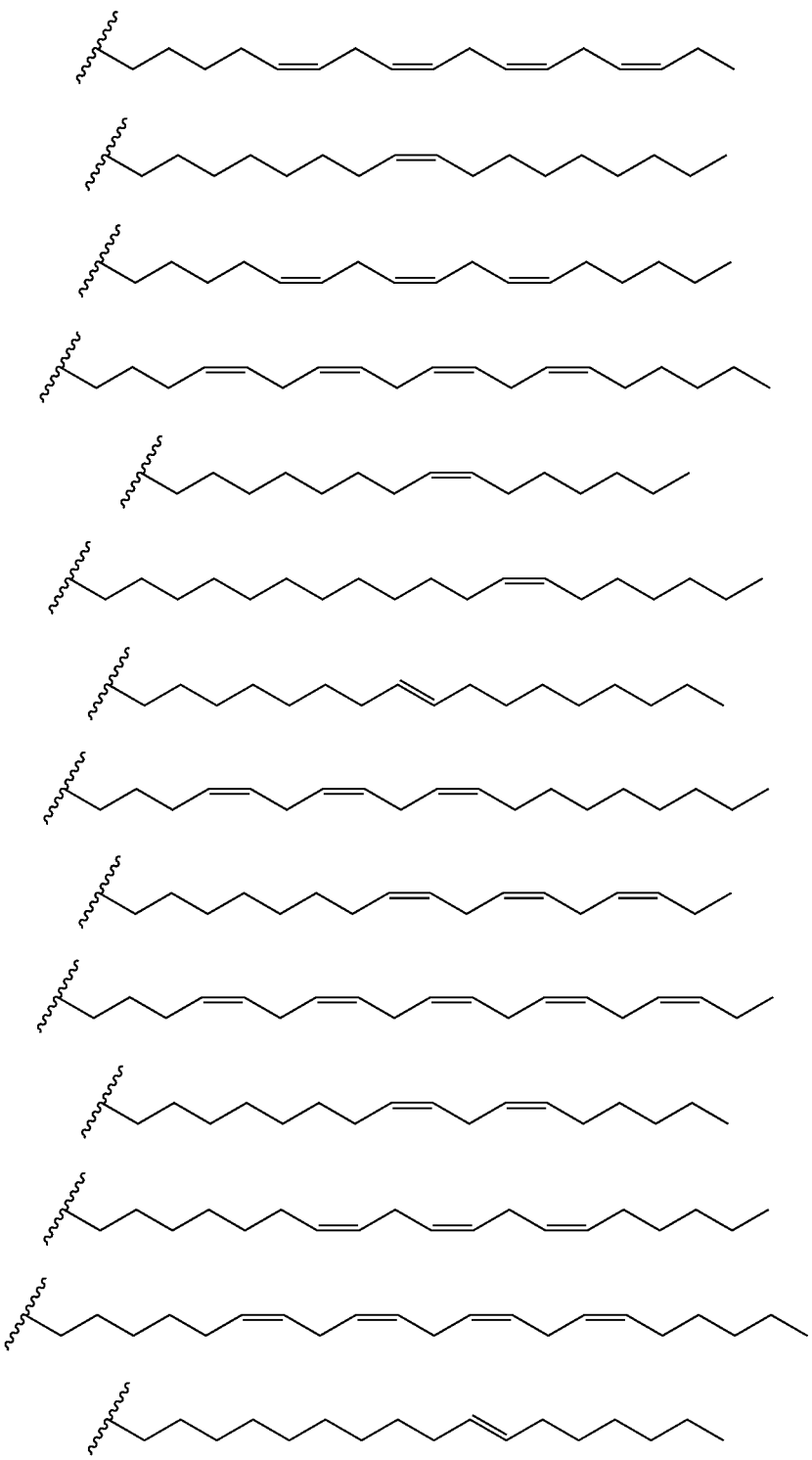

TABLE 3-continued

Exemplary unsubstituted alkenyl moieties.

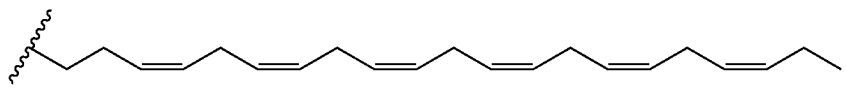 [SMILES: *CC/C=C\C/C=C\C/C=C\C/C=C\C/C=C\C/C=C\CC]

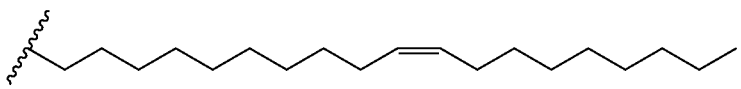 [SMILES: *CCCCCCCCC/C=C\CCCCCCCC]

In certain embodiments, all instances of $R^{A2}$ are the same. In certain embodiments, at least two instances of $R^{A2}$ are different from each other. In certain embodiments, at least one instance of $R^{A2}$ is H. In certain embodiments, each instance of $R^{A2}$ is H. In certain embodiments, at least one instance of $R^{A2}$ is substituted alkyl. In certain embodiments, at least one instance of $R^{A2}$ is unsubstituted alkyl. In certain embodiments, at least one instance of $R^{A2}$ is unsubstituted $C_{1-6}$ alkyl. In certain embodiments, both instances of $R^{A2}$ are unsubstituted $C_{1-6}$ alkyl. In certain embodiments, at least one instance of $R^{A2}$ is substituted $C_{1-6}$ alkyl. In certain embodiments, at least one instance of $R^{A2}$ is $C_{1-6}$ alkyl substituted with at least one halogen. In certain embodiments, at least one instance of $R^{A2}$ is —$CH_3$. In certain embodiments, at least one instance of $R^{A2}$ is substituted methyl. In certain embodiments, at least one instance of $R^{A2}$ is —$CH_2F$, —$CHF_2$, or —$CF_3$. In certain embodiments, at least one instance of $R^{A2}$ is ethyl, propyl, butyl, pentyl, or hexyl.

In certain embodiments, all instances of $R^{A3}$ are the same. In certain embodiments, at least two instances of $R^{A3}$ are different from each other. In certain embodiments, at least one instance of $R^{A3}$ is H. In certain embodiments, each instance of $R^{A3}$ is H. In certain embodiments, at least one instance of $R^{A3}$ is substituted alkyl. In certain embodiments, at least one instance of $R^{A3}$ is unsubstituted alkyl. In certain embodiments, at least one instance of $R^{A3}$ is unsubstituted $C_{1-6}$ alkyl. In certain embodiments, both instances of $R^{A3}$ are unsubstituted $C_{1-6}$ alkyl. In certain embodiments, at least one instance of $R^{A3}$ is substituted $C_{1-6}$ alkyl. In certain embodiments, at least one instance of $R^{A3}$ is $C_{1-6}$ alkyl substituted with at least one halogen. In certain embodiments, at least one instance of $R^{A3}$ is —$CH_3$. In certain embodiments, at least one instance of $R^{A3}$ is substituted methyl. In certain embodiments, at least one instance of $R^{A3}$ is —$CH_2F$, —$CHF_2$, or —$CF_3$. In certain embodiments, at least one instance of $R^{A3}$ is ethyl, propyl, butyl, pentyl, or hexyl.

In certain embodiments, all instances of $R^{A2}$ and $R^{A3}$ are H.

In certain embodiments, each instance of a is 1. In certain embodiments, each instance of a is 2. In certain embodiments, each instance of a is 3. In certain embodiments, each instance of a is 4. In certain embodiments, each instance of a is 5.

In certain embodiments, each instance of k is 0. In certain embodiments, each instance of k is 1. In certain embodiments, each instance of k is 2. In certain embodiments, each instance of k is 3. In certain embodiments, each instance of k is 4. In certain embodiments, each instance of k is 5. In certain embodiments, each instance of k is 6.

In certain embodiments, each instance of u is 1. In certain embodiments, each instance of u is 2. In certain embodiments, each instance of u is 3. In certain embodiments, each instance of u is 4. In certain embodiments, each instance of u is 5. In certain embodiments, each instance of u is 6. In certain embodiments, each instance of u is 7. In certain embodiments, each instance of u is 8. In certain embodiments, each instance of u is 9. In certain embodiments, each instance of u is 10.

In certain embodiments, p is an integer between 1 and 1000, inclusive. In certain embodiments, p is an integer between 1 and 300, inclusive. In certain embodiments, p is an integer between 1 and 100, inclusive. In certain embodiments, p is an integer between 1 and 70, inclusive. In certain embodiments, p is an integer between 1 and 50, inclusive. In certain embodiments, p is an integer between 1 and 30, inclusive. In certain embodiments, p is an integer between 5 and 30, inclusive. In certain embodiments, p is an integer between 10 and 20, inclusive. In certain embodiments, p is an integer between 1 and 15, inclusive. In certain embodiments, p is an integer between 5 and 15, inclusive. In certain embodiments, p is 10 or 11.

In certain embodiments, the polymer of Formula (I) is of the formula:

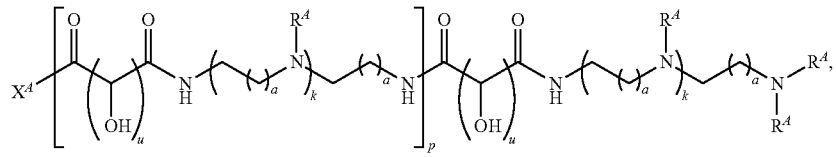

or a salt, solvate, hydrate, polymorph, co-crystal, tautomer, stereoisomer, or isotopically labeled derivative thereof.

In certain embodiments, the polymer of Formula (I) is of the formula:

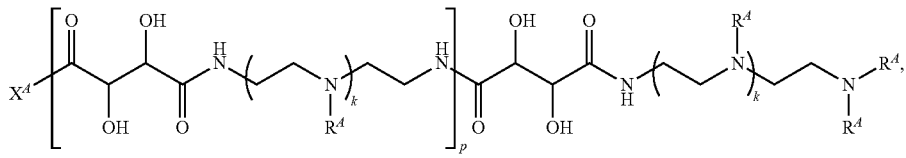

or a salt, solvate, hydrate, polymorph, co-crystal, tautomer, stereoisomer, or isotopically labeled derivative thereof.

In certain embodiments, the polymer of Formula (I) is of the formula:

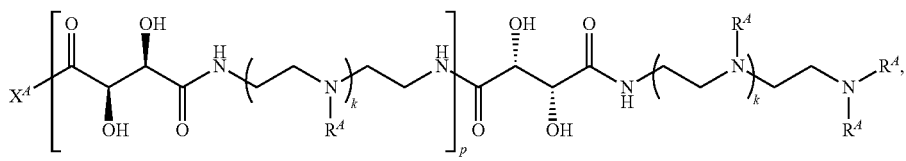

or a salt, solvate, hydrate, polymorph, co-crystal, tautomer, stereoisomer, or isotopically labeled derivative thereof.

In certain embodiments, the polymer of Formula (I) is of the formula:

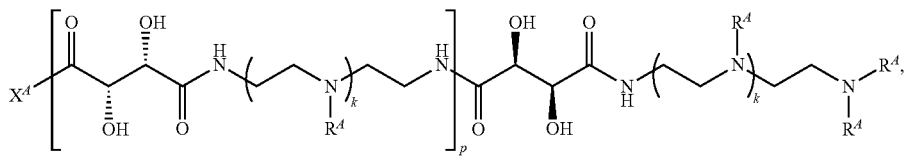

or a salt, solvate, hydrate, polymorph, co-crystal, tautomer, stereoisomer, or isotopically labeled derivative thereof.

In certain embodiments, the polymer of Formula (I) is of the formula:

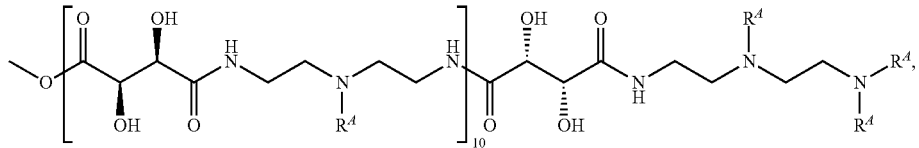

or a salt, solvate, hydrate, polymorph, co-crystal, tautomer, stereoisomer, or isotopically labeled derivative thereof, wherein each instance of $R^A$ is independently H, a moiety of the formula:

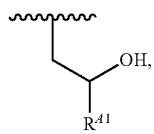

or a moiety of the formula:

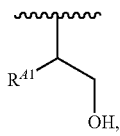

wherein: at least one instance of $R^A$ is of the formula:

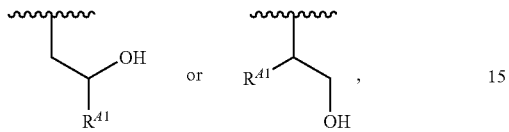

and each instance of $R^{A1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

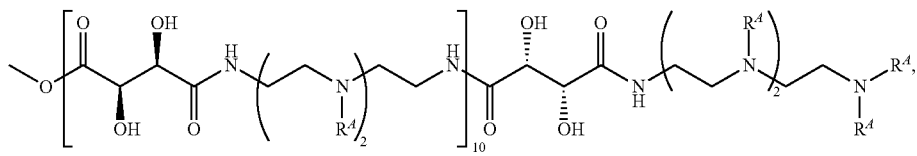

or a salt, solvate, hydrate, polymorph, co-crystal, tautomer, stereoisomer, or isotopically labeled derivative thereof, wherein each instance of $R^A$ is independently H, a moiety of the formula:

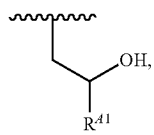

or a moiety of the formula:

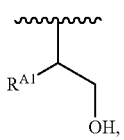

wherein: at least one instance of $R^A$ is of the formula:

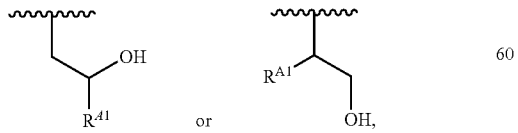

and each instance of $R^{A1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

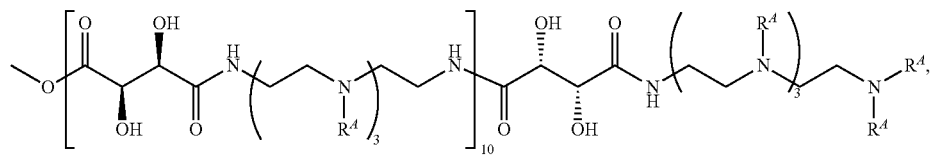

or a salt, solvate, hydrate, polymorph, co-crystal, tautomer, stereoisomer, or isotopically labeled derivative thereof, wherein each instance of $R^A$ is independently H, a moiety of the formula:

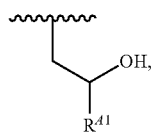

or a moiety of the formula:

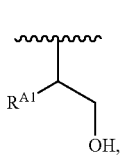

wherein: at least one instance of $R^A$ is of the formula:

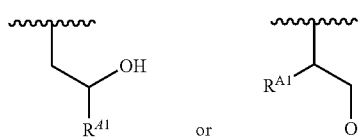 or 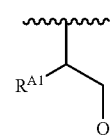

and each instance of $R^{A1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

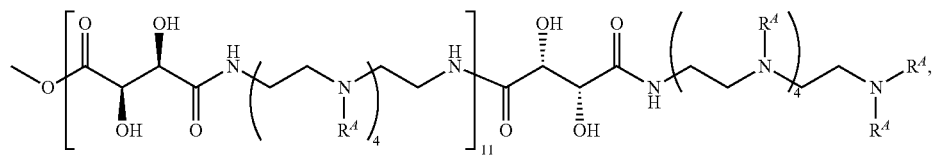

or a salt, solvate, hydrate, polymorph, co-crystal, tautomer, stereoisomer, or isotopically labeled derivative thereof, wherein each instance of $R^A$ is independently H, a moiety of the formula:

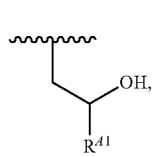

or a moiety of the formula:

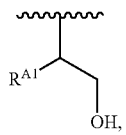

wherein: at least one instance of $R^A$ is of the formula:

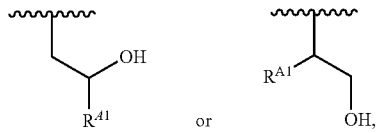

and each instance of $R^{A1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

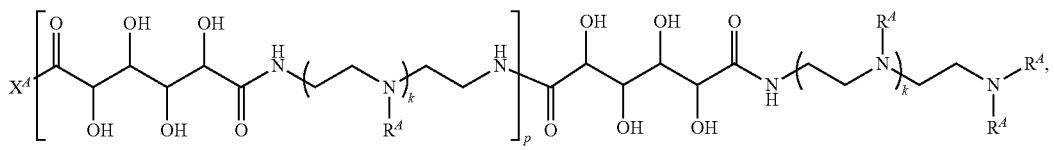

or a salt, solvate, hydrate, polymorph, co-crystal, tautomer, stereoisomer, or isotopically labeled derivative thereof.

In certain embodiments, the polymer of Formula (I) is of the formula:

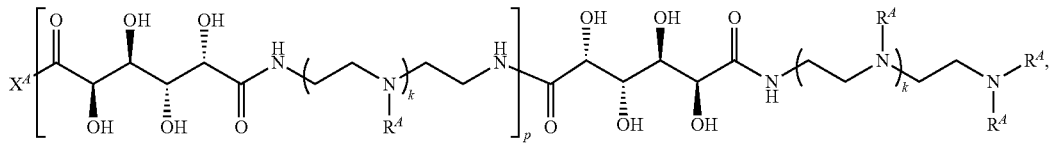

or a salt, solvate, hydrate, polymorph, co-crystal, tautomer, stereoisomer, or isotopically labeled derivative thereof.

In certain embodiments, the polymer of Formula (I) is of the formula:

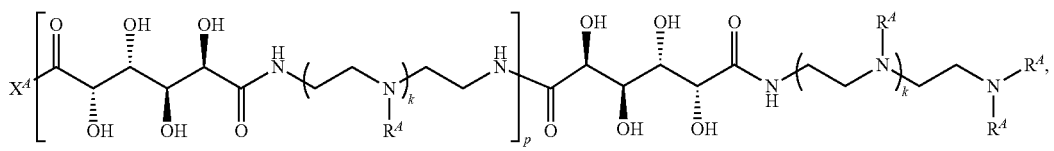

or a salt, solvate, hydrate, polymorph, co-crystal, tautomer, stereoisomer, or isotopically labeled derivative thereof.

In certain embodiments, the polymer of Formula (I) is of the formula:

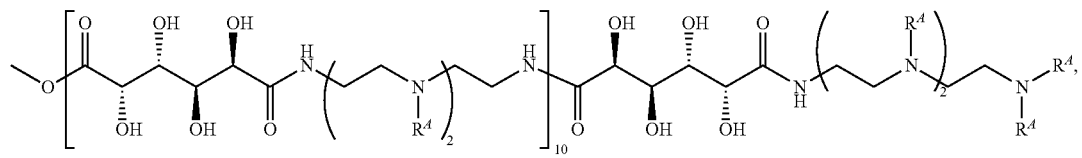

or a salt, solvate, hydrate, polymorph, co-crystal, tautomer, stereoisomer, or isotopically labeled derivative thereof, wherein each instance of $R^A$ is independently H, a moiety of the formula:

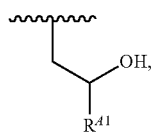

or a moiety of the formula:

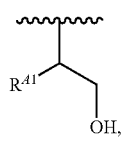

wherein: at least one instance of $R^A$ is of the formula:

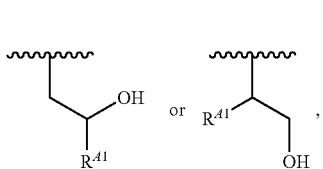

and each instance of $R^{A1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

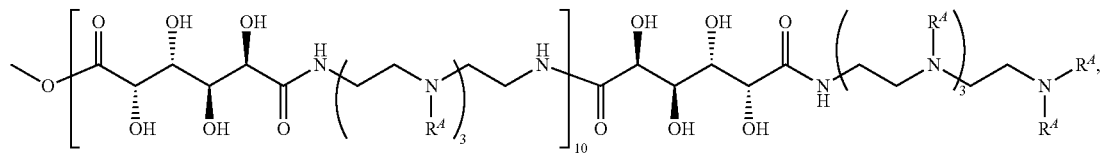

or a salt, solvate, hydrate, polymorph, co-crystal, tautomer, stereoisomer, or isotopically labeled derivative thereof, wherein each instance of $R^A$ is independently H, a moiety of the formula:

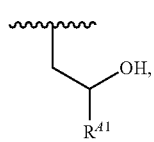

or a moiety of the formula:

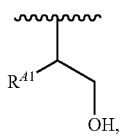

wherein: at least one instance of $R^A$ is of the formula:

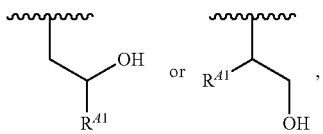

and each instance of $R^{A1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

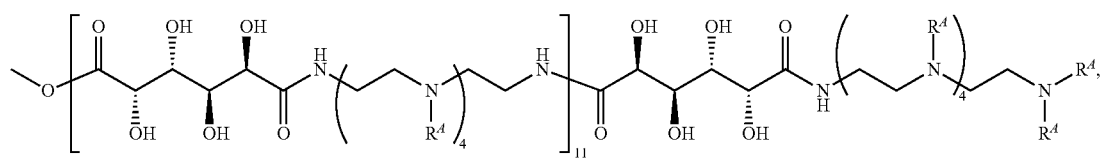

or a salt, solvate, hydrate, polymorph, co-crystal, tautomer, stereoisomer, or isotopically labeled derivative thereof, wherein each instance of $R^A$ is independently H, a moiety of the formula:

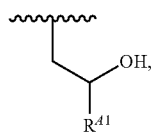

or a moiety of the formula:

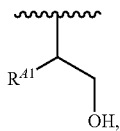

wherein: at least one instance of $R^A$ is of the formula:

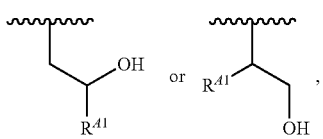

and each instance of $R^{A1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

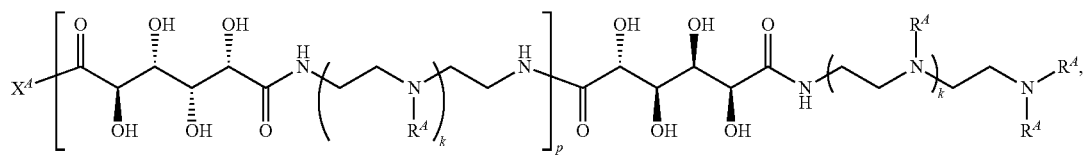

or a salt, solvate, hydrate, polymorph, co-crystal, tautomer, stereoisomer, or isotopically labeled derivative thereof.

In certain embodiments, the polymer of Formula (I) is of the formula:

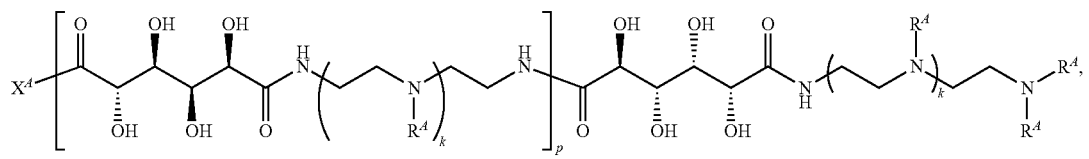

or a salt, solvate, hydrate, polymorph, co-crystal, tautomer, stereoisomer, or isotopically labeled derivative thereof.

In certain embodiments, the polymer of Formula (I) is of the formula:

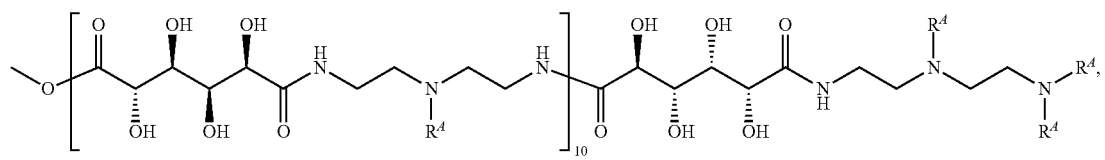

or a salt, solvate, hydrate, polymorph, co-crystal, tautomer, stereoisomer, or isotopically labeled derivative thereof, wherein each instance of $R^A$ is independently H, a moiety of the formula:

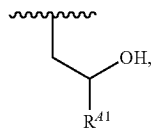

or a moiety of the formula:

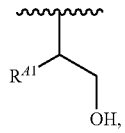

wherein: at least one instance of $R^A$ is of the formula:

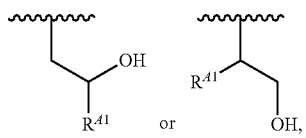

and each instance of $R^{A1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

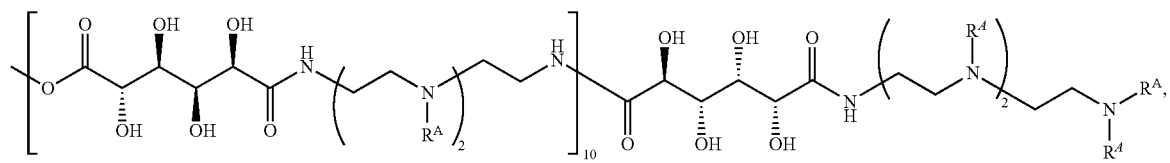

or a salt, solvate, hydrate, polymorph, co-crystal, tautomer, stereoisomer, or isotopically labeled derivative thereof, wherein each instance of $R^A$ is independently H, a moiety of the formula:

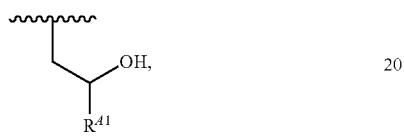

or a moiety of the formula:

wherein: at least one instance of $R^A$ is of the formula:

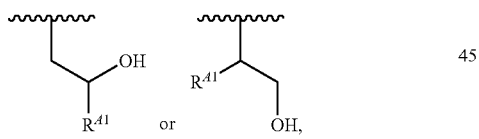

and each instance of $R^{A1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

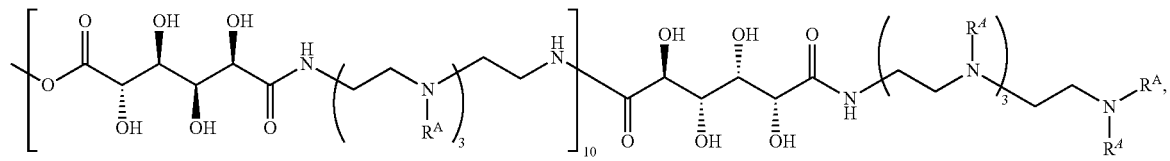

or a salt, solvate, hydrate, polymorph, co-crystal, tautomer, stereoisomer, or isotopically labeled derivative thereof, wherein each instance of $R^A$ is independently H, a moiety of the formula:

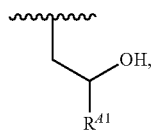

or a moiety of the formula:

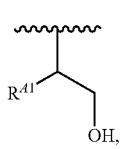

wherein: at least one instance of $R^A$ is of the formula:

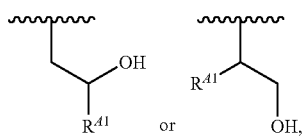

and each instance of $R^{A1}$ is n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

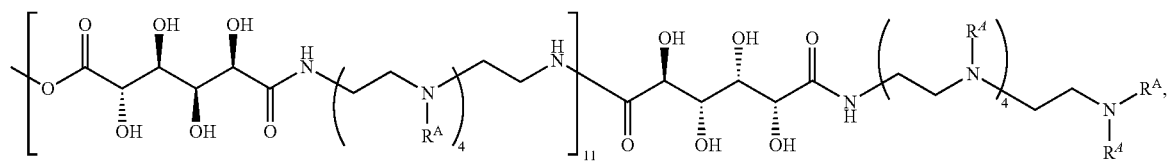

or a salt, solvate, hydrate, polymorph, co-crystal, tautomer, stereoisomer, or isotopically labeled derivative thereof, wherein each instance of $R^A$ is independently H, a moiety of the formula:

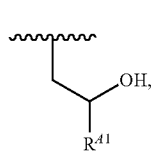

or a moiety of the formula:

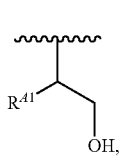

wherein: at least one instance of $R^A$ is of the formula:

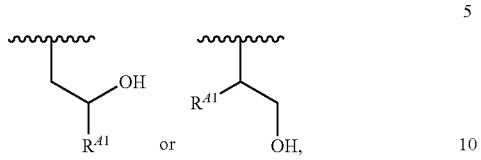

and each instance of $R^{A1}$ is n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, the polymer of Formula (I) is of the formula:

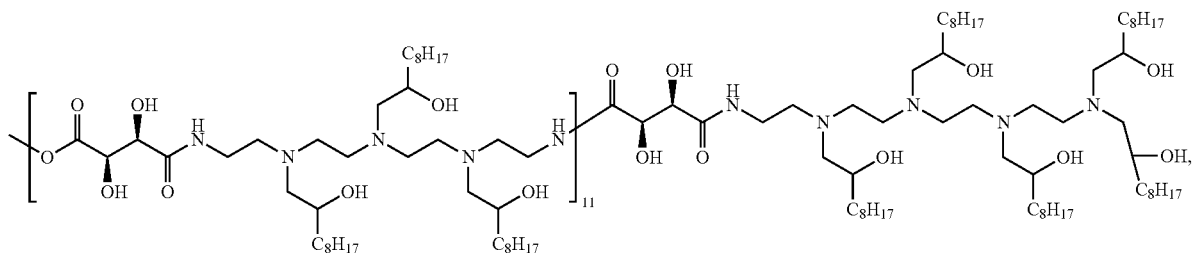

or a salt, solvate, hydrate, polymorph, co-crystal, tautomer, stereoisomer, or isotopically labeled derivative thereof, wherein each instance of $C_8H_{17}$ is n-$C_8H_{17}$.

In certain embodiments, the polymer of Formula (I') is of the formula:

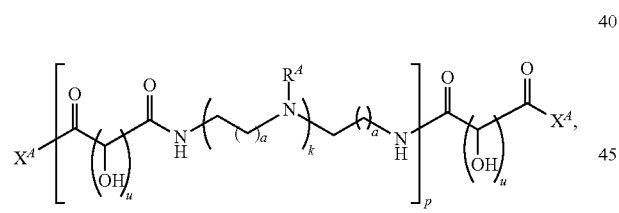

or a salt, solvate, hydrate, polymorph, co-crystal, tautomer, stereoisomer, or isotopically labeled derivative thereof.

In certain embodiments, the polymer of Formula (I') is of the formula:

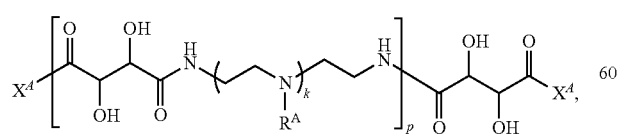

or a salt, solvate, hydrate, polymorph, co-crystal, tautomer, stereoisomer, or isotopically labeled derivative thereof.

In certain embodiments, the polymer of Formula (I') is of the formula:

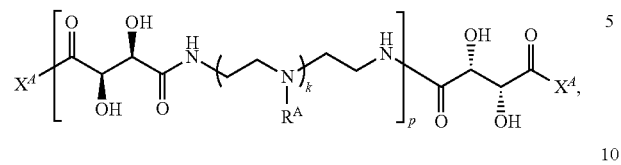

or a salt, solvate, hydrate, polymorph, co-crystal, tautomer, stereoisomer, or isotopically labeled derivative thereof.

In certain embodiments, the polymer of Formula (I') is of the formula:

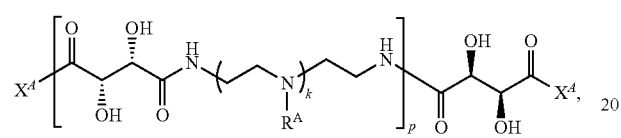

or a salt, solvate, hydrate, polymorph, co-crystal, tautomer, stereoisomer, or isotopically labeled derivative thereof.

In certain embodiments, the polymer of Formula (I') is of the formula:

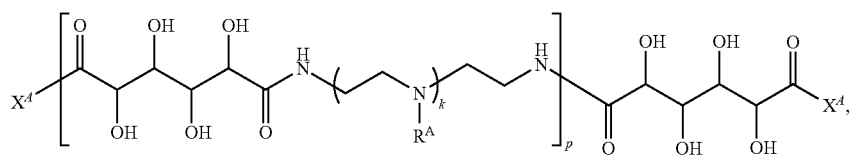

or a salt, solvate, hydrate, polymorph, co-crystal, tautomer, stereoisomer, or isotopically labeled derivative thereof.

In certain embodiments, the polymer of Formula (I') is of the formula:

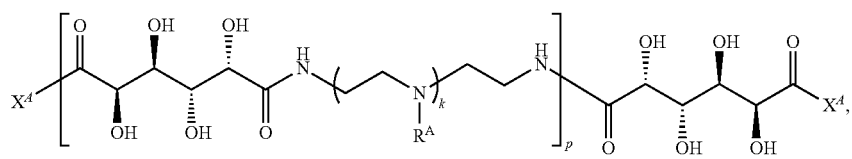

or a salt, solvate, hydrate, polymorph, co-crystal, tautomer, stereoisomer, or isotopically labeled derivative thereof.

In certain embodiments, the polymer of Formula (I') is of the formula:

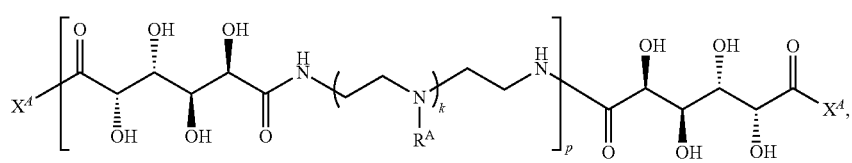

or a salt, solvate, hydrate, polymorph, co-crystal, tautomer, stereoisomer, or isotopically labeled derivative thereof.

In certain embodiments, the polymer of Formula (I') is of the formula:

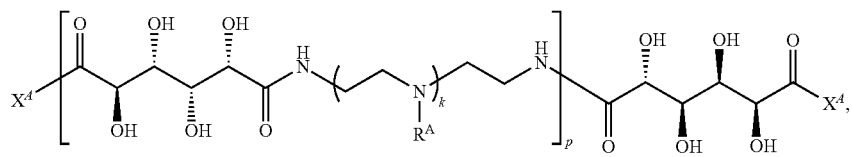

or a salt, solvate, hydrate, polymorph, co-crystal, tautomer, stereoisomer, or isotopically labeled derivative thereof.

In certain embodiments, the polymer of Formula (I") is of the formula:

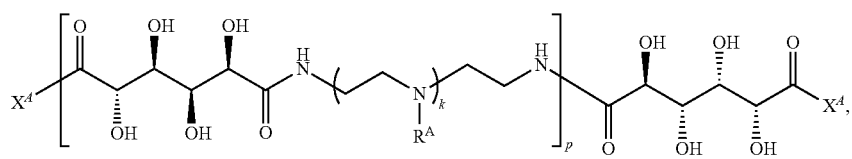

or a salt, solvate, hydrate, polymorph, co-crystal, tautomer, stereoisomer, or isotopically labeled derivative thereof.

In certain embodiments, the polymer of Formula (I") is of the formula:

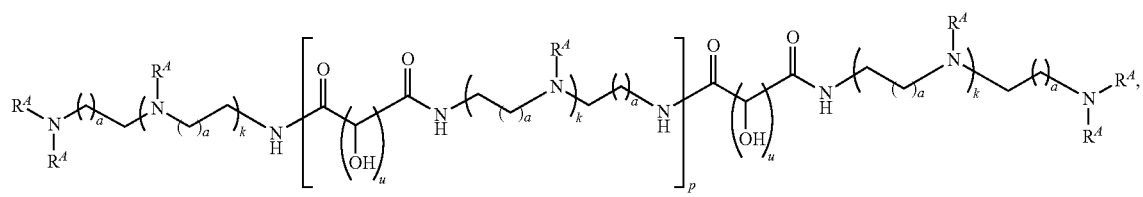

or a salt, solvate, hydrate, polymorph, co-crystal, tautomer, stereoisomer, or isotopically labeled derivative thereof.

In certain embodiments, the polymer of Formula (I') is of the formula:

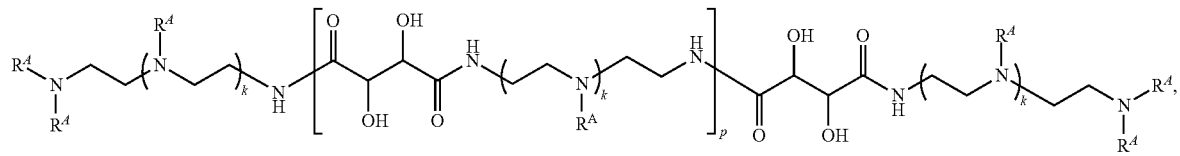

or a salt, solvate, hydrate, polymorph, co-crystal, tautomer, stereoisomer, or isotopically labeled derivative thereof.

In certain embodiments, the polymer of Formula (I") is of the formula:

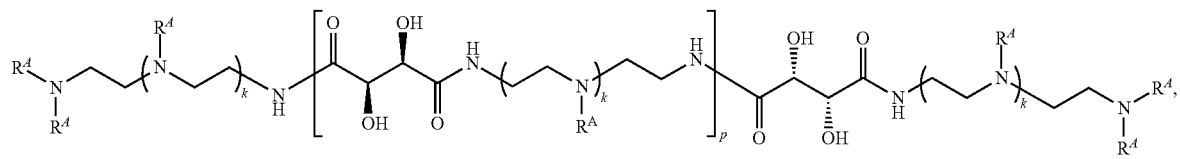

or a salt, solvate, hydrate, polymorph, co-crystal, tautomer, stereoisomer, or isotopically labeled derivative thereof.

In certain embodiments, the polymer of Formula (I″) is of the formula:

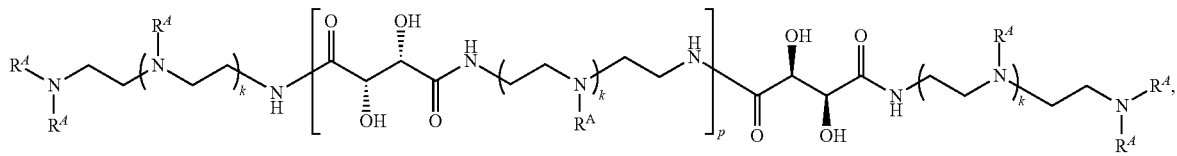

or a salt, solvate, hydrate, polymorph, co-crystal, tautomer, stereoisomer, or isotopically labeled derivative thereof.

In certain embodiments, the polymer of Formula (I″) is of the formula:

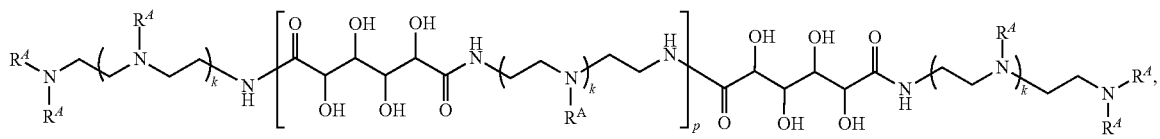

or a salt, solvate, hydrate, polymorph, co-crystal, tautomer, stereoisomer, or isotopically labeled derivative thereof.

In certain embodiments, the polymer of Formula (I″) is of the formula:

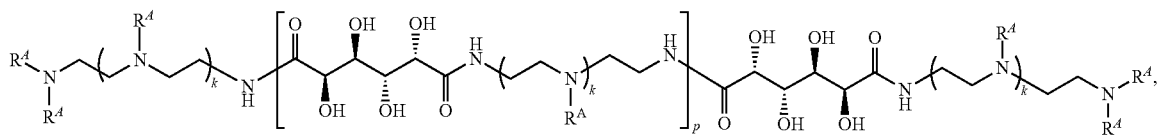

or a salt, solvate, hydrate, polymorph, co-crystal, tautomer, stereoisomer, or isotopically labeled derivative thereof.

In certain embodiments, the polymer of Formula (I″) is of the formula:

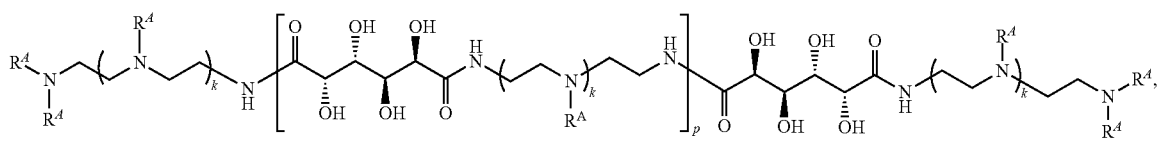

or a salt, solvate, hydrate, polymorph, co-crystal, tautomer, stereoisomer, or isotopically labeled derivative thereof.

In certain embodiments, the polymer of Formula (I″) is of the formula:

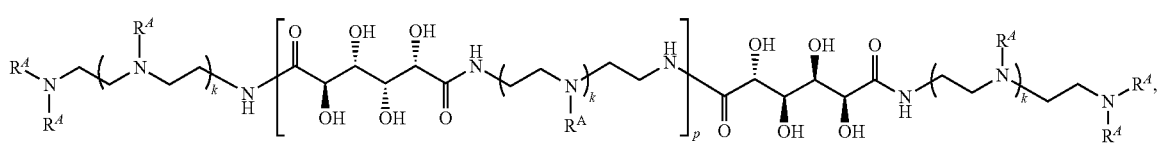

or a salt, solvate, hydrate, polymorph, co-crystal, tautomer, stereoisomer, or isotopically labeled derivative thereof.

In certain embodiments, the polymer of Formula (I″) is of the formula:

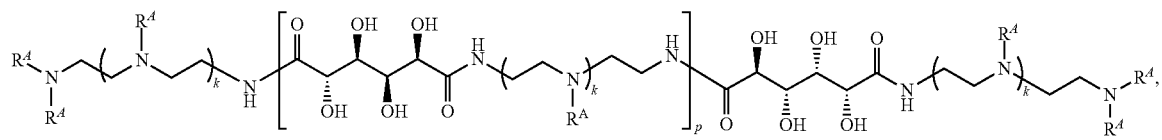

or a salt, solvate, hydrate, polymorph, co-crystal, tautomer, stereoisomer, or isotopically labeled derivative thereof.

In another aspect, the present disclosure provides polymers of Formula (II):

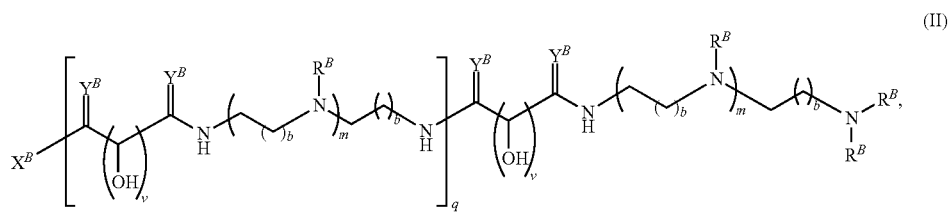

(II)

and salts, solvates, hydrates, polymorphs, co-crystals, tautomers, stereoisomers, and isotopically labeled derivatives thereof, wherein:

$X^B$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{XB}$, —$N(R^{XB})_2$, —$SR^{XB}$, —CN, —SCN, —$C(=NR^{XB})R^{XB}$, —$C(=NR^{XB})OR^{XB}$, —$C(=NR^{XB})N(R^{XB})_2$, —$C(=O)R^{XB}$, —$C(=O)OR^{XB}$, or —$C(=O)N(R^{XB})_2$, —$NO_2$, —$NR^{XB}C(=O)R^{XB}$, —$NR^{XB}C(=O)OR^{XB}$, —$NR^{XB}C(=O)N(R^{XB})_2$, —$OC(=O)R^{XB}$, —$OC(=O)OR^{XB}$, or —$OC(=O)N(R^{XB})_2$, wherein each instance of $R^{XB}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{XB}$ are joined to form a substituted or unsubstituted heterocyclic or substituted or unsubstituted heteroaryl ring;

each instance of $Y^B$ is independently =O, =S, or =$NR^{YB}$, wherein each instance of $R^{YB}$ is independently hydrogen, substituted or unsubstituted $C_{1-6}$ alkyl, or a nitrogen protecting group;

each instance of $R^B$ is independently hydrogen or a moiety of the formula:

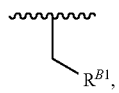

wherein: at least one instance of $R^B$ is of the formula:

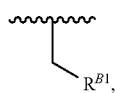

and each instance of $R^{B1}$ is independently substituted or unsubstituted alkyl or substituted or unsubstituted alkenyl;

each instance of b is 1, 2, 3, 4, or 5;
each instance of m is 0, 1, 2, 3, 4, 5, or 6;
each instance of v is 1, 2, 3, 4, 5, 6, 7, 8, 9, or 10; and
q is an integer between 1 and 1000, inclusive.

In another aspect, the present disclosure provides polymers of Formula (II'):

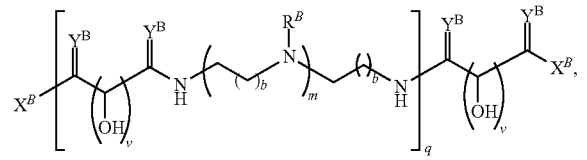

and salts, solvates, hydrates, polymorphs, co-crystals, tautomers, stereoisomers, and isotopically labeled derivatives thereof, wherein:

each instance of $X^B$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^B$, $-N(R^{XB})_2$, $-SR^{XB}$, $-CN$, $-SCN$, $-C(=NR^{XB})R^{XB}$, $-C(=NR^{XB})OR^{XB}$, $-C(=NR^{XB})N(R^{XB})_2$, $-C(=O)R^{XB}$, $-C(=O)OR^{XB}$, or $-C(=O)N(R^{XB})_2$, $-NO_2$, $-NR^{XB}C(=O)R^{XB}$, $-NR^{XB}C(=O)OR^{XB}$, $-NR^{XB}C(=O)N(R^{XB})_2$, $-OC(=O)R^{XB}$, $-OC(=O)OR^{XB}$, or $-OC(=O)N(R^{XB})_2$, wherein each instance of $R^{XB}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{XB}$ are joined to form a substituted or unsubstituted heterocyclic or substituted or unsubstituted heteroaryl ring;

each instance of $Y^B$ is independently $=O$, $=S$, or $=NR^{YB}$, wherein each instance of $R^{YB}$ is independently hydrogen, substituted or unsubstituted $C_{1-6}$ alkyl, or a nitrogen protecting group;

each instance of $R^B$ is independently hydrogen or a moiety of the formula:

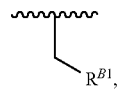

wherein: at least one instance of $R^B$ is of the formula:

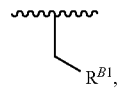

and each instance of $R^{B1}$ is independently substituted or unsubstituted alkyl or substituted or unsubstituted alkenyl;

each instance of b is 1, 2, 3, 4, or 5;
each instance of m is 0, 1, 2, 3, 4, 5, or 6;
each instance of v is 1, 2, 3, 4, 5, 6, 7, 8, 9, or 10; and
q is an integer between 1 and 1000, inclusive.

In another aspect, the present disclosure provides polymers of Formula (II''):

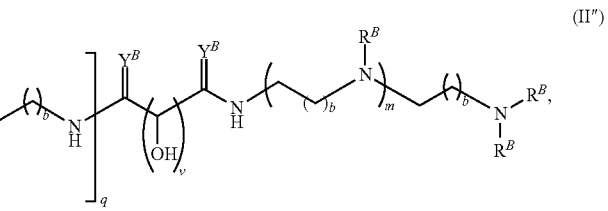

and salts, solvates, hydrates, polymorphs, co-crystals, tautomers, stereoisomers, and isotopically labeled derivatives thereof, wherein:

each instance of $Y^B$ is independently =O, =S, or =$NR^{YB}$, wherein each instance of $R^{YB}$ is independently hydrogen, substituted or unsubstituted $C_{1-6}$ alkyl, or a nitrogen protecting group;

each instance of $R^B$ is independently hydrogen or a moiety of the formula:

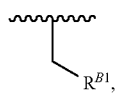

wherein: at least one instance of $R^B$ is of the formula:

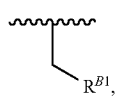

and each instance of $R^{B1}$ is independently substituted or unsubstituted alkyl or substituted or unsubstituted alkenyl;

each instance of b is 1, 2, 3, 4, or 5;

each instance of m is 0, 1, 2, 3, 4, 5, or 6;

each instance of v is 1, 2, 3, 4, 5, 6, 7, 8, 9, or 10; and q is an integer between 1 and 1000, inclusive.

Formula (II) includes end group $X^B$. In certain embodiments, $X^B$ is substituted alkyl. In certain embodiments, $X^B$ is unsubstituted alkyl. In certain embodiments, $X^B$ is unsubstituted $C_{1-6}$ alkyl. In certain embodiments, $X^B$ is substituted $C_{1-6}$ alkyl. In certain embodiments, $X^B$ is $C_{1-6}$ alkyl substituted with at least one halogen. In certain embodiments, $X^B$ is —$CH_3$. In certain embodiments, $X^B$ is substituted methyl. In certain embodiments, $X^B$ is —$CH_2F$. In certain embodiments, $X^B$ is —$CHF_2$. In certain embodiments, $X^B$ is —$CF_3$. In certain embodiments, $X^B$ is ethyl. In certain embodiments, $X^B$ is propyl. In certain embodiments, $X^B$ is butyl. In certain embodiments, $X^B$ is pentyl. In certain embodiments, $X^B$ is hexyl. In certain embodiments, $X^B$ is halogen or substituted or unsubstituted $C_{1-6}$ alkyl. In certain embodiments, $X^B$ is substituted alkenyl. In certain embodiments, $X^B$ is unsubstituted alkenyl. In certain embodiments, $X^B$ is substituted alkynyl. In certain embodiments, $X^B$ is unsubstituted alkynyl. In certain embodiments, $X^B$ is substituted carbocyclyl. In certain embodiments, $X^B$ is unsubstituted carbocyclyl. In certain embodiments, $X^B$ is saturated carbocyclyl. In certain embodiments, $X^B$ is unsaturated carbocyclyl. In certain embodiments, $X^B$ is monocyclic carbocyclyl. In certain embodiments, $X^B$ is 3- to 7-membered, monocyclic carbocyclyl. In certain embodiments, $X^B$ is substituted heterocyclyl. In certain embodiments, $X^B$ is unsubstituted heterocyclyl. In certain embodiments, $X^B$ is saturated heterocyclyl. In certain embodiments, $X^B$ is unsaturated heterocyclyl. In certain embodiments, $X^B$ is heterocyclyl, wherein one, two, or three atoms of the heterocyclic ring system are independently selected from the group consisting of nitrogen, oxygen, and sulfur. In certain embodiments, $X^B$ is monocyclic heterocyclyl. In certain embodiments, $X^B$ is 3- to 7-membered, monocyclic heterocyclyl. In certain embodiments, $X^B$ is substituted aryl. In certain embodiments, $X^B$ is unsubstituted aryl. In certain embodiments, $X^B$ is 6- to 10-membered aryl. In certain embodiments, $X^B$ is substituted phenyl. In certain embodiments, $X^B$ is unsubstituted phenyl. In certain embodiments, $X^B$ is substituted heteroaryl. In certain embodiments, $X^B$ is unsubstituted heteroaryl. In certain embodiments, $X^B$ is heteroaryl, wherein one, two, three, or four atoms of the heteroaryl ring system are independently selected from the group consisting of nitrogen, oxygen, and sulfur. In certain embodiments, $X^B$ is monocyclic heteroaryl. In certain embodiments, $X^B$ is 5-membered, monocyclic heteroaryl. In certain embodiments, $X^B$ is 6-membered, monocyclic heteroaryl. In certain embodiments, $X^B$ is bicyclic heteroaryl, wherein the point of attachment may be on any atom of the bicyclic heteroaryl ring system, as valency permits. In certain embodiments, $X^B$ is 9- or 10-membered, bicyclic heteroaryl. In certain embodiments, $X^B$ is —$OR^{XB}$. In certain embodiments, $X^B$ is —OH. In certain embodiments, $X^B$ is —$OR^{XB}$, wherein $R^{XB}$ is substituted or unsubstituted $C_{1-6}$ alkyl. In certain embodiments, $X^B$ is —OMe. In certain embodiments, $X^B$ is —OEt, —OPr, —OBu, or —OBn. In certain embodiments, $X^B$ is —OPh. In certain embodiments, $X^B$ is —$SR^{XB}$. In certain embodiments, $X^B$ is —SH. In certain embodiments, $X^B$ is —SMe. In certain embodiments, $X^B$ is —$N(R^{XB})_2$. In certain embodiments, $X^B$ is —$NH_2$. In certain embodiments, $X^B$ is —NHMe. In certain embodiments, $X^B$ is —$NMe_2$. In certain embodiments, $X^B$ is —$OR^{XB}$ or —$N(R^{XB})_2$. In certain embodiments, $X^B$ is —C(=$NR^{XB}$)$R^{XB}$, —C(=$NR^{XB}$)$OR^{XB}$, or —C(=$NR^{XB}$)$N(R^{XB})_2$. In certain embodiments, $X^B$ is —C(=O)$R^{XB}$ or —C(=O)$OR^{XB}$. In certain embodiments, $X^B$ is —C(=O)$N(R^{XB})_2$. In certain embodiments, $X^B$ is —C(=O)$NMe_2$, —C(=O)NHMe, or —C(=O)$NH_2$.

Formula (II') includes end groups $X^B$. In certain embodiments, all instances of $X^B$ are the same. In certain embodiments, two instances of $X^B$ are not the same. In certain embodiments, at least one instance of $X^B$ is substituted alkyl. In certain embodiments, at least one instance of $X^B$ is unsubstituted alkyl. In certain embodiments, at least one instance of $X^B$ is unsubstituted $C_{1-6}$ alkyl. In certain embodiments, at least one instance of $X^B$ is substituted $C_{1-6}$ alkyl. In certain embodiments, at least one instance of $X^B$ is $C_{1-6}$ alkyl substituted with at least one halogen. In certain embodiments, at least one instance of $X^B$ is —$CH_3$. In certain embodiments, at least one instance of $X^B$ is substituted methyl. In certain embodiments, at least one instance of $X^B$ is —$CH_2F$. In certain embodiments, at least one instance of $X^B$ is —$CHF_2$. In certain embodiments, at least one instance of $X^B$ is —$CF_3$. In certain embodiments, at least one instance of $X^B$ is ethyl. In certain embodiments, at least one instance of $X^B$ is propyl. In certain embodiments, at least one instance of $X^B$ is butyl. In certain embodiments, at least one instance of $X^B$ is pentyl. In certain embodiments, at least one instance of $X^B$ is hexyl. In certain embodiments, at least one instance of $X^B$ is halogen or substituted or unsubstituted $C_{1-6}$ alkyl. In certain embodiments, at least one instance of $X^B$ is substituted alkenyl. In certain embodiments, at least one instance of $X^B$ is unsubstituted alkenyl. In certain embodiments, at least one instance of $X^B$ is substituted alkynyl. In certain embodiments, at least one instance of $X^B$ is unsubstituted alkynyl. In certain embodiments, at least one instance of $X^B$ is substituted carbocyclyl. In certain embodiments, at least one instance of $X^B$ is unsubstituted carbocyclyl. In certain embodiments, at least one instance of $X^B$ is saturated carbocyclyl. In certain embodiments, at least one instance of $X^B$ is unsaturated carbocyclyl. In certain embodiments, at least one instance of $X^B$ is monocyclic carbocyclyl. In certain embodiments, at least one instance of $X^B$ is 3- to 7-membered, monocyclic carbocyclyl. In certain embodiments, at least one instance of $X^B$ is substituted heterocyclyl. In certain embodiments, at least one instance of $X^B$ is unsubstituted heterocyclyl. In certain embodiments, at least one instance of $X^B$ is saturated heterocyclyl. In certain embodiments, at least one instance of $X^B$ is unsaturated heterocyclyl. In certain embodiments, at least one instance of $X^B$ is heterocyclyl, wherein one, two, or three atoms of the heterocyclic ring system are independently selected from the group consisting of nitrogen, oxygen, and sulfur. In certain embodiments, at least one instance of $X^B$ is monocyclic heterocyclyl. In certain embodiments, at least one instance of $X^B$ is 3- to 7-membered, monocyclic heterocyclyl. In certain embodiments, at least one instance of $X^B$ is substituted aryl. In certain embodiments, at least one instance of $X^B$ is unsubstituted aryl. In certain embodiments, at least one instance of $X^B$ is 6- to 10-membered aryl. In certain embodiments, at least one instance of $X^B$ is substituted phenyl. In certain embodiments, at least one instance of $X^B$ is unsubstituted phenyl. In certain embodiments, at least one instance of $X^B$ is substituted heteroaryl. In certain embodiments, at least one instance of $X^B$ is unsubstituted heteroaryl. In certain embodiments, at least one instance of $X^B$ is heteroaryl, wherein one, two, three, or four atoms of the heteroaryl ring system are independently selected from the group consisting of nitrogen, oxygen, and sulfur. In certain embodiments, at least one instance of $X^B$ is monocyclic heteroaryl. In certain embodiments, at least one instance of $X^B$ is 5-membered, monocyclic heteroaryl. In certain embodiments, at least one instance of $X^B$ is 6-membered, monocyclic heteroaryl. In certain embodiments, at least one instance of $X^B$ is bicyclic heteroaryl, wherein the point of attachment may be on any atom of the bicyclic heteroaryl ring system, as valency permits. In certain embodiments, at least one instance of $X^B$ is 9- or 10-membered, bicyclic heteroaryl. In certain embodiments, at least one instance of $X^B$ is —$OR^B$. In certain embodiments, at least one instance of $X^B$ is —OH. In certain embodiments, at least one instance of $X^B$ is —$OR^{XB}$, wherein $R^{XB}$ is substituted or unsubstituted $C_{1-6}$alkyl. In certain embodiments, at least one instance of $X^B$ is —OMe. In certain embodiments, at least one instance of $X^B$ is —OEt, —OPr, —OBu, or —OBn. In certain embodiments, at least one instance of $X^B$ is —OPh. In certain embodiments, at least one instance of $X^B$ is —$SR^{XB}$. In certain embodiments, at least one instance of $X^B$ is —SH. In certain embodiments, at least one instance of $X^B$ is —SMe. In certain embodiments, at least one instance of $X^B$ is —$N(R^{XB})_2$. In certain embodiments, at least one instance of $X^B$ is —$NH_2$. In certain embodiments, at least one instance of $X^B$ is —NHMe. In certain embodiments, at least one instance of $X^B$ is —$NMe_2$. In certain embodiments, at least one instance of $X^B$ is —$OR^{XB}$ or —$N(R^{XB})_2$. In certain embodiments, at least one instance of $X^B$ is —$C(=NR^{XB})R^{XB}$, —$C(=NR^{XB})OR^{XB}$, or —$C(=NR^{XB})N(R^{XB})_2$. In certain embodiments, at least one instance of $X^B$ is —$C(=O)R^{XB}$ or —$C(=O)OR^{XB}$. In certain embodiments, at least one instance of $X^B$ is —$C(=O)N(R^{XB})_2$. In certain embodiments, at least one instance of $X^B$ is —$C(=O)NMe_2$, —$C(=O)NHMe$, or —$C(=O)NH_2$.

For any of the $X^B$ that include an $R^{XB}$ moiety described herein, any of the following embodiments for $R^{XB}$ may be applicable. In certain embodiments, $R^{XB}$ is H. In certain embodiments, $R^{XB}$ is substituted acyl. In certain embodiments, $R^{XB}$ is unsubstituted acyl. In certain embodiments, $R^{XB}$ is acetyl. In certain embodiments, $R^{XB}$ is substituted alkyl. In certain embodiments, $R^{XB}$ is unsubstituted alkyl. In certain embodiments, $R^{XB}$ is unsubstituted $C_{1-6}$ alkyl. In certain embodiments, $R^{XB}$ is methyl. In certain embodiments, $R^{XB}$ is ethyl. In certain embodiments, $R^{XB}$ is propyl. In certain embodiments, $R^{XB}$ is butyl. In certain embodiments, $R^{XB}$ is pentyl. In certain embodiments, $R^{XB}$ is hexyl. In certain embodiments, $R^{XB}$ is substituted alkenyl. In certain embodiments, $R^{XB}$ is unsubstituted alkenyl. In certain embodiments, $R^{XB}$ is substituted alkynyl. In certain embodiments, $R^{XB}$ is unsubstituted alkynyl. In certain embodiments, $R^{XB}$ is substituted or unsubstituted carbocyclyl. In certain embodiments, $R^{XB}$ is saturated carbocyclyl. In certain embodiments, $R^{XB}$ is unsaturated carbocyclyl. In certain embodiments, $R^{XB}$ is 3- to 7-membered, monocyclic carbocyclyl. In certain embodiments, $R^{XB}$ is substituted or unsubstituted heterocyclyl. In certain embodiments, $R^{XB}$ is saturated heterocyclyl. In certain embodiments, $R^{XB}$ is unsaturated heterocyclyl. In certain embodiments, $R^{XB}$ is heterocyclyl, wherein one, two, or three atoms of the heterocyclic ring system are independently selected from the group consisting of nitrogen, oxygen, and sulfur. In certain embodiments, $R^{XB}$ is 3- to 7-membered, monocyclic heterocyclyl. In certain embodiments, $R^{XB}$ is substituted or unsubstituted aryl. In certain embodiments, $R^{XB}$ is 6- to 10-membered aryl. In certain embodiments, $R^{XB}$ is monocyclic aryl. In certain embodiments, $R^{XB}$ is substituted phenyl. In certain embodiments, $R^{XB}$ is unsubstituted phenyl. In certain embodiments, $R^{XB}$ is bicyclic aryl. In certain embodiments, $R^{XB}$ is substituted or unsubstituted heteroaryl. In certain embodiments, $R^{XB}$ is heteroaryl, wherein one, two, three, or four atoms of the heteroaryl ring system are independently selected from the group consisting of nitrogen, oxygen, and sulfur. In certain embodiments, $R^{XB}$ is monocyclic heteroaryl. In certain embodiments, $R^{XB}$ is 5- or 6-membered, monocyclic heteroaryl. In certain embodiments, $R^{XB}$ is bicyclic heteroaryl, wherein the point of attachment may be on any atom of the bicyclic heteroaryl ring system, as valency permits. In certain embodiments, $R^{XB}$ is a nitrogen protecting group when attached to a nitrogen atom. In certain embodiments, $R^{XB}$ is Bn, Boc, Cbz, Fmoc, trifluoroacetyl, triphenylmethyl, acetyl, or Ts when attached to a nitrogen atom. In certain embodiments, $R^{XB}$ is an oxygen protecting group when attached to an oxygen atom. In certain embodiments, $R^{XB}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{XB}$ is a sulfur protecting group when attached to a sulfur atom. In certain embodiments, $R^{XB}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{XB}$ are joined to form a substituted or unsubstituted heterocyclic ring. In certain embodiments, two instances of $R^{XB}$ are joined to form a saturated or unsaturated heterocyclic ring. In certain embodiments, two instances of $R^{XB}$ are joined to form a heterocyclic ring, wherein one, two, or three atoms of the heterocyclic ring system are independently selected from the group consisting of nitrogen, oxygen, and sulfur. In certain embodiments, two instances of $R^{XB}$ are joined to form a 3- to 7-membered, monocyclic heterocyclic ring. In certain embodiments, two instances of $R^{XB}$ are joined to form a substituted or unsubstituted heteroaryl ring. In certain embodiments, two instances of $R^{XB}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

Any one of Formulae (II), (II'), and (II") includes $Y^B$ moieties. In certain embodiments, all instances of $Y^B$ are the same. In certain embodiments, at least two instances of $Y^B$ are different from each other. In certain embodiments, at least one instance of $Y^B$ is =O. In certain embodiments, each instance of $Y^B$ is =O. In certain embodiments, at least one instance of $Y^B$ is =S. In certain embodiments, at least one instance of $Y^B$ is =NR$^{YB}$. In certain embodiments, at least one instance of $Y^B$ is =NH. In certain embodiments, at least one instance of $Y^B$ is =N(substituted or unsubstituted $C_{1-6}$ alkyl, e.g., methyl).

In certain embodiments, all instances of $R^{YB}$ are the same. In certain embodiments, at least two instances of $R^{YB}$ are different from each other. In certain embodiments, at least one instance of $R^{YB}$ is H. In certain embodiments, at least one instance of $R^{YB}$ is substituted or unsubstituted $C_{1-6}$ alkyl. In certain embodiments, at least one instance of $R^{YB}$ is methyl. In certain embodiments, at least one instance of $R^{YB}$ is ethyl, propyl, butyl, pentyl, or hexyl. In certain embodiments, at least one instance of $R^{YB}$ is a nitrogen protecting group (e.g., Bn, Boc, Cbz, Fmoc, trifluoroacetyl, triphenylmethyl, acetyl, or Ts).

Any one of Formulae (II), (II'), and (II") includes substituents $R^B$. In certain embodiments, at least about 10%, at least about 20%, at least about 30%, or at least about 40% of the total instances of $R^B$ are the same. In certain embodiments, at least about 50% of the total instances of $R^B$ are the same. In certain embodiments, at least about 60% of the total instances of $R^B$ are the same. In certain embodiments, at least about 70% of the total instances of $R^B$ are the same. In certain embodiments, at least about 80% of the total instances of $R^B$ are the same. In certain embodiments, at least about 90% of the total instances of $R^B$ are the same. In certain embodiments, at least about 95% of the total instances of $R^B$ are the same. In certain embodiments, all instances of $R^B$ are the same. In certain embodiments, at least two instances of $R^B$ are different from each other. In certain embodiments, at least one instance of $R^B$ is H. In certain embodiments, at least one instance of $R^B$ is of the formula:

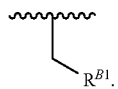

In certain embodiments, at least about 10%, at least about 20%, at least about 30%, at least about 40%, at least about 50%, at least about 60%, at least about 70%, at least about 80%, at least about 90%, or at least about 95% of the total instances of $R^B$ are independently of the formula:

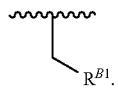

In certain embodiments, all instances of $R^B$ are independently of the formula:

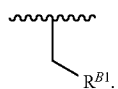

Any one of Formulae (II), (II'), and (II") includes one or more substituents $R^{B1}$. In certain embodiments, all instances of $R^{B1}$ are the same. In certain embodiments, all instances of $R^{B1}$ that are not hydrogen are the same. In certain embodiments, at least two instances of $R^{B1}$ are different from each other. In certain embodiments, at least one instance of $R^{B1}$ is substituted alkyl. In certain embodiments, at least one instance of $R^{B1}$ is unsubstituted alkyl. In certain embodiments, each instance of $R^{B1}$ is independently substituted or unsubstituted $C_{1-30}$ alkyl. In certain embodiments, at least one instance of $R^{B1}$ is substituted $C_{1-30}$ alkyl. In certain embodiments, at least one instance of $R^{B1}$ is a moiety shown in Table 2. In certain embodiments, each instance of $R^{B1}$ is independently a moiety shown in Table 2. In certain embodiments, each instance of $R^{B1}$ is a moiety shown in Table 2. In certain embodiments, at least one instance of $R^{B1}$ is $C_{1-30}$ alkyl substituted with one or more halogen. In certain embodiments, at least one instance of $R^{B1}$ is $C_{1-30}$ alkyl substituted with one or more fluorine. In certain embodiments, at least one instance of $R^{B1}$ is $C_{1-30}$ perfluoroalkyl. In certain embodiments, at least one instance of $R^{B1}$ is unsubstituted $C_{1-30}$ alkyl. In certain embodiments, at least one instance of $R^{B1}$ is a moiety shown in Table 1. In certain embodiments, each instance of $R^{B1}$ is independently a moiety shown in Table 1. In certain embodiments, each instance of $R^{B1}$ is a moiety shown in Table 1. In certain embodiments, at least one instance of $R^{B1}$ is unsubstituted and unbranched $C_{1-30}$ alkyl. In certain embodiments, each instance of $R^{B1}$ is independently substituted or unsubstituted $C_{4-22}$ alkyl (e.g., substituted or unsubstituted $C_{4-18}$ alkyl). In certain embodiments, at least one instance of $R^{B1}$ is substituted $C_{4-18}$ alkyl. In certain embodiments, at least one instance of $R^{B1}$ is $C_{4-18}$ alkyl substituted with one or more halogen. In certain embodiments, at least one instance of $R^{B1}$ is $C_{4-18}$ alkyl substituted with one or more fluorine. In certain embodiments, at least one instance of $R^{B1}$ is $C_{4-18}$ perfluoroalkyl. In certain embodiments, at least one instance of $R^{B1}$ is unsubstituted $C_{4-18}$ alkyl. In certain embodiments, at least one instance of $R^{B1}$ is unsubstituted and unbranched $C_{4-18}$ alkyl. In certain embodiments, each instance of $R^{B1}$ is independently substituted or unsubstituted $C_{6-14}$ alkyl. In certain embodiments, at least one instance of $R^{B1}$ is substituted $C_{6-14}$ alkyl. In certain embodiments, at least one instance of $R^{B1}$ is $C_{6-14}$ alkyl substituted with one or more halogen. In certain embodiments, at least one instance of $R^{B1}$ is $C_{6-14}$ alkyl substituted with one or more fluorine. In certain embodiments, at least one instance of $R^{B1}$ is $C_{6-14}$ perfluoroalkyl. In certain embodiments, at least one instance of $R^{B1}$ is unsubstituted $C_{6-14}$ alkyl. In certain embodiments, at least one instance of $R^{B1}$ is unsubstituted and unbranched $C_{6-14}$ alkyl. In certain embodiments, each instance of $R^{B1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$. In certain embodiments, each instance of $R^{B1}$ is n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, at least one instance of $R^{B1}$ is substituted alkenyl. In certain embodiments, at least one instance of $R^{B1}$ is unsubstituted alkenyl. In certain embodiments, each instance of $R^{B1}$ is independently substituted or unsubstituted $C_{2-30}$ alkenyl. In certain embodiments, at least one instance of $R^{B1}$ is substituted $C_{2-30}$ alkenyl. In certain embodiments, at least one instance of $R^{B1}$ is $C_{2-30}$ alkenyl substituted with one or more halogen. In certain embodiments, at least one instance of $R^{B1}$ is $C_{2-30}$ alkenyl substituted with one or more fluorine. In certain embodiments, at least one instance of $R^{B1}$ is $C_{2-30}$ perfluoroalkenyl. In certain embodiments, at least one instance of $R^{B1}$ is unsubstituted $C_{2-30}$ alkenyl. In certain embodiments, at least one instance of $R^{B1}$ is a moiety shown in Table 3. In certain embodiments, each instance of $R^{B1}$ is independently a moiety shown in Table 3. In certain embodiments, each instance of $R^{B1}$ is a moiety shown in Table 3. In certain embodiments, at least one instance of $R^{B1}$ is unsubstituted and unbranched $C_{2-30}$ alkenyl. In certain embodiments, each instance of $R^{B1}$ is independently substituted or unsubstituted $C_{4-18}$ alkenyl. In certain embodiments, at least one instance of $R^{B1}$ is substituted $C_{4-18}$ alkenyl. In certain embodiments, at least one instance of $R^{B1}$ is $C_{4-18}$ alkenyl substituted with one or more halogen. In certain embodiments, at least one instance of $R^{B1}$ is $C_{4-18}$ alkenyl substituted with one or more fluorine. In certain embodiments, at least one instance of $R^{B1}$ is $C_{4-18}$ perfluoroalkenyl. In certain embodiments, at least one instance of $R^{B1}$ is unsubstituted $C_{4-18}$ alkenyl. In certain embodiments, at least one instance of $R^{B1}$ is unsubstituted and unbranched $C_{4-18}$ alkenyl. In certain embodiments, each instance of $R^{B1}$ is independently substituted or unsubstituted $C_{6-14}$ alkenyl. In certain embodiments, at least one instance of $R^{B1}$ is substituted $C_{6-14}$ alkenyl. In certain embodiments, at least one instance of $R^{B1}$ is $C_{6-14}$ alkenyl substituted with one or more halogen. In certain embodiments, at least one instance of $R^{B1}$ is $C_{6-14}$ alkenyl substituted with one or more fluorine. In certain embodiments, at least one instance of $R^{B1}$ is $C_{6-14}$ perfluoroalkenyl. In certain embodiments, at least one instance of $R^{B1}$ is unsubstituted $C_{6-14}$ alkenyl. In certain embodiments, at least one instance of $R^{B1}$ is unsubstituted and unbranched $C_{6-14}$ alkenyl.

In certain embodiments, each instance of b is 1. In certain embodiments, each instance of b is 2. In certain embodiments, each instance of b is 3. In certain embodiments, each instance of b is 4. In certain embodiments, each instance of b is 5.

In certain embodiments, each instance of m is 0. In certain embodiments, each instance of m is 1. In certain embodiments, each instance of m is 2. In certain embodiments, each instance of m is 3. In certain embodiments, each instance of m is 4. In certain embodiments, each instance of m is 5. In certain embodiments, each instance of m is 6.

In certain embodiments, each instance of v is 1. In certain embodiments, each instance of v is 2. In certain embodiments, each instance of v is 3. In certain embodiments, each instance of v is 4. In certain embodiments, each instance of v is 5. In certain embodiments, each instance of v is 6. In certain embodiments, each instance of v is 7. In certain embodiments, each instance of v is 8. In certain embodiments, each instance of v is 9. In certain embodiments, each instance of v is 10.

In certain embodiments, q is an integer between 1 and 1000, inclusive. In certain embodiments, q is an integer between 1 and 300, inclusive. In certain embodiments, q is an integer between 1 and 100, inclusive. In certain embodiments, q is an integer between 1 and 70, inclusive. In certain embodiments, q is an integer between 1 and 50, inclusive. In certain embodiments, q is an integer between 1 and 30, inclusive. In certain embodiments, q is an integer between 5 and 30, inclusive. In certain embodiments, q is an integer between 10 and 20, inclusive. In certain embodiments, q is an integer between 1 and 15, inclusive. In certain embodiments, q is an integer between 5 and 15, inclusive. In certain embodiments, q is 10 or 11.

In certain embodiments, the polymer of Formula (II) is of the formula:

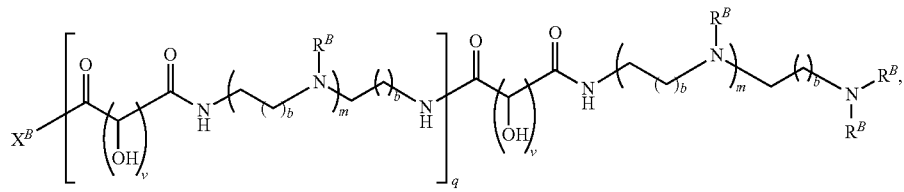

or a salt, solvate, hydrate, polymorph, co-crystal, tautomer, stereoisomer, or isotopically labeled derivative thereof.

In certain embodiments, the polymer of Formula (II) is of the formula:

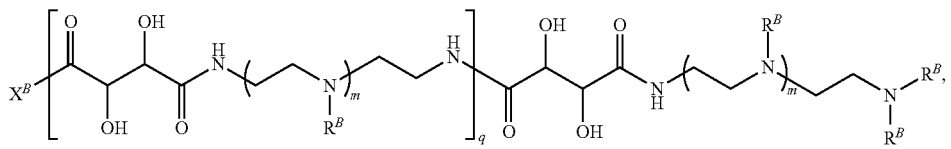

or a salt, solvate, hydrate, polymorph, co-crystal, tautomer, stereoisomer, or isotopically labeled derivative thereof.

In certain embodiments, the polymer of Formula (II) is of the formula:

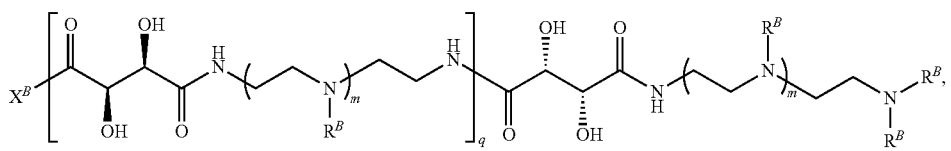

or a salt, solvate, hydrate, polymorph, co-crystal, tautomer, stereoisomer, or isotopically labeled derivative thereof.

In certain embodiments, the polymer of Formula (II) is of the formula:

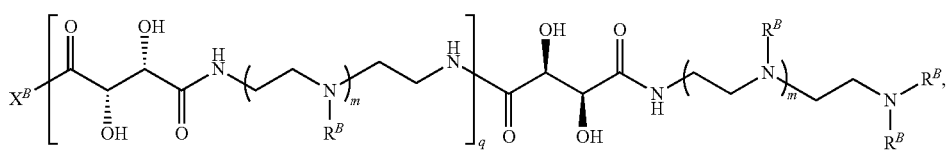

or a salt, solvate, hydrate, polymorph, co-crystal, tautomer, stereoisomer, or isotopically labeled derivative thereof.

In certain embodiments, the polymer of Formula (II) is of the formula:

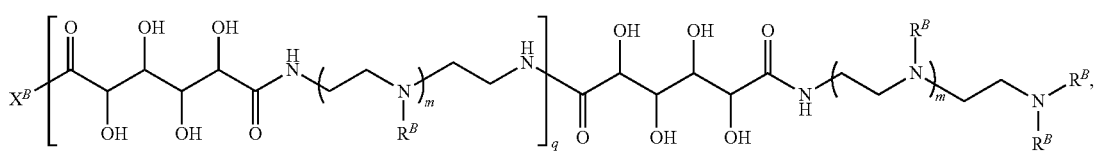

or a salt, solvate, hydrate, polymorph, co-crystal, tautomer, stereoisomer, or isotopically labeled derivative thereof.

In certain embodiments, the polymer of Formula (II) is of the formula:

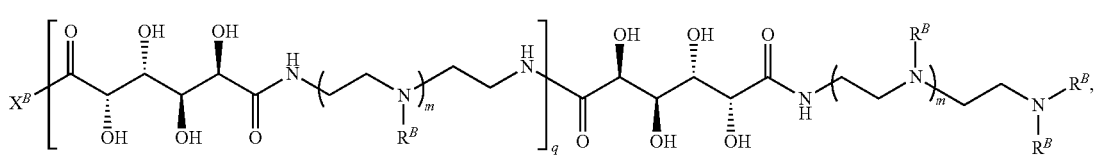

or a salt, solvate, hydrate, polymorph, co-crystal, tautomer, stereoisomer, or isotopically labeled derivative thereof.

In certain embodiments, the polymer of Formula (II) is of the formula:

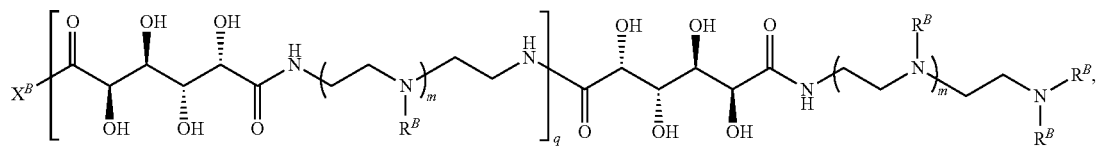

or a salt, solvate, hydrate, polymorph, co-crystal, tautomer, stereoisomer, or isotopically labeled derivative thereof.

In certain embodiments, the polymer of Formula (II) is of the formula:

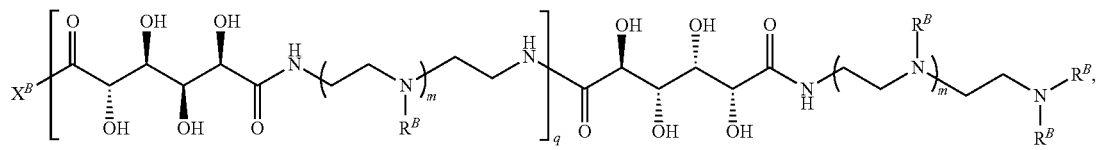

or a salt, solvate, hydrate, polymorph, co-crystal, tautomer, stereoisomer, or isotopically labeled derivative thereof.

In certain embodiments, the polymer of Formula (II) is of the formula:

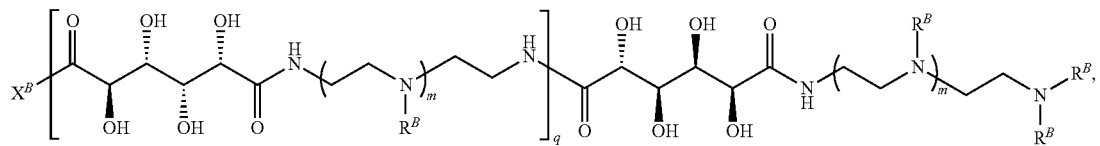

or a salt, solvate, hydrate, polymorph, co-crystal, tautomer, stereoisomer, or isotopically labeled derivative thereof.

In certain embodiments, the polymer of Formula (II') is of the formula:

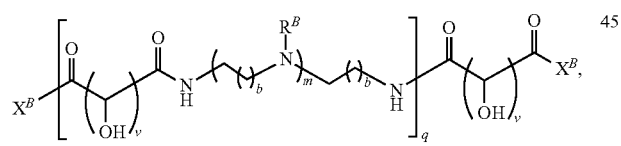

or a salt, solvate, hydrate, polymorph, co-crystal, tautomer, stereoisomer, or isotopically labeled derivative thereof.

In certain embodiments, the polymer of Formula (II') is of the formula:

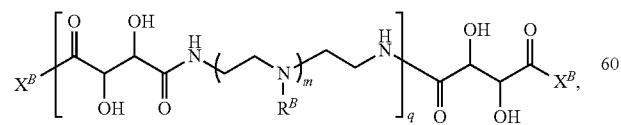

or a salt, solvate, hydrate, polymorph, co-crystal, tautomer, stereoisomer, or isotopically labeled derivative thereof.

In certain embodiments, the polymer of Formula (II') is of the formula:

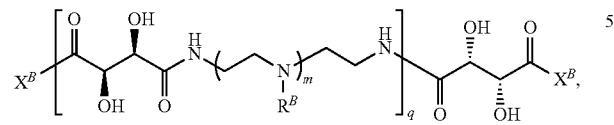

or a salt, solvate, hydrate, polymorph, co-crystal, tautomer, stereoisomer, or isotopically labeled derivative thereof.

In certain embodiments, the polymer of Formula (II') is of the formula:

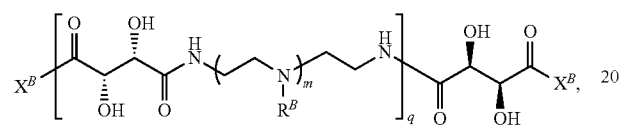

or a salt, solvate, hydrate, polymorph, co-crystal, tautomer, stereoisomer, or isotopically labeled derivative thereof.

In certain embodiments, the polymer of Formula (II') is of the formula:

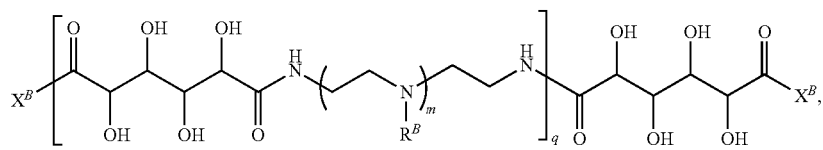

or a salt, solvate, hydrate, polymorph, co-crystal, tautomer, stereoisomer, or isotopically labeled derivative thereof.

In certain embodiments, the polymer of Formula (II') is of the formula:

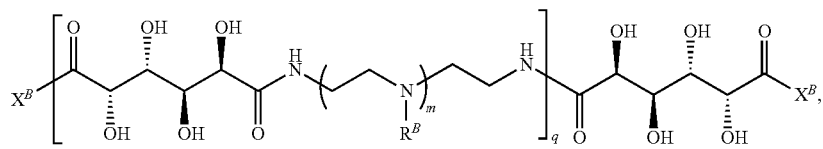

or a salt, solvate, hydrate, polymorph, co-crystal, tautomer, stereoisomer, or isotopically labeled derivative thereof.

In certain embodiments, the polymer of Formula (II') is of the formula:

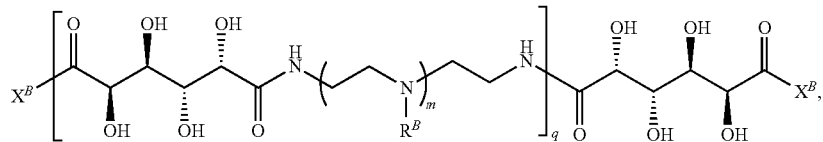

or a salt, solvate, hydrate, polymorph, co-crystal, tautomer, stereoisomer, or isotopically labeled derivative thereof.

In certain embodiments, the polymer of Formula (II') is of the formula:

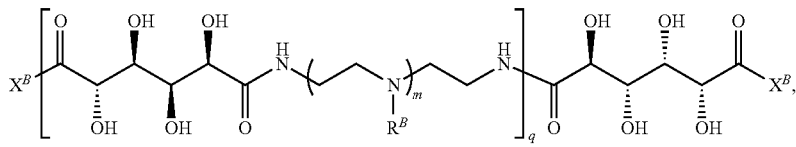

or a salt, solvate, hydrate, polymorph, co-crystal, tautomer, stereoisomer, or isotopically labeled derivative thereof.

In certain embodiments, the polymer of Formula (II') is of the formula:

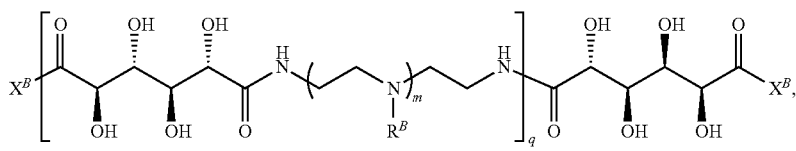

or a salt, solvate, hydrate, polymorph, co-crystal, tautomer, stereoisomer, or isotopically labeled derivative thereof.

In certain embodiments, the polymer of Formula (II") is of the formula:

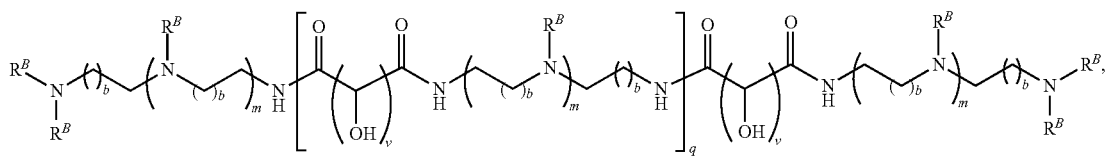

or a salt, solvate, hydrate, polymorph, co-crystal, tautomer, stereoisomer, or isotopically labeled derivative thereof.

In certain embodiments, the polymer of Formula (II") is of the formula:

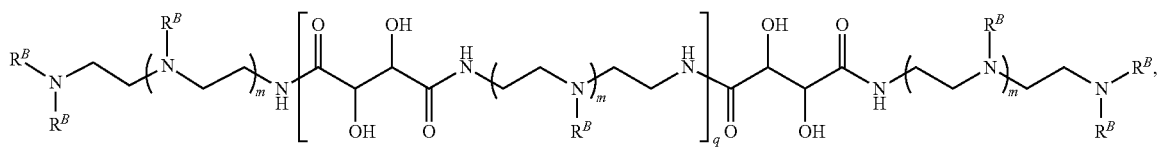

or a salt, solvate, hydrate, polymorph, co-crystal, tautomer, stereoisomer, or isotopically labeled derivative thereof.

In certain embodiments, the polymer of Formula (II") is of the formula:

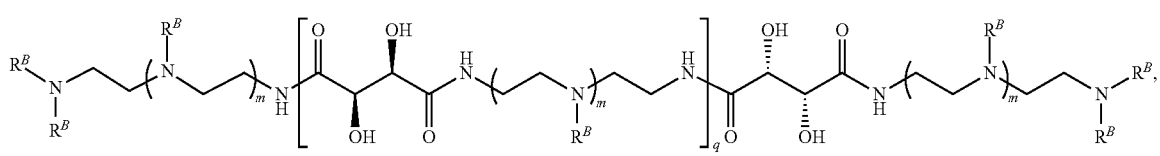

or a salt, solvate, hydrate, polymorph, co-crystal, tautomer, stereoisomer, or isotopically labeled derivative thereof.

In certain embodiments, the polymer of Formula (II″) is of the formula:

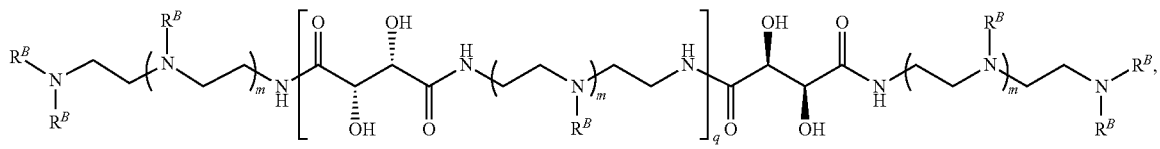

or a salt, solvate, hydrate, polymorph, co-crystal, tautomer, stereoisomer, or isotopically labeled derivative thereof.

In certain embodiments, the polymer of Formula (II″) is of the formula:

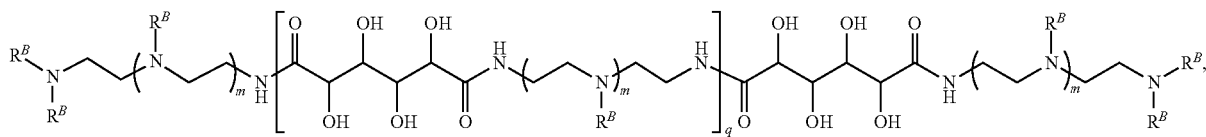

or a salt, solvate, hydrate, polymorph, co-crystal, tautomer, stereoisomer, or isotopically labeled derivative thereof.

In certain embodiments, the polymer of Formula (II″) is of the formula:

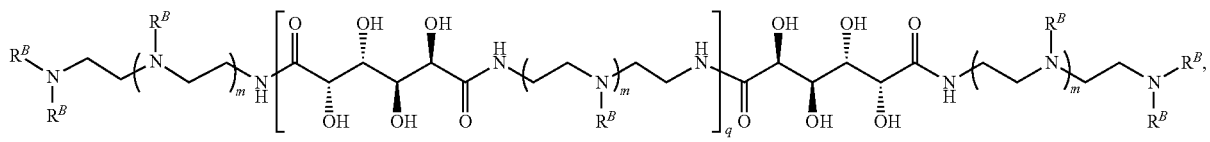

or a salt, solvate, hydrate, polymorph, co-crystal, tautomer, stereoisomer, or isotopically labeled derivative thereof.

In certain embodiments, the polymer of Formula (II″) is of the formula:

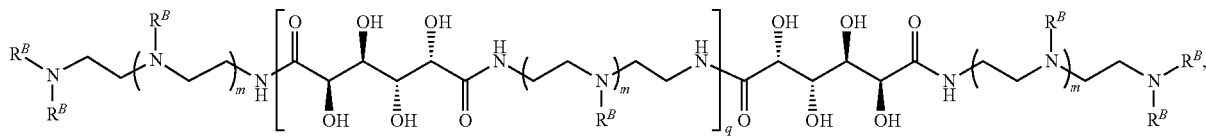

or a salt, solvate, hydrate, polymorph, co-crystal, tautomer, stereoisomer, or isotopically labeled derivative thereof.

In certain embodiments, the polymer of Formula (II″) is of the formula:

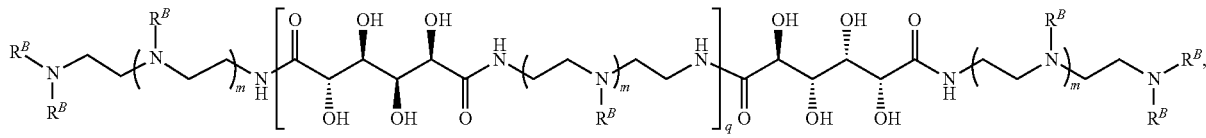

or a salt, solvate, hydrate, polymorph, co-crystal, tautomer, stereoisomer, or isotopically labeled derivative thereof.

In certain embodiments, the polymer of Formula (II″) is of the formula:

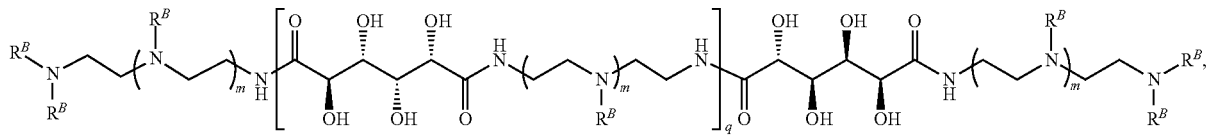

or a salt, solvate, hydrate, polymorph, co-crystal, tautomer, stereoisomer, or isotopically labeled derivative thereof.

In another aspect, the present disclosure provides polymers of Formula (III):

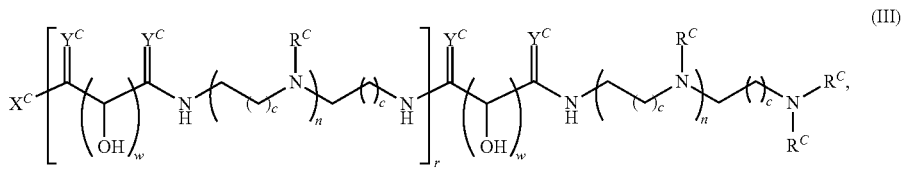

(III)

and salts, solvates, hydrates, polymorphs, co-crystals, tautomers, stereoisomers, and isotopically labeled derivatives thereof, wherein:

$X^C$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{XC}$, —$N(R^{XC})_2$, —$SR^{XC}$, —CN, —SCN, —$C(=NR^{XC})R^{XC}$, —$C(=NR^{XC})OR^{XC}$, —$C(=NR^{XC})N(R^{XC})_2$, —$C(=O)R^{XC}$, —$C(=O)OR^{XC}$, or —$C(=O)N(R^{XC})_2$, —$NO_2$, —$NR^{XC}C(=O)R^{XC}$, —$NR^{XC}C(=O)OR^{XC}$, —$NR^{XC}C(=O)N(R^{XC})_2$, —$OC(=O)R^{XC}$, —$OC(=O)OR^{XC}$, or —$OC(=O)N(R^{XC})_2$, wherein each instance of $R^{XC}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{XC}$ are joined to form a substituted or unsubstituted heterocyclic or substituted or unsubstituted heteroaryl ring;

each instance of $Y^C$ is independently =O, =S, or =$NR^{YC}$, wherein each instance of $R^{YC}$ is independently hydrogen, substituted or unsubstituted $C_{1-6}$ alkyl, or a nitrogen protecting group;

each instance of $R^C$ is independently hydrogen or a moiety of the formula:

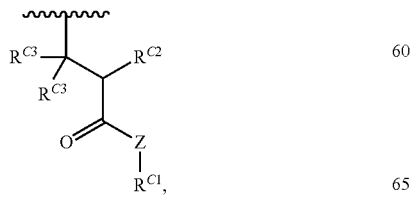

wherein at least one instance of $R^C$ is of the formula:

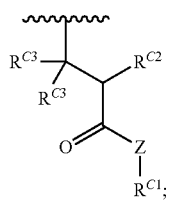

each instance of Z is independently —O— or —$NR^{C4}$—; each instance of $R^{C1}$ is independently hydrogen, substituted or unsubstituted alkyl, or substituted or unsubstituted alkenyl; each instance of $R^{C2}$ is independently hydrogen or substituted or unsubstituted alkyl; each instance of $R^{C3}$ is independently hydrogen or substituted or unsubstituted alkyl; and each instance of $R^{C4}$ is independently hydrogen, substituted or unsubstituted $C_{1-6}$ alkyl, or a nitrogen protecting group;

each instance of c is 1, 2, 3, 4, or 5;
each instance of n is 0, 1, 2, 3, 4, 5, or 6;
each instance of w is 1, 2, 3, 4, 5, 6, 7, 8, 9, or 10; and
r is an integer between 1 and 1000, inclusive.

In another aspect, the present disclosure provides polymers of Formula (III'):

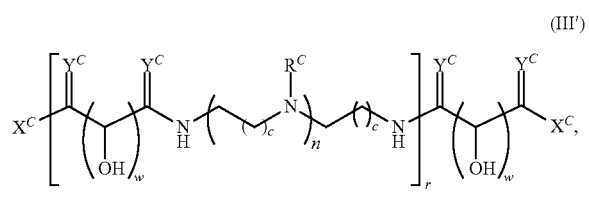

and salts, solvates, hydrates, polymorphs, co-crystals, tautomers, stereoisomers, and isotopically labeled derivatives thereof, wherein:

each instance of $X^C$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{XC}$, —$N(R^{XC})_2$, —$SR^{XC}$, —CN, —SCN, —C(=$NR^{XC}$)$R^{XC}$, —C(=$NR^{XC}$)$OR^{XC}$, —C(=$NR^{XC}$)N($R^{XC}$)$_2$, —C(=O)$R^{XC}$, —C(=O)$OR^{XC}$, or —C(=O)N($R^{XC}$)$_2$, —$NO_2$, —$NR^{XC}$C(=O)$R^{XC}$, —$NR^{XC}$C(=O)$OR^{XC}$, —$NR^{XC}$C(=O)N($R^{XC}$)$_2$, —OC(=O)$R^{XC}$, —OC(=O)$OR^{XC}$, or —OC(=O)N($R^{XC}$)$_2$, wherein each instance of $R^{XC}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{XC}$ are joined to form a substituted or unsubstituted heterocyclic or substituted or unsubstituted heteroaryl ring;

each instance of $Y^C$ is independently =O, =S, or =$NR^{YC}$, wherein each instance of $R^{YC}$ is independently hydrogen, substituted or unsubstituted $C_{1-6}$ alkyl, or a nitrogen protecting group;

each instance of $R^C$ is independently hydrogen or a moiety of the formula:

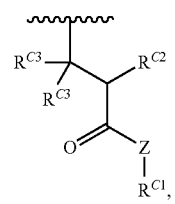

wherein: at least one instance of $R^C$ is of the formula:

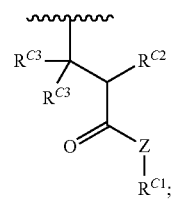

each instance of Z is independently —O— or —$NR^{C4}$—; each instance of $R^{C1}$ is independently hydrogen, substituted or unsubstituted alkyl, or substituted or unsubstituted alkenyl; each instance of $R^{C2}$ is independently hydrogen or substituted or unsubstituted alkyl; each instance of $R^{C3}$ is independently hydrogen or substituted or unsubstituted alkyl; and each instance of $R^{C4}$ is independently hydrogen, substituted or unsubstituted $C_{1-6}$ alkyl, or a nitrogen protecting group;

each instance of c is 1, 2, 3, 4, or 5;
each instance of n is 0, 1, 2, 3, 4, 5, or 6;
each instance of w is 1, 2, 3, 4, 5, 6, 7, 8, 9, or 10; and
r is an integer between 1 and 1000, inclusive.

In another aspect, the present disclosure provides polymers of Formula (III"):

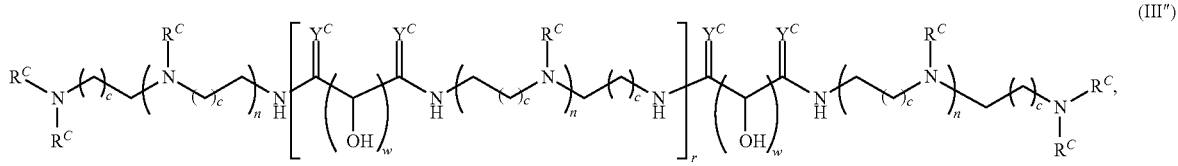

and salts, solvates, hydrates, polymorphs, co-crystals, tautomers, stereoisomers, and isotopically labeled derivatives thereof, wherein:

each instance of $Y^C$ is independently =O, =S, or =$NR^{YC}$, wherein each instance of $R^{YC}$ is independently hydrogen, substituted or unsubstituted $C_{1-6}$ alkyl, or a nitrogen protecting group;

each instance of $R^C$ is independently hydrogen or a moiety of the formula:

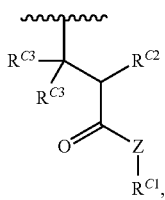

wherein: at least one instance of $R^C$ is of the formula:

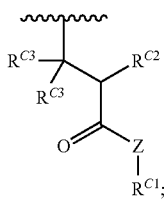

each instance of Z is independently —O— or —$NR^{C4}$—; each instance of $R^{C1}$ is independently hydrogen, substituted or unsubstituted alkyl, or substituted or unsubstituted alkenyl; each instance of $R^{C2}$ is independently hydrogen or substituted or unsubstituted alkyl; each instance of $R^{C3}$ is independently hydrogen or substituted or unsubstituted alkyl; and each instance of $R^{C4}$ is independently hydrogen, substituted or unsubstituted $C_{1-6}$ alkyl, or a nitrogen protecting group;

each instance of c is 1, 2, 3, 4, or 5;
each instance of n is 0, 1, 2, 3, 4, 5, or 6;
each instance of w is 1, 2, 3, 4, 5, 6, 7, 8, 9, or 10; and
r is an integer between 1 and 1000, inclusive.

Formula (III) includes end group $X^C$. In certain embodiments, $X^C$ is substituted alkyl. In certain embodiments, $X^C$ is unsubstituted alkyl. In certain embodiments, $X^C$ is unsubstituted $C_{1-6}$ alkyl. In certain embodiments, $X^C$ is substituted $C_{1-6}$ alkyl. In certain embodiments, $X^C$ is $C_{1-6}$ alkyl substituted with at least one halogen. In certain embodiments, $X^C$ is —$CH_3$. In certain embodiments, $X^C$ is substituted methyl. In certain embodiments, $X^C$ is —$CH_2F$. In certain embodiments, $X^C$ is —$CHF_2$. In certain embodiments, $X^C$ is —$CF_3$. In certain embodiments, $X^C$ is ethyl. In certain embodiments, $X^C$ is propyl. In certain embodiments, $X^C$ is butyl. In certain embodiments, $X^C$ is pentyl. In certain embodiments, $X^C$ is hexyl. In certain embodiments, $X^C$ is halogen or substituted or unsubstituted $C_{1-6}$ alkyl. In certain embodiments, $X^C$ is substituted alkenyl. In certain embodiments, $X^C$ is unsubstituted alkenyl. In certain embodiments, $X^C$ is substituted alkynyl. In certain embodiments, $X^C$ is unsubstituted alkynyl. In certain embodiments, $X^C$ is substituted carbocyclyl. In certain embodiments, $X^C$ is unsubstituted carbocyclyl. In certain embodiments, $X^C$ is saturated carbocyclyl. In certain embodiments, $X^C$ is unsaturated carbocyclyl. In certain embodiments, $X^C$ is monocyclic carbocyclyl. In certain embodiments, $X^C$ is 3- to 7-membered, monocyclic carbocyclyl. In certain embodiments, $X^C$ is substituted heterocyclyl. In certain embodiments, $X^C$ is unsubstituted heterocyclyl. In certain embodiments, $X^C$ is saturated heterocyclyl. In certain embodiments, $X^C$ is unsaturated heterocyclyl. In certain embodiments, $X^C$ is heterocyclyl, wherein one, two, or three atoms of the heterocyclic ring system are independently selected from the group consisting of nitrogen, oxygen, and sulfur. In certain embodiments, $X^C$ is monocyclic heterocyclyl. In certain embodiments, $X^C$ is 3- to 7-membered, monocyclic heterocyclyl. In certain embodiments, $X^C$ is substituted aryl. In certain embodiments, $X^C$ is unsubstituted aryl. In certain embodiments, $X^C$ is 6- to 10-membered aryl. In certain embodiments, $X^C$ is substituted phenyl. In certain embodiments, $X^C$ is unsubstituted phenyl. In certain embodiments, $X^C$ is substituted heteroaryl. In certain embodiments, $X^C$ is unsubstituted heteroaryl. In certain embodiments, $X^C$ is heteroaryl, wherein one, two, three, or four atoms of the heteroaryl ring system are independently selected from the group consisting of nitrogen, oxygen, and sulfur. In certain embodiments, $X^C$ is monocyclic heteroaryl. In certain embodiments, $X^C$ is 5-membered, monocyclic heteroaryl. In certain embodiments, $X^C$ is 6-membered, monocyclic heteroaryl. In certain embodiments, $X^C$ is bicyclic heteroaryl, wherein the point of attachment may be on any atom of the bicyclic heteroaryl ring system, as valency permits. In certain embodiments, $X^C$ is 9- or 10-membered, bicyclic heteroaryl. In certain embodiments, $X^C$ is —$OR^{XC}$. In certain embodiments, $X^C$ is —OH. In certain embodiments, $X^C$ is —$OR^{XC}$, wherein $R^{XC}$ is substituted or unsubstituted $C_{1-6}$ alkyl. In certain embodiments, $X^C$ is —OMe. In certain embodiments, $X^C$ is —OEt, —OPr, —OBu, or —OBn. In certain embodiments, $X^C$ is —OPh. In certain embodiments, $X^C$ is —$SR^{XC}$. In certain embodiments, $X^C$ is —SH. In certain embodiments, $X^C$ is —SMe. In certain embodiments, $X^C$ is —$N(R^{XC})_2$. In certain embodiments, $X^C$ is —$NH_2$. In certain embodiments, $X^C$ is —NHMe. In certain embodiments, $X^C$ is —$NMe_2$. In certain embodiments, $X^C$ is —$OR^{XC}$ or —$N(R^{XC})_2$. In certain embodiments, $X^C$ is —$C(=NR^{XC})R^{XC}$, —$C(=NR^{XC})OR^{XC}$, or —$C(=NR^{XC})N(R^{XC})_2$. In certain embodiments, $X^C$ is —$C(=O)R^{XC}$ or —$C(=O)OR^{XC}$. In certain embodiments, $X^C$ is —$C(=O)N(R^{XC})_2$. In certain embodiments, $X^C$ is —$C(=O)NMe_2$, —$C(=O)NHMe$, or —$C(=O)NH_2$.

Formula (III') includes end groups $X^C$. In certain embodiments, all instances of $X^C$ are the same. In certain embodiments, two instances of $X^C$ are not the same. In certain embodiments, at least one instance of $X^C$ is substituted alkyl. In certain embodiments, at least one instance of X is unsubstituted alkyl. In certain embodiments, at least one instance of $X^C$ is unsubstituted $C_{1-6}$ alkyl. In certain embodiments, at least one instance of $X^C$ is substituted $C_{1-6}$ alkyl. In certain embodiments, at least one instance of X is $C_{1-6}$ alkyl substituted with at least one halogen. In certain embodiments, at least one instance of $X^C$ is —$CH_3$. In certain embodiments, at least one instance of $X^C$ is substituted methyl. In certain embodiments, at least one instance of X is —$CH_2F$. In certain embodiments, at least one instance of $X^C$ is —$CHF_2$. In certain embodiments, at least one instance of $X^C$ is —$CF_3$. In certain embodiments, at least one instance of $X^C$ is ethyl. In certain embodiments, at least one instance of $X^C$ is propyl. In certain embodiments, at least one instance of $X^C$ is butyl. In certain embodiments, at least one instance of $X^C$ is pentyl. In certain embodiments, at least one instance of $X^C$ is hexyl. In certain embodiments, at least one instance of $X^C$ is halogen or substituted or unsubstituted $C_{1-6}$ alkyl. In certain embodiments, at least one instance of $X^C$ is substituted alkenyl. In certain embodiments, at least one instance of $X^C$ is unsubstituted alkenyl. In certain embodiments, at least one instance of $X^C$ is substituted alkynyl. In certain embodiments, at least one instance of $X^C$ is unsubstituted alkynyl. In certain embodiments, at least one instance of $X^C$ is substituted carbocyclyl. In certain embodiments, at least one instance of $X^C$ is unsubstituted carbocyclyl. In certain embodiments, at least one instance of $X^C$ is saturated carbocyclyl. In certain embodiments, at least one instance of $X^C$ is unsaturated carbocyclyl. In certain embodiments, at least one instance of $X^C$ is monocyclic carbocyclyl. In certain embodiments, at least one instance of $X^C$ is 3- to 7-membered, monocyclic carbocyclyl. In certain embodiments, at least one instance of $X^C$ is substituted heterocyclyl. In certain embodiments, at least one instance of $X^C$ is unsubstituted heterocyclyl. In certain embodiments, at least one instance of $X^C$ is saturated heterocyclyl. In certain embodiments, at least one instance of $X^C$ is unsaturated heterocyclyl. In certain embodiments, at least one instance of $X^C$ is heterocyclyl, wherein one, two, or three atoms of the heterocyclic ring system are independently selected from the group consisting of nitrogen, oxygen, and sulfur. In certain embodiments, at least one instance of $X^C$ is monocyclic heterocyclyl. In certain embodiments, at least one instance of $X^C$ is 3- to 7-membered, monocyclic heterocyclyl. In certain embodiments, at least one instance of $X^C$ is substituted aryl. In certain embodiments, at least one instance of $X^C$ is unsubstituted aryl. In certain embodiments, at least one instance of $X^C$ is 6- to 10-membered aryl. In certain embodiments, at least one instance of $X^C$ is substituted phenyl. In certain embodiments, at least one instance of $X^C$ is unsubstituted phenyl. In certain embodiments, at least one instance of $X^C$ is substituted heteroaryl. In certain embodiments, at least one instance of $X^C$ is unsubstituted heteroaryl. In certain embodiments, at least one instance of $X^C$ is heteroaryl, wherein one, two, three, or four atoms of the heteroaryl ring system are independently selected from the group consisting of nitrogen, oxygen, and sulfur. In certain embodiments, at least one instance of $X^C$ is monocyclic heteroaryl. In certain embodiments, at least one instance of $X^C$ is 5-membered, monocyclic heteroaryl. In certain embodiments, at least one instance of X is 6-membered, monocyclic heteroaryl. In certain embodiments, at least one instance of $X^C$ is bicyclic heteroaryl, wherein the point of attachment may be on any atom of the bicyclic heteroaryl ring system, as valency permits. In certain embodiments, at least one instance of $X^C$ is 9- or 10-membered, bicyclic heteroaryl. In certain embodiments, at least one instance of $X^C$ is —$OR^{XC}$. In certain embodiments, at least one instance of $X^C$ is —OH. In certain embodiments, at least one instance of $X^C$ is —$OR^{XC}$, wherein $R^{XC}$ is substituted or unsubstituted $C_{1-6}$ alkyl. In certain embodiments, at least one instance of $X^C$ is —OMe. In certain embodiments, at least one instance of X is —OEt, —OPr, —OBu, or —OBn. In certain embodiments, at least one instance of $X^C$ is —OPh. In certain embodiments, at least one instance of $X^C$ is —$SR^{XC}$. In certain embodiments, at least one instance of $X^C$ is —SH. In certain embodiments, at least one instance of $X^C$ is —SMe. In certain embodiments, at least one instance of $X^C$ is —$N(R^{XC})_2$. In certain embodiments, at least one instance of $X^C$ is —$NH_2$. In certain embodiments, at least one instance of $X^C$ is —NHMe. In certain embodiments, at least one instance of $X^C$ is —$NMe_2$. In certain embodiments, at least one instance of $X^C$ is —$OR^{XC}$ or —$N(R^{XC})_2$. In certain embodiments, at least one instance of $X^C$ is —$C(=NR^{XC})R^{XC}$, —$C(=NR^{XC})OR^{XC}$, or —$C(=NR^{XC})N(R^{XC})_2$. In certain embodiments, at least one instance of $X^C$ is —$C(=O)R^{XC}$ or —$C(=O)OR^{XC}$. In certain embodiments, at least one instance of $X^C$ is —$C(=O)N(R^{XC})_2$. In certain embodiments, at least one instance of $X^C$ is —$C(=O)NMe_2$, —$C(=O)NHMe$, or —$C(=O)NH_2$.

For any of the $X^C$ that include an $R^{XC}$ moiety described herein, any of the following embodiments for $R^{XC}$ may be applicable. In certain embodiments, $R^{XC}$ is H. In certain embodiments, $R^{XC}$ is substituted acyl. In certain embodiments, $R^{XC}$ is unsubstituted acyl. In certain embodiments, $R^{XC}$ is acetyl. In certain embodiments, $R^{XC}$ is substituted alkyl. In certain embodiments, $R^{XC}$ is unsubstituted alkyl. In certain embodiments, $R^{XC}$ is unsubstituted $C_{1-6}$ alkyl. In certain embodiments, $R^{XC}$ is methyl. In certain embodiments, $R^{XC}$ is ethyl. In certain embodiments, $R^{XC}$ is propyl. In certain embodiments, $R^{XC}$ is butyl. In certain embodiments, $R^{XC}$ is pentyl. In certain embodiments, $R^{XC}$ is hexyl. In certain embodiments, $R^{XC}$ is substituted alkenyl. In certain embodiments, $R^{XC}$ is unsubstituted alkenyl. In certain embodiments, $R^{XC}$ is substituted alkynyl. In certain embodiments, $R^{XC}$ is unsubstituted alkynyl. In certain embodiments, $R^{XC}$ is substituted or unsubstituted carbocyclyl. In certain embodiments, $R^{XC}$ is saturated carbocyclyl. In certain embodiments, $R^{XC}$ is unsaturated carbocyclyl. In certain embodiments, $R^{XC}$ is 3- to 7-membered, monocyclic carbocyclyl. In certain embodiments, $R^{XC}$ is substituted or unsubstituted heterocyclyl. In certain embodiments, $R^{XC}$ is saturated heterocyclyl. In certain embodiments, $R^{XC}$ is unsaturated heterocyclyl. In certain embodiments, $R^{XC}$ is heterocyclyl, wherein one, two, or three atoms of the heterocyclic ring system are independently selected from the group consisting of nitrogen, oxygen, and sulfur. In certain embodiments, $R^{XC}$ is 3- to 7-membered, monocyclic heterocyclyl. In certain embodiments, $R^{XC}$ is substituted or unsubstituted aryl. In certain embodiments, $R^{XC}$ is 6- to 10-membered aryl. In certain embodiments, $R^{XC}$ is monocyclic aryl. In certain embodiments, $R^{XC}$ is substituted phenyl. In certain embodiments, $R^{XC}$ is unsubstituted phenyl. In certain embodiments, $R^{XC}$ is bicyclic aryl. In certain embodiments, $R^{XC}$ is substituted or unsubstituted heteroaryl. In certain embodiments, $R^{XC}$ is heteroaryl, wherein one, two, three, or four atoms of the heteroaryl ring system are independently selected from the group consisting of nitrogen, oxygen, and sulfur. In certain embodiments, $R^{XC}$ is monocyclic heteroaryl. In certain embodiments, $R^{XC}$ is 5- or 6-membered, monocyclic heteroaryl. In certain embodiments, $R^{XC}$ is bicyclic heteroaryl, wherein the point of attachment may be on any atom of the bicyclic heteroaryl ring system, as valency permits. In certain embodiments, $R^{XC}$ is a nitrogen protecting group when attached to a nitrogen atom. In certain embodiments, $R^{XC}$ is Bn, Boc, Cbz, Fmoc, trifluoroacetyl, triphenylmethyl, acetyl, or Ts when attached to a nitrogen atom. In certain embodiments, $R^{XC}$ is an oxygen protecting group when attached to an oxygen atom. In certain embodiments, $R^{XC}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{XC}$ is a sulfur protecting group when attached to a sulfur atom. In certain embodiments, $R^{XC}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{XC}$ are joined to form a substituted or unsubstituted heterocyclic ring. In certain embodiments, two instances of $R^{XC}$ are joined to form a saturated or unsaturated heterocyclic ring. In certain embodiments, two instances of $R^{XC}$ are joined to form a heterocyclic ring, wherein one, two, or three atoms of the heterocyclic ring system are independently selected from the group consisting of nitrogen, oxygen, and sulfur. In certain embodiments, two instances of $R^{XC}$ are joined to form a 3- to 7-membered, monocyclic heterocyclic ring. In certain embodiments, two instances of $R^{XC}$ are joined to form a substituted or unsubstituted heteroaryl ring. In certain embodiments, two instances of $R^{XC}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

Any one of Formulae (III), (III'), and (III") includes $Y^C$ moieties. In certain embodiments, all instances of $Y^C$ are the same. In certain embodiments, at least two instances of $Y^C$ are different from each other. In certain embodiments, at least one instance of $Y^C$ is =O. In certain embodiments, each instance of $Y^C$ is =O. In certain embodiments, at least one instance of $Y^C$ is =S. In certain embodiments, at least one instance of $Y^C$ is =$NR^{YC}$. In certain embodiments, at least one instance of $Y^C$ is =NH. In certain embodiments, at least one instance of $Y^C$ is =N(substituted or unsubstituted $C_{1-6}$ alkyl, e.g., methyl).

In certain embodiments, all instances of $R^{YC}$ are the same. In certain embodiments, at least two instances of $R^{YC}$ are different from each other. In certain embodiments, at least one instance of $R^{YC}$ is H. In certain embodiments, at least one instance of $R^{YC}$ is substituted or unsubstituted $C_{1-6}$ alkyl. In certain embodiments, at least one instance of $R^{YC}$ is methyl. In certain embodiments, at least one instance of $R^{YC}$ is ethyl, propyl, butyl, pentyl, or hexyl. In certain embodiments, at least one instance of $R^{YC}$ is a nitrogen protecting group (e.g., Bn, Boc, Cbz, Fmoc, trifluoroacetyl, triphenylmethyl, acetyl, or Ts).

Any one of Formulae (III), (III'), and (III") includes substituents $R^C$. In certain embodiments, at least about 10%, at least about 20%, at least about 30%, or at least about 40% of the total instances of $R^C$ are the same. In certain embodiments, at least about 50% of the total instances of $R^C$ are the same. In certain embodiments, at least about 60% of the total instances of $R^C$ are the same. In certain embodiments, at least about 70% of the total instances of $R^C$ are the same. In certain embodiments, at least about 80% of the total instances of $R^C$ are the same. In certain embodiments, at least about 90% of the total instances of $R^C$ are the same. In certain embodiments, at least about 95% of the total instances of $R^C$ are the same. In certain embodiments, all instances of $R^C$ are the same. In certain embodiments, at least two instances of $R^C$ are different from each other. In certain embodiments, at least one instance of $R^C$ is H. In certain embodiments, at least one instance of $R^C$ is of the formula:

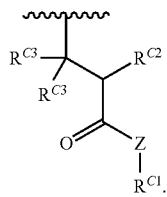

In certain embodiments, at least about 10%, at least about 20%, at least about 30%, at least about 40%, at least about 50%, at least about 60%, at least about 70%, at least about 80%, at least about 90%, or at least about 95% of the total instances of $R^C$ are independently of the formula:

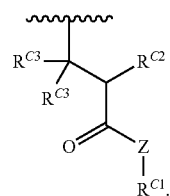

In certain embodiments, all instances of $R^C$ are independently of the formula:

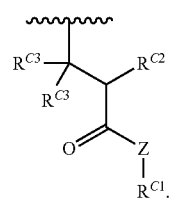

In certain embodiments, at least one instance of $R^C$ is of the formula:

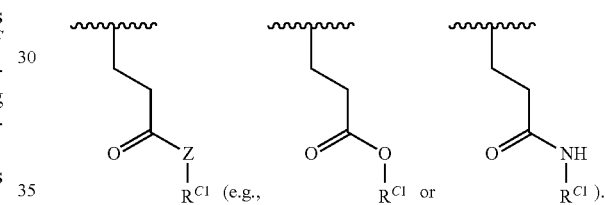

In certain embodiments, at least about 10%, at least about 20%, at least about 30%, at least about 40%, at least about 50%, at least about 60%, at least about 70%, at least about 80%, at least about 90%, or at least about 95% of the total instances of $R^C$ are independently of the formula:

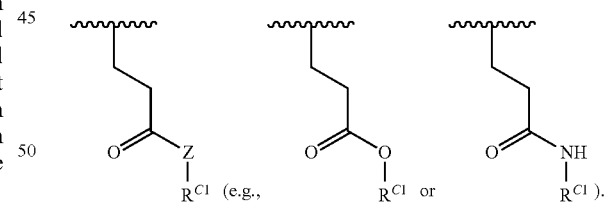

In certain embodiments, all instances of $R^C$ are independently of the formula:

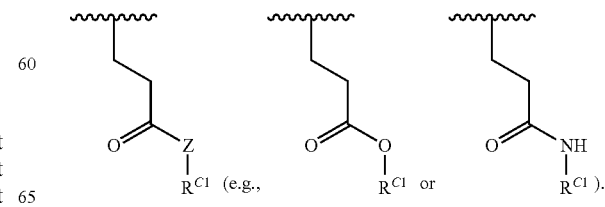

In certain embodiments, at least one instance of $R^C$ is of the formula:

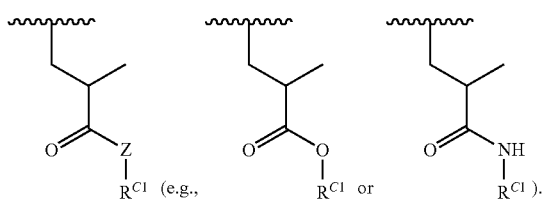

$R^{C1}$ (e.g., [left]), $R^{C1}$ (middle), or $R^{C1}$ (right).

In certain embodiments, at least about 10%, at least about 20%, at least about 30%, at least about 40%, at least about 50%, at least about 60%, at least about 70%, at least about 80%, at least about 90%, or at least about 95% of the total instances of $R^C$ are independently of the formula:

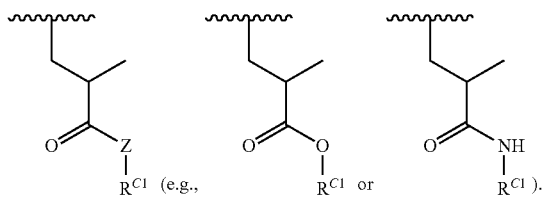

$R^{C1}$ (e.g., [left]), $R^{C1}$ (middle), or $R^{C1}$ (right).

In certain embodiments, all instances of $R^C$ are independently of the formula:

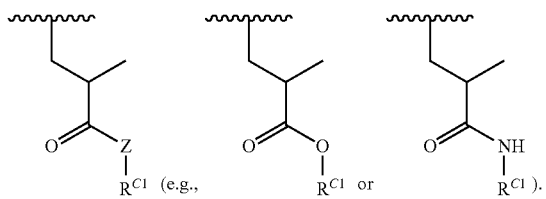

$R^{C1}$ (e.g., [left]), $R^{C1}$ (middle), or $R^{C1}$ (right).

In certain embodiments, each instance of Z is —O—. In certain embodiments, each instance of Z is independently —$NR^{C4}$—. In certain embodiments, each instance of Z is —NH—. In certain embodiments, each instance of Z is independently —$NR^{C4}$—, wherein each instance of $R^{C4}$ is independently substituted or unsubstituted $C_{1-6}$ alkyl. In certain embodiments, each instance of Z is —NMe-.

Any one of Formulae (III), (III'), and (III") includes one or more substituents $R^C$. In certain embodiments, all instances of $R^{C1}$ are the same. In certain embodiments, all instances of $R^{C1}$ that are not hydrogen are the same. In certain embodiments, at least two instances of $R^{C1}$ are different from each other. In certain embodiments, at least one instance of $R^{C1}$ is H. In certain embodiments, each instance of $R^{C1}$ is H. In certain embodiments, at least one instance of $R^{C1}$ is substituted alkyl. In certain embodiments, at least one instance of $R^{C1}$ is unsubstituted alkyl. In certain embodiments, each instance of $R^{C1}$ is independently substituted or unsubstituted $C_{1-30}$ alkyl. In certain embodiments, at least one instance of $R^{C1}$ is substituted $C_{1-30}$ alkyl. In certain embodiments, at least one instance of $R^{C1}$ is a moiety shown in Table 2. In certain embodiments, each instance of $R^{C1}$ is independently a moiety shown in Table 2. In certain embodiments, each instance of $R^{C1}$ is a moiety shown in Table 2. In certain embodiments, at least one instance of $R^{C1}$ is $C_{1-30}$ alkyl substituted with one or more halogen. In certain embodiments, at least one instance of $R^{C1}$ is $C_{1-30}$ alkyl substituted with one or more fluorine. In certain embodiments, at least one instance of $R^{C1}$ is $C_{1-30}$ perfluoroalkyl. In certain embodiments, at least one instance of $R^{C1}$ is unsubstituted $C_{1-30}$ alkyl. In certain embodiments, at least one instance of $R^{C1}$ is a moiety shown in Table 1. In certain embodiments, each instance of $R^{C1}$ is independently a moiety shown in Table 1. In certain embodiments, each instance of $R^{C1}$ is a moiety shown in Table 1. In certain embodiments, at least one instance of $R^{C1}$ is unsubstituted and unbranched $C_{1-30}$ alkyl. In certain embodiments, each instance of $R^{C1}$ is independently substituted or unsubstituted $C_{4-22}$ alkyl (e.g., substituted or unsubstituted $C_{4-18}$ alkyl). In certain embodiments, at least one instance of $R^{C1}$ is substituted $C_{4-18}$ alkyl. In certain embodiments, at least one instance of $R^{C1}$ is $C_{4-18}$ alkyl substituted with one or more halogen. In certain embodiments, at least one instance of $R^{C1}$ is $C_{4-18}$ alkyl substituted with one or more fluorine. In certain embodiments, at least one instance of $R^{C1}$ is $C_{4-18}$ perfluoroalkyl. In certain embodiments, at least one instance of $R^{C1}$ is unsubstituted $C_{4-18}$ alkyl. In certain embodiments, at least one instance of $R^{C1}$ is unsubstituted and unbranched $C_{4-18}$ alkyl. In certain embodiments, each instance of $R^{C1}$ is independently substituted or unsubstituted $C_{6-14}$ alkyl. In certain embodiments, at least one instance of $R^{C1}$ is substituted $C_{6-14}$ alkyl. In certain embodiments, at least one instance of $R^{C1}$ is $C_{6-14}$ alkyl substituted with one or more halogen. In certain embodiments, at least one instance of $R^{C1}$ is $C_{6-14}$ alkyl substituted with one or more fluorine. In certain embodiments, at least one instance of $R^{C1}$ is $C_{6-14}$ perfluoroalkyl. In certain embodiments, at least one instance of $R^{C1}$ is unsubstituted $C_{6-14}$ alkyl. In certain embodiments, at least one instance of $R^{C1}$ is unsubstituted and unbranched $C_{6-14}$ alkyl. In certain embodiments, each instance of $R^{C1}$ is independently n-$C_6H_{13}$, n-$C_8H_{17}$, n-$C_{10}H_{21}$, n-$C_{12}H_{25}$, n-$C_{14}H_{29}$, or n-$C_{16}H_{33}$. In certain embodiments, each instance of $R^{C1}$ is n-$C_6H_{13}$, n-$C_8H_{17}$, n-$C_{10}H_{21}$, n-$C_{12}H_{25}$, n-$C_{14}H_{29}$, or n-$C_{16}H_{33}$.

In certain embodiments, at least one instance of $R^{C1}$ is substituted alkenyl. In certain embodiments, at least one instance of $R^{C1}$ is unsubstituted alkenyl. In certain embodiments, each instance of $R^{C1}$ is independently substituted or unsubstituted $C_{2-30}$ alkenyl. In certain embodiments, at least one instance of $R^{C1}$ is substituted $C_{2-30}$ alkenyl. In certain embodiments, at least one instance of $R^{C1}$ is $C_{2-30}$ alkenyl substituted with one or more halogen. In certain embodiments, at least one instance of $R^{C1}$ is $C_{2-30}$ alkenyl substituted with one or more fluorine. In certain embodiments, at least one instance of $R^{C1}$ is $C_{2-30}$ perfluoroalkenyl. In certain embodiments, at least one instance of $R^{C1}$ is unsubstituted $C_{2-30}$ alkenyl. In certain embodiments, at least one instance of $R^{C1}$ is a moiety shown in Table 3. In certain embodiments, each instance of $R^{C1}$ is independently a moiety shown in Table 3. In certain embodiments, each instance of $R^{C1}$ is a moiety shown in Table 3. In certain embodiments, at least one instance of $R^{C1}$ is unsubstituted and unbranched $C_{2-30}$ alkenyl. In certain embodiments, each instance of $R^{C1}$ is independently substituted or unsubstituted $C_{4-18}$ alkenyl. In certain embodiments, at least one instance of $R^{C1}$ is substituted $C_{4-18}$ alkenyl. In certain embodiments, at least one instance of $R^{C1}$ is $C_{4-18}$ alkenyl substituted with one or more halogen. In certain embodiments, at least one instance of $R^{C1}$ is $C_{4-18}$ alkenyl substituted with one or more fluorine. In certain embodiments, at least one instance of $R^{C1}$ is $C_{4-18}$ perfluoroalkenyl. In certain embodiments, at least one instance of $R^{C1}$ is unsubstituted $C_{4-18}$ alkenyl. In certain embodiments, at least one instance of $R^{C1}$ is unsubstituted and unbranched $C_{4-18}$ alkenyl. In certain embodiments, each instance of $R^{C1}$ is independently substituted or unsubstituted $C_{6-14}$ alkenyl. In certain embodiments, at least one instance of $R^{C1}$ is substituted $C_{6-14}$ alkenyl. In certain embodiments, at least one instance of $R^{C1}$ is $C_{6-14}$ alkenyl substituted with one or more halogen. In certain embodiments, at least one instance of $R^{C1}$ is $C_{6-14}$ alkenyl substituted with one or more fluorine. In certain embodiments, at least one instance of $R^{C1}$ is $C_{6-14}$ perfluoroalkenyl. In certain embodiments, at least one instance of $R^{C1}$ is unsubstituted $C_{6-14}$ alkenyl. In certain embodiments, at least one instance of $R^{C1}$ is unsubstituted and unbranched $C_{6-14}$ alkenyl.

In certain embodiments, all instances of $R^{C2}$ are the same. In certain embodiments, at least two instances of $R^{C2}$ are different from each other. In certain embodiments, at least one instance of $R^{C2}$ is H. In certain embodiments, each instance of $R^{C2}$ is H. In certain embodiments, at least one instance of $R^{C2}$ is substituted alkyl. In certain embodiments, at least one instance of $R^{C2}$ is unsubstituted alkyl. In certain embodiments, at least one instance of $R^{C2}$ is unsubstituted $C_{1-6}$ alkyl. In certain embodiments, both instances of $R^{C2}$ are unsubstituted $C_{1-6}$ alkyl. In certain embodiments, at least one instance of $R^{C2}$ is substituted $C_{1-6}$ alkyl. In certain embodiments, at least one instance of $R^{C2}$ is $C_{1-6}$ alkyl substituted with at least one halogen. In certain embodiments, at least one instance of $R^{C2}$ is —$CH_3$. In certain embodiments, at least one instance of $R^{C2}$ is substituted methyl. In certain embodiments, at least one instance of $R^{C2}$ is —$CH_2F$. In certain embodiments, at least one instance of $R^{C2}$ is —$CHF_2$. In certain embodiments, at least one instance of $R^{C2}$ is —$CF_3$. In certain embodiments, at least one instance of $R^{C2}$ is ethyl. In certain embodiments, at least one instance of $R^{C2}$ is propyl. In certain embodiments, at least one instance of $R^{C2}$ is butyl. In certain embodiments, at least one instance of $R^{C2}$ is pentyl. In certain embodiments, at least one instance of $R^{C2}$ is hexyl.

In certain embodiments, all instances of $R^{C3}$ are the same. In certain embodiments, at least two instances of $R^{C3}$ are different from each other. In certain embodiments, at least one instance of $R^{C3}$ is H. In certain embodiments, each instance of $R^{C3}$ is H. In certain embodiments, at least one instance of $R^{C3}$ is substituted alkyl. In certain embodiments, at least one instance of $R^{C3}$ is unsubstituted alkyl. In certain embodiments, at least one instance of $R^{C3}$ is unsubstituted $C_{1-6}$ alkyl. In certain embodiments, both instances of $R^{C3}$ are unsubstituted $C_{1-6}$ alkyl. In certain embodiments, at least one instance of $R^{C3}$ is substituted $C_{1-6}$ alkyl. In certain embodiments, at least one instance of $R^{C3}$ is $C_{1-6}$ alkyl substituted with at least one halogen. In certain embodiments, at least one instance of $R^{C3}$ is —$CH_3$. In certain embodiments, at least one instance of $R^{C3}$ is substituted methyl. In certain embodiments, at least one instance of $R^{C3}$ is —$CH_2F$. In certain embodiments, at least one instance of $R^{C3}$ is —$CHF_2$. In certain embodiments, at least one instance of $R^{C3}$ is —$CF_3$. In certain embodiments, at least one instance of $R^{C3}$ is ethyl. In certain embodiments, at least one instance of $R^{C3}$ is propyl. In certain embodiments, at least one instance of $R^{C3}$ is butyl. In certain embodiments, at least one instance of $R^{C3}$ is pentyl. In certain embodiments, at least one instance of $R^{C3}$ is hexyl.

In certain embodiments, all instances of $R^{C2}$ and $R^{C3}$ are H.

In certain embodiments, all instances of $R^{C4}$ are the same. In certain embodiments, at least two instances of $R^{C4}$ are different from each other. In certain embodiments, at least one instance of $R^{C4}$ is H. In certain embodiments, each instance of $R^{C4}$ is H. In certain embodiments, at least one instance of $R^{C4}$ is substituted alkyl. In certain embodiments, at least one instance of $R^{C4}$ is unsubstituted alkyl. In certain embodiments, at least one instance of $R^{C4}$ is unsubstituted $C_{1-6}$ alkyl. In certain embodiments, both instances of $R^{C4}$ are unsubstituted $C_{1-6}$ alkyl. In certain embodiments, at least one instance of $R^{C4}$ is substituted $C_{1-6}$ alkyl. In certain embodiments, at least one instance of $R^{C4}$ is $C_{1-6}$ alkyl substituted with at least one halogen. In certain embodiments, at least one instance of $R^{C4}$ is —$CH_3$. In certain embodiments, at least one instance of $R^{C4}$ is substituted methyl. In certain embodiments, at least one instance of $R^{C4}$ is —$CH_2F$. In certain embodiments, at least one instance of $R^{C4}$ is —$CHF_2$. In certain embodiments, at least one instance of $R^{C4}$ is —$CF_3$. In certain embodiments, at least one instance of $R^{C4}$ is ethyl. In certain embodiments, at least one instance of $R^{C4}$ is propyl. In certain embodiments, at least one instance of $R^{C4}$ is butyl. In certain embodiments, at least one instance of $R^{C4}$ is pentyl. In certain embodiments, at least one instance of $R^{C4}$ is hexyl. In certain embodiments, at least one instance of $R^{C4}$ is a nitrogen protecting group. In certain embodiments, at least one instance of $R^{C4}$ is Bn, Boc, Cbz, Fmoc, trifluoroacetyl, triphenylmethyl, acetyl, or Ts.

In certain embodiments, each instance of c is 1. In certain embodiments, each instance of c is 2. In certain embodiments, each instance of c is 3. In certain embodiments, each instance of c is 4. In certain embodiments, each instance of c is 5.

In certain embodiments, each instance of n is 0. In certain embodiments, each instance of n is 1. In certain embodiments, each instance of n is 2. In certain embodiments, each instance of n is 3. In certain embodiments, each instance of n is 4. In certain embodiments, each instance of n is 5. In certain embodiments, each instance of n is 6.

In certain embodiments, each instance of w is 1. In certain embodiments, each instance of w is 2. In certain embodiments, each instance of w is 3. In certain embodiments, each instance of w is 4. In certain embodiments, each instance of w is 5. In certain embodiments, each instance of w is 6. In certain embodiments, each instance of w is 7. In certain embodiments, each instance of w is 8. In certain embodiments, each instance of w is 9. In certain embodiments, each instance of w is 10.

In certain embodiments, r is an integer between 1 and 1000, inclusive. In certain embodiments, r is an integer between 1 and 300, inclusive. In certain embodiments, r is an integer between 1 and 100, inclusive. In certain embodiments, r is an integer between 1 and 70, inclusive. In certain embodiments, r is an integer between 1 and 50, inclusive. In certain embodiments, r is an integer between 1 and 30, inclusive. In certain embodiments, r is an integer between 5 and 30, inclusive. In certain embodiments, r is an integer between 10 and 20, inclusive. In certain embodiments, r is an integer between 1 and 15, inclusive. In certain embodiments, r is an integer between 5 and 15, inclusive. In certain embodiments, r is 10 or 11.

In certain embodiments, the polymer of Formula (III) is of the formula:

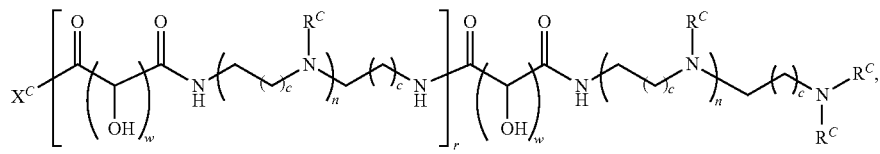

or a salt, solvate, hydrate, polymorph, co-crystal, tautomer, stereoisomer, or isotopically labeled derivative thereof.

In certain embodiments, the polymer of Formula (III) is of the formula:

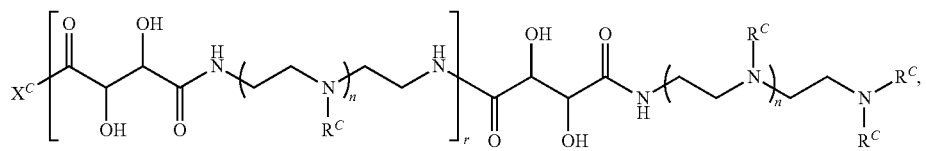

or a salt, solvate, hydrate, polymorph, co-crystal, tautomer, stereoisomer, or isotopically labeled derivative thereof.

In certain embodiments, the polymer of Formula (III) is of the formula:

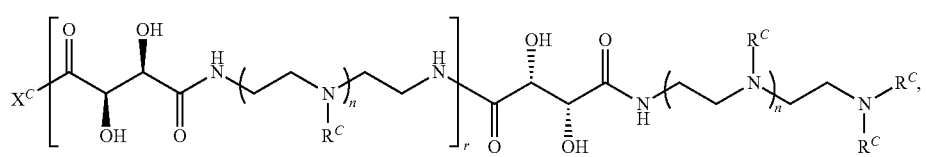

or a salt, solvate, hydrate, polymorph, co-crystal, tautomer, stereoisomer, or isotopically labeled derivative thereof.

In certain embodiments, the polymer of Formula (III) is of the formula:

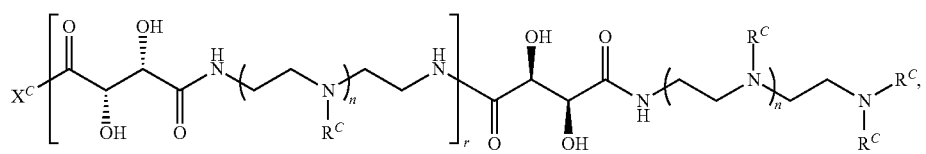

or a salt, solvate, hydrate, polymorph, co-crystal, tautomer, stereoisomer, or isotopically labeled derivative thereof.

In certain embodiments, the polymer of Formula (III) is of the formula:

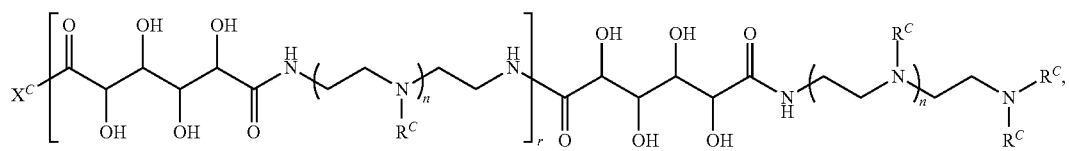

or a salt, solvate, hydrate, polymorph, co-crystal, tautomer, stereoisomer, or isotopically labeled derivative thereof.

In certain embodiments, the polymer of Formula (III) is of the formula:

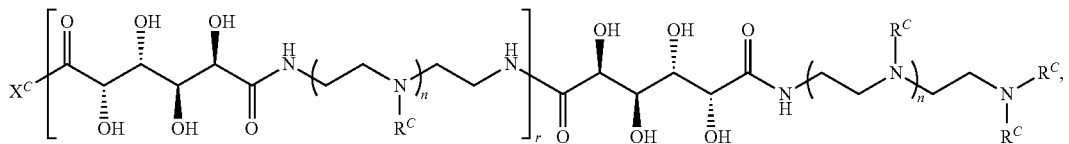

or a salt, solvate, hydrate, polymorph, co-crystal, tautomer, stereoisomer, or isotopically labeled derivative thereof.

In certain embodiments, the polymer of Formula (III) is of the formula:

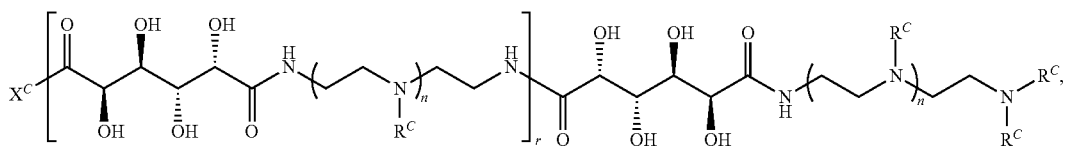

or a salt, solvate, hydrate, polymorph, co-crystal, tautomer, stereoisomer, or isotopically labeled derivative thereof.

In certain embodiments, the polymer of Formula (III) is of the formula:

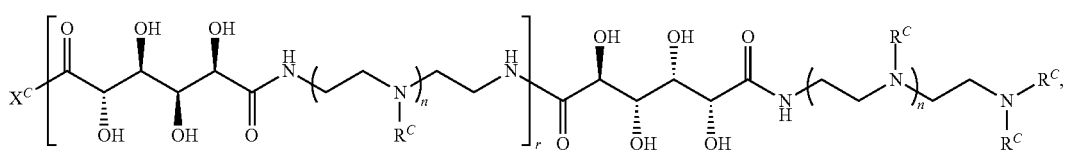

or a salt, solvate, hydrate, polymorph, co-crystal, tautomer, stereoisomer, or isotopically labeled derivative thereof.

In certain embodiments, the polymer of Formula (III) is of the formula:

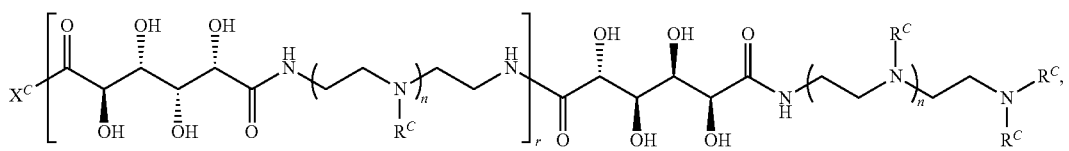

or a salt, solvate, hydrate, polymorph, co-crystal, tautomer, stereoisomer, or isotopically labeled derivative thereof.

In certain embodiments, the polymer of Formula (III') is of the formula:

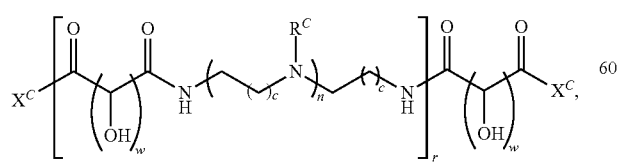

or a salt, solvate, hydrate, polymorph, co-crystal, tautomer, stereoisomer, or isotopically labeled derivative thereof.

In certain embodiments, the polymer of Formula (III') is of the formula:

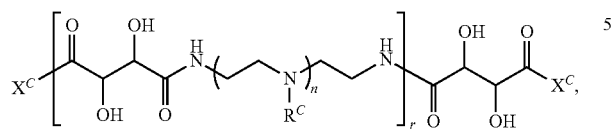

or a salt, solvate, hydrate, polymorph, co-crystal, tautomer, stereoisomer, or isotopically labeled derivative thereof.

In certain embodiments, the polymer of Formula (III') is of the formula:

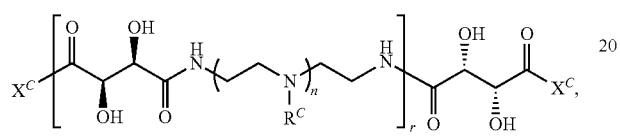

or a salt, solvate, hydrate, polymorph, co-crystal, tautomer, stereoisomer, or isotopically labeled derivative thereof.

In certain embodiments, the polymer of Formula (III') is of the formula:

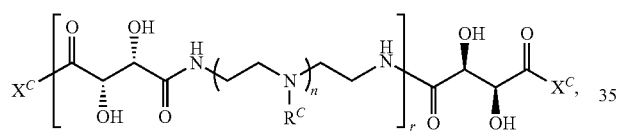

or a salt, solvate, hydrate, polymorph, co-crystal, tautomer, stereoisomer, or isotopically labeled derivative thereof.

In certain embodiments, the polymer of Formula (III') is of the formula:

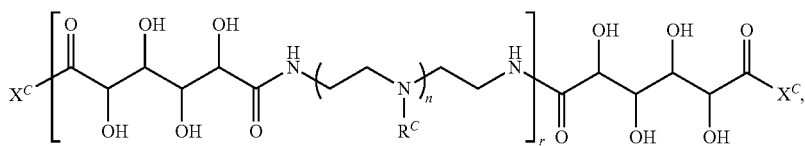

or a salt, solvate, hydrate, polymorph, co-crystal, tautomer, stereoisomer, or isotopically labeled derivative thereof.

In certain embodiments, the polymer of Formula (III') is of the formula:

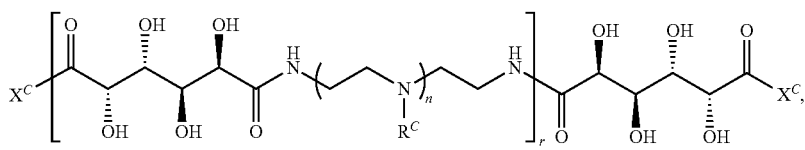

or a salt, solvate, hydrate, polymorph, co-crystal, tautomer, stereoisomer, or isotopically labeled derivative thereof.

In certain embodiments, the polymer of Formula (III') is of the formula:

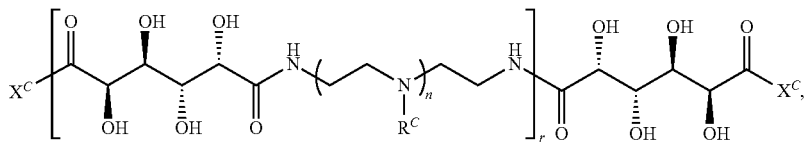

or a salt, solvate, hydrate, polymorph, co-crystal, tautomer, stereoisomer, or isotopically labeled derivative thereof.

In certain embodiments, the polymer of Formula (III') is of the formula:

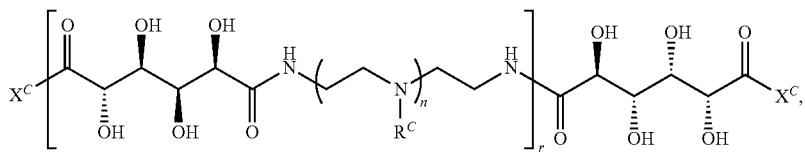

or a salt, solvate, hydrate, polymorph, co-crystal, tautomer, stereoisomer, or isotopically labeled derivative thereof.

In certain embodiments, the polymer of Formula (III') is of the formula:

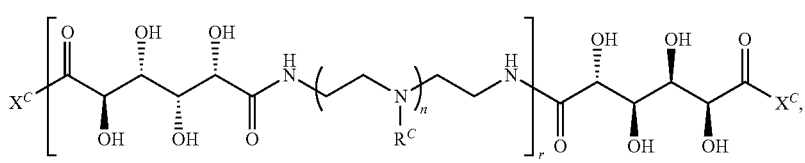

or a salt, solvate, hydrate, polymorph, co-crystal, tautomer, stereoisomer, or isotopically labeled derivative thereof.

In certain embodiments, the polymer of Formula (III") is of the formula:

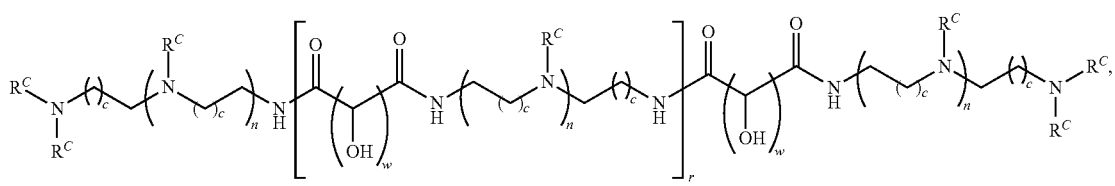

or a salt, solvate, hydrate, polymorph, co-crystal, tautomer, stereoisomer, or isotopically labeled derivative thereof.

In certain embodiments, the polymer of Formula (III") is of the formula:

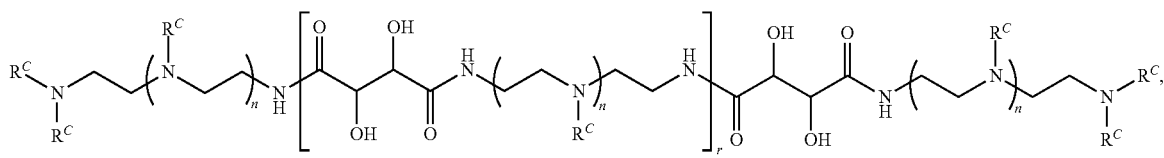

or a salt, solvate, hydrate, polymorph, co-crystal, tautomer, stereoisomer, or isotopically labeled derivative thereof.

In certain embodiments, the polymer of Formula (III″) is of the formula:

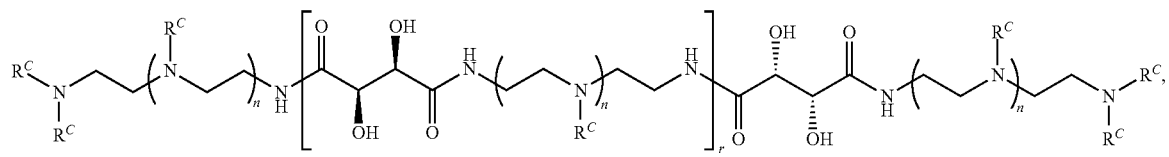

or a salt, solvate, hydrate, polymorph, co-crystal, tautomer, stereoisomer, or isotopically labeled derivative thereof.

In certain embodiments, the polymer of Formula (III″) is of the formula:

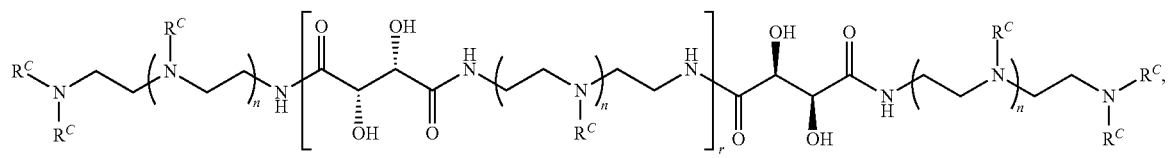

or a salt, solvate, hydrate, polymorph, co-crystal, tautomer, stereoisomer, or isotopically labeled derivative thereof.

In certain embodiments, the polymer of Formula (III″) is of the formula:

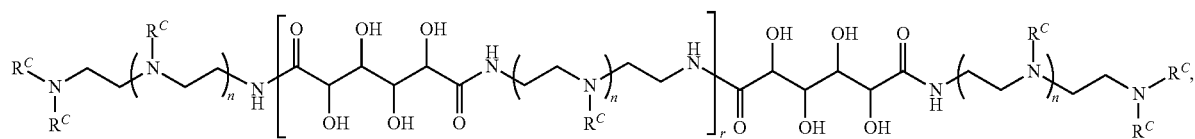

or a salt, solvate, hydrate, polymorph, co-crystal, tautomer, stereoisomer, or isotopically labeled derivative thereof.

In certain embodiments, the polymer of Formula (III″) is of the formula:

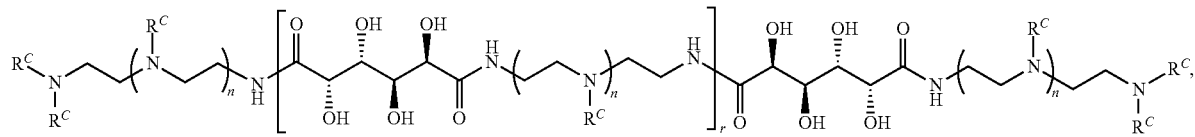

or a salt, solvate, hydrate, polymorph, co-crystal, tautomer, stereoisomer, or isotopically labeled derivative thereof.

In certain embodiments, the polymer of Formula (III″) is of the formula:

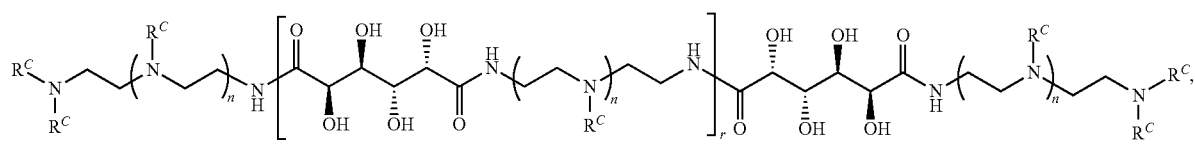

or a salt, solvate, hydrate, polymorph, co-crystal, tautomer, stereoisomer, or isotopically labeled derivative thereof.

In certain embodiments, the polymer of Formula (III") is of the formula:

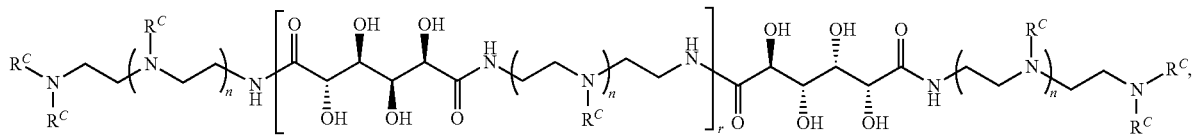

or a salt, solvate, hydrate, polymorph, co-crystal, tautomer, stereoisomer, or isotopically labeled derivative thereof.

In certain embodiments, the polymer of Formula (III") is of the formula:

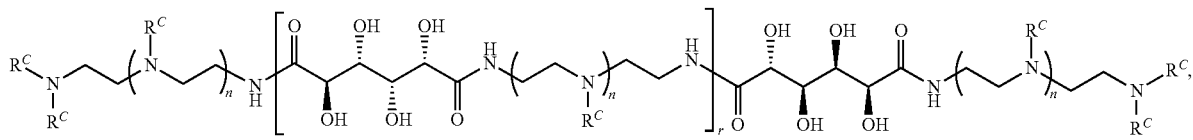

or a salt, solvate, hydrate, polymorph, co-crystal, tautomer, stereoisomer, or isotopically labeled derivative thereof.

In another aspect, the present disclosure provides polymers of Formula (IV):

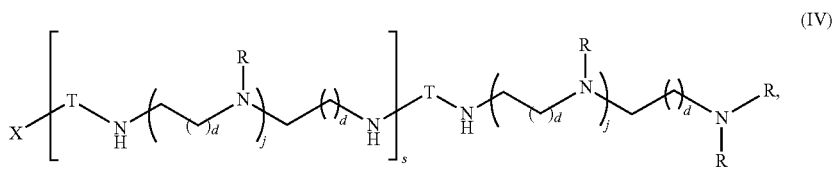

(IV)

and salts, solvates, hydrates, polymorphs, co-crystals, tautomers, stereoisomers, and isotopically labeled derivatives thereof, wherein:
- each instance of T is a divalent carbohydrate moiety;
- X is $X^A$, $X^B$, or $X^C$;
- each instance of R is independently $R^A$, $R^B$, or $R^C$;
- each instance of d is a, b, or c;
- each instance of j is k, m, or n; and
- s is p, q, or r;

wherein $X^A$, $X^B$, $X^C$, $R^A$, $R^B$, $R^C$, a, b, c, k, m, n, p, q, and r are as described herein.

In certain embodiments, each instance of T is a divalent monosaccharide moiety. In certain embodiments, each instance of T is a divalent disaccharide moiety. In certain embodiments, the disaccharide is sucrose, lactulose, lactose, maltose, isomaltose, trehalose, cellobiose, xylobiose, laminaribiose, gentiobiose, mannobiose, melibiose, nigerose, or rutinose. In certain embodiments, each instance of T is a divalent polysaccharide moiety. In certain embodiments, the polysaccharide is alginate or chitosan. In certain embodiments, the polysaccharide is dextran, hyarulonan, pullulan, cyclodextrin, schizopyllan, cellulose, or lipopolysaccharide.

In certain embodiments, each instance of R is independently $R^A$. In certain embodiments, each instance of R is independently $R^B$. In certain embodiments, each instance of R is independently $R^C$.

In certain embodiments, a polymer described herein is a polymer of Formula (I), or a salt, hydrate, solvate, polymorph, tautomer, stereoisomer, and isotopically labeled derivative thereof. In certain embodiments, a polymer described herein is a polymer of Formula (I), or a salt thereof. In certain embodiments, a polymer described herein is a polymer of Formula (I), or a pharmaceutically acceptable salt thereof. In certain embodiments, a polymer described herein is a polymer of Formula (I') or (I"), or a salt, hydrate, solvate, polymorph, tautomer, stereoisomer, and isotopically labeled derivative thereof. In certain embodiments, a polymer described herein is a polymer of Formula (I') or (I"), or a salt thereof. In certain embodiments, a polymer described herein is a polymer of Formula (I') or (I") or a pharmaceutically acceptable salt thereof. In certain embodiments, a polymer described herein is a polymer of Formula (II), or a salt, hydrate, solvate, polymorph, tautomer, stereoisomer, and isotopically labeled derivative thereof. In certain embodiments, a polymer described herein is a polymer of Formula (II), or a salt thereof. In certain embodiments, a polymer described herein is a polymer of Formula (II), or a pharmaceutically acceptable salt thereof. In certain embodiments, a polymer described herein is a polymer of Formula (II') or (II"), or a salt, hydrate, solvate, polymorph, tautomer, stereoisomer, and isotopically labeled derivative thereof. In certain embodiments, a polymer described herein is a polymer of Formula (II') or (II"), or a salt thereof. In certain embodiments, a polymer described herein is a polymer of Formula (II') or (II"), or a pharmaceutically acceptable salt thereof. In certain embodiments, a polymer described herein is a polymer of Formula (III), or a salt, hydrate, solvate, polymorph, tautomer, stereoisomer, and isotopically labeled derivative thereof. In certain embodiments, a polymer described herein is a polymer of Formula (III), or a salt thereof. In certain embodiments, a polymer described herein is a polymer of Formula (III), or a pharmaceutically acceptable salt thereof. In certain embodiments, a polymer described herein is a polymer of Formula (III') or (III"), or a salt, hydrate, solvate, polymorph, tautomer, stereoisomer, and isotopically labeled derivative thereof. In certain embodiments, a polymer described herein is a polymer of Formula (III') or (III"), or a salt thereof. In certain embodiments, a polymer described herein is a polymer of Formula (III') or (III"), or a pharmaceutically acceptable salt thereof. In certain embodiments, a polymer described herein is a polymer of Formula (IV), or a salt, hydrate, solvate, polymorph, tautomer, stereoisomer, and isotopically labeled derivative thereof. In certain embodiments, a polymer described herein is a polymer of Formula (IV), or a salt thereof. In certain embodiments, a polymer described herein is a polymer of Formula (IV), or a pharmaceutically acceptable salt thereof.

There is a growing interest in use of messenger RNA (mRNA) as a therapeutic strategy.[1-5] For example, preclinical and clinical studies have explored mRNA for use as vaccines through local administration of naked mRNA or mRNA-transfected dendritic cells to induce antigen-specific immune response.[1-3] Recently, Phua compared the delivery efficiency of different administration methods using stemfect mRNA transfection agents in mice.[4] Su developed lipid based nanoparticles for intranasal delivery of mRNA to induce luciferase expression in mice.[6] Through intratracheal delivery of mRNA for surfactant protein B (SP-B), Kormann reported therapeutic activity in a mouse model of lethal congenital lung disease caused by SP-B deficiency.[7] Zangi has reported local administration of modified mRNA in mice for the treatment of myocardial infarction.[7, 8] The potential utility of mRNA as a method to promote protein secretion was reported by Kariko, who demonstrated delivery of erythropoietin (EPO) mRNA via intraperitoneal administration in mice and macaques.[9]

Compared with targeting through local administration, systemic administration has the potential to access more organs and cell types through the bloodstream.[10] However, several physiologic barriers impede access of mRNA formulations following systemic administration.[1-3] In general, after intravenous administration, mRNA formulations must traverse the vascular endothelial barrier and then pass through extracellular matrix to access the tissue of interest.[10] Additionally, intravascular therapies must avoid filtration by the kidneys and uptake by immune cells. After cell internalization, the mRNA must survive and escape the endocytic pathway in order to access translational machinery in the cytosol. The efficient and safe delivery of mRNA remains a key challenge to the broad clinical application of mRNA therapeutics.[1]

The polymers described herein may be useful in delivering an agent, such as a polynucleotide (e.g., DNA (e.g., plasmid DNA) or RNA (e.g., siRNA, mRNA), or a combination thereof), to a subject, tissue, or cell. The polymers include amino groups, which may increase electrostatic complexation and entrapment of negatively-charged agents (e.g., polynucleotide, e.g., mRNA). In addition, the polymers may include multiple hydroxyl groups, which may increase hydrophilicity, while alkyl tails (brushes) included in the polymers may enable incorporation of the polymers into nanoparticle formulations (e.g., lipid-based nanoparticle formulations). This modular design offers the ability to tune the agent-delivery system through modification of a number of chemical and structural properties. The polymers described herein may also be useful in treating and/or preventing a disease (e.g., a genetic disease, proliferative disease, hematological disease, neurological disease, gastrointestinal disease, spleen disease, respiratory disease, painful condition, psychiatric disorder, musculoskeletal disease, genitourinary disease, or metabolic disorder) in a subject in need thereof. In certain embodiments, the polymers described herein are useful in gene therapy. The polymers described herein may also be useful for other applications, e.g., as an emulsion, emulsifier, or coating, each of which may be useful as a food component, for extinguishing fires, for disinfecting surfaces, or for oil cleanup; and/or as a bulk material.

Methods of Preparing the Polymers and Polymers Prepared by the Methods

Polymers described herein may be prepared using epoxide-amine addition reactions (e.g., Methods A, A', and A"), reductive amination reactions (e.g., Methods B-1, B-1', B-1", and B-2), and Michael addition reactions (e.g., Methods C, C', and C"). In another aspect, the present disclosure provides methods of preparing the polymers of Formula (I), and salts thereof (Method A), the methods including reacting a polymer of Formula (A1), or a salt thereof, with an epoxide of Formula (A2) to provide the polymer of Formula (I), or a salt thereof:

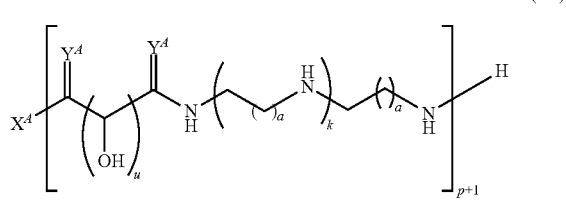

(A1)

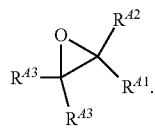
(A2)

In another aspect, the present disclosure provides methods of preparing the polymers of Formula (I'), and salts thereof (Method A'), the methods including reacting a polymer of Formula (A3), or a salt thereof, with an epoxide of Formula (A2) to provide the polymer of Formula (I'), or a salt thereof:

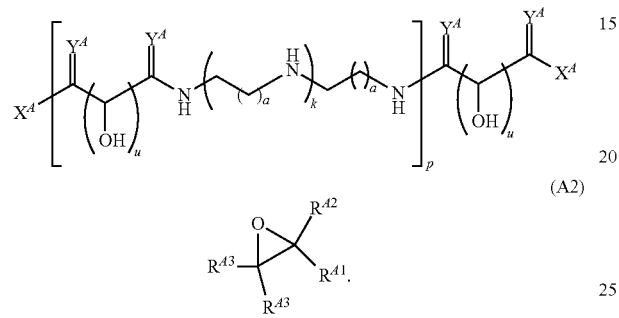

(A3)

(A2)

In another aspect, the present disclosure provides methods of preparing the polymers of Formula (I"), and salts thereof (Method A"), the methods including reacting a polymer of Formula (A4), or a salt thereof, with an epoxide of Formula (A2) to provide the polymer of Formula (I"), or a salt thereof:

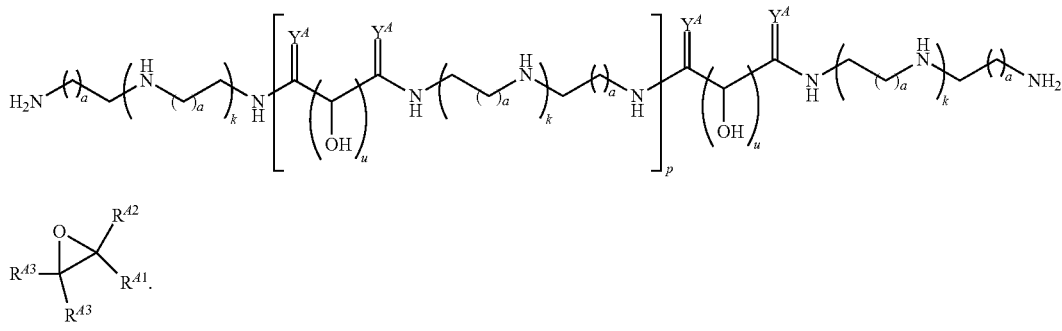

(A4)

(A2)

Another aspect of the present disclosure relates to methods of preparing the polymers of Formula (II), and salts thereof (Method B-1), the methods including reacting a polymer of Formula (B1), or a salt thereof, with an aldehyde of Formula (B2) in the presence of a reductant to provide the polymer of Formula (II), or a salt thereof:

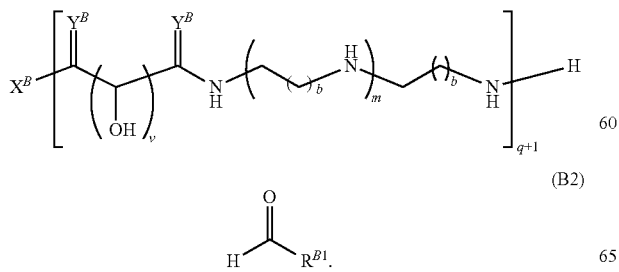

(B1)

(B2)

Another aspect of the present disclosure relates to methods of preparing the polymers of Formula (II'), and salts thereof (Method B-1'), the methods including reacting a polymer of Formula (B4), or a salt thereof, with an aldehyde of Formula (B2) in the presence of a reductant to provide the polymer of Formula (II'), or a salt thereof:

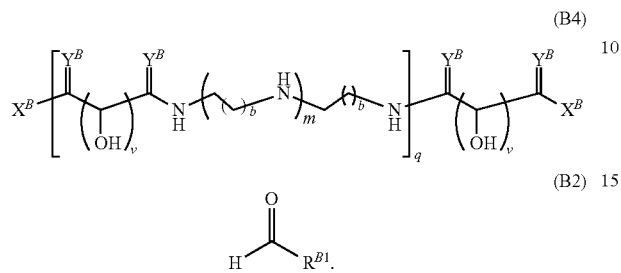
(B4)

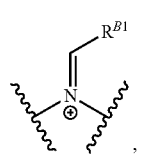
(B2)

Another aspect of the present disclosure relates to methods of preparing the polymers of Formula (II''), and salts thereof (Method B-1''), the methods including reacting a polymer of Formula (B5), or a salt thereof, with an aldehyde of Formula (B2) in the presence of a reductant to provide the polymer of Formula (II''), or a salt thereof:

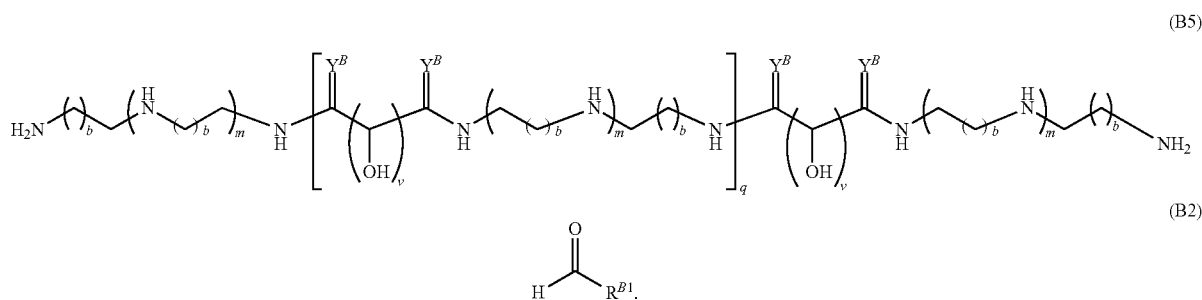
(B5)

(B2)

Another aspect of the present disclosure relates to methods of preparing the polymers of Formula (II), and salts thereof (Method B-2), the methods including reducing a polymer of Formula (B3), or a salt thereof, with a reductant to provide the polymer of Formula (II), or a salt thereof:

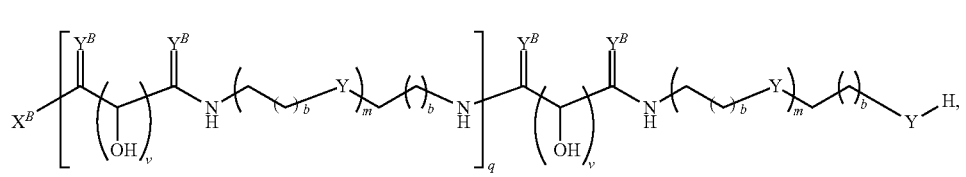
(B3)

wherein each instance of Y is independently —NH— or a moiety of the formula:

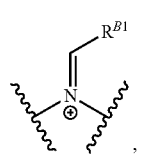

wherein at least one instance of Y is a moiety of the formula:

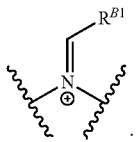

In certain embodiments, at least about 10%, at least about 20%, at least about 30%, or at least about 40% of the total instances of Y are the same. In certain embodiments, at least about 50% of the total instances of Y are the same. In certain embodiments, at least about 60% of the total instances of Y are the same. In certain embodiments, at least about 70% of the total instances of Y are the same. In certain embodiments, at least about 80% of the total instances of Y are the same. In certain embodiments, at least about 90% of the total instances of Y are the same. In certain embodiments, at least about 95% of the total instances of Y are the same. In certain embodiments, all instances of Y are the same. In certain embodiments, at least two instances of Y are different from each other. In certain embodiments, at least one instance of Y is —NH—. In certain embodiments, at least one instance of Y is of the formula:

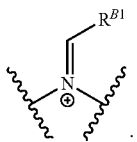

In certain embodiments, at least about 10%, at least about 20%, at least about 30%, at least about 40%, at least about 50%, at least about 60%, at least about 70%, at least about 80%, at least about 90%, or at least about 95% of the total instances of Y are independently of the formula:

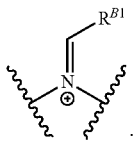

In certain embodiments, all instances of Y are independently of the formula:

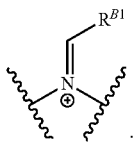

In certain embodiments, Method B-2 further includes reacting a polymer of Formula (B1), or a salt thereof, with an aldehyde of Formula (B2) to provide the polymer of Formula (B3), or a salt thereof. Polymers of Formulae (II') and (II") can also be prepared using a method similar to Method B-2.

The reductant employed in Method B-1, B-1', B-1", or B-2 may be any reductant known in the art. In certain embodiments, the reductant is a borohydride (e.g., sodium borohydride, potassium borohydride, calcium borohydride, magnesium borohydride, tetramethylammonium borohydride, tetraethylammonium borohydride, tetrabutylammonium borohydride, methyltrioctylammonium borohydride, cetyltrimethylammonium borohydride, bis(triphenylphosphine)copper(I) borohydride, potassium tri(1-pyrazolyl) borohydride, potassium tri(3,5-dimethyl-1-pyrazolyl)borohydride, sodium cyanoborohydride, sodium triacetoxyborohydride, or polymer-supported borohydride). In certain embodiments, the reductant is a borane (e.g., a borane tetrahydrofuran complex, borane dimethyl sulfide complex, borane dimethylamine complex, borane pyridine complex, borane trimethylamine complex, borane triethylamine complex, borane morpholine complex, borane tert-butylamine complex, borane-ammonia complex, borane triphenylphosphine complex, borane N,N-diethylaniline complex, borane di(tert-butyl)phosphine complex, borane diphenylphosphine complex, borane 4-methylmorpholine complex, borane N,N-diisopropylethylamine complex, borane isoamylsulfide complex, borane ethylenediamine complex, acetylthiomethyl-diphenylphosphine borane complex, 2-methylpyridine borane complex, tert-butyldimethylphosphine borane, 5-ethyl-2-methylpyridine borane complex, lithium ammonia borane, (11bR)-4,5-dihydro-3H-dinaphtho[2,1-c:1',2'-e]phosphepine borane, (methoxycarbonyl)borane trimethylamine complex, dibromoborane dimethyl sulfide complex, mono-bromoborane methyl sulfide complex, dichloroborane methyl sulfide complex, 1,3-dimethylimidazol-2-ylidene borane). In certain embodiments, the reductant is a silane. In certain embodiments, the silane is of the formula: $HSi(R^1)_3$, wherein each instance of $R^1$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or —$OR^{1a}$, wherein each instance of $R^{1a}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group). In certain embodiments, the silane is a monoalkylsilane (e.g., $BuSiH_3$), dialkylsilane (e.g., $Et_2SiH_2$), or trialkylsilane (e.g., $Me_3SiH$ or $Et_3SiH$). In certain embodiments, the silane is a poly(alkylhydrosiloxane) (e.g., poly(methylhydrosiloxane) (PMHS)). In certain embodiments, the reductant is an alcohol. In certain embodiments, the alcohol is of the formula: $(R^2)_2CHOH$, wherein each instance of $R^2$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, the alcohol is methanol, ethanol, propanol (e.g., n-propanol or isopropanol), or butanol (e.g., t-butanol). In certain embodiments, the reductant is $H_2$. In certain embodiments, the reductant is commercially available.

Another aspect of the present disclosure relates to methods of preparing the polymers of Formula (III), and salts thereof (Method C), the methods including reacting a polymer of Formula (C1), or a salt thereof, with a compound of Formula (C2) to provide the polymer of Formula (III), or a salt thereof:

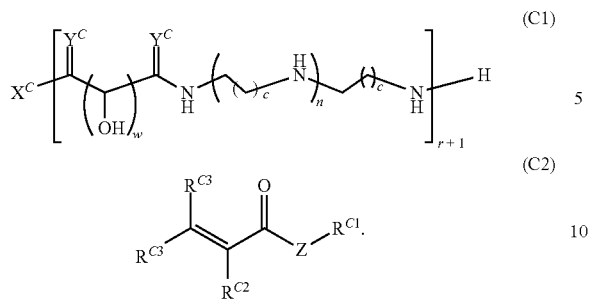

(C1)

(C2)

Another aspect of the present disclosure relates to methods of preparing the polymers of Formula (III'), and salts thereof (Method C'), the methods including reacting a polymer of Formula (C3), or a salt thereof, with a compound of Formula (C2) to provide the polymer of Formula (III'), or a salt thereof:

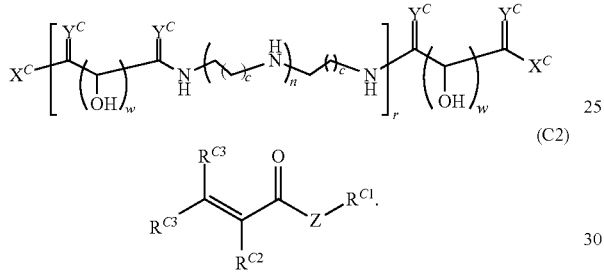

(C3)

(C2)

Another aspect of the present disclosure relates to methods of preparing the polymers of Formula (III"), and salts thereof (Method C"), the methods including reacting a polymer of Formula (C4), or a salt thereof, with a compound of Formula (C2) to provide the polymer of Formula (III"), or a salt thereof:

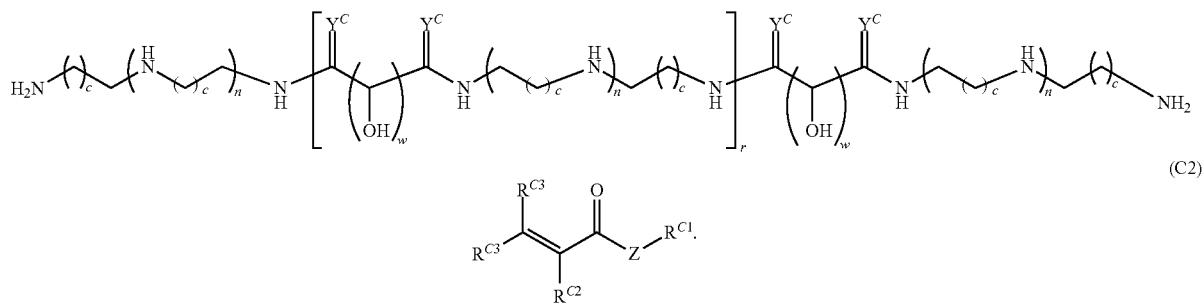

(C4)

(C2)

Another aspect of the present disclosure relates to methods of preparing the polymers of Formula (IV), and salts thereof. In certain embodiments, when X is $X^A$, each instance of R is independently $R^A$, each instance of d is a, each instance of j is k, and s is p, a method of preparing a polymer of Formula (IV), or a salt thereof (Method D-A), includes reacting a polymer of Formula (A), or a salt thereof, with an epoxide of Formula (A2):

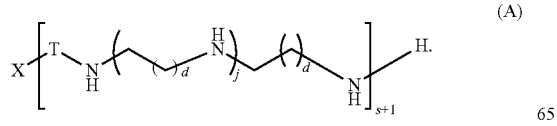

(A)

In certain embodiments, when X is $X^B$, each instance of R is independently $R^B$, each instance of d is b, each instance of j is m, and s is q, a method of preparing a polymer of Formula (IV), or a salt thereof (Method D-B-1), includes reacting a polymer of Formula (A), or a salt thereof, with an aldehyde of Formula (B2) in the presence of a reductant.

In certain embodiments, when X is $X^B$, each instance of R is independently $R^B$, each instance of d is b, each instance of j is m, and s is q, a method of preparing a polymer of Formula (IV), or a salt thereof (Method D-B-2), includes reducing a polymer of Formula (B), or a salt thereof, with a reductant:

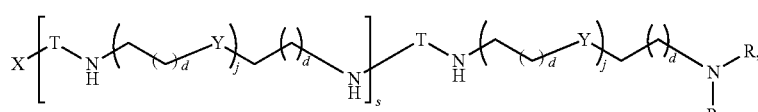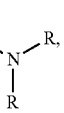

(B)

wherein each instance of Y is as described herein.

In certain embodiments, when X is $X^C$, each instance of R is independently $R^C$, each instance of d is c, each instance of j is n, and s is r, a method of preparing a polymer of Formula (IV), or a salt thereof (Method D-C), includes reacting a polymer of Formula (A), or a salt thereof, with a compound of Formula (C2).

The step(s) of the methods of preparing the polymers described herein may be performed under any suitable conditions. A suitable condition is a combination of physical and chemical parameters under which an intended product (e.g., a polymer described herein) or intermediate may be formed using the methods.

A suitable condition may include the absence of a solvent (i.e., neat). A suitable condition may include a suitable solvent. In certain embodiments, the suitable solvent is an organic solvent. In certain embodiments, the suitable solvent is an aprotic organic solvent (e.g., acetonitrile, N,N-dimethylformamide (DMF), N,N-dimethylacetamide (DMA), N-methyl-2-pyrrolidone (NMP), dimethyl sulfoxide (DMSO), tetrahydrofuran (THF), 2-methyl-tetrahydrofuran, tetrahydropyran, dioxane, diethyl ether, methyl t-butyl ether (MTBE), dimethoxyethane (DME), diglyme, acetone, butanone, dichloromethane, chloroform, carbon tetrachloride, or 1,2-dichloroethane). In certain embodiments, the suitable solvent is a protic organic solvent (e.g., an alcohol, such as methanol, ethanol, propanol, or butanol). In certain embodiments, the suitable solvent is an inorganic solvent (e.g., water). In certain embodiments, the suitable solvent is a mixture of two or more solvents. In certain embodiments, the suitable solvent is commercially available.

A suitable condition may also include a suitable temperature under which a step of a method of preparing a polymer described herein is performed. In certain embodiments, the suitable temperature is at least about 0° C., at least about 23° C., at least about 40° C., at least about 60° C., at least about 80° C., or at least about 100° C. In certain embodiments, the suitable temperature is not more than about 100° C., not more than about 80° C., not more than about 60° C., not more than about 40° C., not more than about 23° C., or not more than about 0° C. Combinations of the above-referenced ranges (e.g., at least about 23° C. and not more than about 60° C.) are also within the scope of the disclosure. A suitable temperature may be a variable temperature (e.g., from 23° C. to about 60° C.) during a step of a method of preparing a polymer described herein.

A suitable condition may also include a suitable pressure under which a step of a method of preparing a polymer described herein is performed. In certain embodiments, the suitable pressure is about 1 atmosphere. In certain embodiments, the suitable pressure is at least about 2 atmosphere, at least about 5 atmosphere, at least about 10 atmosphere, at least about 30 atmosphere, or at least about 100 atmosphere.

A suitable condition may also include a suitable atmosphere under which a step of a method of preparing a polymer described herein is performed. In certain embodiments, the suitable atmosphere is air. In certain embodiments, the suitable atmosphere is an inert atmosphere. In certain embodiments, the suitable atmosphere is a nitrogen or argon atmosphere.

A suitable condition may also include a suitable time duration that a step of a method of preparing a polymer described herein lasts. In certain embodiments, the suitable time duration is in the order of minutes (e.g., about 10 minutes or about 30 minutes), hours (e.g., about 1 hour, about 2 hours, about 3 hours, about 4 hours, about 6 hours, or about 12 hours), or days (e.g., about 1 day or 2 days).

A suitable condition may also include a suitable molar ratio between the reactants and/or reagents employed in a method of preparing the polymers described herein. In certain embodiments, a suitable molar ratio of (1) the nucleophilic amino groups of a polymer of Formula (A1), (A3), or (A4), to (2) an epoxide of Formula (A2) is about 1:1, about 1:1.2, about 1:1.5, about 1:2, about 1:5, or about 1:10. In certain embodiments, a suitable molar ratio of (1) the nucleophilic amino groups of a polymer of Formula (B1), (B4), (B5), to (2) an aldehyde of Formula (B2) is about 1:1, about 1:1.2, about 1:1.5, about 1:2, about 1:5, or about 1:10. In certain embodiments, a suitable molar ratio of (1) the nucleophilic amino groups of a polymer of Formula (C1), (C3), or (C4), to (2) a compound of Formula (C2) is about 1:1, about 1:1.2, about 1:1.5, about 1:2, about 1:5, or about 1:10.

One or more intermediates resulting from a step of a method of preparing the polymers described herein may be isolated and/or purified, and the isolated and/or purified intermediates may be reacted in a next step of the method. The isolated and/or purified intermediates may be substantially free of impurities or may contain one or more other components, such as reagents and solvents employed in the step yielding the intermediates, and byproducts. The intermediates may also be reacted in a next step without being isolated and/or purified. The intermediates and/or intended products of a method of preparing a polymer described herein may be isolated and/or purified using methods known in the art, such as distillation, chromatography (e.g., normal phase chromatography (e.g., silica gel flash chromatography), reverse phase chromatography (e.g., high performance liquid chromatography (HPLC)), precipitation, decanting, filtration, centrifuge, trituration, crystallization, recrystallization, liquid-liquid phase separation, evaporation, and drying.

Another aspect of the present disclosure relates to polymers prepared by a method described herein. In certain embodiments, described herein are polymers prepared by Method A, A', or A", wherein the polymer of Formula (A1), (A3), or (A4) is a poly(glycoamidoamine) in Table 4, or a salt thereof, and the epoxide of Formula (A2) is an epoxide in Table 5 or 6. In certain embodiments, the epoxide of Formula (A2) is not of the formula:

TABLE 4

Exemplary poly(glycoamidoamines) that are useful in Method A, A', A", B-1, B-1', B-1", B-2, C', C"

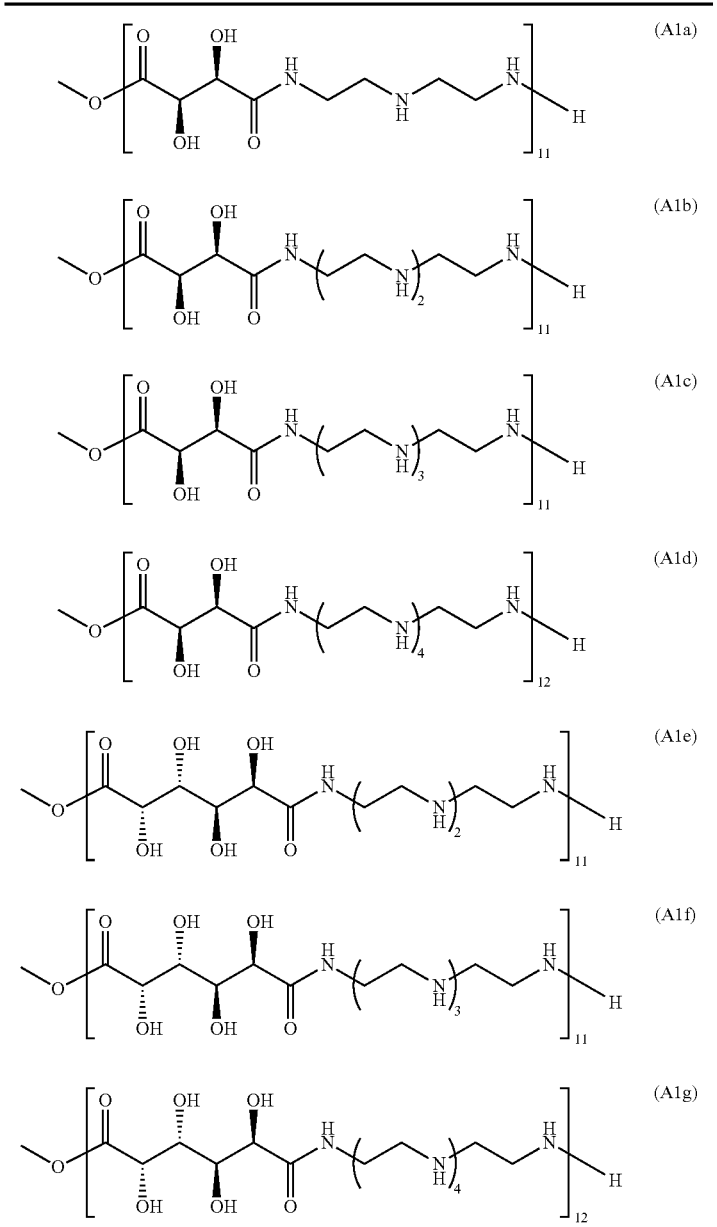

TABLE 4-continued
Exemplary poly(glycoamidoamines) that are useful in Method A, A', A", B-1, B-1', B-1", B-2, C', C"
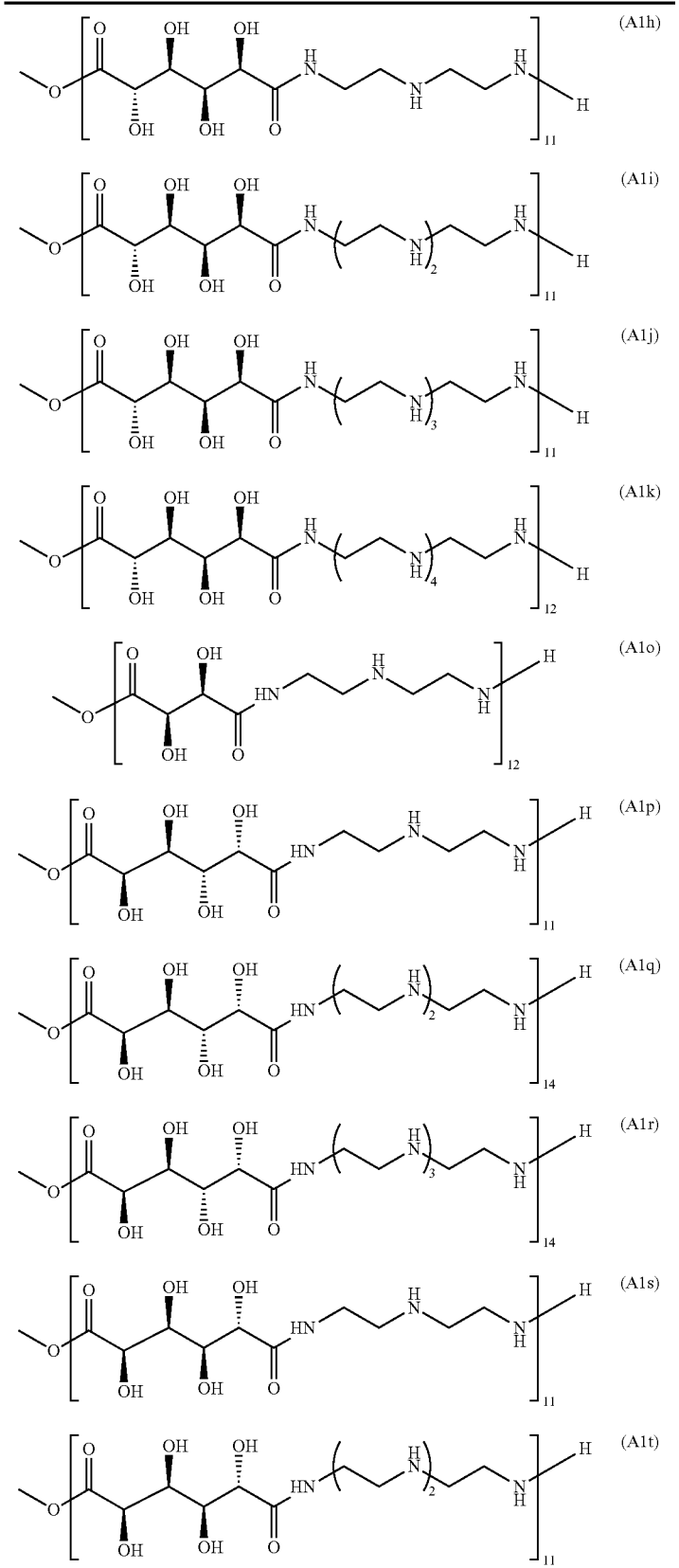

TABLE 4-continued

Exemplary poly(glycoamidoamines) that are useful in Method A, A', A", B-1, B-1', B-1", B-2, C', C"

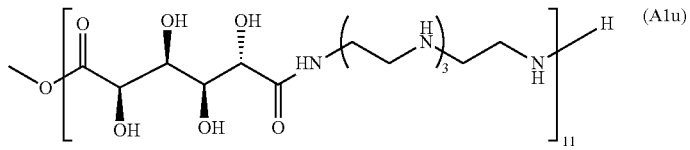
(A1u)

TABLE 5

Exemplary epoxides that are useful in Methods A, A', and A".

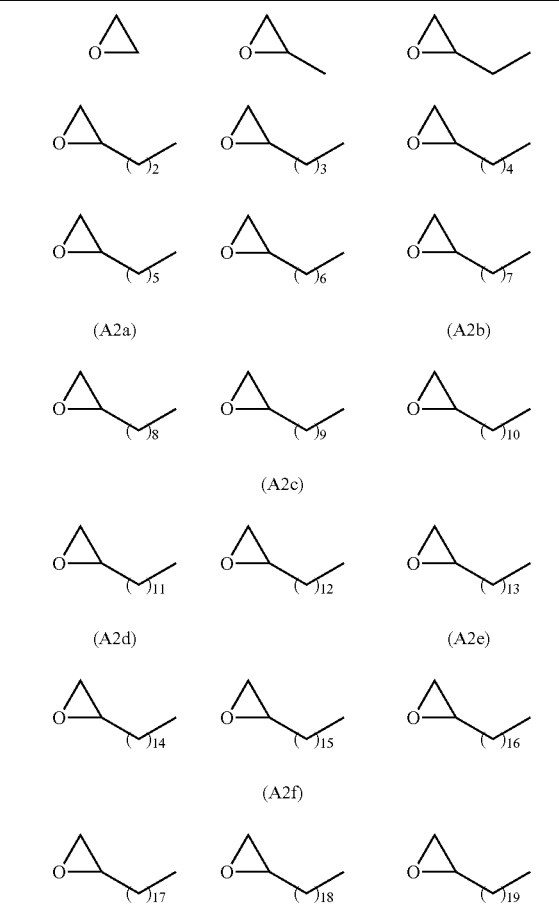

TABLE 6

Exemplary epoxides that are useful in Methods A, A', and A".

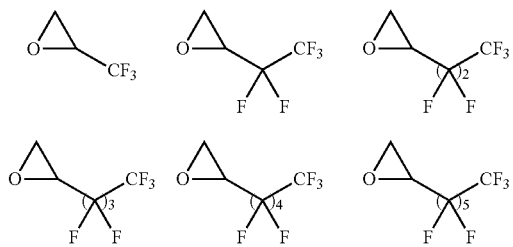

TABLE 6-continued

Exemplary epoxides that are useful in Methods A, A', and A".

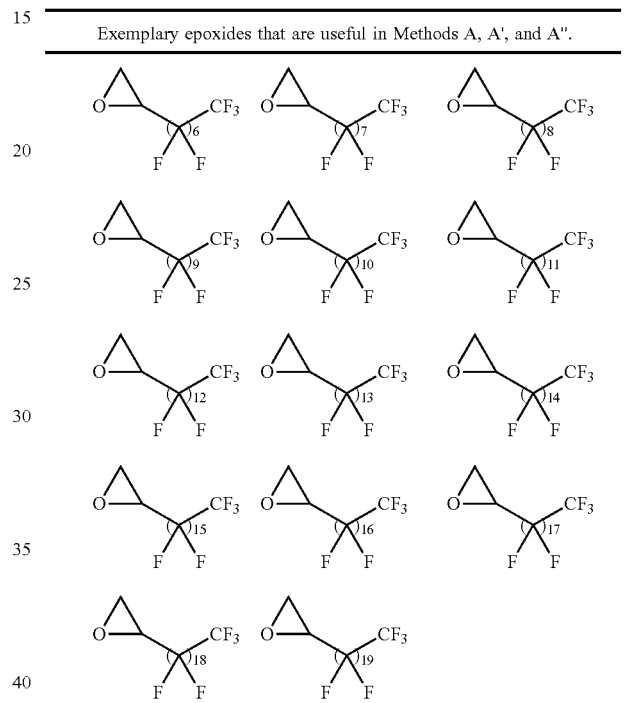

In certain embodiments, a polymer described herein is a polymer prepared according to Method A, A', or A" using the poly(glycoamidoamines) and epoxides in Table 7.

TABLE 7

Exemplary polymers prepared according to Method A, A', or A" using poly(glycoamidoamines) and epoxides.

| Polymer | Poly(glyco-amidoamine) | Epoxide |
|---|---|---|
| TarN1C8 | A1a | A2b |
| TarN1C10 | A1a | A2c |
| TarN1C12 | A1a | A2d |
| TarN1C14 | A1a | A2e |
| TarN2C8 | A1b | A2b |
| TarN2C10 | A1b | A2c |
| TarN2C12 | A1b | A2d |
| TarN2C14 | A1b | A2e |
| TarN3C8 | A1c | A2b |
| TarN3C10 | A1c | A2c |
| TarN3C12 | A1c | A2d |
| TarN3C14 | A1c | A2e |
| TarN4C8 | A1d | A2b |
| TarN4C10 | A1d | A2c |
| TarN4C12 | A1d | A2d |

TABLE 7-continued

Exemplary polymers prepared according to Method A, A', or A" using poly(glycoamidoamines) and epoxides.

| Polymer | Poly(glyco-amidoamine) | Epoxide |
|---|---|---|
| TarN4C14 | A1d | A2e |
| GalN2C8 | A1e | A2b |
| GalN2C10 | A1e | A2c |
| GalN2C12 | A1e | A2d |
| GalN2C14 | A1e | A2e |
| GalN3C8 | A1f | A2b |
| GalN3C10 | A1f | A2c |
| GalN3C12 | A1f | A2d |
| GalN3C14 | A1f | A2e |
| GalN4C8 | A1g | A2b |
| GalN4C10 | A1g | A2c |
| GalN4C12 | A1g | A2d |
| GalN4C14 | A1g | A2e |
| GluN1C10 | A1h | A2c |
| GluN1C12 | A1h | A2d |
| GluN1C14 | A1h | A2e |
| GluN2C8 | A1i | A2b |
| GluN2C10 | A1i | A2c |
| GluN2C12 | A1i | A2d |
| GluN2C14 | A1i | A2e |
| GluN3C6 | A1j | A2a |
| GluN3C8 | A1j | A2b |
| GluN3C10 | A1j | A2c |
| GluN3C12 | A1j | A2d |
| GluN3C14 | A1j | A2e |
| GluN4C8 | A1k | A2b |
| GluN4C10 | A1k | A2c |
| GluN4C12 | A1k | A2d |
| GluN4C14 | A1k | A2e |
| TarN1C16 | A1o | A2f |
| TarN2C16 | A1b | A2f |
| TarN3C16 | A1c | A2f |
| GalN2C10' | A1q | A2c |
| GalN3C10' | A1r | A2c |
| GalN2C12' | A1q | A2d |
| GalN3C12' | A1r | A2d |
| GalN2C14' | A1q | A2e |
| GalN3C14' | A1r | A2e |
| GalN2C16' | A1q | A2f |
| GalN3C16' | A1r | A2f |
| GluN2C10' | A1t | A2c |
| GluN3C10' | A1u | A2c |
| GluN1C12' | A1s | A2d |
| GluN2C12' | A1t | A2d |
| GluN3C12' | A1u | A2d |
| GluN1C14' | A1s | A2e |
| GluN2C14' | A1t | A2e |
| GluN3C14' | A1u | A2e |
| GluN1C16' | A1s | A2f |
| GluN2C16' | A1t | A2f |
| GluN3C16' | A1u | A2f |

In certain embodiments, described herein are polymers prepared by Method B-1, B-1', B-1", or B-2, wherein the polymer of Formula (B1) is a poly(glycoamidoamine) in Table 4, or a salt thereof, and the aldehyde of Formula (B2) is an aldehyde in Table 8 or 9.

TABLE 8

Exemplary aldehydes that are useful in Methods B-1, B-1', B-1", and B-2.

Me—CHO, CHO-(CH₂)₂, CHO-(CH₂)₃, CHO-(CH₂)₄, CHO-(CH₂)₅, CHO-(CH₂)₆, CHO-(CH₂)₇, CHO-(CH₂)₈, CHO-(CH₂)₉, CHO-(CH₂)₁₀, CHO-(CH₂)₁₁, CHO-(CH₂)₁₂, CHO-(CH₂)₁₃, CHO-(CH₂)₁₄, CHO-(CH₂)₁₅, CHO-(CH₂)₁₆, CHO-(CH₂)₁₇, CHO-(CH₂)₁₈, CHO-(CH₂)₁₉

TABLE 9

Exemplary aldehydes that are useful in Methods B-1, B-1', B-1", and B-2.

$F_3C$—CHO, and various fluorinated aldehydes with $F_3C$ and $F$ substituents bearing CHO groups with chain lengths 2 through 19.

In certain embodiments, described herein are polymers prepared by Method C, C', or C", wherein the polymer of Formula (C1) is a poly(glycoamidoamine) in Table 4, or a salt thereof, and the compound of Formula (C2) is an acrylate in Table 10 or an acrylamide in Table 11.

TABLE 10

Exemplary acrylates that are useful in Method C, C', or C".

TABLE 10-continued

Exemplary acrylates that are useful in Method C, C', or C''.

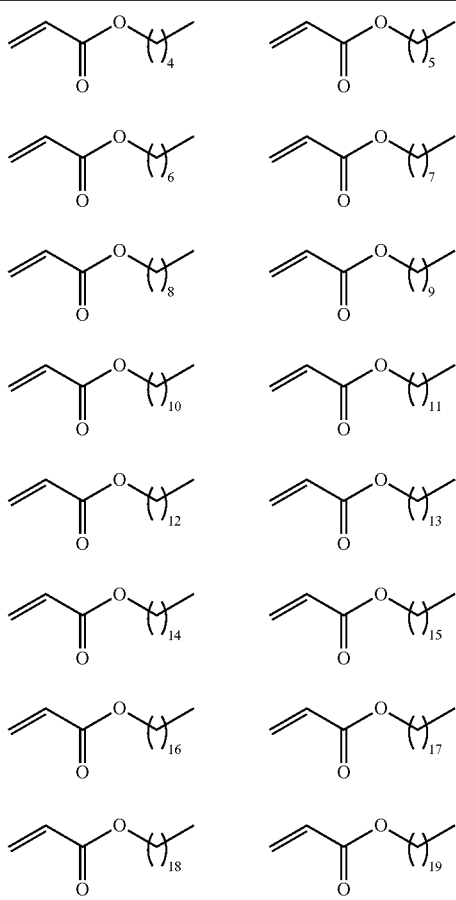

TABLE 11

Exemplary acrylamides that are useful in Method C, C', or C''.

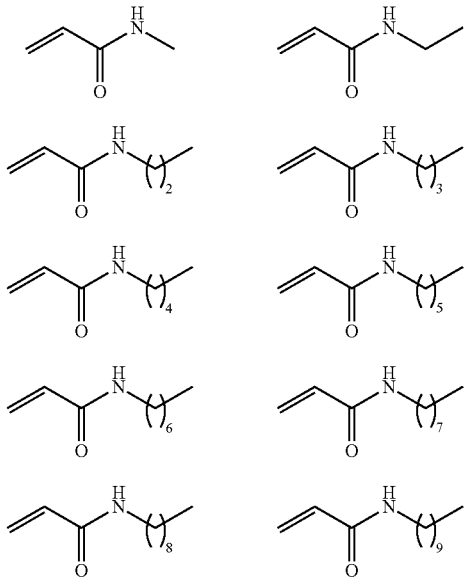

TABLE 11-continued

Exemplary acrylamides that are useful in Method C, C', or C''.

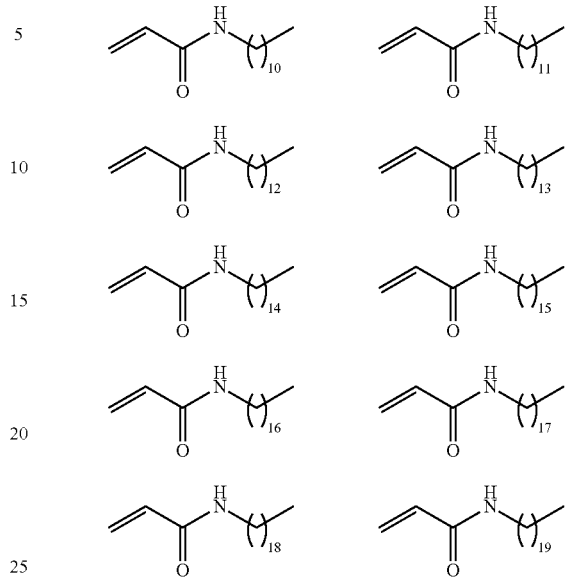

In certain embodiments, described herein are polymers prepared by Method D-A. In certain embodiments, described herein are polymers prepared by Method D-B-1 or D-B-2. In certain embodiments, described herein are polymers prepared by Method D-C.

A polymer of any one of Formulae (A1), (A3), (A4), (B1), (B3), (B4), (B5), (C1), (C3), and (C4) can be prepared using methods known in the art, e.g., methods disclosed in Liu et al., *J. Am. Chem. Soc.*, 2004, 126, (24), 7422-3; Liu et al., *J. Am. Chem. Soc.*, 2005, 127, 3004-3015; and McLendon et al., *Molecular Pharmaceutics*, 2010, 7, 738-750. In certain embodiments, the polydispersity index (PDI, determined by dynamic light scattering) of a polymer of any one of Formulae (A1), (A3), (A4), (B1), (B3), (B4), (B5), (C1), (C3), and (C4) is between 1.02 and 10, between 1.02 and 5, between 1.02 and 3, between 1.1 and 5, between 1.1 and 3, or between 1.2 and 2.

In certain embodiments, a polymer prepared using a method described herein is a fully-substituted poly(glycoamidoamine) (e.g., no instance of $R^A$ is H, no instance of $R^B$ is H, or no instance of $R^C$ is H). In other embodiments, a polymer prepared using a method described herein is a partially substituted poly(glycoamidoamine) (e.g., at least one instance of $R^A$ is H, at least one instances of $R^B$ is H, or at least one instances of $R^C$ is H). In certain embodiments, provided are mixtures of polymers prepared by a method described herein. In certain embodiments, a provided mixture of polymers is a mixture of partially substituted poly(glycoamidoamines) described herein. In certain embodiments, a provided mixture of polymers is a mixture of partially substituted poly(glycoamidoamines) described herein and fully-substituted poly(glycoamidoamines) described herein. In certain embodiments, the polydispersity index (PDI, determined by dynamic light scattering) of a polymer prepared using a method described herein is between 1.02 and 10, between 1.02 and 5, between 1.02 and 3, between 1.1 and 5, between 1.1 and 3, or between 1.2 and 2.

Compositions

In another aspect, the present disclosure provides compositions comprising a polymer described herein and optionally an excipient. In certain embodiments, a composition described herein comprises a polymer described herein and an excipient. In certain embodiments, a composition described herein is a pharmaceutical composition. In certain embodiments, a composition described herein comprises a polymer described herein and a pharmaceutically acceptable excipient. In certain embodiments, a composition described herein is a composition for non-medical applications. In certain embodiments, a composition described herein is a cosmetic composition. In certain embodiments, a composition described herein comprises a polymer described herein and a cosmetically acceptable excipient. In certain embodiments, a composition described herein is a dietary composition. In certain embodiments, a composition described herein comprises a polymer described herein and a dietarily acceptable excipient. In certain embodiments, a composition described herein is a nutraceutical composition. In certain embodiments, a composition described herein comprises a polymer described herein and a nutraceutically acceptable excipient.

A composition described herein may further comprise an agent (e.g., a pharmaceutical agent or diagnostic agent). In a composition described herein, an agent may form a complex with a polymer described herein. In certain embodiments, a composition described herein is useful in the delivery of the agent to a subject, tissue, or cell. In certain embodiments, a composition described herein is useful in the delivery of an effective amount of the agent to the subject, tissue, or cell.

Compositions of the disclosure may improve or increase the delivery of an agent described herein to a subject, tissue, or cell. In certain embodiments, the compositions increase the delivery of the agent to a target tissue or target cell. In certain embodiments, the target tissue is liver, spleen, and/or lung. In certain embodiments, the target cell is a liver cell, spleen cell, and/or lung cell. In certain embodiments, the compositions selectively deliver the agent to the target tissue or target cell (e.g., the compositions deliver the agent to the target tissue in a greater quantity in unit time than to a non-target tissue or deliver the agent to the target cell in a greater quantity in unit time than to a non-target cell).

The delivery of an agent described herein may be characterized in various ways, such as the exposure, concentration, and bioavailability of the agent. The exposure of an agent in a subject, tissue, or cell may be defined as the area under the curve (AUC) of the concentration of the agent in the subject, tissue, or cell after administering or dosing the agent. In general, an increase in exposure may be calculated by first taking the difference in: (1) a first AUC, which is the AUC measured in a subject, tissue, or cell administered or dosed with a composition described herein; and (2) a second AUC, which is the AUC measured in a subject, tissue, or cell administered or dosed with a control composition; and then by dividing the difference by the second AUC. Exposure of an agent may be measured in an appropriate animal model. The concentration of an agent and, when appropriate, its metabolite(s), in a subject, tissue, or cell is measured as a function of time after administering or dosing the agent.

Concentration of an agent, and, when appropriate, of its metabolite(s), in a subject, tissue, or cell, may be measured as a function of time in vivo using an appropriate animal model. In certain embodiments, the concentration of the agent is the concentration of the agent in a target tissue or target cell. One exemplary method of determining the concentration of an agent involves dissecting of a tissue. The concentration of the agent may be determined by HPLC or LC/MS analysis.

In some embodiments, a composition of the disclosure increases the delivery of an agent described herein to a subject, tissue, or cell by due to the presence of a polymer described herein. In some embodiments, the composition increases the delivery of the agent due to the presence of a complex formed between the polymer and the agent. In some embodiments, the presence of a polymer described herein increase the delivery of the agent by at least about 10%, at least about 20%, at least about 30%, at least about 40%, at least about 50%, at least about 100%, at least about 2-fold, at least about 3-fold, at least about 10-fold, at least about 30-fold, at least about 100-fold, at least about 300-fold, or at least about 1000-fold. In certain embodiments, a polymer described herein is present in the composition in an amount sufficient to increase the delivery of the agent by an amount described herein when administered in the composition compared to the delivery of the agent when administered in the absence of the polymer.

Compositions described herein may deliver an agent selectively to a tissue or cell. In certain embodiments, the tissue or cell to which the agent is selectively delivered is a target tissue or target cell, respectively. In certain embodiments, the compositions deliver at least about 10%, at least about 20%, at least about 30%, at least about 40%, at least about 50%, at least about 70%, at least about 100%, at least about 3-fold, at least about 10-fold, at least about 30-fold, at least about 100-fold, at least about 300-fold, or at least about 1000-fold more amount of the agent in unit time to a target tissue than to a non-target tissue or to a target cell than to a non-target cell. The amount of agent may be measured by the exposure, concentration, and/or bioavailability of the agent in a tissue or cell as described herein.

The compositions described herein (e.g., pharmaceutical compositions) including one or more agents (e.g., pharmaceutical agents) may be useful in treating and/or preventing a disease. In certain embodiments, the compositions are useful in gene therapy. In certain embodiments, the compositions are useful for treating and/or preventing a genetic disease. In certain embodiments, the compositions are useful for treating and/or preventing a proliferative disease. In certain embodiments, the compositions are useful for treating and/or preventing cancer. In certain embodiments, the compositions are useful for treating and/or preventing a benign neoplasm. In certain embodiments, the compositions are useful for treating and/or preventing pathological angiogenesis. In certain embodiments, the compositions are useful for treating and/or preventing an inflammatory disease. In certain embodiments, the compositions are useful for treating and/or preventing an autoimmune disease. In certain embodiments, the compositions are useful for treating and/or preventing a hematological disease. In certain embodiments, the compositions are useful for treating and/or preventing a neurological disease. In certain embodiments, the compositions are useful for treating and/or preventing a gastrointestinal disease. In certain embodiments, the compositions are useful for treating and/or preventing a liver disease. In certain embodiments, the compositions are useful for treating and/or preventing a spleen disease. In certain embodiments, the compositions are useful for treating and/or preventing a respiratory disease. In certain embodiments, the compositions are useful for treating and/or preventing a lung disease. In certain embodiments, the compositions are useful for treating and/or preventing a painful condition. In certain embodiments, the compositions are useful for treating and/or preventing a psychiatric disorder. In certain embodiments, the compositions are useful for treating and/or preventing a musculoskeletal disease. In certain embodiments, the compositions are useful for treating and/or preventing a genitourinary diseases. In certain embodiments, the compositions are useful for treating and/or preventing a metabolic disorder.

The agents may be provided in an effective amount in a composition described herein. In certain embodiments, the effective amount is a therapeutically effective amount. In certain embodiments, the effective amount is a prophylactically effective amount. In certain embodiments, the effective amount is an amount effective for treating a disease described herein. In certain embodiments, the effective amount is an amount effective for preventing a disease described herein.

An effective amount of an agent may vary from about 0.001 mg/kg to about 1000 mg/kg in one or more dose administrations for one or several days (depending on the mode of administration). In certain embodiments, the effective amount per dose varies from about 0.001 to about 1000 mg/kg, from about 0.01 to about 750 mg/kg, from about 0.1 to about 500 mg/kg, from about 1.0 to about 250 mg/kg, and from about 10.0 to about 150 mg/kg.

A composition of the disclosure may include a particle described herein. In certain embodiments, the composition is in the form of a particle. In certain embodiments, the particle is a nanoparticle or microparticle. In certain embodiments, a composition described herein is in the form of liposomes or micelles. It is understood that, in certain embodiments, the particles, micelles, or liposomes result from self-assembly of the components of the composition. In certain embodiments, the particle, micelle, or liposome encapsulates an agent. The agent to be delivered by the particle, micelle, or liposome may be in the form of a gas, liquid, or solid. The polymers described herein may be combined with polymers (synthetic or natural), surfactants, cholesterol, carbohydrates, proteins, lipids, lipidoids, etc. to form the particles. These particles may be further combined with an excipient to form the composition. The particles, micelles, and liposomes are described in more detail herein.

The compositions described herein (e.g., pharmaceutical compositions) can be prepared by any method known in the art (e.g., pharmacology). In certain embodiments, such preparatory methods include the steps of bringing a polymer described herein into association with an agent described herein (i.e., the "active ingredient"), optionally with a carrier or excipient, and/or one or more other accessory ingredients, and then, if necessary and/or desirable, shaping, and/or packaging the product into a desired single- or multi-dose unit.

Compositions can be prepared, packaged, and/or sold in bulk, as a single unit dose, and/or as a plurality of single unit doses. A unit dose is a discrete amount of the composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the excipient (e.g., the pharmaceutically or cosmetically acceptable excipient), and/or any additional ingredients in a composition described herein will vary, depending upon the identity, size, and/or condition of the subject to whom the composition is administered and further depending upon the route by which the composition is to be administered. The composition may comprise between 0.1% and 100% (w/w) active ingredient.

Excipients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, and mixtures thereof.

Exemplary chelating agents include ethylenediaminetetraacetic acid (EDTA) and salts and hydrates thereof (e.g., sodium edetate, disodium edetate, trisodium edetate, calcium disodium edetate, and dipotassium edetateke), citric acid and salts and hydrates thereof (e.g., citric acid monohydrate), fumaric acid and salts and hydrates thereof, malic acid and salts and hydrates thereof, phosphoric acid and salts and hydrates thereof, tartaric acid and salts and hydrates thereof, and mixtures thereof.

Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, thimerosal, and mixtures thereof.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, sorbic acid, and mixtures thereof.

Exemplary alcohol preservatives include ethanol, polyethylene glycol, phenol, phenolic compounds, bisphenol, chlorobutanol, hydroxybenzoate, phenylethyl alcohol, and mixtures thereof.

Exemplary acidic preservatives include vitamin A, vitamin C, vitamin E, beta-carotene, citric acid, acetic acid, dehydroacetic acid, ascorbic acid, sorbic acid, phytic acid, and mixtures thereof.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, Euxyl®, and mixtures thereof.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Additionally, the composition may further comprise an apolipoprotein. Previous studies have reported that Apolipoprotein E (ApoE) was able to enhance cell uptake and gene silencing for a certain type of materials. See, e.g., Akinc, A., et al., *Targeted delivery of RNAi therapeutics with endogenous and exogenous ligand-based mechanisms*. Mol Ther. 18(7): p. 1357-64. In certain embodiments, the apolipoprotein is ApoA, ApoB, ApoC, ApoE, or ApoH, or an isoform thereof.

Liquid dosage forms for oral and parenteral administration include emulsions, microemulsions, solutions, suspensions, syrups and elixirs. In certain embodiments, the emulsions, microemulsions, solutions, suspensions, syrups and elixirs are or cosmetically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, excipient or carrier (e.g., pharmaceutically or cosmetically acceptable excipient or carrier) such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the formulation art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a composition of this disclosure may include ointments, pastes, creams, lotions, gels, powders, solutions, sprays, inhalants, and/or patches. Generally, the active ingredient is admixed under sterile conditions with a carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599, 302; 5,334,144; 5,993,412; 5,649,912; 5,569,189; 5,704, 911; 5,383,851; 5,893,397; 5,466,220; 5,339,163; 5,312, 335; 5,503,627; 5,064,413; 5,520,639; 4,596,556; 4,790, 824; 4,941,880; 4,940,460; and PCT publications WO 97/37705 and WO 97/13537. Ballistic powder/particle delivery devices which use compressed gas to accelerate the agent in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A composition described herein can be prepared, packaged, and/or sold in a formulation suitable for pulmonary administration via the buccal cavity. Such a formulation may comprise dry particles which comprise the active ingredient. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A composition described herein can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Polymers described herein are typically formulated in dosage unit form for ease of administration and uniformity of dosage. It will be understood, however, that the total daily usage of the compositions of the present disclosure will be decided by the attending physician within the scope of sound medical judgment. The specific therapeutically effective dose level for any particular subject or organism will depend upon a variety of factors including the disease being treated and the severity of the disorder, the activity of the specific active ingredient employed, the specific composition employed, the age, body weight, general health, sex, and diet of the subject, the time of administration, route of administration, and rate of excretion of the specific active ingredient employed, the duration of the treatment, drugs used in combination or coincidental with the specific active ingredient employed, and like factors well known in the medical arts.

The compositions described herein can be administered by any suitable route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In certain embodiments, the compositions are administered by oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of an agent required to achieve an effective amount will vary from subject to subject, depending, for example, on species, age, and general condition of a subject, severity of the side effects or disorder, identity of the particular agent, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an agent for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an agent per unit dosage form.

In certain embodiments, the agents described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided compositions to an adult. The amount to be administered to, for example, a child or an adolescent can be determined by a medical practitioner or person skilled in the art and can be lower or the same as that administered to an adult.

Compositions described herein may further include a hydrophilic polymer (e.g., polyethylene glycol (PEG)). The compositions described herein may further include a lipid (e.g., a steroid, a substituted or unsubstituted cholesterol, or a polyethylene glycol (PEG)-containing material). In certain embodiments, the lipid included in the compositions is a triglyceride, a driglyceride, a PEGylated lipid, a phospholipid (e.g., 1,2-distearoyl-sn-glycero-3-phosphocholine (DSPC)), a steroid, a substituted or unsubstituted cholesterol, an apolipoprotein, or a combination thereof. In certain embodiments, the compositions include two components selected from the group consisting of the following components: a hydrophilic polymer, a triglyceride, a driglyceride, a PEGylated lipid, a phospholipid, a steroid, a substituted or unsubstituted cholesterol, and an apolipoprotein. In certain embodiments, the compositions include three components selected from the group consisting of the following components: a hydrophilic polymer, a triglyceride, a driglyceride, a PEGylated lipid, a phospholipid, a steroid, a substituted or unsubstituted cholesterol, and an apolipoprotein. In certain embodiments, the compositions include at least four components selected from the group consisting of the following components: a hydrophilic polymer, a triglyceride, a driglyceride, a PEGylated lipid, a phospholipid, a steroid, a substituted or unsubstituted cholesterol, and an apolipoprotein. In certain embodiments, the compositions include a hydrophilic polymer, a phospholipid, a steroid, and a substituted or unsubstituted cholesterol. In certain embodiments, the compositions include PEG, DSPC, and substituted or unsubstituted cholesterol.

Compositions described herein may be useful in other applications, e.g., non-medical applications. Nutraceutical compositions described herein may be useful in the delivery of an effective amount of a nutraceutical, e.g., a dietary supplement, to a subject in need thereof. Cosmetic compositions described herein may be formulated as a cream, ointment, balm, paste, film, or liquid, etc., and may be useful in the application of make-up, hair products, and materials useful for personal hygiene, etc. Compositions described herein may be useful for other non-medical applications, e.g., such as an emulsion, emulsifier, or coating, useful, for example, as a food component, for extinguishing fires, for disinfecting surfaces, for oil cleanup, and/or as a bulk material.

Agents

Agents that are delivered by the compositions described herein (e.g., pharmaceutical compositions) may be pharmaceutical (e.g., therapeutic or prophylactic), diagnostic, cosmetic, or nutraceutical agents. Any chemical compound to be administered to a subject or to be contacted with a tissue or cell may be delivered using the compositions, complexes, particles, micelles, or liposomes described herein. The agent may be a small molecule (e.g., a small organic molecule or small inorganic molecule), protein, peptide, polynucleotide, targeting agent, isotopically labeled chemical compound, vaccine, or immunological agent. The agent may be an agent useful in bioprocessing (e.g., intracellular manufacturing of proteins, such as a cell's bioprocessing of a commercially useful chemical or fuel). For example, intracellular delivery of an agent may be useful in bioprocessing by maintaining the cell's health and/or growth, e.g., in the manufacturing of proteins. Any chemical compound to be administered to a subject or contacted with a tissue or cell may be delivered to the subject, tissue, or cell using the compositions described herein.

Exemplary agents that may be included in a composition described herein include, but are not limited to, small molecules, organometallic compounds, polynucleotides, proteins, peptides, carbohydrates, monosaccharides, oligosaccharides, polysaccharides, nucleoproteins, mucoproteins, lipoproteins, small molecules linked to proteins, glycoproteins, steroids, nucleotides, oligonucleotides, polynucleotides, nucleosides, antisense oligonucleotides, lipids, hormones, vitamins, cells, metals, targeting agents, isotopically labeled chemical compounds, drugs (e.g., compounds approved for human or veterinary use by the U.S. Food and Drug Administration as provided in the Code of Federal Regulations), vaccines, immunological agents, agents useful in bioprocessing, and mixtures thereof. The targeting agents are described in more detail herein. In certain embodiments, the agents are nutraceutical agents. In certain embodiments, the agents are pharmaceutical agents (e.g., a therapeutic or prophylactic agent). In certain embodiments, the agent is an antibiotic agent (e.g., an anti-bacterial, anti-viral, or anti-fungal agent), anesthetic, steroidal agent, anti-proliferative agent, anti-inflammatory agent, anti-angiogenesis agent, anti-neoplastic agent, anti-cancer agent, anti-diabetic agent, antigen, vaccine, antibody, decongestant, antihypertensive, sedative, birth control agent, progestational agent, anti-cholinergic, analgesic, immunosuppressant, anti-depressant, anti-psychotic, β-adrenergic blocking agent, diuretic, cardiovascular active agent, vasoactive agent, non-steroidal, nutritional agent, anti-allergic agent, or pain-relieving agent. Vaccines may comprise isolated proteins or peptides, inactivated organisms and viruses, dead organisms and viruses, genetically altered organisms or viruses, and cell extracts. Therapeutic and prophylactic agents may be combined with interleukins, interferon, cytokines, and adjuvants such as cholera toxin, alum, and Freund's adjuvant, etc.

In certain embodiments, an agent to be delivered or used in a composition described herein is a polynucleotide. In certain embodiments, the agent is plasmid DNA (pDNA). In certain embodiments, the agent is single-stranded DNA (ssDNA), double-stranded DNA (dsDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA. In certain embodiments, the agent is RNA. In certain embodiments, the agent is small interfering RNA (siRNA). In certain embodiments, the agent is messenger RNA (mRNA). In certain embodiments, the agent is single-stranded RNA (ssRNA), double-stranded RNA (dsRNA), small interfering RNA (siRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA. In certain embodiments, the agent is an RNA that carries out RNA interference (RNAi). The phenomenon of RNAi is discussed in greater detail, for example, in the following references: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, upon delivery of an RNA into a subject, tissue, or cell, the RNA is able to interfere with the expression of a specific gene in the subject, tissue, or cell. In certain embodiments, the agent is a pDNA, siRNA, mRNA, or a combination thereof.

In certain embodiments, the polynucleotide may be provided as an antisense agent or RNAi. See, e.g., Fire et al., *Nature* 391:806-811, 1998. Antisense therapy is meant to include, e.g., administration or in situ provision of single- or double-stranded polynucleotides, or derivatives thereof, which specifically hybridize, e.g., bind, under cellular conditions, with cellular mRNA and/or genomic DNA, or mutants thereof, so as to inhibit the expression of the encoded protein, e.g., by inhibiting transcription and/or translation. See, e.g., Crooke, "Molecular mechanisms of action of antisense drugs," *Biochim. Biophys. Acta* 1489(1): 31-44, 1999; Crooke, "Evaluating the mechanism of action of anti-proliferative antisense drugs," *Antisense Nucleic Acid Drug Dev.* 10(2):123-126, discussion 127, 2000; *Methods in Enzymology* volumes 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

The RNA and/or RNAi described herein can be designed and/or predicted using one or more of a large number of available algorithms. To give but a few examples, the following resources can be utilized to design and/or predict polynucleotides: algorithms found at Alnylum Online; Dharmacon Online; OligoEngine Online; Molecula Online; Ambion Online; BioPredsi Online; RNAi Web Online; Chang Bioscience Online; Invitrogen Online; LentiWeb Online GenScript Online; Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7: 271.

The polynucleotide included in a composition described herein may be of any size or sequence, and they may be single- or double-stranded. In certain embodiments, the polynucleotide includes at least about 30, at least about 100, at least about 300, at least about 1,000, at least about 3,000, or at least about 10,000 base pairs. In certain embodiments, the polynucleotide includes less than about 10,000, less than about 3,000, less than about 1,000, less than about 300, less than about 100, or less than about 30 base pairs. Combinations of the above ranges (e.g., at least about 100 and less than about 1,000) are also within the scope of the disclosure. The polynucleotide may be provided by any suitable means known in the art. In certain embodiments, the polynucleotide is engineered using recombinant techniques. See, e.g., Ausubel et al., *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry. The polynucleotide may be isolated and/or purified. In certain embodiments, the polynucleotide is substantially free of impurities. In certain embodiments, the polynucleotide is at least about 50%, at least about 60%, at least about 70%, at least about 80%, at least about 90%, at least about 95%, or at least about 99% free of impurities.

The polynucleotide may be modified by physical, chemical, and/or biological means. The modifications include methylation, phosphorylation, and/or end-capping, etc. In certain embodiments, the modifications lead to increased stability of the polynucleotide.

Wherever a polynucleotide is employed in the present disclosure, a derivative of the polynucleotide may also be used. These derivatives include products resulted from modifications of the polynucleotide in the base moieties, sugar moieties, and/or phosphate moieties of the polynucleotide. Modified base moieties include, but are not limited to, 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugar moieties include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any suitable means known in the art; however, as will be appreciated by those of skill in the art, the modified polynucleotides may be prepared using synthetic chemistry in vitro.

The polynucleotide described herein may be in any form, such as a circular plasmid, a linearized plasmid, a cosmid, a viral genome, a modified viral genome, or an artificial chromosome.

The polynucleotide described herein may be of any sequence. In certain embodiments, the polynucleotide encodes a protein or peptide. The encoded protein may be an enzyme, structural protein, receptor, soluble receptor, ion channel, active (e.g., pharmaceutically active) protein, cytokine, interleukin, antibody, antibody fragment, antigen, coagulation factor, albumin, growth factor, hormone, or insulin, etc. The polynucleotide may also comprise regulatory regions to control the expression of a gene. These regulatory regions may include, but are not limited to, promoters, enhancer elements, repressor elements, TATA boxes, ribosomal binding sites, and stop sites for transcription. In certain embodiments, the polynucleotide is not intended to encode a protein. For example, the polynucleotide may be used to fix an error in the genome of the cell being transfected.

In certain embodiments, the polynucleotide described herein comprises a sequence encoding an antigenic peptide or protein. A composition containing the polynucleotide can be delivered to a subject to induce an immunologic response sufficient to decrease the chance of a subsequent infection and/or lessen the symptoms associated with such an infection. The polynucleotide of these vaccines may be combined with interleukins, interferon, cytokines, and/or adjuvants described herein.

The antigenic protein or peptides encoded by the polynucleotide may be derived from bacterial organisms, such as *Streptococcus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi*, and *Camphylobacter jejuni*; from viruses, such as smallpox virus, influenza A virus, influenza B virus, respiratory syncytial virus, parainfluenza virus, measles virus, HIV virus, varicella-zoster virus, herpes simplex 1 virus, herpes simplex 2 virus, cytomegalovirus, Epstein-Barr virus, rotavirus, rhinovirus, adenovirus, papillomavirus, poliovirus, mumps virus, rabies virus, rubella virus, coxsackieviruses, equine encephalitis virus, Japanese encephalitis virus, yellow fever virus, Rift Valley fever virus, hepatitis A virus, hepatitis B virus, hepatitis C virus, hepatitis D virus, and hepatitis E virus; and from fungal, protozoan, or parasitic organisms, such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis*, and *Schistosoma mansoni.*

An agent described herein may be covalently or non-covalently (e.g., complexed or encapsulated) attached to a polymer described herein, or included in a composition described herein. In certain embodiments, upon delivery of the agent into a cell, the agent is able to interfere with the expression of a specific gene in the cell.

In certain embodiments, an agent described herein may be a mixture of two or more agents that may be useful as, e.g., combination therapies. A composition including the mixture can be used to achieve a synergistic effect. In certain embodiments, the composition including the mixture can be used to improve the activity and/or bioavailability, reduce and/or modify the metabolism, inhibit the excretion, and/or modify the distribution of at least one of the two or more agents in a subject, tissue, or cell to which the mixture is administered or dosed. It will also be appreciated that the composition including the mixture may achieve a desired effect for the same disorder, and/or it may achieve different effects. The two or more agents in the mixture may be useful for treating and/or preventing a same disease or different diseases described herein.

The compositions (e.g., pharmaceutical compositions) described herein can be administered concurrently with, prior to, or subsequent to the one or more agents (e.g., pharmaceutical agents). Each one of the agents may be administered at a dose and/or on a time schedule determined for that agent. The agents may also be administered together with each other and/or with the composition described herein in a single dose or administered separately in different doses. The particular combination to employ in a regimen will take into account compatibility of the agents and/or the desired therapeutic and/or prophylactic effect to be achieved. In general, it is expected that the agents utilized in combination be utilized at levels that do not exceed the levels at which they are utilized individually. In some embodiments, the levels utilized in combination will be lower than those utilized individually.

Targeting Agents

Since it is often desirable to target a particular cell, collection of cells, or tissue, polymers described herein, and the compositions, complexes, liposomes, micelles, and particles thereof, may be modified to include targeting moieties or targeting agents. For example, the polymers may include a targeting moiety or targeting agent. The targeting agent may be included throughout a particle of a polymer described herein or may be only on the surface (e.g., outer or inner surface) of the particle. A targeting agent may be a protein, peptide, carbohydrate, glycoprotein, lipid, small molecule, or polynucleotide, and a targeting moiety may be a fragment of the targeting agent. The targeting moiety or targeting agent may be used to target specific cells or tissues or may be used to promote endocytosis or phagocytosis of the particle. The targeting moieties or targeting agents include the ones known in the art. See, e.g., Cotten et al., *Methods Enzym.* 217:618, 1993. Examples of the targeting moieties and targeting agents include, but are not limited to, antibodies, antibodies, proteins, peptides, carbohydrates, receptor ligands, sialic acid, aptamers, and fragments thereof. If a targeting agent is included throughout a particle, the targeting agent may be included in the mixture that is used to form the particle. If the targeting agent is only on the surface of a particle, the targeting agent may be associated with (e.g., by covalent or non-covalent (e.g., electrostatic, hydrophobic, hydrogen bonding, van der Waals, π-π stacking) interactions) the formed particle using standard chemical techniques.

Complexes of a Lipidoid and an Agent

The present disclosure contemplates that the polymers described herein are useful in the delivery of an agent described herein to a subject, tissue, or cell. Without wishing to be bound by any particular theory, the polymers have several desirable properties that make a composition that includes the polymer and an agent suitable for delivering the agent to a subject, tissue, or cell. The desirable properties include: 1) the ability of the polymer to complex with and "protect" the agent that may otherwise be labile; 2) the ability of the polymer to buffer the pH in an endosome of the cell; 3) the ability of the polymer to act as a "proton sponge" and cause endosomolysis; and 4) the ability of the polymer to substantially neutralize the negative charges of the agent.

A polymer and agent described herein may form a complex in a composition of the disclosure. For example, a polymer described herein comprises secondary or tertiary amino moieties, which may be useful in enhancing the ability of a composition that includes an agent to deliver the agent to a subject, tissue, or cell. The amino moieties, sterically hindered or not, may non-covalently interact with the agent, such as a polynucleotide. The agent may be contacted with the polymer under conditions suitable to form a complex. In certain embodiments, the agent binds to the polymer to form a complex through non-covalent interactions. In certain embodiments, the agent binds to the polymer to form a complex through electrostatic interactions. Without wishing to be bound by any particular theory, one or more amino moieties of a polymer described herein may be positively charged, and an agent described herein may be negatively charged (e.g., at the monophosphate, diphosphate, and/or triphosphate moieties of a polynucleotide), when the polymer, or a composition thereof, is delivered to a subject, tissue, or cell (e.g., under physiological conditions). The agent may bind to the polymer to form a complex through electrostatic interactions between the negative charges of the polymer and the positive charges of the agent. By substantially neutralizing the charges (e.g., negative charges) of the agent, the resulting complex may be able to more easily pass through the hydrophobic membranes (e.g., cytoplasmic, lysosomal, endosomal, or nuclear) of a cell, compared to an agent whose charges are not neutralized. In certain embodiments, the complex is substantially neutral. In certain embodiments, the complex is slightly positively charged. In certain embodiments, the complex has a positive $\zeta$-potential. In certain embodiments the $\zeta$-potential is between 0 and +30.

An agent described herein, such as a polynucleotide, may be degraded chemically and/or enzymatically (e.g., by nucleases). The interaction of a polymer described herein with the agent is thought to at least partially prevent the degradation of the agent.

A polymer described herein may be at least partially provided as a salt (e.g., being protonated) so as to form a complex with a negatively charged agent. In certain embodiments, the complex form particles that are useful in the delivery of the agent to a subject, tissue, or cell. In certain embodiments, more than one polymer described herein are associated with an agent. For example, the complex may include 1-10, 1-100, 1-1,000, 10-1,000, 100-1,000, or 100-10,000 polymers described herein associated with an agent.

The ratio of the amount of a polymer described herein to the amount of an agent to be delivered in a described composition that includes the polymer and agent (e.g., as a complex) may be adjusted so that the agent may be more efficiently delivered to a subject, tissue, or cell and/or the toxicity of the composition is decreased. In certain embodiments, the ratio of the polymer to the agent is at least about 1:1, at least about 2:1, at least about 5:1, at least about 10:1, at least about 20:1, at least about 50:1, at least about 100:1, at least about 200:1, or at least about 500:1 mol/mol. In certain embodiments, the ratio of the polymer to the agent is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the disclosure.

The ratio of the amount of the amino moieties of a polymer described herein to the amount of the phosphate moieties of a polynucleotide (i.e., nitrogen:phosphate ratio) in a described composition that includes the polymer and polynucleotide (e.g., as a complex) may also be adjusted so that the polynucleotide may be more efficiently delivered to a subject, tissue, or cell and/or the toxicity of the composition is decreased. See, e.g., Incani et al., *Soft Matter* (2010) 6:2124-2138. In certain embodiments, the nitrogen:phosphate ratio is at least about 1:1, at least about 2:1, at least about 5:1, at least about 10:1, at least about 20:1, at least about 50:1, at least about 100:1, at least about 200:1, or at least about 500:1 mol/mol. In certain embodiments, the nitrogen:phosphate ratio is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the disclosure.

Particles

A composition that includes a polymer and agent described herein may be in the form of a particle. In certain embodiments, the polymer is in the form of a particle. In certain embodiments, the agent is in the form of a particle. In certain embodiments, the polymer and agent form a complex, and the complex is in the form of a particle. In certain embodiments, the polymer encapsulates the agent and is in the form of a particle. In certain embodiments, the polymer is mixed with the agent, and the mixture is in the form of a particle.

Encapsulation of an agent (e.g., a polynucleotide, such as an siRNA) within particles (e.g., nanoparticles) may offer numerous benefits for delivering the agent to a subject, tissue, or cell, including protection from degradation of the agent by ubiquitous nucleases, passive and active targeting, and/or evasion of endosomal Toll-like receptors. To date, several polymeric, lipid, and dendritic nanoparticles have been developed for the encapsulation and delivery of siRNAs. Despite the delivery successes met by some of these carriers, challenges to efficient delivery exist, including particle dissociation via serum proteins, cellular uptake, endosomal escape, and appropriate intracellular disassembly. To address some of these challenges, single parameter studies that evaluate the effect of chemical structure on a single biological property or on delivery performance have been reported. Furthermore, high-throughput synthetic methods have been exploited for the accelerated discovery of potent lipid nanoparticles (LNPs) and evaluation of structure activity relationships (SARs). In spite of these efforts, the relationships between physicochemical properties of nanoparticles and biological barriers, and that between biological barriers and gene silencing activity remain unclear. This lack of clarity has also resulted in poor in vitro-in vivo translation.

In certain embodiments, a polymer described herein (e.g., a plurality of molecules of the polymer) is in the form of a particle. In certain embodiments, a complex of a polymer and agent described herein in a described composition is in the form of a particle. In certain embodiments, the particle is a microparticle. In certain embodiments, the particle is a nanoparticle. Such a nanoparticle may be referred to as a "lipid nanoparticle" (LNP). In certain embodiments, the average diameter of the particle is less than about 1 mm, less than about 300 µm, less than about 100 µm, less than about 30 µm less than about 10 µm, less than about 3 µm, less than about 1 µm, less than about 300 nm, less than about 100 nm, less than about 30 nm, or less than about 10 nm. In certain embodiments, the average diameter of the particle is at least about 10 nm, at least about 30 nm, at least about 100 nm, at least about 300 nm, at least about 1 µm, at least about 3 µm, at least about 10 µm, at least about 30 µm, at least about 100 µm, at least about 300 µm, or at least about 1 mm. Combinations of the above ranges (e.g., at least about 100 nm and less than about 1 µm) are also within the scope of the present disclosure.

In certain embodiments, a particle described herein includes an agent described herein. The particle may encapsulate the agent. A particle described herein may further include additional materials such as polymers (e.g., synthetic polymers (e.g., PEG, PLGA) and natural polymers (e.g., phospholipids, proteins)). In certain embodiments, the particle further includes a lipid (e.g., a steroid, a substituted or unsubstituted cholesterol, or a polyethylene glycol (PEG)-containing material). In certain embodiments, the additional materials are approved by a regulatory agency, such as the U.S. FDA, for human and/or veterinary use.

A particle described herein may be prepared using any suitable method known in the art, such as precipitation, milling, spray drying, single and double emulsion solvent evaporation, solvent extraction, phase separation, and simple and complex coacervation. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, and polydispersity). The method of preparing the particles and the conditions (e.g., solvent, temperature, concentration, and air flow rate) used may also depend on the agent being complexed, encapsulated, or mixed, and/or the composition of the matrix.

Methods developed for making particles for delivery of agents that are included in the particles are described in the literature. See, e.g., Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988.

If the particles prepared by any of the methods described herein have a size range outside of the desired range, the particles can be sized, for example, using a sieve. The particles may also be coated. In certain embodiments, the particles are coated with a targeting agent. In certain embodiments, the particles are coated with a surface-altering agent. In some embodiments, the particles are coated to achieve desirable surface properties (e.g., a particular charge).

Particles described herein may also be a micelle, liposome, or lipoplex.

In certain embodiments, the polydispersity index (PDI, determined by dynamic light scattering) of the particles described herein (e.g., particles included in a composition described herein) is between 0.01 and 0.9, between 0.1 and 0.9, between 0.1 and 0.7, between 0.1 and 0.5, between 0.01 and 0.4, between 0.03 and 0.4, between 0.1 and 0.4, between 0.01 and 0.3, between 0.03 and 0.3, or between 0.1 and 0.3.

Micelles, Liposomes, and Lipoplexes

A composition including a polymer and agent described herein may be in the form of a micelle or liposome. In certain embodiments, the polymer is in the form of a micelle or liposome. An agent described herein may be inside a micelle or liposome, and a lipidoid described herein may be inside the micelle or liposome. In certain embodiments, in a micelle or liposome, an agent is encapsulated in a lipidoid. Micelles and liposomes are typically useful in delivering an agent, such as a hydrophobic agent, to a subject, tissue, or cell. When the micelle or liposome is complexed with (e.g., encapsulates or covers) a polynucleotide, the resulting complex may be referred to as a "lipoplex." Many techniques for preparing micelles and liposomes are known in the art, and any such method may be used to make micelles and liposomes.

In certain embodiments, liposomes are formed through spontaneous assembly. In some embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This may prevent interaction of water with the hydrocarbon core of the bilayers at the edges. Once these liposomes have formed, reducing the size of the liposomes can be modified through input of sonic energy (sonication) or mechanical energy (extrusion). See, e.g., Walde, P. "Preparation of Vesicles (Liposomes)" In *Encyclopedia of Nanoscience and Nanotechnology*; Nalwa, H. S. Ed. American Scientific Publishers: Los Angeles, 2004; Vol. 9, pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein by reference. The preparation of lipsomes may involve preparing a polymer described herein for hydration, hydrating the polymer with agitation, and sizing the vesicles to achieve a homogenous distribution of liposomes. A polymer described herein may be first dissolved in a solvent in a container to result in a homogeneous mixture. The solvent is then removed to form a film. This film is thoroughly dried to remove residual amount of the solvent, e.g., by placing the container in vacuo for a period of time. Hydration of the film may be accomplished by adding an aqueous medium and agitating the resulting mixture. Disruption of LMV suspensions using sonic energy typically produces small unilamellar vesicles (SUV) with diameters in the range of 15-50 nm. Lipid extrusion is a technique in which a lipid suspension is forced through a polycarbonate filter with a defined pore size to yield particles having a diameter near the pore size of the filter used. Extrusion through filters with 100 nm pores typically yields large, unilamellar vesicles (LUV) with a mean diameter of 120-140 nm. In certain embodiments, the amount of a polymer described herein in the liposome is between about 30 mol % and about 80 mol %, between about 40 mol % and about 70 mol %, or between about 60 mol % and about 70 mol %, inclusive. In certain embodiments, the polymer further complexes an agent, such as a polynucleotide.

Liposomes and micelles may also be prepared according to methods in the following scientific papers: Narang et al., "Cationic Lipids with Increased DNA Binding Affinity for Nonviral Gene Transfer in Dividing and Nondividing Cells," *Bioconjugate Chem.* 16:156-68, 2005; Hofland et al., "Formation of stable cationic lipid/DNA complexes for gene transfer," *Proc. Natl. Acad. Sci. USA* 93:7305-7309, July 1996; Byk et al., "Synthesis, Activity, and Structure—Activity Relationship Studies of Novel Cationic Lipids for DNA Transfer," *J. Med. Chem.* 41(2):224-235, 1998; Wu et al., "Cationic Lipid Polymerization as a Novel Approach for Constructing New DNA Delivery Agents," *Bioconjugate Chem.* 12:251-57, 2001; Lukyanov et al., "Micelles from lipid derivatives of water-soluble polymers as delivery systems for poorly soluble drugs," *Advanced Drug Delivery Reviews* 56:1273-1289, 2004; Tranchant et al., "Physicochemical optimisation of plasmid delivery by cationic lipids," *J. Gene Med.* 6:S24-S35, 2004; van Balen et al., "Liposome/Water Lipophilicity: Methods, Information Content, and Pharmaceutical Applications," *Medicinal Research Rev.* 24(3):299-324, 2004.

Kits

Also described herein are kits (e.g., packs). The kits provided may comprise a polymer or composition described herein and a container (e.g., a vial, ampule, bottle, syringe, and/or dispenser package, or other suitable container). In some embodiments, a kit described herein further includes a second container comprising an excipient for dilution or suspension of a polymer or composition described herein. In some embodiments, the polymer or composition provided in the first container and the polymer or composition provided in the second container are combined to form one unit dosage form.

In certain embodiments, the kits described herein are useful for delivering an agent to a subject, tissue, or cell. In certain embodiments, the kits are useful for delivering an agent to a target tissue described herein. In certain embodiments, the kits are useful for treating a disease described herein. In certain embodiments, the kits are useful for preventing a disease described herein.

In certain embodiments, the described kits further include instructions for administering a polymer or composition described herein. The kits may also include information as required by a regulatory agency such as the U.S. Food and Drug Administration (FDA). In certain embodiments, the information included in the kits is prescribing information. In certain embodiments, the kits, including the instructions, provide for delivering an agent described herein to a subject, tissue, or cell. In certain embodiments, the kits, including the instructions, provide for treating a disease described herein. In certain embodiments, the kits, including the instructions, provide for preventing a disease described herein. The kit described herein may include one or more agents described herein as a separate composition.

Methods of Treatment and Uses

It is estimated that over 10,000 human diseases are caused by genetic disorders, which are abnormalities in genes or chromosomes. See, e.g., McClellan, J. and M. C. King, *Genetic heterogeneity in human disease*. Cell. 141(2): p. 210-7; Leachman, S. A., et al., *J. Dermatol. Sci.*, 2008. 51(3): p. 151-7. Many of these diseases are fatal, such as cancer, severe hypercholesterolemia, and familial amyloidotic polyneuropathy. See, e.g., Frank-Kamenetsky, M., et al., *Proc. Natl. Acad. Sci. U.S.A.* 2008. 105(33): p. 11915-20; Coelho, T., *Curr. Opin. Neurol.*, 1996. 9(5): p. 355-9. Since the discovery of gene expression silencing via RNA interference (RNAi) by Fire and Mello (Fire, A., et al., *Nature*, 1998. 391(6669): p. 806-11), there has been extensive effort toward developing therapeutic applications for RNAi in humans. See, e.g., Davis, M. E., *Mol. Pharm.* 2009. 6(3): p. 659-68; Whitehead, K. A., R. Langer, and D. G. Anderson, *Nat. Rev. Drug Discovery,* 2009. 8(2): p. 129-138; Tan, S. J., et al., *Small.* 7(7): p. 841-56; Castanotto, D. and J. J. Rossi, *Nature,* 2009. 457(7228): p. 426-33; Chen, Y. and L. Huang, *Expert Opin. Drug Deliv.* 2008. 5(12): p. 1301-11; Weinstein, S. and D. Peer, *Nanotechnology.* 21(23): p. 232001; Fenske, D. B. and P. R. Cullis, *Expert Opin. Drug Deliv.* 2008. 5(1): p. 25-44; and Thiel, K. W. and P. H. Giangrande, *Oligonucleotides,* 2009. 19(3): p. 209-22. Currently, there are more than 20 clinical trials ongoing or completed involving siRNA therapeutics, which have shown promising results for the treatment of various diseases. See, e.g., Burnett, J. C., J. J. Rossi, and K. Tiemann, *Biotechnol. J.* 6(9): p. 1130-46. However, the efficient and safe delivery of siRNA is still a key challenge in the development of siRNA therapeutics. See, e.g., Juliano, R., et al., *Mol. Pharm.* 2009. 6(3): p. 686-95.

In another aspect, the present disclosure provides methods of delivering an agent described herein (e.g., polynucleotide) to a subject, tissue, or cell. In certain embodiments, described herein are methods of delivering the agent to a target tissue or target cell described herein. In certain embodiments, described herein are methods of selectively delivering the agent to a target tissue, compared to a non-target tissue. In certain embodiments, described herein are methods of selectively delivering the agent to a target cell, compared to a non-target cell. In certain embodiments, the agent is delivered into the subject, tissue, or cell by the methods described herein. In certain embodiments, the agent is selectively delivered into the target tissue or target cell by the methods described herein, compared to a non-target tissue or non-target cell, respectively.

Another aspect of the present disclosure relates to methods of increasing the delivery of an agent to a subject, tissue, or cell. In certain embodiments, the delivery of the agent to the subject, tissue, or cell is increased by a method described herein. In certain embodiments, the delivery of the agent to the subject, tissue, or cell by a method described herein is increased compared to the delivery of the agent to the subject, tissue, or cell by a control method that does not involve a polymer described herein.

In another aspect, the present disclosure provides methods of treating a disease described herein in a subject in need thereof.

In another aspect, the present disclosure provides methods of preventing a disease described herein in a subject in need thereof.

In certain embodiments, a disease described herein is a genetic disease. In certain embodiments, the disease is a proliferative disease. In certain embodiments, the disease is cancer. In certain embodiments, the disease is a benign neoplasm. In certain embodiments, the disease is pathological angiogenesis. In certain embodiments, the disease is an inflammatory disease. In certain embodiments, the disease is an autoimmune disease. In certain embodiments, the disease is a hematological disease. In certain embodiments, the disease is a neurological disease. In certain embodiments, the disease is a gastrointestinal disease. In certain embodiments, the disease is a liver disease. In certain embodiments, the disease is a spleen disease. In certain embodiments, the disease is a respiratory disease. In certain embodiments, the disease is a lung disease. In certain embodiments, the disease is a painful condition. In certain embodiments, the painful condition is inflammatory pain. In certain embodiments, the painful condition is associated with an inflammatory disorder and/or an autoimmune disorder. In certain embodiments, the disease is a psychiatric disorder. In certain embodiments, the disease is a musculoskeletal disease. In certain embodiments, the disease is a genitourinary disease. In certain embodiments, the disease is a metabolic disorder.

Another aspect of the present disclosure relates to methods of genetically engineering a subject. In certain embodiments, the subject is genetically engineered to increase the growth of the subject. In certain embodiments, the subject is genetically engineered to increase the subject's resistance to pathogenic organisms and/or microorganisms (e.g., viruses, bacteria, fungi, protozoa, and parasites).

In certain embodiments, a method described herein includes administering to the subject a composition described herein. In certain embodiments, a method described herein includes administering to the subject an effective amount of a composition described herein. In certain embodiments, a method described herein includes administering to the subject a therapeutically effective amount of a pharmaceutical composition described herein.

In certain embodiments, a method described herein includes contacting the tissue with a composition described herein. In certain embodiments, a method described herein includes contacting the tissue with an effective amount of a composition described herein. In certain embodiments, a method described herein includes contacting the tissue with a therapeutically effective amount of a pharmaceutical composition described herein.

In certain embodiments, a method described herein includes contacting the cell with a composition described herein. In certain embodiments, a method described herein includes contacting the cell with an effective amount of a composition described herein. In certain embodiments, a method described herein includes contacting the cell with a therapeutically effective amount of a pharmaceutical composition described herein.

In certain embodiments, a subject described herein is a human. In certain embodiments, the subject is an animal. In certain embodiments, the subject is a non-human animal. The animal may be of either sex and may be at any stage of development. In certain embodiments, the subject is a fish. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is a human with a disease described herein. In certain embodiments, the subject is a human suspected of having a disease described. In certain embodiments, the subject is a human at risk of developing a disease described herein.

In certain embodiments, a cell described herein is in vivo. In certain embodiments, a cell described herein is in vitro.

Another aspect of the present disclosure relates to methods of screening a library of polymers to identify a polymer that is useful in the methods described herein. In certain embodiments, the methods of screening a library of polymers are useful in identifying a polymer with desired or undesired properties. In certain embodiments, the desired property is solubility in water, solubility at different pH, ability to bind polynucleotides, ability to bind heparin, ability to bind small molecules, ability to bind protein, ability to form microparticles, ability to increase transfection efficiency, ability to support normal cell growth, ability to inhibit abnormal cell growth, ability to support cell attachment, ability to support tissue growth, and/or intracellular delivery of an agent described herein and/or an agent complexed or attached thereto to aid in bioprocessing. In certain embodiments, the undesired property is the lack of a desired property. In certain embodiments, the polymer identified is useful for delivering an agent described herein to a subject, tissue, or cell. In certain embodiments, the polymer identified is useful for treating and/or preventing a disease described herein. In certain embodiments, the library of polymers is a library of polymers described herein. In certain embodiments, the methods of screening a library include providing at least two different polymers described herein; and performing at least one assay using the polymers. In certain embodiments, at least one assay is useful in identifying a polymer that is useful in a method described herein. The assay may be an immunoassay, such as a sandwich-type assay, competitive binding assay, one-step direct test, two-step test, or blot assay. The step of performing at least one assay may be performed robotically or manually.

Another aspect of the present disclosure relates to uses of a polymer described herein in a method described herein (e.g., uses for delivering an agent to a subject, tissue, or cell; uses for treating a disease in a subject in need thereof; and uses for preventing a disease in a subject).

Another aspect of the present disclosure relates to uses of a composition described herein (e.g., a composition including a described polymer, agent, and optionally a pharmaceutical excipient) in a method described herein (e.g., uses for delivering an agent to a subject, tissue, or cell; uses for treating a disease in a subject in need thereof; and uses for preventing a disease in a subject).

EXAMPLES

In order that the invention described herein may be more fully understood, the following examples are set forth. The synthetic and biological examples described in this application are offered to illustrate the polymers, pharmaceutical compositions, and methods provided herein and are not to be construed in any way as limiting their scope.

Example 1. Preparation of the Polymers

Reineke and co-workers previously reported on the development of poly(glycoamidoamines) (PGAAs), which contain amines and multiple hydroxyl groups along their polymer backbone. These polymers previously demonstrated efficient delivery of both DNA and siRNA in different cell types.[11-13, 15, 16] Beginning with the PGAA polymer backbone,[16-18] we prepared modified PGAAs to create new polymer-brush materials for incorporation into lipid nanoparticle formulations. First, we synthesized three different PGAA polymers based on tartarate, galactarate, or glucarate sugars combined with three different amine-containing monomers using the synthetic methods reported by Reineke.[11-14] $^1$HNMR of PGAA polymers is consistent with reported data. Next, alkyl tails were added onto amines on the PGAA backbone using ring opening reactions with epoxides to afford a modified polymer-brush materials.[18-21] Structures of polymers were confirmed by $^1$HNMR and their molecular weight was calculated based on the results reported by Reineke and $^1$HNMR of final products.[12] The nomenclature for polymer identification signifies the combination of these three structural building blocks; a three letter code (Tar—tartarate, Gal—galactarate, or Glu—glucarate) denoting the sugar used to prepare the PGAA backbone followed by the number of amines in the amine-containing monomer (N1, N2, or N3), and finally the number of carbons (C8, C10, C12, C14, or C16) on the epoxides used for modification.

The polymers provided herein can be prepared from readily available starting materials using the following general methods and procedures (e.g., the method shown in Scheme 1, 2, or 3). It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization.

Scheme 1. An exemplary preparation of the polymers described herein

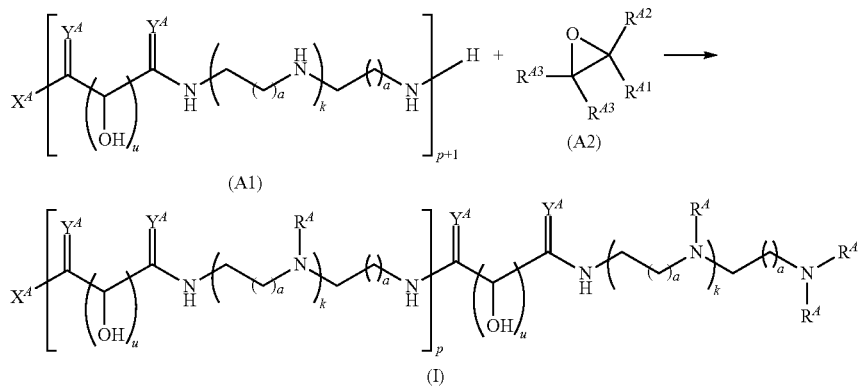

In an exemplary reaction, a mixture of a polymer of Formula (A1) and an epoxide of Formula (A2) in a suitable solvent (e.g., EtOH) was heated in a microwave reactor at 150° C. for 5 h. The resulting reaction mixture was purified by flash chromatography to yield the desired polymer of Formula (I) (e.g., a polymer in Table 7).

Scheme 2. An exemplary preparation of the polymers described herein

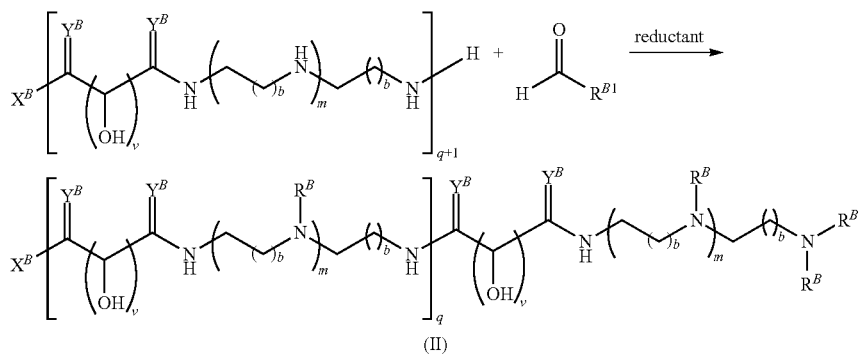

Scheme 3. An exemplary preparation of the polymers described herein

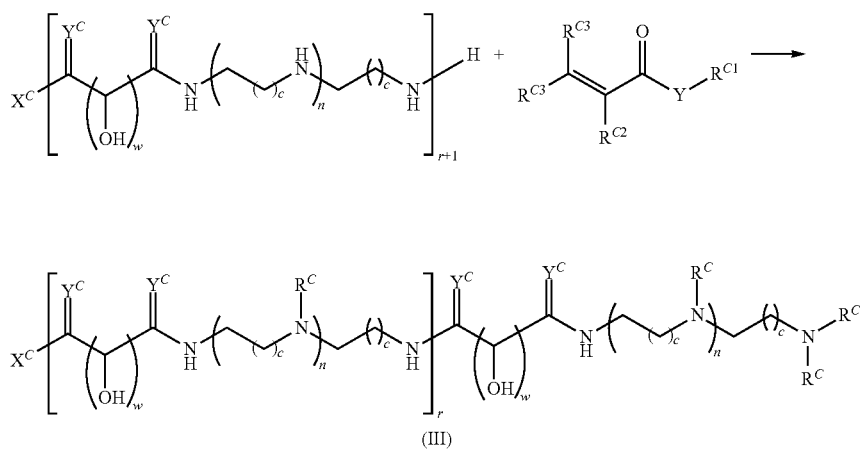

General Methods and Materials

Microwave irradiations were performed in a BIOTAGE INITIATOR. $^1$H NMR spectra were measured on a 300 & 500 MHz VARIAN spectrometer using TMS as internal standard. Mass spectra were measured on a WATERS ACQUITY LC-MS instrument. Thin-layer chromatography (TLC) was performed on precoated silica gel GF plates purchased from Merck, Inc. ISCO COMBIFLASH systems were used for flash chromatography. All other chemicals were obtained from commercial sources and were used as received.

An exemplary preparation of the polymers described herein was through ring opening reactions between poly (glycoamidoamine) (PGAAs) and epoxides. TarN, GalN, and GluN were synthesized using the methods reported by Reineke.[11-14] $^1$HNMR of PGAA polymers is consistent with reported data.[11, 14] Different analytical data are shown below when different batches of a polymer was characterized.

Polymers of any one of Formulae (I') and (I") can be prepared using methods similar to the methods of preparing the polymers of Formula (I). Polymers of any one of Formulae (II') and (II") can be prepared using methods similar to the methods of preparing the polymers of Formula (II). Polymers of any one of Formulae (III') and (III") can be prepared using methods similar to the methods of preparing the polymers of Formula (III).

Polymer A1o
$^1$HNMR (500 MHz, D$_2$O): δ 4.53 (s, 2H), 3.28-3.50 (m, 4H), 2.65-2.80 (m, 4H).

Polymer A1b
$^1$HNMR (500 MHz, D$_2$O): δ 4.51 (s, 2H), 3.28-3.57 (m, 4H), 2.63-2.85 (m, 8H).

Polymer A1c
$^1$HNMR (500 MHz, D$_2$O): δ 4.52 (s, 2H), 3.28-3.47 (m, 4H), 2.65-2.81 (m, 12H).

Polymer A1p
$^1$HNMR (500 MHz, D$_2$O): δ 4.41 (s, 2H), 4.00 (s, 2H), 3.31-3.48 (m, 4H), 2.71-2.80 (m, 4H).

Polymer A1q
$^1$HNMR (500 MHz, D$_2$O): δ 4.40 (m, 2H), 4.00 (s, 2H), 3.31-3.43 (m, 4H), 2.69-2.79 (m, 8H).

Polymer A1r
$^1$HNMR (500 MHz, D$_2$O): δ 4.35-4.43 (m, 2H), 3.92-4.04 (m, 2H), 3.30-3.47 (m, 4H), 2.65-2.85 (m, 12H).

Polymer A1s
$^1$HNMR (500 MHz, D$_2$O): δ 4.34-4.39 (m, 1H), 4.21-4.29 (m, 1H), 4.07-4.13 (m, 1H), 3.92-3.98 (t, 1H), 3.36-3.54 (m, 4H), 2.80-2.99 (m, 4H).

Polymer A1t
$^1$HNMR (500 MHz, D$_2$O): δ 4.29-4.38 (m, 1H), 4.22-4.26 (m, 1H), 4.06-4.13 (m, 1H), 3.91-3.99 (t, 1H), 3.30-3.55 (m, 4H), 2.73-2.98 (m, 8H).

Polymer A1u
$^1$HNMR (500 MHz, D$_2$O): δ 4.18-4.38 (m, 2H), 4.02-4.12 (m, 1H), 3.87-3.98 (m, 1H), 3.23-3.53 (m, 4H), 2.74-2.96 (m, 12H).

Polymer TarN1C8
$^1$HNMR (500 MHz, CDCl$_3$): δ 8.10 (s, 1H), 3.96-4.91 (m, 3H), 3.21-3.8 (m, 4H), 2.06-3.15 (m, 6H), 1.15-1.37 (m, 14H), 0.79-0.94 (t, 3H).

Polymer TarN1C10
$^1$HNMR (500 MHz, CDCl$_3$): δ 8.08 (s, 1H), 3.22-5.40 (m, 7H), 2.09-3.05 (m, 6H), 1.18-1.50 (m, 18H), 0.82-0.95 (t, 3H).

Polymer TarN1C12
$^1$HNMR (500 MHz, CDCl$_3$): δ 8.10 (s, 1H), 3.87-4.98 (m, 3H), 3.09-3.86 (m, 4H), 1.98-3.04 (m, 6H), 1.17-1.52 (m, 22H), 0.79-0.94 (t, 3H).

Polymer TarN1C14
$^1$HNMR (500 MHz, CDCl$_3$): δ 8.08 (s, 1H), 3.91-4.96 (m, 3H), 3.09-3.90 (m, 4H), 2.00-3.06 (m, 6H), 1.14-1.52 (m, 26H), 0.78-0.95 (t, 3H).

Polymer TarN2C8
$^1$HNMR (500 MHz, CDCl$_3$): δ 8.02 (s, 1H), 3.98-4.79 (m, 4H), 3.40-3.84 (m, 4H), 2.02-3.02 (m, 12H), 1.16-1.55 (m, 28H), 0.79-0.96 (t, 6H).

Polymer TarN2C10
$^1$HNMR (500 MHz, CDCl$_3$): δ 7.96 (s, 1H), 4.00-4.83 (m, 4H), 3.40-3.84 (m, 4H), 2.19-3.06 (m, 12H), 1.18-1.52 (m, 36H), 0.78-0.94 (t, 6H).

Polymer TarN2C12
$^1$HNMR (500 MHz, CDCl$_3$): δ 7.90-8.23 (br, 1H), 4.00-4.87 (m, 4H), 3.40-3.84 (m, 4H), 2.09-3.02 (m, 12H), 1.17-1.51 (m, 44H), 0.79-0.95 (t, 6H).

Polymer TarN2C14
$^1$HNMR (500 MHz, CDCl$_3$): δ 7.88-8.25 (br, 1H), 3.99-4.80 (m, 4H), 3.24-3.87 (m, 4H), 2.14-3.02 (m, 12H), 1.17-1.52 (m, 52H), 0.82-0.94 (t, 6H).

Polymer TarN3C8
$^1$HNMR (500 MHz, CDCl$_3$): δ 8.05 (s, 1H), 3.30-3.80 (m, 9H), 2.02-2.98 (m, 18H), 1.17-1.52 (m, 42H), 0.83-0.96 (t, 9H).

Polymer TarN3C10
$^1$HNMR (500 MHz, CDCl$_3$): δ 7.84-8.15 (br, 1H), 3.95-4.95 (m, 5H), 3.47-3.80 (m, 4H), 2.15-3.01 (m, 18H), 1.16-1.51 (m, 54H), 0.79-0.93 (t, 9H).

Polymer TarN3C12
$^1$HNMR (500 MHz, CDCl$_3$): δ 7.88-8.19 (br, 1H), 3.93-4.67 (m, 5H), 3.45-3.76 (m, 4H), 2.20-2.97 (m, 18H), 1.18-1.50 (m, 66H), 0.78-0.95 (t, 9H).

Polymer TarN3C14
$^1$HNMR (500 MHz, CDCl$_3$): δ 7.88-8.14 (br, 1H), 4.00-4.66 (m, 5H), 3.47-3.76 (m, 4H), 2.16-2.93 (m, 18H), 1.19-1.50 (m, 78H), 0.82-0.95 (t, 9H).

Polymer TarN4C8
$^1$HNMR (500 MHz, CDCl$_3$): δ 7.92-8.07 (br, 1H), 4.20-4.91 (m, 6H), 3.50-3.75 (m, 4H), 2.01-3.07 (m, 26H), 1.18-1.52 (m, 56H), 0.82-0.98 (t, 12H).

Polymer TarN4C10
$^1$HNMR (500 MHz, CDCl$_3$): δ 7.97-8.13 (br, 1H), 4.00-4.77 (m, 6H), 3.45-3.80 (m, 4H), 1.98-3.21 (m, 26H), 1.03-1.58 (m, 72H), 0.78-0.96 (t, 12H).

Polymer TarN4C12
$^1$HNMR (500 MHz, CDCl$_3$): δ 8.08 (s, 1H), 3.51-3.82 (m, 4NHCO, 4-6OH), 2.07-2.97 (m, 26H), 1.18-1.52 (m, 88H), 0.82-0.96 (t, 12H).

Polymer TarN4C14
$^1$HNMR (500 MHz, CDCl$_3$): δ 8.05 (s, 1H), 3.38-3.85 (m, 10H), 2.18-2.92 (m, 26H), 1.17-1.49 (m, 104H), 0.82-0.96 (t, 12H).

Polymer GalN2C8
$^1$HNMR (500 MHz, CDCl$_3$): δ 8.00 (s, 1H), 3.18-4.76 (m, 10H), 2.19-3.05 (m, 12H), 1.17-1.50 (m, 28H), 0.81-0.91 (t, 6H).

Polymer GalN2C10
$^1$HNMR (500 MHz, CDCl$_3$): δ 8.00 (s, 1H), 3.19-4.99 (m, 10H), 2.21-3.03 (m, 12H), 1.12-1.54 (m, 36H), 0.82-0.95 (t, 6H).

Polymer GalN2C12
$^1$HNMR (500 MHz, CDCl$_3$): δ 8.01 (s, 1H), 3.97-5.19 (m, 6H), 3.41-3.84 (m, 4H), 2.20-3.04 (m, 12H), 1.16-1.52 (m, 44H), 0.84-0.95 (t, 6H).

Polymer GalN2C14
$^1$HNMR (500 MHz, CDCl$_3$): δ 7.98 (s, 1H), 4.27-5.06 (m, 6H), 3.51-3.86 (m, 4H), 2.26-3.05 (m, 12H), 1.19-1.56 (m, 52H), 0.82-1.00 (t, 6H).

Polymer GalN3C8
$^1$HNMR (500 MHz, CDCl$_3$): δ 7.95-8.21 (br, 1H), 3.25-4.78 (m, 11H), 2.15-2.94 (m, 18H), 1.18-1.52 (m, 42H), 0.82-0.93 (t, 9H).

Polymer GalN3C10
$^1$HNMR (500 MHz, CDCl$_3$): δ 8.03 (s, 1H), 3.44-4.77 (m, 11H), 2.22-2.95 (m, 18H), 1.19-1.55 (m, 54H), 0.82-0.96 (t, 9H).

Polymer GalN3C12
$^1$HNMR (500 MHz, CDCl$_3$): δ 7.99 (s, 1H), 3.37-3.94 (m, 11H), 2.25-2.97 (m, 18H), 1.16-1.54 (m, 66H), 0.84-0.96 (t, 9H).

Polymer GalN3C14
$^1$HNMR (500 MHz, CDCl$_3$): δ 7.99 (s, 1H), 3.17-4.22 (m, 11H), 2.15-2.91 (m, 18H), 1.15-1.58 (m, 78H), 0.79-0.94 (t, 9H).

Polymer GalN4C8
$^1$HNMR (500 MHz, CDCl$_3$): δ 8.03 (s, 1H), 3.45-5.15 (m, 12H), 2.09-2.98 (m, 24H), 1.18-1.53 (m, 56H), 0.81-0.97 (t, 12H).

Polymer GalN4C10
$^1$HNMR (500 MHz, CDCl$_3$): δ 8.02 (s, 1H), 3.34-4.46 (m, 12H), 2.16-2.99 (m, 24H), 1.19-1.53 (m, 72H), 0.82-0.94 (t, 12H).

Polymer GalN4C12
$^1$HNMR (500 MHz, CDCl$_3$): δ 8.02 (s, 1H), 3.34-4.34 (m, 12H), 2.10-2.97 (m, 24H), 1.19-1.53 (m, 88H), 0.81-0.94 (t, 12H).

Polymer GalN4C14
$^1$HNMR (500 MHz, CDCl$_3$): δ 7.99 (s, 1H), 3.43-4.31 (m, 12H), 2.09-2.98 (m, 24H), 1.18-1.51 (m, 104H), 0.84-0.95 (t, 12H).

Polymer GluN1C10
$^1$HNMR (500 MHz, CDCl$_3$): δ 8.09 (s, 1H), 3.14-4.53 (m, 9H), 2.09-3.00 (m, 6H), 1.20-1.54 (m, 18H), 0.80-0.97 (t, 3H).

Polymer GluN1C12
$^1$HNMR (500 MHz, CDCl$_3$): δ 8.10 (s, 1H), 3.10-4.75 (m, 9H), 2.01-2.99 (m, 6H), 1.17-1.54 (m, 22H), 0.82-0.95 (t, 3H).

Polymer GluN1C14
$^1$HNMR (500 MHz, CDCl$_3$): δ 8.01 (s, 1H), 3.09-4.85 (m, 9H), 2.11-3.00 (m, 6H), 1.18-1.53 (m, 26H), 0.82-0.94 (t, 3H).

Polymer GluN2C8
$^1$HNMR (500 MHz, CDCl$_3$): δ 8.06 (s, 1H), 3.09-4.45 (m, 10H), 2.22-3.00 (m, 12H), 1.16-1.49 (m, 28H), 0.82-0.93 (t, 6H).

Polymer GluN2C10
$^1$HNMR (500 MHz, CDCl$_3$): δ 8.04 (s, 1H), 3.21-4.84 (m, 10H), 2.11-3.12 (m, 12H), 1.22-1.54 (m, 36H), 0.85-0.97 (t, 6H).

Polymer GluN2C12
$^1$HNMR (500 MHz, CDCl$_3$): δ 8.06 (s, 1H), 3.07-4.82 (m, 10H), 2.00-3.00 (m, 12H), 1.05-1.82 (m, 44H), 0.78-1.01 (t, 6H).

Polymer GluN2C14
$^1$HNMR (500 MHz, CDCl$_3$): δ 8.08 (s, 1H), 3.20-4.40 (m, 10H), 2.06-3.10 (m, 12H), 1.15-1.82 (m, 52H), 0.79-1.04 (t, 6H).

Polymer GluN3C6
$^1$HNMR (500 MHz, CDCl$_3$): δ 8.06 (s, 1H), 3.31-4.80 (m, 11H), 1.98-3.12 (m, 18H), 1.15-1.62 (m, 30H), 0.83-1.06 (t, 9H).

Polymer GluN3C8
$^1$HNMR (500 MHz, CDCl$_3$): δ 8.02 (s, 1H), 3.12-4.31 (m, 11H), 2.22-3.01 (m, 18H), 1.14-1.50 (m, 42H), 0.77-0.92 (t, 9H).

Polymer GluN3C10
$^1$HNMR (500 MHz, CDCl$_3$): δ 8.05 (s, 1H), 3.33-4.38 (m, 11H), 2.02-3.05 (m, 18H), 1.16-1.58 (m, 54H), 0.79-0.98 (t, 9H).

Polymer GluN3C12
$^1$HNMR (500 MHz, CDCl$_3$): δ 8.01 (s, 1H), 3.15-4.53 (m, 11H), 1.89-3.04 (m, 18H), 1.16-1.53 (m, 66H), 0.83-0.94 (t, 9H).

Polymer GluN3C14
$^1$HNMR (500 MHz, CDCl$_3$): δ 8.04 (s, 1H), 3.20-4.09 (m, 11H), 2.13-3.00 (m, 18H), 1.17-1.51 (m, 78H), 0.81-0.95 (t, 9H).

Polymer GluN4C8
$^1$HNMR (500 MHz, CDCl$_3$): δ 8.04 (s, 1H), 3.35-4.33 (m, 12H), 1.99-3.10 (m, 24H), 1.18-1.53 (m, 56H), 0.81-0.94 (t, 12H).

Polymer GluN4C10
$^1$HNMR (500 MHz, CDCl$_3$): δ 8.00 (s, 1H), 3.43-4.34 (m, 12H), 2.02-3.07 (m, 24H), 1.16-1.54 (m, 72H), 0.80-0.93 (t, 12H).

Polymer GluN4C12
$^1$HNMR (500 MHz, CDCl$_3$): δ 8.01 (s, 1H), 3.09-4.16 (m, 12H), 2.06-2.92 (m, 24H), 1.18-1.56 (m, 88H), 0.81-0.94 (t, 12H).

Polymer GluN4C14
$^1$HNMR (500 MHz, CDCl$_3$): δ 8.01 (s, 1H), 3.18-4.22 (m, 12H), 2.16-2.95 (m, 24H), 1.07-1.54 (m, 104H), 0.79-0.96 (t, 12H).

Polymer TarN1C10
$^1$HNMR (500 MHz, CDCl3): δ 8.10 (s, 1H), 3.96-4.91 (m, 3H), 3.21-3.8 (m, 4H), 2.06-3.15 (m, 6H), 1.15-1.37 (m, 14H), 0.79-0.94 (t, 3H).

Polymer TarN2C10
$^1$HNMR (500 MHz, CDCl3): δ 8.02 (s, 1H), 3.98-4.79 (m, 4H), 3.40-3.84 (m, 4H), 2.02-3.02 (m, 12H), 1.16-1.55 (m, 28H), 0.79-0.96 (t, 6H).

Polymer TarN3C10
$^1$HNMR (500 MHz, CDCl3): δ 8.05 (s, 1H), 3.30-3.80 (m, 9H), 2.02-2.98 (m, 18H), 1.17-1.52 (m, 42H), 0.83-0.96 (t, 9H).

Polymer TarN1C12
$^1$HNMR (500 MHz, CDCl3): δ 8.08 (s, 1H), 3.22-5.40 (m, 7H), 2.09-3.05 (m, 6H), 1.18-1.50 (m, 18H), 0.82-0.95 (t, 3H).

Polymer TarN2C12
$^1$HNMR (500 MHz, CDCl3): δ 7.96 (s, 1H), 4.00-4.83 (m, 4H), 3.40-3.84 (m, 4H), 2.19-3.06 (m, 12H), 1.18-1.52 (m, 36H), 0.78-0.94 (t, 6H).

Polymer TarN3C12
$^1$HNMR (500 MHz, CDCl3): δ 7.84-8.15 (br, 1H), 3.95-4.95 (m, 5H), 3.47-3.80 (m, 4H), 2.15-3.01 (m, 18H), 1.16-1.51 (m, 54H), 0.79-0.93 (t, 9H).

Polymer TarN1C14
$^1$HNMR (500 MHz, CDCl3): δ 8.10 (s, 1H), 3.87-4.98 (m, 3H), 3.09-3.86 (m, 4H), 1.98-3.04 (m, 6H), 1.17-1.52 (m, 22H), 0.79-0.94 (t, 3H).

Polymer TarN2C14
$^1$HNMR (500 MHz, CDCl3): δ 7.90-8.23 (br, 1H), 4.00-4.87 (m, 4H), 3.40-3.84 (m, 4H), 2.09-3.02 (m, 12H), 1.17-1.51 (m, 44H), 0.79-0.95 (t, 6H).

Polymer TarN3C14

¹HNMR (500 MHz, CDCl3): δ 7.88-8.19 (br, 1H), 3.93-4.67 (m, 5H), 3.45-3.76 (m, 4H), 2.20-2.97 (m, 18H), 1.18-1.50 (m, 66H), 0.78-0.95 (t, 9H).

Polymer TarN1C16

¹HNMR (500 MHz, CDCl3): δ 8.08 (s, 1H), 3.91-4.96 (m, 3H), 3.09-3.90 (m, 4H), 2.00-3.06 (m, 6H), 1.14-1.52 (m, 26H), 0.78-0.95 (t, 3H).

Polymer TarN2C16

¹HNMR (500 MHz, CDCl3): δ 7.88-8.25 (br, 1H), 3.99-4.80 (m, 4H), 3.24-3.87 (m, 4H), 2.14-3.02 (m, 12H), 1.17-1.52 (m, 52H), 0.82-0.94 (t, 6H).

Polymer TarN3C16

¹HNMR (500 MHz, CDCl3): δ 7.88-8.14 (br, 1H), 4.00-4.66 (m, 5H), 3.47-3.76 (m, 4H), 2.16-2.93 (m, 18H), 1.19-1.50 (m, 78H), 0.82-0.95 (t, 9H).

Polymer GalN2C10'

¹HNMR (500 MHz, CDCl3): δ 8.00 (s, 1H), 3.18-4.76 (m, 10H), 2.19-3.05 (m, 12H), 1.17-1.50 (m, 28H), 0.81-0.91 (t, 6H).

Polymer GalN3C10'

¹HNMR (500 MHz, CDCl3): δ 7.95-8.21 (br, 1H), 3.25-4.78 (m, 11H), 2.15-2.94 (m, 18H), 1.18-1.52 (m, 42H), 0.82-0.93 (t, 9H).

Polymer GalN2C12'

¹HNMR (500 MHz, CDCl3): δ 8.00 (s, 1H), 3.19-4.99 (m, 10H), 2.21-3.03 (m, 12H), 1.12-1.54 (m, 36H), 0.82-0.95 (t, 6H).

Polymer GalN3C12'

¹HNMR (500 MHz, CDCl3): δ 8.03 (s, 1H), 3.44-4.77 (m, 11H), 2.22-2.95 (m, 18H), 1.19-1.55 (m, 54H), 0.82-0.96 (t, 9H).

Polymer GalN2C14'

¹HNMR (500 MHz, CDCl3): δ 8.01 (s, 1H), 3.97-5.19 (m, 6H), 3.41-3.84 (m, 4H), 2.20-3.04 (m, 12H), 1.16-1.52 (m, 44H), 0.84-0.95 (t, 6H).

Polymer GalN3C14'

¹HNMR (500 MHz, CDCl3): δ 7.99 (s, 1H), 3.37-3.94 (m, 11H), 2.25-2.97 (m, 18H), 1.16-1.54 (m, 66H), 0.84-0.96 (t, 9H).

Polymer GalN2C16'

¹HNMR (500 MHz, CDCl3): δ 7.98 (s, 1H), 4.27-5.06 (m, 6H), 3.51-3.86 (m, 4H), 2.26-3.05 (m, 12H), 1.19-1.56 (m, 52H), 0.82-1.00 (t, 6H).

Polymer GalN3C16'

¹HNMR (500 MHz, CDCl3): δ 7.99 (s, 1H), 3.17-4.22 (m, 11H), 2.15-2.91 (m, 18H), 1.15-1.58 (m, 78H), 0.79-0.94 (t, 9H).

Polymer GluN2C10'

¹HNMR (500 MHz, CDCl3): δ 8.06 (s, 1H), 3.09-4.45 (m, 10H), 2.22-3.00 (m, 12H), 1.16-1.49 (m, 28H), 0.82-0.93 (t, 6H).

Polymer GluN3C10'

¹HNMR (500 MHz, CDCl3): δ 8.02 (s, 1H), 3.12-4.31 (m, 11H), 2.22-3.01 (m, 18H), 1.14-1.50 (m, 42H), 0.77-0.92 (t, 9H).

Polymer GluN1C12'

¹HNMR (500 MHz, CDCl3): δ 8.09 (s, 1H), 3.14-4.53 (m, 9H), 2.09-3.00 (m, 6H), 1.20-1.54 (m, 18H), 0.80-0.97 (t, 3H).

Polymer GluN2C12'

¹HNMR (500 MHz, CDCl3): δ 8.04 (s, 1H), 3.21-4.84 (m, 10H), 2.11-3.12 (m, 12H), 1.22-1.54 (m, 36H), 0.85-0.97 (t, 6H).

Polymer GluN3C12'

¹HNMR (500 MHz, CDCl3): δ 8.05 (s, 1H), 3.33-4.38 (m, 11H), 2.02-3.05 (m, 18H), 1.16-1.58 (m, 54H), 0.79-0.98 (t, 9H).

Polymer GluN1C14'

¹HNMR (500 MHz, CDCl3): δ 8.10 (s, 1H), 3.10-4.75 (m, 9H), 2.01-2.99 (m, 6H), 1.17-1.54 (m, 22H), 0.82-0.95 (t, 3H).

Polymer GluN2C14'

¹HNMR (500 MHz, CDCl3): δ 8.06 (s, 1H), 3.07-4.82 (m, 10H), 2.00-3.00 (m, 12H), 1.05-1.82 (m, 44H), 0.78-1.01 (t, 6H).

Polymer GluN3C14'

¹HNMR (500 MHz, CDCl3): δ 8.01 (s, 1H), 3.15-4.53 (m, 11H), 1.89-3.04 (m, 18H), 1.16-1.53 (m, 66H), 0.83-0.94 (t, 9H).

Polymer GluN1C16'

¹HNMR (500 MHz, CDCl3): δ 8.01 (s, 1H), 3.09-4.85 (m, 9H), 2.11-3.00 (m, 6H), 1.18-1.53 (m, 26H), 0.82-0.94 (t, 3H).

Polymer GluN2C16'

¹HNMR (500 MHz, CDCl3): δ 8.08 (s, 1H), 3.20-4.40 (m, 10H), 2.06-3.10 (m, 12H), 1.15-1.82 (m, 52H), 0.79-1.04 (t, 6H).

Polymer GluN3C16'

¹HNMR (500 MHz, CDCl3): δ 8.04 (s, 1H), 3.20-4.09 (m, 11H), 2.13-3.00 (m, 18H), 1.17-1.51 (m, 78H), 0.81-0.95 (t, 9H).

Example 2. Biological Assays of the Polymers Materials

Cholesterol was purchased from Sigma Aldrich; DOPE (1,2-dioleoyl-sn-glycero-3-phosphoethanolamine) and mPEG2000-DMG (1,2-dimyristoyl-sn-glycero-3-phosphoethanolamine-N-[methoxy(polyethylene glycol)-2000](ammonium salt)) were purchased from Avanti Polar Lipids. Slide-A-Lyzer dialysis cassettes were obtained from Pierce Thermo Scientific. The microfluidics devices were made as previously published.[22] The RiboGreen was ordered from Invitrogen Life Technologies, and used as according to the manufacturer guidelines. The EPO and luciferase mRNA used were generously provided by Shire. Serum separator tubes were purchased from BD biosciences. The EPO ELISA kits were from R&D Systems Inc.

General Procedures for Synthesis of Polymer Brush Materials.

Poly(glycoamidoamine) (PGAA) was synthesized according to synthetic methods reported by Reineke.[11] Polymer structures were confirmed with ¹HNMR. PGAAs undergo ring opening reactions with diverse epoxides to afford the desired polymer brush materials. A mixture of PGAA and epoxides (a ratio of 1.5:1 epoxides/amine) in EtOH was irradiated in a microwave oven at 140° C. for 5 h. The reaction mixture was purified by flash chromatography using a solvent system $CH_2Cl_2$:MeOH:$NH_4OH$ (aqueous) 87.5:11:1.5.

Formulation Procedure

Liposomes were formed using a microfluidics devices, as previously described.[22] Briefly, the polymer brush, DOPE, cholesterol, and mPEG2000-DMG were dissolved in ethanol and combined in a 5:2:2:1 weight ratio. The mRNA was dissolved in a 10 mM citrate buffer, pH3.0. The polymer:mRNA weight ratio was 10:1. The ethanol and aqueous solutions were combined in a 1:1 ratio using the microfluidics device, and immediately diluted two-fold in PBS. Formulations were then dialyzed against PBS dialysis cassettes. The relative mRNA entrapment was determined using a RIBOGREEN fluorescent assay and the particle size (e.g., volume mean particle diameter) was determined via dynamic light scattering (ZETAPALS, Brookhaven Instruments).

Cryo-Transmission Electron Microscopy (Cryo-TEM)

Cryo-TEM samples are prepared in a controlled environment vitrification system (CEVS) or using the commercial environmentally controlled automated VITROBOT (FEI, Netherlands), always at a controlled temperature (25° C.) and at saturation. A 6 µl drop of the suspension is placed on a 400-mesh TEM copper grid covered with a perforated carbon film. To remove excess solution and produce a thin liquid film the drop is blotted—manually in the CEVS and automatically in the VITROBOT. The blotted sample is then plunged into liquid ethane (−183° C.) to form a vitrified specimen and transferred to liquid nitrogen (−196° C.) for storage. Vitrified specimens are examined at temperatures below −175° C. using a GATAN 626 cryo holder either in a TECNAI T12 G2 TEM (FEI, Netherlands) or a PHILIPS CM120 TEM operating at 120 kV. Images are recorded on a GATAN MULTISCAN 791 camera or GATAN ULTRASCAN 1000 using the DIGITALMICROGRAPH software (Gatan, U.K.) in the low-dose imaging mode to minimize beam exposure and electron-beam radiation damage, as described.[26, 31]

Preparation of FFL and Human EPO Messenger RNA

Firefly Luciferase (FFL) and human erythropoietin (hEPO) messenger RNA were synthesized via in vitro transcription from a plasmid DNA template encoding the respective gene. The subsequent transcript was further reacted by the enzymatic addition of a 5' cap structure (Cap 1) and a 3' poly (A) tail of approximately 300 nucleotides in length as determined by gel electrophoresis.[32] The messenger RNA was purified using commercially available silica-based spin column technology.

In Vivo EPO mRNA Delivery in Mice

All procedures used in animal studies conducted at MIT were approved by the Institutional Animal Care and Use Committee (IACUC) and were also consistent with local, state and federal regulations as applicable. Formulated mRNA was administered intravenously via tail vein injection using C57BL/6 mice (Charles River Labs, 6 to 8 weeks old, 18-22 grams) were for mRNA expression experiments. After 6 hours, blood was collected from the mice via the tail vein, and serum was obtained using serum separation tubes. EPO levels were measured by an ELISA assay using standard EPO protein.

Biodistribution of TarN3C10-mRNA Nanoparticles in Mice

C57BL/6 mice were administered intravenously via tail vein injection for luciferase mRNA expression experiments. The mice were sacrificed 24 hours post injection; the pancreas, spleen, liver, kidneys, ovaries/uterus, heart, lungs, and thymus as well as a section of the adipose tissue and muscle tissue were then dissected. The tissues were examined with an IVIS imaging system from Caliper. Signal strength of the individual tissue was normalized against tissue weight.

Toxicity Study in Mice

Figure 4:
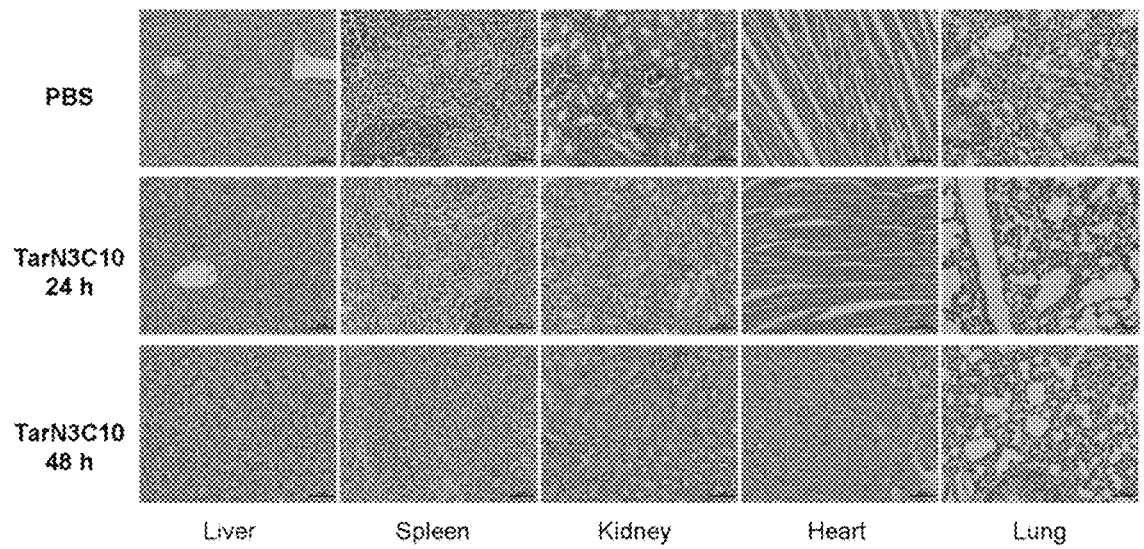
FIG. 4. Histology images of select tissues (liver, spleen, kidney, heart, and lung) of mice (Scale bar=50 μm). The mice were treated with PBS (control) or with TarN3C10 at 0.5 mg/kg at 24 hours or 48 hours. No histological abnormalities were observed in the treated tissues at either time.
Figure 6:
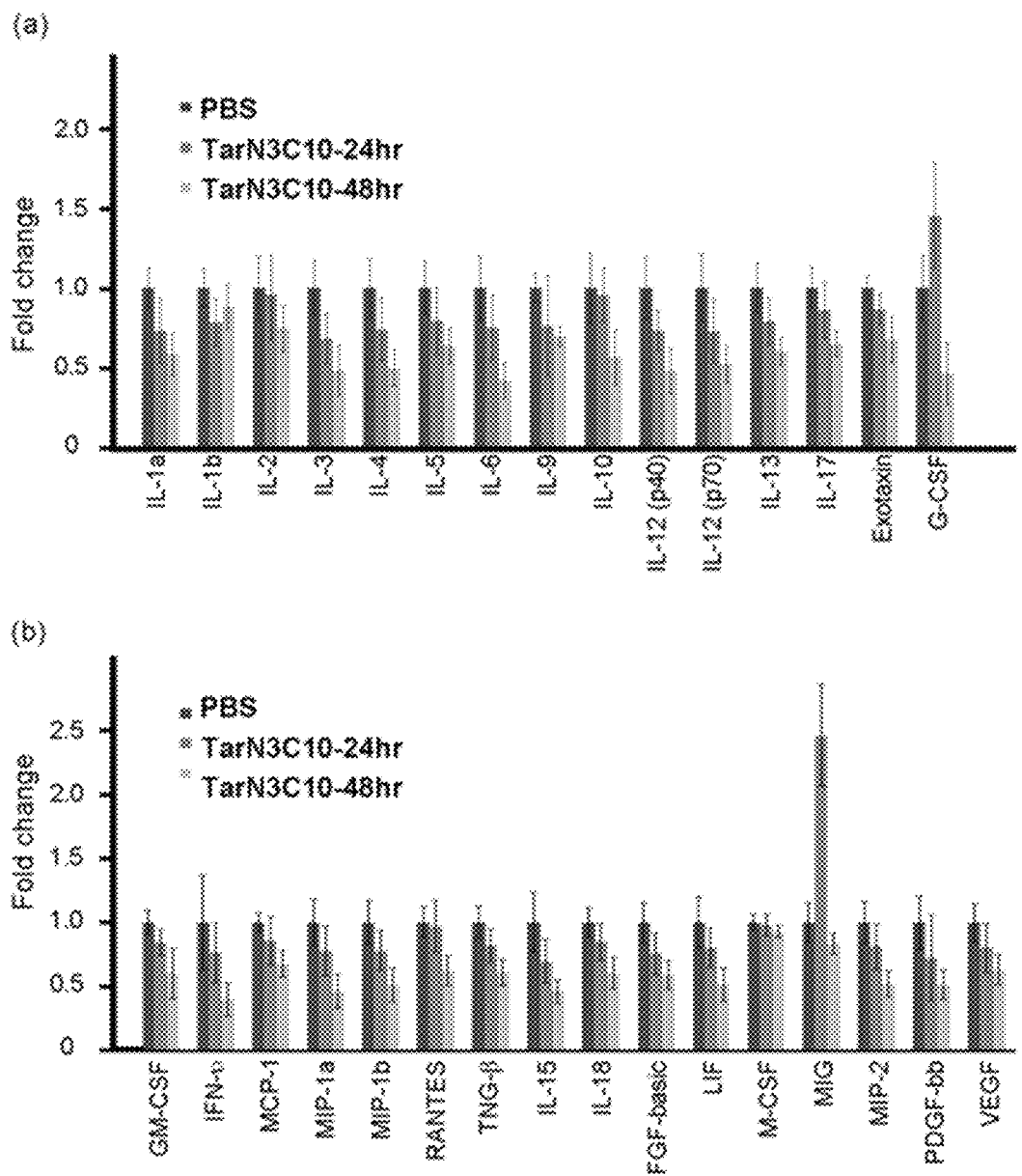
FIG. 6. Cytokine induction of TarN3C10 nanoparticles at 24 and 48 hours compared with PBS control group.

C57Bl/6 mice were administered intravenously TarN3C10 nanoparticles via tail vein injection. Blood and tissue samples were collected 24 and 48 hours after injection from the animals. Histopathology on liver, spleen, kidneys, heart, and lungs were processed and evaluated by the histology core facility of Koch Institute. Immunoassays were used to measure the levels of cytokines in a 96-well plate using BIO-PLEX PRO™ assays formatted on magnetic beads. 30 different cytokines were analyzed: IL-1, IL-2, IL-3, IL-4, IL-5, IL-6, IL-9, IL-10, IL-12 (p40), IL-12 (p70), IL-13, IL-17, Exotaxin, G-CSF, GM-CSF, IFN-γ, KC, MCP-1, MIP-1a, MIP-1b, RANTES, TNG-α, IL-18, FGF-basic, LIF, M-CSF, MIG, MIP-2, PDGF-bb, and VEGF. Clinical chemistry of ALT, AST, and total bilirubin were measured by IDEXX Laboratories. Exemplary results are shown in FIGS. 4 and 6 and Table 12.

TABLE 12

Liver chemistry for TarN3C10-treated mice

| Treatment | Time (hour) | ALT (U/L) | AST (U/L) | TBILI (mg/dL) |
| --- | --- | --- | --- | --- |
| PBS | 24 | 39.6 ± 6.4 | 198.2 ± 75.8 | 0.2 ± 0.1 |
| TarN3C10 | 24 | 44.8 ± 3.5 | 323.5 ± 93.2 | 0.2 ± 0.0 |
| TarN3C10 | 48 | 38.4 ± 3.4 | 227 ± 55.6 | 0.2 ± 0.0 |

Blood samples were taken at 24 & 48 h after administration. Control: PBS. ALT: alanine aminotransferase. AST: aspartate aminotransferase. TBILI: total bilirubin (n=4 or 5).

In Vivo Factor VII (FVII) Silencing in Mice

Figure 1B:
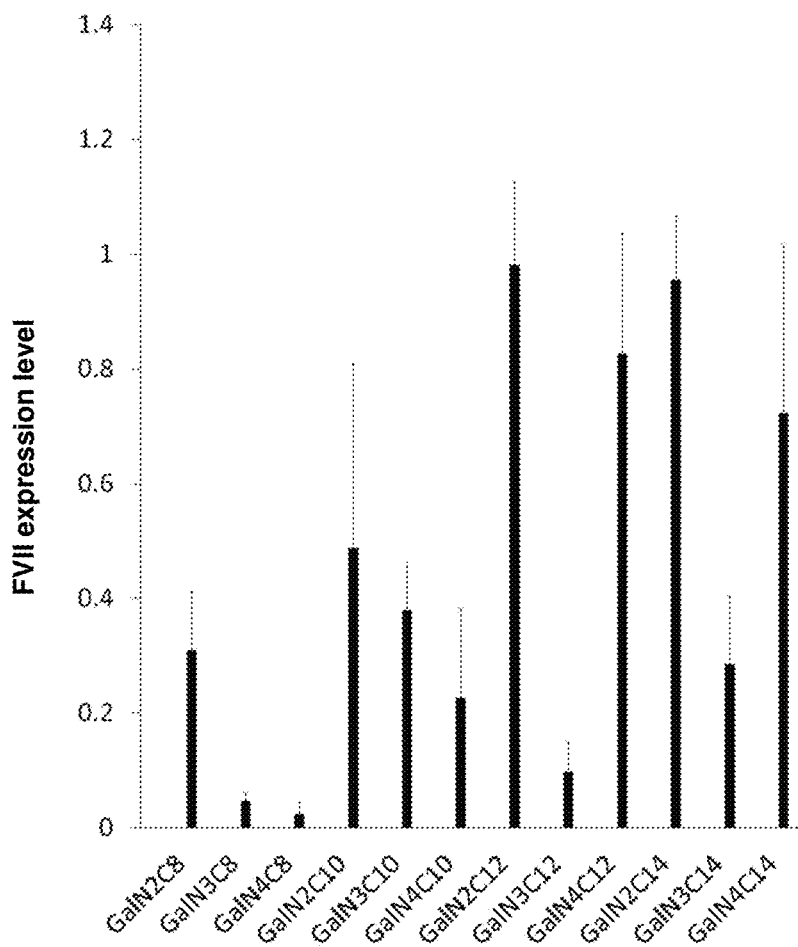
Figure 1C:
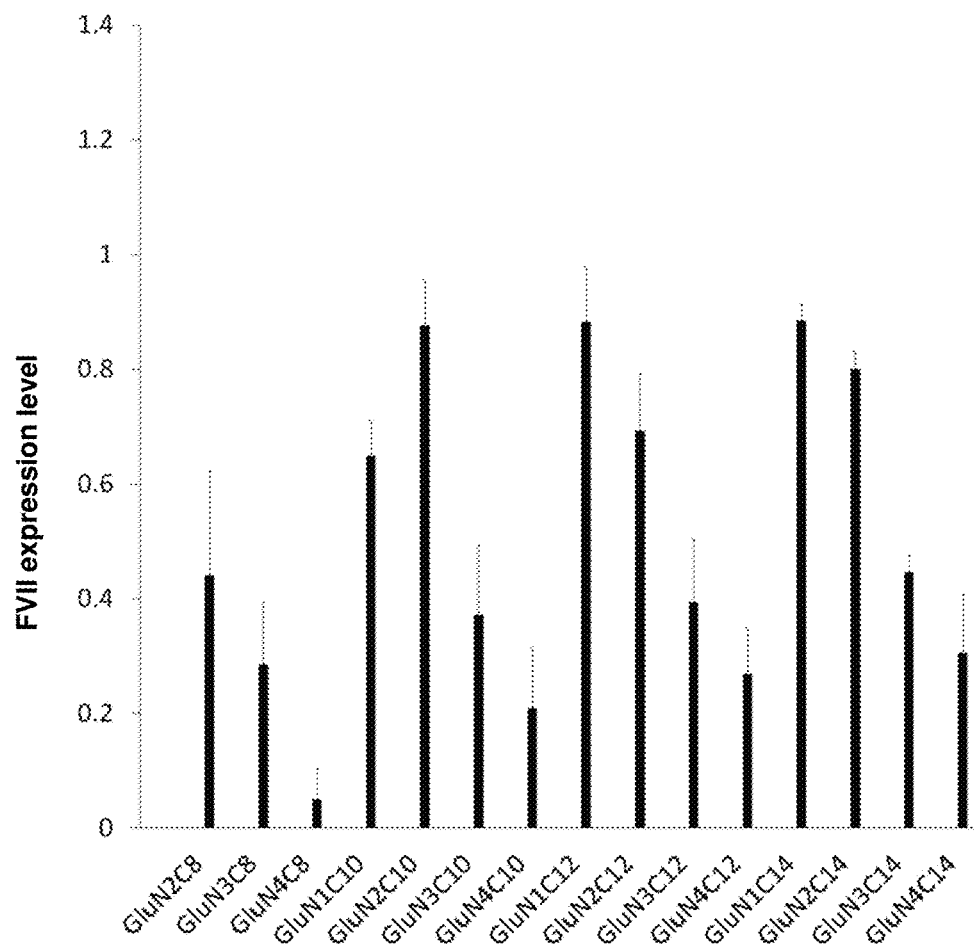
Figure 2:
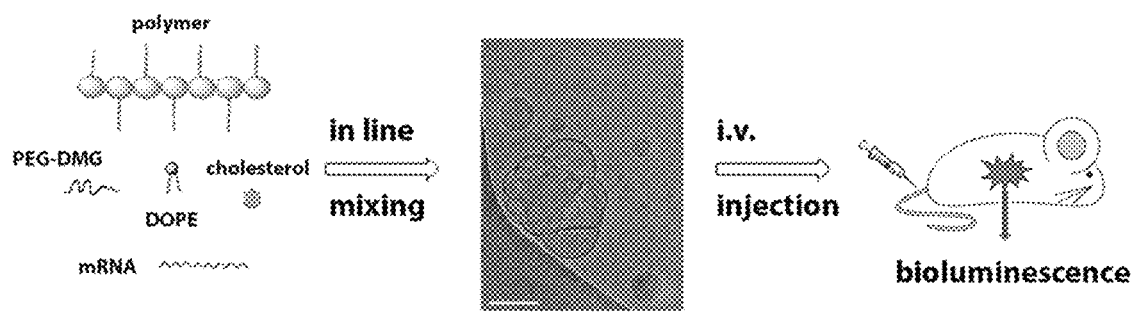
FIG. 2. Illustration of particle formulation with cholesterol, DOPE, mPEG2000-DMG, and mRNA via a microfluidic based mixing device, and evaluation through intravenous delivery of luciferase mRNA. Scale bar is 100 nm.

All procedures used in animal studies conducted at MIT were approved by the Institutional Animal Care and Use Committee (IACUC) and were also consistent with local, state and federal regulations as applicable. PBS (phosphate buffered saline) solutions containing Factor VII siRNA and a polymer described herein were administered to C57BL/6 mice (Charles River Labs, 6 to 8 weeks old, 18-22 grams) at 10 µl or 0.03 µg per gram of mouse body weight intravenously via tail vein injection for siRNA silencing experiments. After 24 or 48 h, the mice were anaesthetized by isofluorane inhalation for blood sample collection by retroorbital eye bleed using serum separation tubes (Falcon tubes, Becton Dickinson). Protein levels of Factor VII were calculated by chromogenic assay (Biophen FVII, Aniara Corporation) with a standard curve obtained from control mice. Exemplary results are shown in FIGS. 1A to 1C. FVII expression levels were significantly reduced by the polymers.

Exemplary Results

Figure 5:
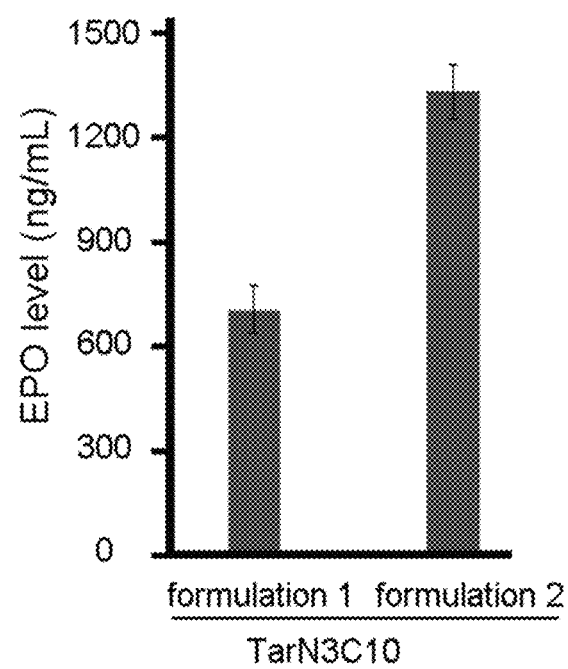
FIG. 5. Expression of EPO in mouse serum. Polymer TarN3C10 was formulated using two formulation methods: formulation 1 (polymer brush, DSPC, cholesterol, and mPEG2000-DMG), formulation 2 (polymer brush, DOPE, cholesterol, and mPEG2000-DMG). TarN3C10 nanoparticles with formulation 2 showed higher expression of EPO in comparison to formulation 1.

To formulate polymer-mRNA nanoparticles, we first mixed polymers with mRNA without adding additional components. For example, the particle size of TarN3C12-mRNA and GalN3C12'-mRNA is 647 and 536 nm, respectively (Table 13). Their PDI is 0.43 and 0.83. In order reduce particle size and improve polydispersity, we incorporated additional formulation components based on our research experience in siRNA delivery.[20] The polymer brush materials were subsequently formulated into nanoparticles through combination with cholesterol, DSPC (1,2-distearoyl-sn-glycero-3-phosphocholine)/or DOPE (1,2-dioleoyl-sn-glycero-3-phosphoethanolamine), mPEG2000-DMG (1,2-dimyristoyl-sn-glycero-3-phosphoethanolamine-N-[methoxy(polyethyleneglycol)-2000]), and mRNA using a microfluidic based mixing device.[22] To evaluate the delivery efficiency of these polymer-brush nanoparticles, mRNA for human erythropoietin (EPO) was incorporated into the formulations. EPO functions to regulate red blood cell production,[7] and is used therapeutically by patients with anemia and myelodysplasia.[23] Preliminary study indicated that TarN3C10 formulated with DOPE showed higher expression of EPO than that formulated with DSPC (FIG. 5). Therefore, we formulated all other polymers using DOPE. Characterization of the formulated nanoparticles by dynamic light scattering revealed particle sizes ranging from 56 to 96 nm (Table 13). All formulations produced fine nanoparticles with polydispersity index (PDI) between 0.11-

Figure 3A:
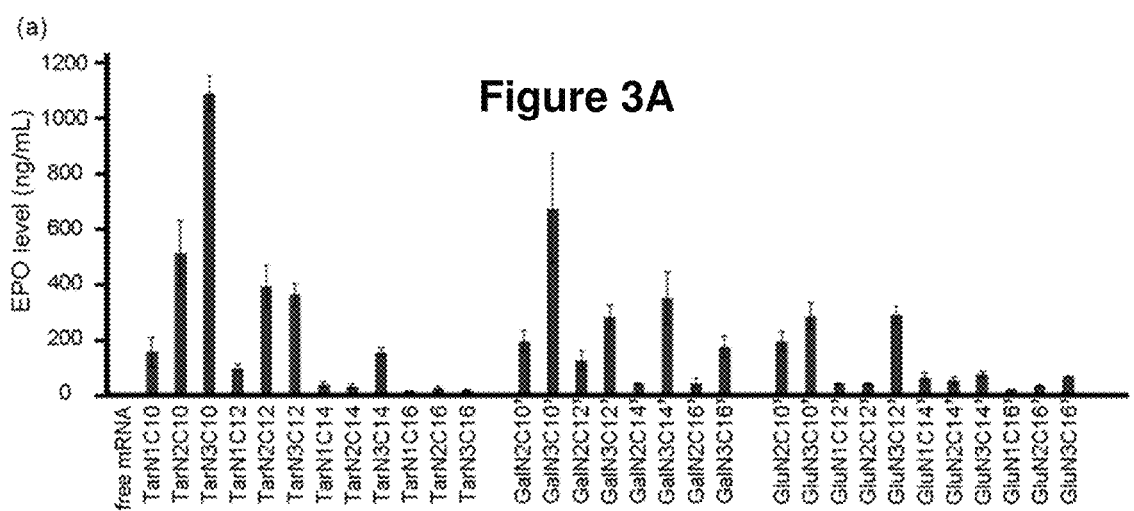
FIGS. 3A to 3E. mRNA delivery efficiency of nanoparticles of exemplary polymers described herein.

0.27. Additionally, the mRNA loading efficiency, measured using the RiboGreen assay,[17] was as high as 81% for these formulations. Polymer-brush nanoparticles were administered intravenously via tail vein in mice (EPO mRNA dose=0.3 mg/kg) with free mRNA as a control. According to the literature, protein expression with mRNA delivery normally peaks around five to seven hours.[4] Six hours following injection, blood was collected and EPO levels were measured by ELISA, with several polymer-brush nanoparticles demonstrating efficacy in delivery of functional EPO mRNA (FIG. 3A).

TABLE 13

Particle size, polydispersity index (PDI), and percentage of mRNA entrapment.

| Polymer | Particle size (nm) | PDI | mRNA entrapment % |
|---|---|---|---|
| TarN1C10 | 67 | 0.16 | 60 |
| TarN2C10 | 70 | 0.16 | 69 |
| TarN3C10 | 73 | 0.14 | 67 |
| TarN1C12 | 71* | 0.23 | 76 |
| TarN2C12 | 57* | 0.22 | 81 |
| TarN3C12 | 68* | 0.18 | 74 |
| TarN3C12 (without other formulation components) | 647 | 0.43 | 2 |
| TarN1C14 | 66 | 0.20 | 67 |
| TarN2C14 | 69 | 0.21 | 67 |
| TarN3C14 | 60* | 0.23 | 68 |
| TarN1C16 | 65* | 0.17 | 70 |
| TarN2C16 | 64 | 0.19 | 66 |
| TarN3C16 | 63* | 0.19 | 63 |
| GalN2C10' | 74 | 0.15 | 35 |
| GalN3C10' | 96 | 0.14 | 39 |
| GalN2C12' | 74 | 0.13 | 16 |
| GalN3C12' | 68 | 0.15 | 6 |
| GalN3C12' (without other formulation components) | 536 | 0.83 | 7 |
| GalN2C14' | 94 | 0.11 | 15 |
| GalN3C14' | 93 | 0.22 | 14 |
| GalN2C16' | 97 | 0.28 | 34 |
| GalN3C16' | 84 | 0.24 | 22 |
| GluN2C10' | 76 | 0.12 | 32 |
| GluN3C10' | 56 | 0.17 | 24 |
| GluN1C12' | 77 | 0.15 | 17 |
| GluN2C12' | 75 | 0.13 | 19 |
| GluN3C12' | 91 | 0.22 | 14 |
| GluN1C14' | 82* | 0.27 | 38 |
| GluN2C14' | 91 | 0.14 | 38 |
| GluN3C14' | 85 | 0.12 | 26 |
| GluN1C16' | 85 | 0.16 | 53 |
| GluN2C16' | 90 | 0.13 | 27 |
| GluN3C16' | 85 | 0.11 | 35 |

*More than one peak.

Analyzing the results from the screen demonstrates that members of the polymer building blocks were able to facilitate some amount of mRNA delivery. If the sugar unit

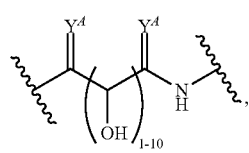

such as glycoamido moieties

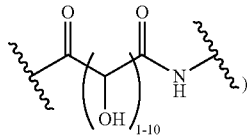

and alkyl tails are kept constant, efficiency is increased as the number of amino groups is increased (N1<N2<N3; e.g. TarN1C10 vs TarN2C10 vs TarN3C10; GalN2C10' vs GalN3C10'; GluN2C10' vs GluN3C10'). When comparing the significance of sugar, the tartarate (Tar) series was more efficient than either the galactarate (Gal) or glucarate (Glu) series (e.g. TarN2C10 vs GalN2C10' vs GluN2C10'; TarN3C10 vs GalN3C10' vs TarN3C10). The galactarate series demonstrated similar or better efficiency when compared to the glucarate series (e.g. GalN2C10' vs GluN2C10'; GalN3C10' vs TarN3C10). Taken together, these results indicate that the number of hydroxyl groups may be important to delivery efficiency. When comparing the polymers described herein on the basis of alkyl tail length, in general, polymers with shorter tails showed better efficiency than those with longer tails (C10>C12>C14>C16, e.g. TarN1C10 vs TarN1C12 vs TarN1C14 vs TarN1C16; TarN2C10 vs TarN2C12 vs TarN2C14 vs TarN2C16; TarN3C10 vs TarN3C12 vs TarN3C14 vs TarN3C16). All together (under current formulation methods), these results suggest guidelines for structure-activity relationships: (1) efficiency is increased as then number of amino groups is increased (N3>N2>N1); (2) the tartarate sugar improves efficiency relative to the galactarate or glucarate sugar; and/or (3) shorter alkyl tails improve efficiency (C10>C12>C14>C16). TarN3C10 was found to be one of the best-performing polymers. TarN3C10 induced EPO expression that resulted in serum EPO concentrations of 1080 ng/mL at a dose of 0.3 mg/kg. This was over one thousand-fold higher than expression following delivery of free EPO mRNA. To our knowledge, this is one of the most efficient mRNA intravenous delivery systems.

Figure 3B:
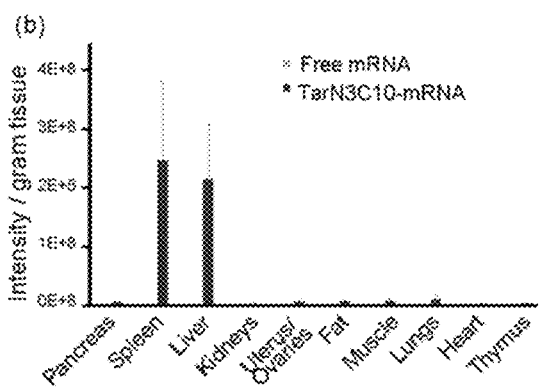

We next evaluated the biodistribution by formulating TarN3C10 with luciferase mRNA. In these studies, TarN3C10 nanoparticles were injected intravenously at an mRNA dose of 1 mg/kg. Through luminescence imaging, we measured signal arising from the pancreas, liver, spleen, kidneys, uterus/ovaries, fat, muscle, lungs, heart, and thymus (FIG. 3B). Luciferase expression following mRNA delivery with TarN3C10 nanoparticles was over one thousand fold higher in the liver and spleen compared to the administration of free mRNA, normalized by tissue weight. Additionally, over ten-fold higher luciferase expression was detected in the pancreas, uterus/ovaries, fat, kidneys, muscle, lungs, heart, and thymus for TarN3C10-treated animals relative to the free mRNA control.

Figures 3C, 3D, 3E:
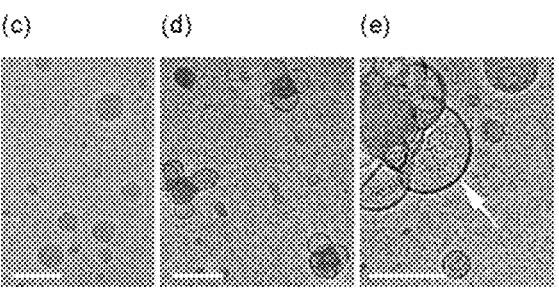

TarN3C10 nanoparticles were further characterized using cryogenic transmission electron microscopy.[24-26] Without mRNA (FIG. 3C), the TarN3C10 nanoparticles form round spherical particles. The addition of mRNA (FIGS. 3D and 3E) results in the formation of more complex structures. It is proposed that TarN3C10 and other formulation components may compose the core of the observed structures, surrounded by internally ordered domains. At higher magnification, the nanoparticles demonstrated multiple envelope domains (FIG. 3E, arrow).[27, 28]

CONCLUSION

We have described the synthesis and evaluation of novel polymer-brush nanoparticles for efficient mRNA delivery. A modular design strategy enabled the creation of polymers with building blocks consisting of amino groups, multiple hydroxyl groups, and alkyl tails. Analyzing structure-activity relationships indicates that all three building blocks contribute to efficient mRNA encapsulation and delivery. The key structural features of top performing revealed that more amino groups may be favorable, the tartarate series may be more potent than the galactarate or glucarate series, and alkyl tails may improve performance. These guidelines can be used to inform the design of next-generation mRNA delivery systems. Our study indicated that polymer/mRNA polyplex formed particles with larger size and higher polydispersity index in comparison to formulations with DOPE, cholesterol, and PEG-DMG. We note that humans with chemotherapy-related anemia receive EPO at 40,000 units/week, translating to approximately 308 μg.[30] TarN3C10 induced EPO expression of 1080 ng/mL with an mRNA dose of 0.3 mg/kg. This would translate to a dose roughly 10-fold higher than that used clinically for EPO. Finally, a single dose toxicity study revealed TarN3C10 nanoparticles are well tolerated based on histopathology, broad panel cytokine screening, and liver blood chemistry profiles. As such, strategies based on the platform of polymer-brush nanoparticles reported here may have promise for use in mRNA-based therapy.

REFERENCES

1. Tavernier, G.; Andries, O.; Demeester, J.; Sanders, N. N.; De Smedt, S. C.; Rejman, J., mRNA as gene therapeutic: how to control protein expression. *J Control Release* 2011, 150, (3), 238-247.
2. Pascolo, S., Vaccination with messenger RNA (mRNA). *Handb Exp Pharmacol* 2008, (183), 221-235.
3. Sahin, U.; Kariko, K.; Tureci, O., mRNA-based therapeutics—developing a new class of drugs. *Nat Rev Drug Discov* 2014, 13, (10), 759-780.
4. Phua, K. K.; Leong, K. W.; Nair, S. K., Transfection efficiency and transgene expression kinetics of mRNA delivered in naked and nanoparticle format. *J Control Release* 2013, 166, (3), 227-233.
5. McIvor, R. S., Therapeutic delivery of mRNA: the medium is the message. *Mol Ther* 2011, 19, (5), 822-823.
6. Su, X.; Fricke, J.; Kavanagh, D. G.; Irvine, D. J., In vitro and in vivo mRNA delivery using lipid-enveloped pH-responsive polymer nanoparticles. *Mol Pharm* 2011, 8, (3), 774-787.
7. Kormann, M. S.; Hasenpusch, G.; Aneja, M. K.; Nica, G.; Flemmer, A. W.; Herber-Jonat, S.; Huppmann, M.; Mays, L. E.; Illenyi, M.; Schams, A.; Griese, M.; Bittmann, I.; Handgretinger, R.; Hartl, D.; Rosenecker, J.; Rudolph, C., Expression of therapeutic proteins after delivery of chemically modified mRNA in mice. *Nat Biotechnol* 2011, 29, (2), 154-157.
8. Zangi, L.; Lui, K. O.; von Gise, A.; Ma, Q.; Ebina, W.; Ptaszek, L. M.; Spater, D.; Xu, H.; Tabebordbar, M.; Gorbatov, R.; Sena, B.; Nahrendorf, M.; Briscoe, D. M.; Li, R. A.; Wagers, A. J.; Rossi, D. J.; Pu, W. T.; Chien, K. R., Modified mRNA directs the fate of heart progenitor cells and induces vascular regeneration after myocardial infarction. *Nat Biotechnol* 2013, 31, 898-907.
9. Kariko, K.; Muramatsu, H.; Keller, J. M.; Weissman, D., Increased erythropoiesis in mice injected with submicrogram quantities of pseudouridine-containing mRNA encoding erythropoietin. *Mol Ther* 2012, 20, (5), 948-953.
10. Whitehead, K. A.; Langer, R.; Anderson, D. G., Knocking down barriers: advances in siRNA delivery. *Nature Reviews Drug Discovery* 2009, 8, (2), 129-138.
11. Liu, Y.; Wenning, L.; Lynch, M.; Reineke, T. M., New poly(d-glucaramidoamine)s induce DNA nanoparticle formation and efficient gene delivery into mammalian cells. *J Am Chem Soc* 2004, 126, (24), 7422-3.
12. Liu, Y.; Reineke, T. M., Degradation of poly(glycoamidoamine) DNA delivery vehicles: polyamide hydrolysis at physiological conditions promotes DNA release. *Biomacromolecules* 2010, 11, (2), 316-25.
13. McLendon, P. M.; Fichter, K. M.; Reineke, T. M., Poly(glycoamidoamine) vehicles promote pDNA uptake through multiple routes and efficient gene expression via caveolae-mediated endocytosis. *Mol Pharm* 2010, 7, (3), 738-50.
14. Liu, Y.; Wenning, L.; Lynch, M.; Reineke, T. M., Gene delivery with novel poly(L-tartaramidoamine)s. *ACS Symposium Series* 2006, 923, (Polymeric Drug Delivery I), 217-227.
15. Ingle, N. P.; Malone, B.; Reineke, T. M., Poly(glycoamidoamine)s: a broad class of carbohydrate-containing polycations for nucleic acid delivery. *Trends in biotechnology* 2011, 29, (9), 443-53.
16. Tranter, M.; Liu, Y.; He, S.; Gulick, J.; Ren, X.; Robbins, J.; Jones, W. K.; Reineke, T. M., In vivo delivery of nucleic acids via glycopolymer vehicles affords therapeutic infarct size reduction in vivo. *Mol Ther* 2012, 20, (3), 601-8.
17. Akinc, A.; Zumbuehl, A.; Goldberg, M.; Leshchiner, E. S.; Busini, V.; Hossain, N.; Bacallado, S. A.; Nguyen, D. N.; Fuller, J.; Alvarez, R.; Borodovsky, A.; Borland, T.; Constien, R.; de Fougerolles, A.; Dorkin, J. R.; Narayanannair Jayaprakash, K.; Jayaraman, M.; John, M.; Koteliansky, V.; Manoharan, M.; Nechev, L.; Qin, J.; Racie, T.; Raitcheva, D.; Rajeev, K. G.; Sah, D. W.; Soutschek, J.; Toudjarska, I.; Vornlocher, H. P.; Zimmermann, T. S.; Langer, R.; Anderson, D. G., A combinatorial library of lipid-like materials for delivery of RNAi therapeutics. *Nat Biotechnol* 2008, 26, (5), 561-9.
18. Love Kevin, T.; Mahon Kerry, P.; Levins Christopher, G.; Whitehead Kathryn, A.; Querbes, W.; Dorkin, J. R.; Qin, J.; Cantley, W.; Qin Liu, L.; Racie, T.; Frank-Kamenetsky, M.; Yip Ka, N.; Alvarez, R.; Sah Dinah, W. Y.; de Fougerolles, A.; Fitzgerald, K.; Koteliansky, V.; Akinc, A.; Langer, R.; Anderson Daniel, G., Lipid-like materials for low-dose, in vivo gene silencing. *Proc Natl Acad Sci USA* 2010, 107, (5), 1864-9.
19. Siegwart, D. J.; Whitehead, K. A.; Nuhn, L.; Sahay, G.; Cheng, H.; Jiang, S.; Ma, M.; Lytton-Jean, A.; Vegas, A.; Fenton, P.; Levins, C. G.; Love, K. T.; Lee, H.; Cortez, C.; Collins, S. P.; Li, Y. F.; Jang, J.; Querbes, W.; Zurenko, C.; Novobrantseva, T.; Langer, R.; Anderson, D. G., Combinatorial synthesis of chemically diverse core-shell nanoparticles for intracellular delivery. *Proc Natl Acad Sci USA* 2011, 108, (32), 12996-3001.
20. Dong, Y.; Love, K. T.; Dorkin, J. R.; Sirirungruang, S.; Zhang, Y.; Chen, D.; Bogorad, R. L.; Yin, H.; Chen, Y.; Vegas, A. J.; Alabi, C. A.; Sahay, G.; Olejnik, K. T.; Wang, W.; Schroeder, A.; Lytton-Jean, A. K.; Siegwart, D. J.; Akinc, A.; Barnes, C.; Barros, S. A.; Carioto, M.; Fitzgerald, K.; Hettinger, J.; Kumar, V.; Novobrantseva, T. I.; Qin, J.; Querbes, W.; Koteliansky, V.; Langer, R.; Anderson, D. G., Lipopeptide nanoparticles for potent and selective siRNA delivery in rodents and nonhuman primates. *Proc Natl Acad Sci USA* 2014, 111, (11), 3955-3960.

21. Zhang, Y.; Pelet, J. M.; Heller, D. A.; Dong, Y.; Chen, D.; Gu, Z.; Joseph, B. J.; Wallas, J.; Anderson, D. G., Lipid-modified aminoglycoside derivatives for in vivo siRNA delivery. *Adv Mater* 2013, 25, (33), 4641-4645.

22. Chen, D.; Love, K. T.; Chen, Y.; Eltoukhy, A. A.; Kastrup, C.; Sahay, G.; Jeon, A.; Dong, Y.; Whitehead, K. A.; Anderson, D. G., Rapid Discovery of Potent siRNA-Containing Lipid Nanoparticles Enabled by Controlled Microfluidic Formulation. *J Am Chem Soc* 2012, 134, (16), 6948-6951.

23. Coleman, T.; Brines, M., Science review: recombinant human erythropoietin in critical illness: a role beyond anemia? *Crit Care* 2004, 8, (5), 337-41.

24. Dahlman, J. E.; Barnes, C.; Khan, O. F.; Thiriot, A.; Jhunjunwala, S.; Shaw, T. E.; Xing, Y.; Sager, H. B.; Sahay, G.; Speciner, L.; Bader, A.; Bogorad, R. L.; Yin, H.; Racie, T.; Dong, Y.; Jiang, S.; Seedorf, D.; Dave, A.; Singh Sandhu, K.; Webber, M. J.; Novobrantseva, T.; Ruda, V. M.; Lytton-Jean, A. K.; Levins, C. G.; Kalish, B.; Mudge, D. K.; Perez, M.; Abezgauz, L.; Dutta, P.; Smith, L.; Charisse, K.; Kieran, M. W.; Fitzgerald, K.; Nahrendorf, M.; Danino, D.; Tuder, R. M.; von Andrian, U. H.; Akinc, A.; Panigrahy, D.; Schroeder, A.; Koteliansky, V.; Langer, R.; Anderson, D. G., In vivo endothelial siRNA delivery using polymeric nanoparticles with low molecular weight. *Nat Nanotechnol* 2014, 9, (8), 648-655.

25. Michel, R.; Kesselman, E.; Plostica, T.; Danino, D.; Gradzielski, M., Internalization of Silica Nanoparticles into Fluid Liposomes: Formation of Interesting Hybrid Colloids. *Angew Chem Int Ed Engl* 2014, 53, 12441-12445.

26. Danino, D., Cryo-TEM of soft molecular assemblies. *Curr Opin Colloid In* 2012, 17, (6), 316-329.

27. Semple, S. C.; Akinc, A.; Chen, J.; Sandhu, A. P.; Mui, B. L.; Cho, C. K.; Sah, D. W.; Stebbing, D.; Crosley, E. J.; Yaworski, E.; Hafez, I. M.; Dorkin, J. R.; Qin, J.; Lam, K.; Rajeev, K. G.; Wong, K. F.; Jeffs, L. B.; Nechev, L.; Eisenhardt, M. L.; Jayaraman, M.; Kazem, M.; Maier, M. A.; Srinivasulu, M.; Weinstein, M. J.; Chen, Q.; Alvarez, R.; Barros, S. A.; De, S.; Klimuk, S. K.; Borland, T.; Kosovrasti, V.; Cantley, W. L.; Tam, Y. K.; Manoharan, M.; Ciufolini, M. A.; Tracy, M. A.; de Fougerolles, A.; MacLachlan, I.; Cullis, P. R.; Madden, T. D.; Hope, M. J., Rational design of cationic lipids for siRNA delivery. *Nat Biotechnol* 2010, 28, (2), 172-6.

28. Leung, A. K.; Hafez, I. M.; Baoukina, S.; Belliveau, N. M.; Zhigaltsev, I. V.; Afshinmanesh, E.; Tieleman, D. P.; Hansen, C. L.; Hope, M. J.; Cullis, P. R., Lipid Nanoparticles Containing siRNA Synthesized by Microfluidic Mixing Exhibit an Electron-Dense Nanostructured Core. *J Phys Chem C Nanomater Interfaces* 2012, 116, (34), 18440-18450.

29. Barros, S. A.; Gollob, J. A., Safety profile of RNAi nanomedicines. *Adv Drug Deliv Rev* 2012, 64, (15), 1730-7.

30. Jelkmann, W., Efficacy of recombinant erythropoietins: is there unity of international units? *Nephrology, dialysis, transplantation: official publication of the European Dialysis and Transplant Association—European Renal Association* 2009, 24, (5), 1366-8.

31. Danino, D.; Bernheim-Groswasser, A.; Talmon, Y., Digital cryogenic transmission electron microscopy: an advanced tool for direct imaging of complex fluids. *Colloid Surface A* 2001, 183, 113-122.

32. Fechter, P.; Brownlee, G. G., Recognition of mRNA cap structures by viral and cellular proteins. *The Journal of general virology* 2005, 86, (Pt 5), 1239-1249.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A polymer of the formula:

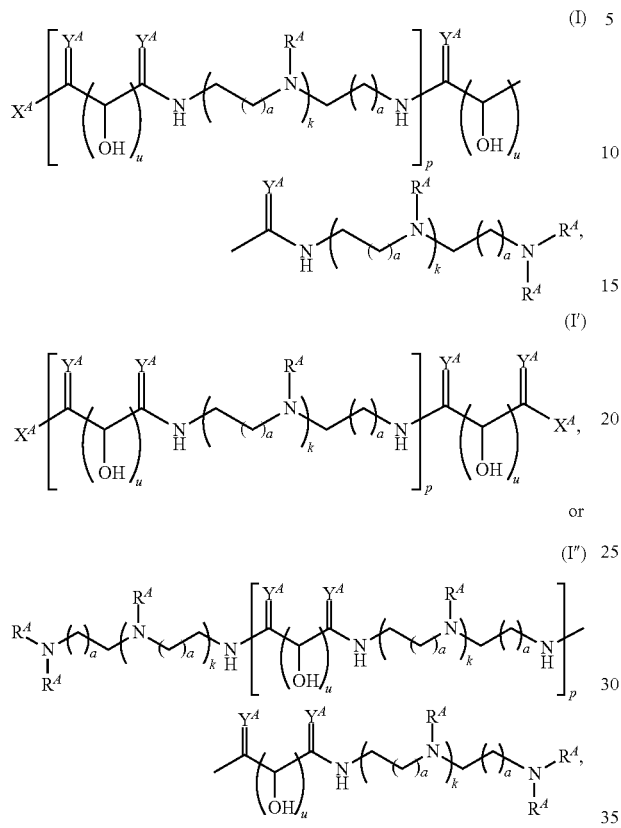

or a salt thereof, wherein:
each instance of $X^A$ is independently substituted alkyl, unsubstituted alkyl, substituted alkenyl, unsubstituted alkenyl, substituted alkynyl, unsubstituted alkynyl, substituted carbocyclyl, unsubstituted carbocyclyl, substituted heterocyclyl, unsubstituted heterocyclyl, substituted aryl, unsubstituted aryl, substituted heteroaryl, unsubstituted heteroaryl, —OR$^{XA}$, —N(R$^{XA}$)$_2$, —SR$^{XA}$, —C(=NR$^{XA}$)R$^{XA}$, —C(=NR$^{XA}$)OR$^{XA}$, —C(=NR$^{XA}$)N(R$^{XA}$)$_2$, —C(=O)R$^{XA}$, —C(=O)OR$^{XA}$, or —C(=O)N(R$^{XA}$)$_2$, wherein each instance of R$^{XA}$ is independently hydrogen, substituted acyl, unsubstituted acyl, substituted alkyl, unsubstituted alkyl, substituted alkenyl, unsubstituted alkenyl, substituted alkynyl, unsubstituted alkynyl, substituted carbocyclyl, unsubstituted carbocyclyl, substituted heterocyclyl, unsubstituted heterocyclyl, substituted aryl, unsubstituted aryl, substituted heteroaryl, unsubstituted heteroaryl, a nitrogen protecting group when attached to a nitrogen atom, an oxygen protecting group when attached to an oxygen atom, or a sulfur protecting group when attached to a sulfur atom, or two instances of R$^{XA}$ are joined to form a substituted heterocyclic ring, unsubstituted heterocyclic ring, substituted heteroaryl ring, or unsubstituted heteroaryl ring;

each instance of $Y^A$ is independently =O, =S, or =NR$^{YA}$, wherein each instance of R$^{YA}$ is independently hydrogen, substituted C$_{1-6}$ alkyl, unsubstituted C$_{1-6}$ alkyl, or a nitrogen protecting group;

each instance of R$^A$ is independently hydrogen, a moiety of the formula:

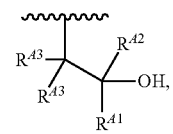

or a moiety of the formula:

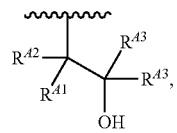

provided that at least about 60% of the total instances of R$^A$ are of the formula:

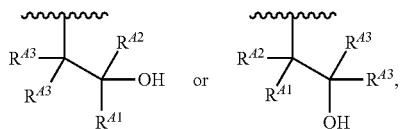

wherein:
each instance of R$^{A1}$ is independently hydrogen, substituted alkyl, unsubstituted alkyl, substituted alkenyl, or unsubstituted alkenyl;
each instance of R$^{A2}$ is independently hydrogen substituted alkyl, or unsubstituted alkyl; and
each instance of R$^{A3}$ is independently hydrogen substituted alkyl, or unsubstituted alkyl;
each instance of a is 1, 2, 3, 4, or 5;
each instance of k is 1, 2, 3, 4, 5, or 6;
each instance of u is 1, 2, 3, 4, 5, 6, 7, 8, 9, or 10; and
p is an integer between 1 and 1000, inclusive.

2. The polymer of claim 1, wherein the polymer is of the formula:

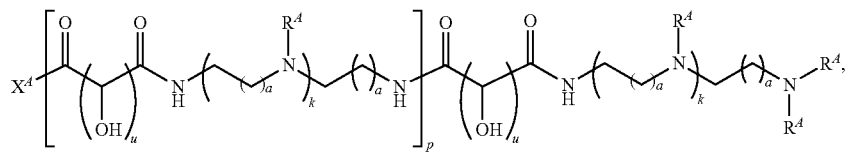

-continued
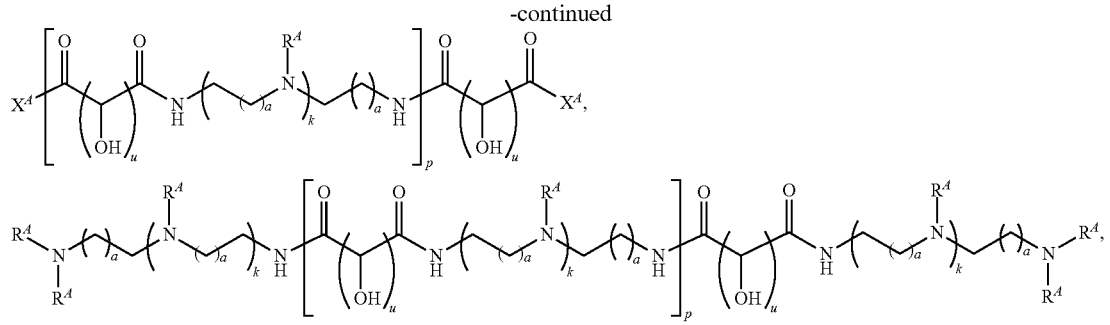
or a salt thereof.
3. The polymer of claim 1, wherein the polymer is of the formula:
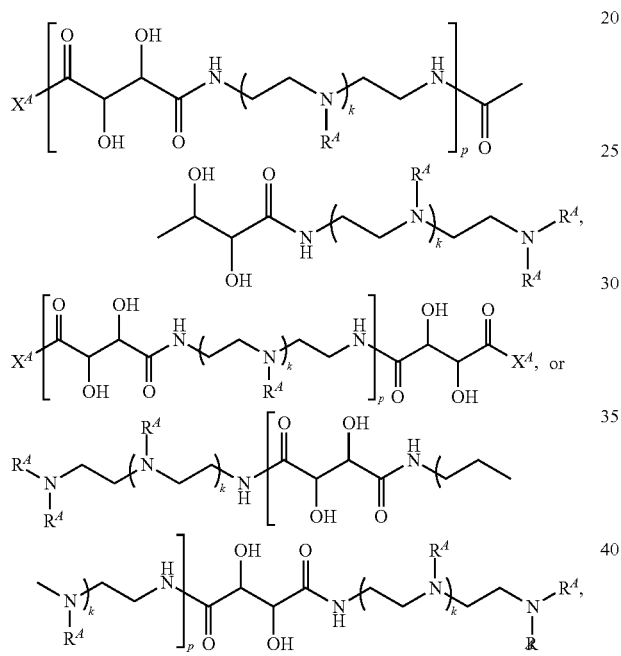
or a salt thereof.
4. The polymer of claim 1, wherein the polymer is of the formula:
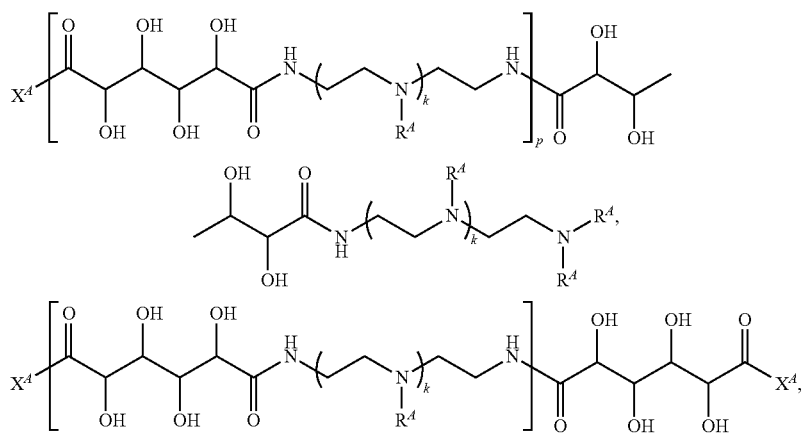

-continued

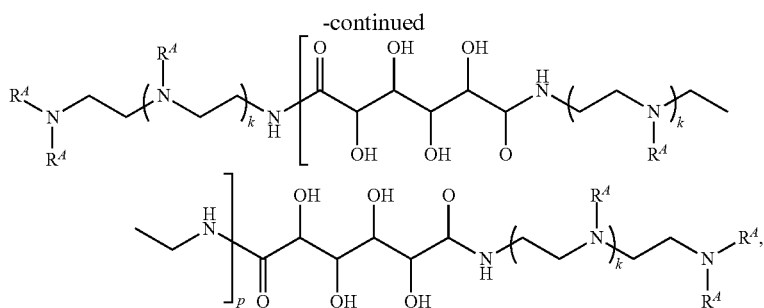

or a salt thereof.

5. The polymer of claim 1, or a salt thereof, wherein each instance of $R^A$ is independently H, a moiety of the formula:

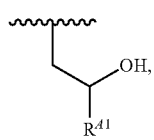

or a moiety of the formula:

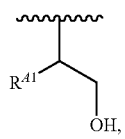

provided that at least one instance of $R^A$ is of the formula:

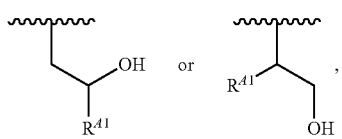

wherein each instance of $R^{A1}$ is independently unsubstituted $C_{4-18}$ alkyl.

6. The polymer of claim 1, or a salt thereof, wherein at least one instance of $X^A$ is —$OR^{XA}$ or —$N(R^{XA})_2$.

7. The polymer of claim 1, or a salt thereof, wherein at least about 60% of the total instances of $R^A$ are independently of the formula:

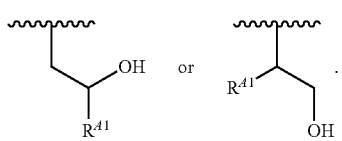

8. The polymer of claim 1, or a salt thereof, wherein each instance of $R^{A1}$ is independently substituted $C_{1-30}$ alkyl, unsubstituted $C_{1-30}$ alkyl, substituted $C_{2-30}$ alkenyl, or unsubstituted $C_{2-30}$ alkenyl.

9. The polymer of claim 1, or a salt thereof, wherein each instance of $R^{A2}$ is hydrogen.

10. The polymer of claim 1, or a salt thereof, wherein each instance of $R^{A3}$ is hydrogen.

11. The polymer of claim 1, or a salt thereof, wherein each instance of a is 1 or 2.

12. The polymer of claim 1, or a salt thereof, wherein each instance of k is 1, 2, 3, or 4.

13. The polymer of claim 1, or a salt thereof, wherein each instance of u is 2, 3, or 4.

14. The polymer of claim 1, or a salt thereof, wherein p is an integer between 1 and 30, inclusive.

15. A polymer of the formula:

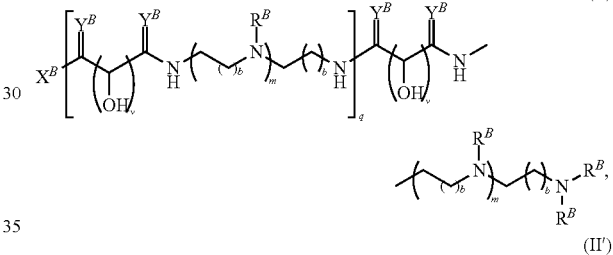

(II)

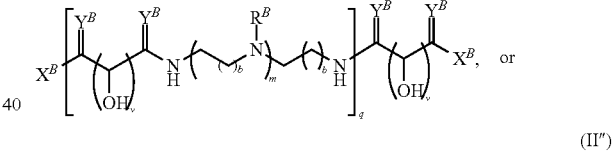

(II')

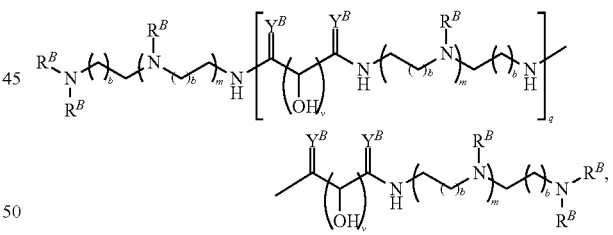

(II'')

or a salt thereof, wherein:

each instance of $X^B$ is independently substituted alkyl, unsubstituted alkyl, substituted alkenyl, unsubstituted alkenyl, substituted alkynyl, unsubstituted alkynyl, substituted carbocyclyl, unsubstituted carbocyclyl, substituted heterocyclyl, unsubstituted heterocyclyl, substituted aryl, unsubstituted aryl, substituted heteroaryl, unsubstituted heteroaryl, —$OR^{XB}$, —$N(R^{XB})_2$, —$SR^{XB}$, —CN, —SCN, —$C(=NR^{XB})R^{XB}$, —$C(=NR^{XB})OR^{XB}$, —$C(=NR^{XB})N(R^{XB})_2$, —$C(=O)R^{XB}$, —$C(=O)OR^{XB}$, or —$C(=O)N(R^{XB})_2$, —$NO_2$, —$NR^{XB}C(=O)R^{XB}$, —$NR^{XB}C(=O)OR^{XB}$, —$NR^{XB}C(=O)N(R^{XB})_2$, —$OC(=O)R^{XB}$, —$OC(=O)OR^{XB}$, or —$OC(=O)N(R^{XB})_2$, wherein each instance of $R^{XB}$ is independently hydrogen, substituted acyl, unsubstituted acyl, substituted alkyl, unsubstituted alkyl, substituted alkenyl, unsubstituted alkenyl, substituted alkynyl, unsubstituted alkynyl, substituted carbocyclyl, unsubstituted carbocyclyl, substituted heterocyclyl, unsubstituted heterocyclyl, substituted aryl, unsubstituted aryl, substituted heteroaryl, unsubstituted heteroaryl, a nitrogen protecting group when attached to a nitrogen atom, an oxygen protecting group when attached to an oxygen atom, or a sulfur protecting group when attached to a sulfur atom, or two instances of $R^{XB}$ are joined to form a substituted heterocyclic ring, unsubstituted heterocyclic ring, substituted heteroaryl ring, or unsubstituted heteroaryl ring;

each instance of $Y^B$ is independently =O, =S, or =NR$^{YB}$, wherein each instance of $R^{YB}$ is independently hydrogen, substituted $C_{1-6}$ alkyl, unsubstituted $C_{1-6}$ alkyl, or a nitrogen protecting group;

each instance of $R^B$ is independently hydrogen or a moiety of the formula:

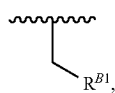

provided that at least about 60% of the total instances of $R^B$ are of the formula:

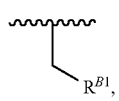

wherein each instance of $R^{B1}$ is independently substituted alkyl, unsubstituted alkyl, substituted alkenyl, or unsubstituted alkenyl;

each instance of b is 1, 2, 3, 4, or 5;
each instance of m is 1, 2, 3, 4, 5, or 6;
each instance of v is 1, 2, 3, 4, 5, 6, 7, 8, 9, or 10; and
q is an integer between 1 and 1000, inclusive.

16. A polymer of the formula:

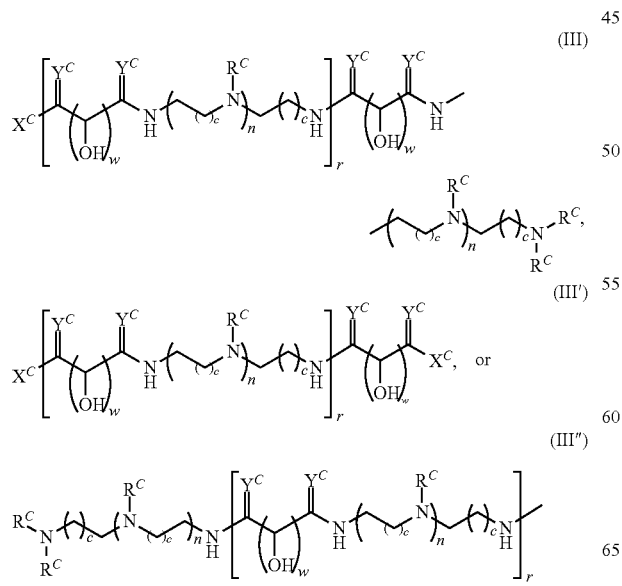

-continued

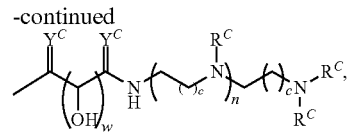

or a salt thereof, wherein:

each instance of $X^C$ is independently substituted alkyl, unsubstituted alkyl, substituted alkenyl, unsubstituted alkenyl, substituted alkynyl, unsubstituted alkynyl, substituted carbocyclyl, unsubstituted carbocyclyl, substituted heterocyclyl, unsubstituted heterocyclyl, substituted aryl, unsubstituted aryl, substituted heteroaryl, unsubstituted heteroaryl, —OR$^{XC}$, —N(R$^{XC}$)$_2$, —SR$^{XC}$, —CN, —SCN, —C(=NR$^{XC}$)R$^{XC}$, C(=NR$^{XC}$)OR$^{XC}$, —C(=NR$^{XC}$)N(R$^{XC}$)$_2$, —C(=O)R$^{XC}$, —C(=O)OR$^{XC}$, or —C(=O)N(R$^{XC}$)$_2$, —NO$_2$, —NR$^{XC}$C(=O)R$^{XC}$, —NR$^{XC}$C(=O)OR$^{XC}$, —NR$^{XC}$C(=O)N(R$^{XC}$)$_2$, —OC(=O)R$^{XC}$, —OC(=O)OR$^{XC}$, or —OC(=O)N(R$^{XC}$)$_2$, wherein each instance of $R^{XC}$ is independently hydrogen, substituted acyl, unsubstituted acyl, substituted alkyl, unsubstituted alkyl, substituted alkenyl, unsubstituted alkenyl, substituted alkynyl, unsubstituted alkynyl, substituted carbocyclyl, unsubstituted carbocyclyl, substituted heterocyclyl, unsubstituted heterocyclyl, substituted aryl, unsubstituted aryl, substituted heteroaryl, unsubstituted heteroaryl, a nitrogen protecting group when attached to a nitrogen atom, an oxygen protecting group when attached to an oxygen atom, or a sulfur protecting group when attached to a sulfur atom, or two instances of $R^{XC}$ are joined to form a substituted heterocyclic ring, unsubstituted heterocyclic ring, substituted heteroaryl ring, or unsubstituted heteroaryl ring;

each instance of $Y^C$ is independently =O, =S, or =NR$^{YC}$, wherein each instance of $R^{YC}$ is independently hydrogen, substituted $C_{1-6}$ alkyl, unsubstituted $C_{1-6}$ alkyl, or a nitrogen protecting group;

each instance of $R^C$ is independently hydrogen or a moiety of the formula:

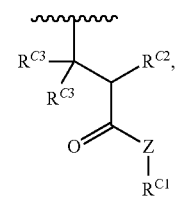

provided that at least one instance of $R^C$ is of the formula:

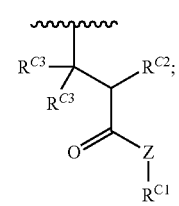

wherein:
each instance of Z is independently —O— or —NR$^{C4}$—;
each instance of R$^{C1}$ is independently hydrogen, substituted alkyl, unsubstituted alkyl, substituted alkenyl, or unsubstituted alkenyl;
each instance of R$^{C2}$ is independently hydrogen substituted alkyl, or unsubstituted alkyl;
each instance of R$^{C3}$ is independently hydrogen substituted alkyl, or unsubstituted alkyl; and
each instance of R$^{C4}$ is independently hydrogen, substituted C$_{1-6}$ alkyl, unsubstituted C$_{1-6}$ alkyl, or a nitrogen protecting group;
each instance of c is 1, 2, 3, 4, or 5;
each instance of n is 0, 1, 2, 3, 4, 5, or 6;
each instance of w is 1, 2, 3, 4, 5, 6, 7, 8, 9, or 10; and
r is an integer between 1 and 1000, inclusive.

17. A particle comprising a polymer of claim 1, or a salt thereof, and an agent.

18. A composition comprising:
a polymer of claim 1, or a salt thereof;
an agent; and
optionally an excipient.

19. A method of delivering an agent to a subject or cell, the method comprising administering to the subject or contacting the cell with a composition of claim 18.

20. The polymer of claim 1, or a salt thereof, wherein each instance of R$^{A1}$ is independently unsubstituted C$_{4-18}$ alkyl.

21. The polymer of claim 1, wherein the polymer is prepared by reacting a poly(glycoamidoamine) and an epoxide as shown in the table below:

| Polymer Number | Poly(glycoamidoamine) Number | Epoxide Number |
|---|---|---|
| TarN1C8 | A1a | A2b |
| TarN1C10 | A1a | A2c |
| TarN1C12 | A1a | A2d |
| TarN1C14 | A1a | A2e |
| TarN2C8 | A1b | A2b |
| TarN2C10 | A1b | A2c |
| TarN2C12 | A1b | A2d |
| TarN2C14 | A1b | A2e |
| TarN3C8 | A1c | A2b |
|  | A1c | A2c |
| TarN3C12 | A1c | A2d |
| TarN3C14 | A1c | A2e |
| TarN4C8 | A1d | A2b |
| TarN4C10 | A1d | A2c |
| TarN4C12 | A1d | A2d |
| TarN4C14 | A1d | A2e |
| GalN2C8 | A1e | A2b |
| GalN2C10 | A1e | A2c |
| GalN2C12 | A1e | A2d |
| GalN2C14 | A1e | A2e |
| GalN3C8 | A1f | A2b |
| GalN3C10 | A1f | A2c |
| GalN3C12 | A1f | A2d |
| GalN3C14 | A1f | A2e |
| GalN4C8 | A1g | A2b |
| GalN4C10 | A1g | A2c |
| GalN4C12 | A1g | A2d |
| GalN4C14 | A1g | A2e |
| GluN1C10 | A1h | A2c |
| GluN1C12 | A1h | A2d |
| GluN1C14 | A1h | A2e |
| GluN2C8 | A1i | A2b |
| GluN2C10 | A1i | A2c |
| GluN2C12 | A1i | A2d |
| GluN2C14 | A1i | A2e |
| GluN3C6 | A1j | A2a |
| GluN3C8 | A1j | A2b |
| GluN3C10 | A1j | A2c |
| GluN3C12 | A1j | A2d |
| GluN3C14 | A1j | A2e |
| GluN4C8 | A1k | A2b |
| GluN4C10 | A1k | A2c |
| GluN4C12 | A1k | A2d |
| GluN4C14 | A1k | A2e |
| TarN1C16 | A1o | A2f |
| TarN2C16 | A1b | A2f |
| TarN3C16 | A1c | A2f |
| GalN2C10" | A1q | A2c |
| GalN3C10" | A1r | A2c |
| GalN2C12" | A1q | A2d |
| GalN3C12" | A1r | A2d |
| GalN2C14" | A1q | A2e |
| GalN3C14" | A1r | A2e |
| GalN2C16" | A1q | A2f |
| GalN3C16" | A1r | A2f |
| GluN2C10" | A1t | A2c |
| GluN3C10" | A1u | A2c |
| GluN1C12" | A1s | A2d |
| GluN2C12" | A1t | A2d |
| GluN3C12" | A1u | A2d |
| GluN1C14" | A1s | A2e |
| GluN2C14" | A1t | A2e |
| GluN3C14" | A1u | A2e |
| GluN1C16" | A1s | A2f |
| GluN2C16" | A1t | A2f |
| GluN3C16" | A1u | A2f; | wherein:
the poly(glycoamidoamine) is of the formula as shown in the table below:

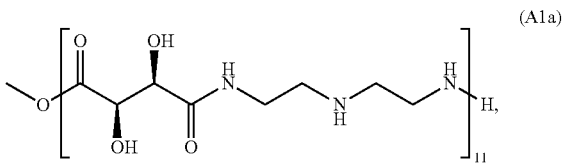

(A1a)

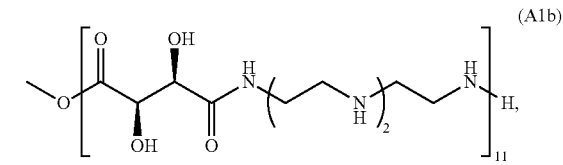

(A1b)

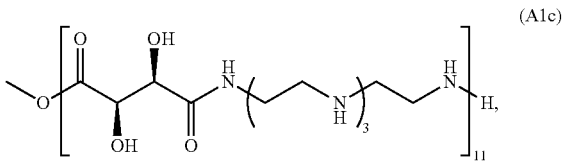

(A1c)

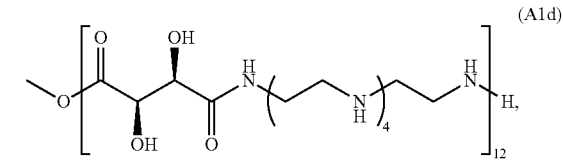

(A1d)

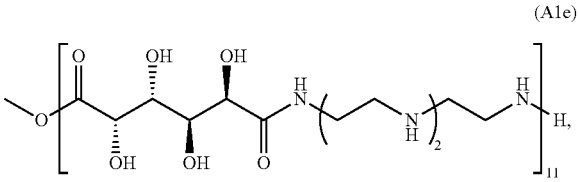

(A1e)

the epoxide is of the formula as shown in the table below:

or a salt thereof.

22. The composition of claim 18, wherein the agent is a polynucleotide, small molecule, protein, or peptide.

23. The composition of claim 18, wherein the agent is a polynucleotide.

24. The composition of claim 23, wherein the polynucleotide is DNA.

25. The composition of claim 24, wherein the DNA is is single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA.

26. The composition of claim 23, wherein the polynucleotide is RNA.

27. The composition of claim 25, wherein the RNA is mRNA, siRNA, single-stranded RNA (ssRNA), double-stranded RNA (dsRNA), small interfering RNA (siRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA.

* * * * *